United States Patent
Askem et al.

(10) Patent No.: US 10,682,446 B2
(45) Date of Patent: Jun. 16, 2020

(54) DRESSING STATUS DETECTION FOR NEGATIVE PRESSURE WOUND THERAPY

(71) Applicant: Smith & Nephew PLC, Watford, Hertfordshire (GB)

(72) Inventors: Ben Alan Askem, Brough (GB); Iacopo Claudio Ferrari, Milan (IT); Matteo Foini, Milan (IT); Paolo Forzani, Milan (IT); Christopher John Fryer, York (GB); Allan Kenneth Frazer Grugeon Hunt, Beverley (GB); Christian Riva, Milan (IT)

(73) Assignee: Smith & Nephew PLC, Watford (GB)

( * ) Notice: Subject to any disclaimer, the term of this patent is extended or adjusted under 35 U.S.C. 154(b) by 343 days.

(21) Appl. No.: 15/536,260

(22) PCT Filed: Dec. 21, 2015

(86) PCT No.: PCT/IB2015/002535
§ 371 (c)(1),
(2) Date: Jun. 15, 2017

(87) PCT Pub. No.: WO2016/103032
PCT Pub. Date: Jun. 30, 2016

(65) Prior Publication Data
US 2018/0133378 A1   May 17, 2018

Related U.S. Application Data

(60) Provisional application No. 62/095,721, filed on Dec. 22, 2014.

(51) Int. Cl.
*A61M 1/00*        (2006.01)
*F04B 43/04*       (2006.01)
(Continued)

(52) U.S. Cl.
CPC ........ *A61M 1/0088* (2013.01); *A61M 1/0025* (2014.02); *A61M 1/0027* (2014.02);
(Continued)

(58) Field of Classification Search
CPC .............. A61M 1/0025; A61M 1/0027; A61M 1/0031; A61M 1/0035; A61M 1/0072;
(Continued)

(56) References Cited

U.S. PATENT DOCUMENTS 3,787,882 A   1/1974  Fillmore et al.
3,885,892 A   5/1975  Dwyer et al.
(Continued)

FOREIGN PATENT DOCUMENTS

CN   101676563    3/2010
DE   34 43 101    5/1986
(Continued)

OTHER PUBLICATIONS

Invitation to Pay Additional Fees and Partial Search Report, re PCT Application No. PCT/IB2015/002536, dated Apr. 22, 2016.
(Continued)

*Primary Examiner* — Benjamin J Klein
(74) *Attorney, Agent, or Firm* — Knobbe, Martens, Olson & Bear LLP

(57) ABSTRACT

Systems and methods for controlling a pump system for use in negative pressure wound therapy are described herein. In some embodiments, a method for controlling a pump system includes causing provision of negative pressure, via a flow path, to a wound dressing configured to be positioned over a wound, the flow path configured to fluidically connect the pump system to the wound dressing, measuring a first pressure value in the flow path at a first time, measuring a second pressure value in the flow path at a second time, calculating a first rate of pressure change using the first and
(Continued)

second pressure values, and in response to determining that the calculated first rate of pressure change satisfies a threshold rate of change, providing an indication that the wound dressing is full, wherein the method is performed under control of a controller of the pump system.

30 Claims, 52 Drawing Sheets

(51) Int. Cl.
*F04B 45/047* (2006.01)
*F04B 49/06* (2006.01)
*B29C 65/16* (2006.01)
*F04B 51/00* (2006.01)
*B29C 65/00* (2006.01)
*B29C 65/78* (2006.01)
*F04B 49/12* (2006.01)
*B29L 31/00* (2006.01)

(52) U.S. Cl.
CPC ........ *A61M 1/0031* (2013.01); *A61M 1/0035* (2014.02); *A61M 1/0072* (2014.02); *A61M 1/0086* (2014.02); *B29C 65/1635* (2013.01); *B29C 65/1677* (2013.01); *B29C 65/7802* (2013.01); *B29C 65/7805* (2013.01); *B29C 66/54* (2013.01); *B29C 66/7392* (2013.01); *F04B 43/04* (2013.01); *F04B 45/047* (2013.01); *F04B 49/065* (2013.01); *F04B 49/12* (2013.01); *F04B 51/00* (2013.01); *A61M 2205/0272* (2013.01); *A61M 2205/15* (2013.01); *A61M 2205/18* (2013.01); *A61M 2205/3331* (2013.01); *A61M 2205/42* (2013.01); *A61M 2205/50* (2013.01); *A61M 2205/505* (2013.01); *A61M 2205/52* (2013.01); *A61M 2205/581* (2013.01); *A61M 2205/583* (2013.01); *A61M 2205/584* (2013.01); *A61M 2205/587* (2013.01); *A61M 2205/70* (2013.01); *A61M 2205/7536* (2013.01); *A61M 2205/8206* (2013.01); *A61M 2207/00* (2013.01); *B29C 65/7808* (2013.01); *B29C 66/71* (2013.01); *B29C 66/8227* (2013.01); *B29C 66/8242* (2013.01); *B29L 2031/7496* (2013.01); *B29L 2031/753* (2013.01)

(58) Field of Classification Search
CPC .............. A61M 1/0086; A61M 1/0088; A61M 2205/0272; A61M 2205/15; A61M 2205/18; A61M 2205/3331; A61M 2205/42; A61M 2205/50; A61M 2205/505; A61M 2205/52; A61M 2205/581; A61M 2205/583; A61M 2205/584; A61M 2205/587; A61M 2205/70
See application file for complete search history.

(56) References Cited

U.S. PATENT DOCUMENTS

| | | |
|---|---|---|
| 3,900,276 A | 8/1975 | Dilworth |
| 3,972,328 A | 8/1976 | Chen |
| 4,015,912 A | 4/1977 | Kofink |
| 4,029,598 A | 6/1977 | Neisius et al. |
| 4,293,609 A | 10/1981 | Erickson |
| 4,321,020 A | 3/1982 | Mittal |
| 4,460,642 A | 7/1984 | Errede et al. |
| 4,578,060 A | 3/1986 | Huck et al. |
| 4,585,397 A | 4/1986 | Crawford et al. |
| 4,599,052 A | 7/1986 | Langen et al. |
| 4,604,313 A | 8/1986 | McFarland et al. |
| 4,643,641 A | 2/1987 | Clausen et al. |
| 4,728,499 A | 3/1988 | Fehder |
| 4,813,942 A | 3/1989 | Alvarez |
| 4,846,164 A | 7/1989 | Martz |
| 4,969,880 A | 11/1990 | Zamierowski |
| 4,979,944 A | 12/1990 | Luzsicza |
| 4,988,345 A | 1/1991 | Reising |
| 5,056,510 A | 10/1991 | Gilman |
| 5,115,801 A | 5/1992 | Cartmell et al. |
| 5,160,328 A | 11/1992 | Cartmell et al. |
| 5,181,905 A | 1/1993 | Flam |
| 5,197,945 A | 3/1993 | Cole et al. |
| 5,222,714 A | 6/1993 | Morinigo et al. |
| 5,238,732 A | 8/1993 | Krishnan |
| 5,246,353 A | 9/1993 | Sohn |
| 5,291,822 A | 3/1994 | Alsobrooks et al. |
| 5,336,219 A | 8/1994 | Krantz |
| 5,349,896 A | 9/1994 | Connelly et al. |
| 5,354,261 A | 10/1994 | Clark et al. |
| 5,358,494 A | 10/1994 | Svedman |
| 5,360,445 A | 11/1994 | Goldowsky |
| 5,364,381 A | 11/1994 | Soga et al. |
| 5,380,294 A | 1/1995 | Persson |
| 5,391,179 A | 2/1995 | Mezzoli |
| 5,417,743 A | 5/1995 | Dauber |
| 5,447,492 A | 9/1995 | Cartmell et al. |
| 5,449,003 A | 9/1995 | Sugimura |
| 5,449,347 A | 9/1995 | Preen et al. |
| 5,456,660 A | 10/1995 | Reich et al. |
| 5,466,229 A | 11/1995 | Elson |
| 5,470,585 A | 11/1995 | Gilchrist |
| 5,480,377 A | 1/1996 | Cartmell et al. |
| 5,492,313 A | 2/1996 | Pan et al. |
| 5,497,788 A | 3/1996 | Inman et al. |
| 5,538,500 A | 7/1996 | Peterson |
| 5,545,151 A | 8/1996 | O'Connor et al. |
| 5,549,584 A | 8/1996 | Gross |
| 5,562,107 A | 10/1996 | Lavender et al. |
| 5,579,765 A | 12/1996 | Cox et al. |
| 5,591,297 A | 1/1997 | Ahr |
| 5,603,946 A | 2/1997 | Constantine |
| 5,630,855 A | 5/1997 | Lundback |
| 5,634,391 A | 6/1997 | Eady |
| 5,636,643 A | 6/1997 | Argenta et al. |
| 5,637,080 A | 6/1997 | Geng |
| 5,645,081 A | 7/1997 | Argenta et al. |
| 5,662,599 A | 9/1997 | Reich et al. |
| 5,676,525 A | 10/1997 | Berner et al. |
| 5,685,214 A | 11/1997 | Neff et al. |
| 5,687,633 A | 11/1997 | Eady |
| 5,688,516 A | 11/1997 | Raad et al. |
| 5,693,013 A | 12/1997 | Geuder |
| 5,702,356 A | 12/1997 | Hathman |
| 5,704,905 A | 1/1998 | Jensen et al. |
| 5,707,173 A | 1/1998 | Cottone et al. |
| 5,707,499 A | 1/1998 | Joshi et al. |
| 5,713,384 A | 2/1998 | Roach et al. |
| 5,730,587 A | 3/1998 | Snyder et al. |
| 5,743,170 A | 4/1998 | Forman et al. |
| 5,759,570 A | 6/1998 | Arnold |
| 5,762,638 A | 6/1998 | Shikani et al. |
| 5,769,608 A | 6/1998 | Seale |
| 5,785,508 A | 7/1998 | Bolt |
| 5,827,213 A | 10/1998 | Jensen |
| 5,840,052 A | 11/1998 | Johns |
| 5,843,025 A | 12/1998 | Shaari |
| 5,852,126 A | 12/1998 | Barnard et al. |
| 5,863,184 A | 1/1999 | Juterbock et al. |
| 5,882,743 A | 3/1999 | McConnell |
| 5,897,296 A | 4/1999 | Yamamoto et al. |
| 5,897,541 A | 4/1999 | Uitenbrock et al. |
| 5,950,523 A | 9/1999 | Reynolds |
| 6,040,493 A | 3/2000 | Cooke et al. |
| 6,056,519 A | 5/2000 | Morita et al. |
| 6,068,588 A | 5/2000 | Goldowsky |
| 6,071,267 A | 6/2000 | Zamierowski |
| 6,075,177 A | 6/2000 | Bahia et al. |

(56) References Cited

U.S. PATENT DOCUMENTS

| | | |
|---|---|---|
| 6,080,685 A | 6/2000 | Eady |
| 6,102,205 A | 8/2000 | Greff et al. |
| 6,102,680 A | 8/2000 | Fraser et al. |
| 6,124,520 A | 9/2000 | Roberts |
| 6,124,521 A | 9/2000 | Roberts |
| 6,138,550 A | 10/2000 | Fingar, Jr. |
| 6,142,982 A | 11/2000 | Hunt et al. |
| 6,145,430 A | 11/2000 | Able et al. |
| 6,158,327 A | 12/2000 | Huss |
| 6,162,194 A | 12/2000 | Shipp |
| 6,174,136 B1 | 1/2001 | Kilayko et al. |
| 6,174,306 B1 | 1/2001 | Fleischmann |
| 6,227,825 B1 | 5/2001 | Vay |
| 6,230,609 B1 | 5/2001 | Fingar |
| 6,231,310 B1 | 5/2001 | Tojo et al. |
| 6,249,198 B1 | 6/2001 | Clark et al. |
| 6,297,423 B1 | 10/2001 | Schoenfeldt et al. |
| 6,323,568 B1 | 11/2001 | Zabar |
| 6,327,960 B1 | 12/2001 | Heimueller et al. |
| 6,343,539 B1 | 2/2002 | Du |
| 6,362,390 B1 | 3/2002 | Carlucci et al. |
| 6,388,417 B1 | 5/2002 | Keith |
| 6,413,057 B1 | 7/2002 | Hong et al. |
| 6,458,109 B1 | 10/2002 | Henley et al. |
| 6,506,175 B1 | 1/2003 | Goldstein |
| 6,514,047 B2 | 2/2003 | Burr et al. |
| 6,528,696 B1 | 3/2003 | Ireland |
| 6,540,490 B1 | 4/2003 | Lilie |
| 6,589,028 B1 | 7/2003 | Eckerbom et al. |
| 6,604,908 B1 | 8/2003 | Bryant et al. |
| 6,613,953 B1 | 9/2003 | Altura |
| 6,618,221 B2 | 9/2003 | Gillis et al. |
| 6,623,255 B2 | 9/2003 | Joong et al. |
| 6,626,891 B2 | 9/2003 | Ohmstede |
| 6,638,035 B1 | 10/2003 | Puff |
| 6,648,862 B2 | 11/2003 | Watson |
| 6,652,252 B2 | 11/2003 | Zabar |
| 6,655,257 B1 | 12/2003 | Meyer |
| 6,673,036 B1 | 1/2004 | Britto |
| 6,685,681 B2 | 2/2004 | Lockwood et al. |
| 6,719,742 B1 | 4/2004 | McCormack et al. |
| 6,752,794 B2 | 6/2004 | Lockwood et al. |
| 6,755,807 B2 | 6/2004 | Risk et al. |
| 6,764,459 B1 | 7/2004 | Donaldson |
| 6,776,769 B2 | 8/2004 | Smith |
| 6,800,074 B2 | 10/2004 | Henley et al. |
| 6,815,846 B2 | 11/2004 | Godkin |
| 6,823,905 B1 | 11/2004 | Smith et al. |
| 6,824,533 B2 | 11/2004 | Risk, Jr. et al. |
| 6,877,419 B2 | 4/2005 | Ohrle et al. |
| 6,885,116 B2 | 4/2005 | Knirck |
| 6,886,116 B1 | 4/2005 | MacLellan et al. |
| 6,936,037 B2 | 8/2005 | Bubb et al. |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,041,057 B1 | 5/2006 | Faupel et al. |
| 7,049,478 B1 | 5/2006 | Smith et al. |
| 7,070,584 B2 | 7/2006 | Johnson et al. |
| 7,108,683 B2 | 9/2006 | Zamierowski |
| 7,128,735 B2 | 10/2006 | Weston |
| 7,151,348 B1 | 12/2006 | Ueda et al. |
| 7,216,651 B2 | 5/2007 | Argenta et al. |
| 7,294,752 B1 | 11/2007 | Propp |
| 7,361,184 B2 | 4/2008 | Joshi |
| 7,363,850 B2 | 4/2008 | Becker |
| 7,374,409 B2 | 5/2008 | Kawamura |
| 7,381,859 B2 | 6/2008 | Hunt et al. |
| 7,401,703 B2 | 7/2008 | McMichael et al. |
| 7,438,705 B2 | 10/2008 | Karpowicz et al. |
| 7,447,327 B2 | 11/2008 | Kitamura et al. |
| 7,524,315 B2 | 4/2009 | Blott et al. |
| 7,534,927 B2 | 5/2009 | Lockwood |
| 7,550,034 B2 | 6/2009 | Janse Van Rensburg et al. |
| 7,553,306 B1 | 6/2009 | Hunt et al. |
| 7,569,742 B2 | 8/2009 | Haggstrom et al. |
| 7,605,298 B2 | 10/2009 | Bechert et al. |
| 7,611,500 B1 | 11/2009 | Lina et al. |
| 7,615,036 B2 | 11/2009 | Joshi et al. |
| 7,622,629 B2 | 11/2009 | Aail |
| 7,625,362 B2 | 12/2009 | Boehringer et al. |
| 7,670,323 B2 | 3/2010 | Hunt et al. |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,718,249 B2 | 5/2010 | Russell et al. |
| 7,722,582 B2 | 5/2010 | Lina et al. |
| 7,749,531 B2 | 7/2010 | Booher |
| 7,758,555 B2 | 7/2010 | Kelch et al. |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| 7,785,247 B2 | 8/2010 | Tatum et al. |
| 7,811,269 B2 | 10/2010 | Boynton et al. |
| 7,838,717 B2 | 11/2010 | Haggstrom et al. |
| 7,846,141 B2 | 12/2010 | Weston |
| 7,857,806 B2 | 12/2010 | Karpowicz et al. |
| 7,883,494 B2 | 2/2011 | Martin |
| 7,909,805 B2 | 3/2011 | Weston |
| 7,910,791 B2 | 3/2011 | Coffey |
| 7,922,703 B2 | 4/2011 | Riesinger |
| 7,959,624 B2 | 6/2011 | Riesinger |
| 7,964,766 B2 | 6/2011 | Blott et al. |
| 7,976,519 B2 | 7/2011 | Bubb et al. |
| 8,007,257 B2 | 8/2011 | Heaton et al. |
| 8,034,037 B2 | 10/2011 | Adams et al. |
| 8,048,046 B2 | 11/2011 | Hudspeth et al. |
| 8,062,272 B2 | 11/2011 | Weston |
| 8,062,273 B2 | 11/2011 | Weston |
| 8,062,331 B2 | 11/2011 | Zamierowski |
| 8,080,702 B2 | 12/2011 | Blott et al. |
| 8,105,295 B2 | 1/2012 | Blott et al. |
| 8,118,794 B2 | 2/2012 | Weston et al. |
| 8,152,785 B2 | 4/2012 | Vitaris |
| 8,162,907 B2 | 4/2012 | Heagle |
| 8,167,869 B2 | 5/2012 | Wudyka |
| 8,186,978 B2 | 5/2012 | Tinholt et al. |
| 8,188,331 B2 | 5/2012 | Barta et al. |
| 8,192,409 B2 | 6/2012 | Hardman et al. |
| 8,202,262 B2 | 6/2012 | Lina et al. |
| 8,207,392 B2 | 6/2012 | Haggstrom et al. |
| 8,215,929 B2 | 7/2012 | Shen et al. |
| 8,241,015 B2 | 8/2012 | Lillie |
| 8,241,261 B2 | 8/2012 | Randolph et al. |
| 8,257,327 B2 | 9/2012 | Blott et al. |
| 8,257,328 B2 | 9/2012 | Augustine et al. |
| 8,267,918 B2 | 9/2012 | Johnson et al. |
| 8,282,611 B2 | 10/2012 | Weston |
| 8,294,586 B2 | 10/2012 | Pidgeon et al. |
| 8,303,552 B2 | 11/2012 | Weston |
| 8,323,264 B2 | 12/2012 | Weston et al. |
| 8,350,116 B2 | 1/2013 | Lockwood et al. |
| 8,363,881 B2 | 1/2013 | Godkin |
| 8,366,690 B2 | 2/2013 | Locke et al. |
| 8,366,692 B2 | 2/2013 | Weston |
| 8,372,049 B2 | 2/2013 | Jaeb et al. |
| 8,372,050 B2 | 2/2013 | Jaeb et al. |
| 8,398,614 B2 | 3/2013 | Blott et al. |
| 8,404,921 B2 | 3/2013 | Lee et al. |
| 8,409,157 B2 | 4/2013 | Haggstrom et al. |
| 8,409,160 B2 | 4/2013 | Locke et al. |
| 8,409,170 B2 | 4/2013 | Locke et al. |
| 8,414,519 B2 | 4/2013 | Hudspeth et al. |
| 8,425,478 B2 | 4/2013 | Olson |
| 8,429,778 B2 | 4/2013 | Receveur et al. |
| 8,439,882 B2 | 5/2013 | Kelch |
| 8,444,392 B2 | 5/2013 | Turner et al. |
| 8,444,612 B2 | 5/2013 | Patel et al. |
| 8,449,267 B2 | 5/2013 | Debrito et al. |
| 8,460,255 B2 | 6/2013 | Joshi et al. |
| 8,513,481 B2 | 8/2013 | Gergeley et al. |
| 8,535,296 B2 | 9/2013 | Blott et al. |
| 8,540,688 B2 | 9/2013 | Eckstein et al. |

(56) References Cited

U.S. PATENT DOCUMENTS

| | | |
|---|---|---|
| 8,545,464 B2 | 10/2013 | Weston |
| 8,545,466 B2 | 10/2013 | Andresen et al. |
| 8,568,386 B2 | 10/2013 | Malhi |
| 8,569,566 B2 | 10/2013 | Blott et al. |
| 8,579,872 B2 | 11/2013 | Coulthard et al. |
| 8,617,129 B2 | 12/2013 | Hartwell |
| 8,622,981 B2 | 1/2014 | Hartwell et al. |
| 8,628,505 B2 | 1/2014 | Weston |
| 8,641,691 B2 | 2/2014 | Fink |
| 8,646,479 B2 | 2/2014 | Jaeb et al. |
| 8,663,198 B2 | 3/2014 | Buan et al. |
| 8,708,984 B2 | 4/2014 | Robinson et al. |
| 8,715,256 B2 | 5/2014 | Greener |
| 8,734,131 B2 | 5/2014 | McCrone et al. |
| 8,764,732 B2 | 7/2014 | Hartwell |
| 8,791,316 B2 | 7/2014 | Greener |
| 8,795,243 B2 | 8/2014 | Weston |
| 8,795,800 B2 | 8/2014 | Evans |
| 8,808,274 B2 | 8/2014 | Hartwell |
| 8,827,983 B2 | 9/2014 | Braga et al. |
| 8,829,263 B2 | 9/2014 | Haggstrom et al. |
| 8,834,451 B2 | 9/2014 | Blott et al. |
| 8,834,452 B2 | 9/2014 | Hudspeth et al. |
| 8,843,327 B2 | 9/2014 | Vernon-Harcourt et al. |
| 8,845,603 B2 | 9/2014 | Middleton et al. |
| 8,905,985 B2 | 12/2014 | Allen et al. |
| 8,945,074 B2 | 2/2015 | Buan et al. |
| 8,951,235 B2 | 2/2015 | Allen et al. |
| 8,956,336 B2 | 2/2015 | Haggstrom et al. |
| 8,974,429 B2 | 3/2015 | Gordon et al. |
| 9,012,714 B2 | 4/2015 | Fleischmann |
| 9,061,095 B2 | 6/2015 | Adie et al. |
| 9,067,003 B2 | 6/2015 | Buan et al. |
| 9,084,845 B2 | 7/2015 | Adie et al. |
| 9,127,665 B2 | 9/2015 | Locke et al. |
| 9,168,330 B2 | 10/2015 | Joshi et al. |
| 9,180,231 B2 | 11/2015 | Greener |
| 9,199,011 B2 | 12/2015 | Locke et al. |
| 9,199,012 B2 | 12/2015 | Vitaris et al. |
| 9,220,822 B2 | 12/2015 | Hartwell et al. |
| 9,227,000 B2 | 1/2016 | Fink et al. |
| 9,265,665 B2 | 2/2016 | Robinson et al. |
| 9,283,118 B2 | 3/2016 | Locke et al. |
| 9,302,033 B2 | 4/2016 | Riesinger |
| 9,314,557 B2 | 4/2016 | Ricci et al. |
| 9,375,353 B2 | 6/2016 | Vitaris et al. |
| 9,375,521 B2 | 6/2016 | Hudspeth et al. |
| 9,381,283 B2 | 7/2016 | Adams et al. |
| 9,421,309 B2 | 8/2016 | Robinson et al. |
| 9,427,505 B2 | 8/2016 | Askem et al. |
| 9,446,178 B2 | 9/2016 | Blott et al. |
| 9,452,248 B2 | 9/2016 | Blott et al. |
| 9,474,661 B2 | 10/2016 | Fouillet et al. |
| 9,506,463 B2 | 11/2016 | Locke et al. |
| 9,518,575 B2 | 12/2016 | Felber |
| 9,545,465 B2 | 1/2017 | Allen et al. |
| 9,629,986 B2 | 4/2017 | Patel et al. |
| 9,669,138 B2 | 6/2017 | Joshi et al. |
| 9,681,993 B2 | 6/2017 | Wu et al. |
| 9,737,649 B2 | 8/2017 | Begin et al. |
| 9,795,725 B2 | 10/2017 | Joshi et al. |
| 9,808,561 B2 | 11/2017 | Adie et al. |
| 9,829,471 B2 | 11/2017 | Hammond et al. |
| 9,844,473 B2 | 12/2017 | Blott et al. |
| 9,877,872 B2 | 1/2018 | Mumby et al. |
| 9,901,664 B2 | 2/2018 | Askem |
| 9,956,121 B2 | 5/2018 | Hartwell |
| 9,962,474 B2 | 5/2018 | Greener |
| 10,016,309 B2 | 7/2018 | Hartwell |
| 10,046,096 B2 | 8/2018 | Askem et al. |
| 10,058,642 B2 | 8/2018 | Weston |
| 10,105,471 B2 | 10/2018 | Weston |
| 10,143,783 B2 | 12/2018 | Adie et al. |
| 10,155,070 B2 | 12/2018 | Childress et al. |
| 10,201,644 B2 | 2/2019 | Haggstrom et al. |
| 10,299,964 B2 | 5/2019 | Askem et al. |
| 10,307,517 B2 | 6/2019 | Allen et al. |
| 10,328,188 B2 | 6/2019 | Begin et al. |
| 10,478,536 B2 | 11/2019 | Pratt et al. |
| 2001/0001278 A1 | 5/2001 | Drevet |
| 2001/0033795 A1 | 10/2001 | Humpheries |
| 2001/0043870 A1 | 11/2001 | Song |
| 2002/0002906 A1 | 1/2002 | Fuesser |
| 2002/0026946 A1 | 3/2002 | McKay |
| 2002/0106282 A1 | 8/2002 | Sharp et al. |
| 2002/0122732 A1 | 9/2002 | Oh et al. |
| 2002/0164255 A1 | 11/2002 | Burr et al. |
| 2003/0031573 A1 | 2/2003 | Tearle |
| 2003/0035743 A1 | 2/2003 | Lee et al. |
| 2003/0065292 A1 | 4/2003 | Darouiche |
| 2003/0095879 A1 | 5/2003 | Oh et al. |
| 2003/0099558 A1 | 5/2003 | Chang |
| 2003/0108430 A1 | 6/2003 | Yoshida et al. |
| 2003/0110939 A1 | 6/2003 | Able et al. |
| 2003/0125646 A1 | 7/2003 | Whitlock |
| 2003/0133812 A1 | 7/2003 | Puff et al. |
| 2003/0161735 A1 | 8/2003 | Kim et al. |
| 2003/0162071 A1 | 8/2003 | Yasuda |
| 2003/0175125 A1 | 9/2003 | Kwon et al. |
| 2003/0175135 A1 | 9/2003 | Heo et al. |
| 2003/0230191 A1 | 12/2003 | Ohrle et al. |
| 2004/0005222 A1 | 1/2004 | Yoshida et al. |
| 2004/0021123 A1 | 2/2004 | Howell et al. |
| 2004/0057855 A1 | 3/2004 | Gerlach et al. |
| 2004/0066097 A1 | 4/2004 | Kobayashi et al. |
| 2004/0071568 A1 | 4/2004 | Hyeon |
| 2004/0071572 A1 | 4/2004 | Greter et al. |
| 2004/0115076 A1 | 6/2004 | Lilie et al. |
| 2004/0116551 A1 | 6/2004 | Terry |
| 2004/0118460 A1 | 6/2004 | Stinson |
| 2004/0126250 A1 | 7/2004 | Tsuchiya et al. |
| 2004/0155741 A1 | 8/2004 | Godin |
| 2004/0156527 A1 | 8/2004 | Stiles et al. |
| 2004/0156730 A1 | 8/2004 | Lilie et al. |
| 2004/0163713 A1 | 8/2004 | Schulze et al. |
| 2004/0182237 A1 | 9/2004 | Headley et al. |
| 2004/0189103 A1 | 9/2004 | Duncan et al. |
| 2004/0219059 A1 | 11/2004 | Barringer et al. |
| 2005/0031458 A1 | 2/2005 | Brashears |
| 2005/0031470 A1 | 2/2005 | Lee |
| 2005/0098031 A1 | 5/2005 | Yoon et al. |
| 2005/0100450 A1 | 5/2005 | Bryant et al. |
| 2005/0110190 A1 | 5/2005 | Giardini |
| 2005/0111987 A1 | 5/2005 | Yoo et al. |
| 2005/0123422 A1 | 6/2005 | Lilie |
| 2005/0124966 A1 | 6/2005 | Karpowicz et al. |
| 2005/0129540 A1 | 6/2005 | Puff |
| 2005/0135946 A1 | 6/2005 | Kang et al. |
| 2005/0142007 A1 | 6/2005 | Lee et al. |
| 2005/0142008 A1 | 6/2005 | Jung et al. |
| 2005/0155657 A1 | 7/2005 | Kack et al. |
| 2005/0163635 A1 | 7/2005 | Berwanger et al. |
| 2005/0209560 A1 | 9/2005 | Boukhny et al. |
| 2005/0235988 A1 | 10/2005 | Hansen et al. |
| 2005/0251117 A1 | 11/2005 | Anderson et al. |
| 2005/0271526 A1 | 12/2005 | Chang et al. |
| 2005/0272142 A1 | 12/2005 | Horita |
| 2005/0276706 A1 | 12/2005 | Radue |
| 2006/0009744 A1 | 1/2006 | Edrman et al. |
| 2006/0017332 A1 | 1/2006 | Kang et al. |
| 2006/0018771 A1 | 1/2006 | Song et al. |
| 2006/0019144 A1 | 1/2006 | Hidaka et al. |
| 2006/0024181 A1 | 2/2006 | Kim |
| 2006/0029675 A1 | 2/2006 | Ginther |
| 2006/0039806 A1 | 2/2006 | Becker |
| 2006/0056979 A1 | 3/2006 | Yoo et al. |
| 2006/0056980 A1 | 3/2006 | Yoo et al. |
| 2006/0057000 A1 | 3/2006 | Hyeon |
| 2006/0061024 A1 | 3/2006 | Jung et al. |
| 2006/0073036 A1 | 4/2006 | Debrito et al. |
| 2006/0110259 A1 | 5/2006 | Puff et al. |
| 2006/0118190 A1 | 6/2006 | Takehana et al. |
| 2006/0122558 A1 | 6/2006 | Sherman et al. |
| 2006/0191575 A1 | 8/2006 | Naesje |

(56) References Cited

U.S. PATENT DOCUMENTS

| | | |
|---|---|---|
| 2006/0192259 A1 | 8/2006 | Silverbrook |
| 2006/0210411 A1 | 9/2006 | Hyeon |
| 2006/0216165 A1 | 9/2006 | Lee |
| 2006/0222532 A1 | 10/2006 | Lee et al. |
| 2006/0228224 A1 | 10/2006 | Hong et al. |
| 2006/0245947 A1 | 11/2006 | Seto et al. |
| 2006/0251523 A1 | 11/2006 | Lee et al. |
| 2006/0271020 A1 | 11/2006 | Huang et al. |
| 2006/0282174 A1 | 12/2006 | Haines |
| 2006/0287632 A1 | 12/2006 | Sarangapani |
| 2007/0032741 A1 | 2/2007 | Hibner et al. |
| 2007/0040454 A1 | 2/2007 | Freudenberger et al. |
| 2007/0041856 A1 | 2/2007 | Hansen et al. |
| 2007/0052144 A1 | 3/2007 | Knirck et al. |
| 2007/0055209 A1 | 3/2007 | Patel et al. |
| 2007/0078444 A1 | 4/2007 | Larsson |
| 2007/0091614 A1 | 4/2007 | Kaisser et al. |
| 2007/0179460 A1 | 8/2007 | Adahan |
| 2007/0196214 A1 | 8/2007 | Bocchiola |
| 2007/0225663 A1 | 9/2007 | Watt et al. |
| 2007/0256428 A1 | 11/2007 | Unger et al. |
| 2007/0260226 A1 | 11/2007 | Jaeb et al. |
| 2007/0282283 A1 | 12/2007 | Kaern et al. |
| 2007/0292286 A1 | 12/2007 | Hell et al. |
| 2007/0295201 A1 | 12/2007 | Dadd |
| 2008/0008607 A1 | 1/2008 | Schade et al. |
| 2008/0015526 A1 | 1/2008 | Reiner et al. |
| 2008/0020178 A1 | 1/2008 | Oehrle et al. |
| 2008/0031748 A1 | 2/2008 | Ihle et al. |
| 2008/0051708 A1 | 2/2008 | Kumar et al. |
| 2008/0082040 A1 | 4/2008 | Kubler et al. |
| 2008/0089796 A1 | 4/2008 | Schade et al. |
| 2008/0094753 A1 | 4/2008 | Brodkin et al. |
| 2008/0110336 A1 | 5/2008 | Bovill et al. |
| 2008/0125697 A1 | 5/2008 | Gao |
| 2008/0125698 A1 | 5/2008 | Gerg et al. |
| 2008/0132821 A1 | 6/2008 | Propp et al. |
| 2008/0191399 A1 | 8/2008 | Chang |
| 2008/0211435 A1 | 9/2008 | Imagawa |
| 2008/0240942 A1 | 10/2008 | Heinrich et al. |
| 2008/0260551 A1 | 10/2008 | Simmons |
| 2008/0267797 A1 | 10/2008 | Hell et al. |
| 2008/0281281 A1 | 11/2008 | Meyer et al. |
| 2008/0306456 A1 | 12/2008 | Riesinger |
| 2008/0310980 A1 | 12/2008 | Ramsdorf et al. |
| 2009/0012441 A1 | 1/2009 | Mulligan |
| 2009/0028733 A1 | 1/2009 | Duwel |
| 2009/0030383 A1 | 1/2009 | Larsen et al. |
| 2009/0030402 A1 | 1/2009 | Adahan |
| 2009/0053081 A1 | 2/2009 | Griffiths |
| 2009/0054855 A1 | 2/2009 | Blott et al. |
| 2009/0060750 A1 | 3/2009 | Chen et al. |
| 2009/0071551 A1 | 3/2009 | Chalich |
| 2009/0081049 A1 | 3/2009 | Tian et al. |
| 2009/0087323 A1 | 4/2009 | Blakey et al. |
| 2009/0114293 A1 | 5/2009 | Kanai et al. |
| 2009/0118711 A1 | 5/2009 | Haase et al. |
| 2009/0125004 A1 | 5/2009 | Shen et al. |
| 2009/0129955 A1 | 5/2009 | Schubert |
| 2009/0129986 A1 | 5/2009 | Wimberger-Friedl et al. |
| 2009/0148320 A1 | 6/2009 | Lucas |
| 2009/0149821 A1 | 6/2009 | Scherson et al. |
| 2009/0157024 A1 | 6/2009 | Song |
| 2009/0163882 A1 | 6/2009 | Koch et al. |
| 2009/0166411 A1 | 7/2009 | Kramer et al. |
| 2009/0169402 A1 | 7/2009 | Stenberg |
| 2009/0206778 A1 | 8/2009 | Roh et al. |
| 2009/0234306 A1 | 9/2009 | Vitaris |
| 2009/0299251 A1 | 12/2009 | Buan |
| 2009/0299306 A1 | 12/2009 | Buan |
| 2009/0304534 A1 | 12/2009 | Richter |
| 2009/0312725 A1 | 12/2009 | Braga |
| 2010/0042059 A1 | 2/2010 | Pratt et al. |
| 2010/0068820 A1 | 3/2010 | Meathrel et al. |
| 2010/0074775 A1 | 3/2010 | Yamamoto et al. |
| 2010/0098566 A1 | 4/2010 | Kang |
| 2010/0125258 A1 | 5/2010 | Coulthard et al. |
| 2010/0160881 A1 | 6/2010 | Lin et al. |
| 2010/0185048 A1 | 7/2010 | Lonky et al. |
| 2010/0191178 A1 | 7/2010 | Ross et al. |
| 2010/0211030 A1 | 8/2010 | Turner et al. |
| 2010/0244780 A1 | 9/2010 | Turner |
| 2010/0259406 A1 | 10/2010 | Caso et al. |
| 2010/0265649 A1 | 10/2010 | Singh et al. |
| 2010/0268179 A1 | 10/2010 | Kelch et al. |
| 2010/0280435 A1 | 11/2010 | Raney et al. |
| 2010/0280469 A1 | 11/2010 | Hall |
| 2010/0318052 A1 | 12/2010 | Ha et al. |
| 2010/0318071 A1 | 12/2010 | Wudyka |
| 2010/0320659 A1 | 12/2010 | Chen et al. |
| 2011/0000069 A1 | 1/2011 | Ramsdorf et al. |
| 2011/0004172 A1 | 1/2011 | Eckstein et al. |
| 2011/0015587 A1 | 1/2011 | Tumey et al. |
| 2011/0020588 A1 | 1/2011 | Kinugawa et al. |
| 2011/0038741 A1 | 2/2011 | Lissner et al. |
| 2011/0043055 A1 | 2/2011 | Chiang |
| 2011/0071415 A1 | 3/2011 | Karwoski et al. |
| 2011/0081267 A1 | 4/2011 | McCrone et al. |
| 2011/0098600 A1 | 4/2011 | Matsumura et al. |
| 2011/0103984 A1 | 5/2011 | Santa |
| 2011/0112492 A1 | 5/2011 | Bharti et al. |
| 2011/0169348 A1 | 7/2011 | Park |
| 2011/0171044 A1 | 7/2011 | Flanigan |
| 2011/0176945 A1 | 7/2011 | Drevet |
| 2011/0176946 A1 | 7/2011 | Drevet |
| 2011/0184341 A1 | 7/2011 | Baker et al. |
| 2011/0186765 A1 | 8/2011 | Jaeb et al. |
| 2011/0196321 A1 | 8/2011 | Wudyka |
| 2011/0205646 A1 | 8/2011 | Sato et al. |
| 2011/0205647 A1 | 8/2011 | Osaka et al. |
| 2011/0224631 A1 | 9/2011 | Simmons |
| 2011/0229352 A1 | 9/2011 | Herbert |
| 2011/0236265 A1 | 9/2011 | Hasui et al. |
| 2011/0236277 A1 | 9/2011 | Lee et al. |
| 2011/0251569 A1 | 10/2011 | Turner et al. |
| 2011/0257572 A1 | 10/2011 | Locke et al. |
| 2011/0311379 A1 | 12/2011 | Hale et al. |
| 2012/0000208 A1 | 1/2012 | Hon et al. |
| 2012/0008817 A1 | 1/2012 | Grinker et al. |
| 2012/0034109 A1 | 2/2012 | Tout et al. |
| 2012/0046625 A1 | 2/2012 | Johannison |
| 2012/0051945 A1 | 3/2012 | Orndorff et al. |
| 2012/0053543 A1 | 3/2012 | Miau et al. |
| 2012/0160091 A1 | 6/2012 | Dadd et al. |
| 2012/0177513 A1 | 7/2012 | Lilie et al. |
| 2012/0184930 A1 | 7/2012 | Johannison |
| 2012/0220960 A1 | 8/2012 | Ruland |
| 2012/0232502 A1 | 9/2012 | Lowing |
| 2012/0251359 A1 | 10/2012 | Neelakantan et al. |
| 2012/0259299 A1 | 10/2012 | Ryu et al. |
| 2012/0271256 A1 | 10/2012 | Locke et al. |
| 2012/0289895 A1 | 11/2012 | Tsoukalis |
| 2012/0289913 A1 | 11/2012 | Eckstein et al. |
| 2012/0301341 A1 | 11/2012 | Ota et al. |
| 2013/0017110 A1 | 1/2013 | Villagomez et al. |
| 2013/0042753 A1 | 2/2013 | Becker et al. |
| 2013/0058802 A1 | 3/2013 | Roman et al. |
| 2013/0062140 A1 | 3/2013 | White et al. |
| 2013/0066285 A1 | 3/2013 | Locke et al. |
| 2013/0066289 A1 | 3/2013 | Song et al. |
| 2013/0085462 A1 | 4/2013 | Nip et al. |
| 2013/0090613 A1 | 4/2013 | Kelch et al. |
| 2013/0090616 A1 | 4/2013 | Neubauer |
| 2013/0118622 A1 | 5/2013 | Patzold et al. |
| 2013/0123755 A1 | 5/2013 | Locke et al. |
| 2013/0138054 A1 | 5/2013 | Fleischmann |
| 2013/0144227 A1* | 6/2013 | Locke ............... A61M 1/0031 604/318 |
| 2013/0150814 A1 | 6/2013 | Buan |
| 2013/0165878 A1 | 6/2013 | Heagle |
| 2013/0209277 A1 | 8/2013 | Locke et al. |
| 2013/0209278 A1 | 8/2013 | Locke et al. |
| 2013/0209279 A1 | 8/2013 | Locke et al. |
| 2013/0209281 A1 | 8/2013 | Locke et al. |

(56) References Cited

U.S. PATENT DOCUMENTS

| | | |
|---|---|---|
| 2013/0213506 A1 | 8/2013 | Chen et al. |
| 2013/0223979 A1 | 8/2013 | Locke et al. |
| 2013/0267917 A1 | 10/2013 | Pan et al. |
| 2013/0276906 A1 | 10/2013 | Locke et al. |
| 2013/0280113 A1 | 10/2013 | Miranda et al. |
| 2013/0296762 A1 | 11/2013 | Toth |
| 2013/0302545 A1 | 11/2013 | Schnelker et al. |
| 2013/0340870 A1 | 12/2013 | Ito et al. |
| 2014/0010673 A1 | 1/2014 | Locke et al. |
| 2014/0014746 A1 | 1/2014 | Watanabe |
| 2014/0017093 A1 | 1/2014 | Locke et al. |
| 2014/0030126 A1 | 1/2014 | God et al. |
| 2014/0072149 A1 | 3/2014 | Yan et al. |
| 2014/0100516 A1 | 4/2014 | Hunt et al. |
| 2014/0114236 A1 | 4/2014 | Gordon |
| 2014/0114237 A1 | 4/2014 | Gordon |
| 2014/0114268 A1 | 4/2014 | Auguste et al. |
| 2014/0127148 A1 | 5/2014 | Derain |
| 2014/0163490 A1 | 6/2014 | Locke et al. |
| 2014/0194835 A1 | 7/2014 | Ehlert |
| 2014/0200533 A1 | 7/2014 | Whyte et al. |
| 2014/0276487 A1 | 9/2014 | Locke et al. |
| 2014/0303551 A1 | 10/2014 | Germain et al. |
| 2014/0303575 A1 | 10/2014 | May |
| 2014/0316359 A1 | 10/2014 | Collinson et al. |
| 2014/0323906 A1 | 10/2014 | Peatfield et al. |
| 2014/0350496 A1 | 11/2014 | Riesinger |
| 2015/0032035 A1 | 1/2015 | Banwell et al. |
| 2015/0057625 A1 | 2/2015 | Coulthard et al. |
| 2015/0073363 A1 | 3/2015 | Kelch et al. |
| 2015/0094673 A1 | 4/2015 | Pratt et al. |
| 2015/0094674 A1 | 4/2015 | Pratt et al. |
| 2015/0119831 A1 | 4/2015 | Robinson et al. |
| 2015/0119832 A1 | 4/2015 | Locke |
| 2015/0119833 A1 | 4/2015 | Coulthard et al. |
| 2015/0159066 A1 | 6/2015 | Hartwell et al. |
| 2015/0165182 A1 | 6/2015 | Pratt et al. |
| 2015/0335798 A1 | 11/2015 | De Samber et al. |
| 2016/0000610 A1 | 1/2016 | Riesinger |
| 2016/0000611 A1 | 1/2016 | Niederauer et al. |
| 2016/0136339 A1* | 5/2016 | Begin ................ A61M 1/0086 604/319 |
| 2016/0144084 A1 | 5/2016 | Collinson et al. |
| 2016/0262942 A1 | 9/2016 | Riesinger |
| 2016/0298620 A1 | 10/2016 | Cordoba et al. |
| 2016/0317357 A1 | 11/2016 | Vitaris et al. |
| 2016/0319957 A1 | 11/2016 | Jaeb et al. |
| 2017/0128642 A1 | 5/2017 | Buan |
| 2017/0181894 A1 | 6/2017 | Allen et al. |
| 2017/0181896 A1 | 6/2017 | Hartwell |
| 2017/0181897 A1 | 6/2017 | Hartwell |
| 2017/0354767 A1 | 12/2017 | Carr et al. |
| 2017/0368239 A1 | 12/2017 | Askem et al. |
| 2018/0296397 A1 | 10/2018 | Askem et al. |
| 2018/0318476 A1 | 11/2018 | Askem et al. |
| 2018/0326129 A1 | 11/2018 | Askem et al. |
| 2019/0167863 A1 | 6/2019 | Adie et al. |
| 2019/0307611 A1 | 10/2019 | Askem et al. |
| 2019/0307934 A1 | 10/2019 | Allen et al. |

FOREIGN PATENT DOCUMENTS

| | | |
|---|---|---|
| DE | 39 16 648 | 9/1990 |
| DE | 90 17 289 | 4/1992 |
| DE | 198 44 355 | 4/2000 |
| DE | 20 2004 017 052 | 7/2005 |
| DE | 10 2005 007016 | 8/2006 |
| EP | 0 208 395 | 1/1987 |
| EP | 0 340 018 | 11/1989 |
| EP | 0 411 564 | 2/1991 |
| EP | 0 541 251 | 5/1993 |
| EP | 0 578 999 | 1/1994 |
| EP | 0 604 953 | 7/1994 |
| EP | 0 759 521 | 2/1997 |
| EP | 0 775 825 | 5/1997 |
| EP | 0 793 019 | 9/1997 |
| EP | 0 809 028 | 11/1997 |
| EP | 0 898 076 | 2/1999 |
| EP | 0 909 895 | 4/1999 |
| EP | 0 941 726 | 9/1999 |
| EP | 1 114 933 | 7/2001 |
| EP | 1 153 218 | 11/2001 |
| EP | 0 708 620 | 5/2003 |
| EP | 0 993 317 | 9/2003 |
| EP | 1 406 020 | 4/2004 |
| EP | 1 430 588 | 6/2004 |
| EP | 1 449 971 | 8/2004 |
| EP | 1 452 156 | 9/2004 |
| EP | 1 554 737 | 7/2005 |
| EP | 1 556 942 | 7/2005 |
| EP | 1 469 580 | 12/2005 |
| EP | 1 757 809 | 2/2007 |
| EP | 1 850 005 | 10/2007 |
| EP | 1 460 270 | 6/2008 |
| EP | 1 955 887 | 8/2008 |
| EP | 1 791 579 | 7/2009 |
| EP | 2 161 011 | 3/2010 |
| EP | 2 161 448 | 3/2010 |
| EP | 1 932 481 | 6/2010 |
| EP | 2 216 573 | 8/2010 |
| EP | 2 253 353 | 11/2010 |
| EP | 2 302 127 | 3/2011 |
| EP | 1 956 242 | 4/2011 |
| EP | 2 366 721 | 9/2011 |
| EP | 2 462 908 | 6/2012 |
| EP | 1 875 081 | 12/2013 |
| EP | 2 616 116 | 12/2014 |
| EP | 3 037 116 | 6/2016 |
| FR | 1 163 907 | 10/1958 |
| FR | 2 939 320 | 6/2010 |
| GB | 1039145 | 8/1966 |
| GB | 1220857 | 1/1971 |
| GB | 1255395 | 12/1971 |
| GB | 2099306 | 12/1982 |
| GB | 2235877 | 3/1991 |
| GB | 2273133 | 6/1994 |
| GB | 2306580 | 5/1997 |
| GB | 2433298 | 6/2007 |
| GB | 2435422 | 8/2007 |
| JP | 52-040804 | 3/1977 |
| JP | S61-81584 | 4/1986 |
| JP | H07-127577 | 5/1995 |
| JP | 2000-220570 | 8/2000 |
| JP | 2006-233925 | 9/2006 |
| JP | 2006-316711 | 11/2006 |
| JP | 2012-219692 | 11/2012 |
| JP | 2014-098393 | 1/2014 |
| KR | 10 2010 0138195 | 12/2010 |
| RU | 62504 | 4/2007 |
| WO | WO 1983/00742 | 3/1983 |
| WO | WO 1987/007683 | 12/1987 |
| WO | WO 1994/21312 | 9/1994 |
| WO | WO 1994/023677 | 10/1994 |
| WO | WO 1995/004511 | 2/1995 |
| WO | WO 1995/014451 | 6/1995 |
| WO | WO 1996/21410 | 7/1996 |
| WO | WO 1997/11658 | 4/1997 |
| WO | WO 1999/39671 | 8/1999 |
| WO | WO 2000/000743 | 1/2000 |
| WO | WO 2000/022298 | 4/2000 |
| WO | WO 2000/42957 | 7/2000 |
| WO | WO 2000/49968 | 8/2000 |
| WO | WO 2000/56378 | 9/2000 |
| WO | WO 2000/061206 | 10/2000 |
| WO | WO 2000/079154 | 12/2000 |
| WO | WO 2001/016488 | 3/2001 |
| WO | WO 2001/079693 | 10/2001 |
| WO | WO 2002/17840 | 3/2002 |
| WO | WO 2002/026180 | 4/2002 |
| WO | WO 2002/038096 | 5/2002 |
| WO | WO 2002/076379 | 10/2002 |
| WO | WO 2002/087058 | 10/2002 |
| WO | WO 2002/090772 | 11/2002 |

(56) References Cited

FOREIGN PATENT DOCUMENTS

| | | |
|---|---|---|
| WO | WO 2003/057071 | 7/2003 |
| WO | WO 2003/057307 | 7/2003 |
| WO | WO 2003/085810 | 10/2003 |
| WO | WO 2003/101508 | 12/2003 |
| WO | WO 2004/007960 | 1/2004 |
| WO | WO 2004/060225 | 7/2004 |
| WO | WO 2004/073566 | 9/2004 |
| WO | WO 2004/077387 | 9/2004 |
| WO | WO 2004/081421 | 9/2004 |
| WO | WO 2005/001286 | 1/2005 |
| WO | WO 2005/001287 | 1/2005 |
| WO | WO 2005/009488 | 2/2005 |
| WO | WO 2005/025447 | 3/2005 |
| WO | WO 2006/058801 | 6/2006 |
| WO | WO 2006/059098 | 6/2006 |
| WO | WO 2006/062276 | 6/2006 |
| WO | WO 2006/069875 | 7/2006 |
| WO | WO 2006/069884 | 7/2006 |
| WO | WO 2006/069885 | 7/2006 |
| WO | WO 2006/092333 | 9/2006 |
| WO | WO 2006/111775 | 10/2006 |
| WO | WO 2006/117207 | 11/2006 |
| WO | WO 2006/122268 | 11/2006 |
| WO | WO 2007/030601 | 3/2007 |
| WO | WO 2007/049876 | 5/2007 |
| WO | WO 2007/055642 | 5/2007 |
| WO | WO 2007/067359 | 6/2007 |
| WO | WO 2007/087811 | 8/2007 |
| WO | WO 2008/013896 | 1/2008 |
| WO | WO 2008/027449 | 3/2008 |
| WO | WO 2008/031418 | 3/2008 |
| WO | WO 2008/039223 | 4/2008 |
| WO | WO 2008/049277 | 5/2008 |
| WO | WO 2008/110022 | 9/2008 |
| WO | WO 2008/131895 | 11/2008 |
| WO | WO 2008/135997 | 11/2008 |
| WO | WO 2009/019415 | 2/2009 |
| WO | WO 2009/047524 | 4/2009 |
| WO | WO 2009/066104 | 5/2009 |
| WO | WO 2009/066105 | 5/2009 |
| WO | WO 2009/095170 | 8/2009 |
| WO | WO 2009/124100 | 10/2009 |
| WO | WO 2009/126103 | 10/2009 |
| WO | WO 2009/146441 | 12/2009 |
| WO | WO 2009/158128 | 12/2009 |
| WO | WO 2010/051068 | 5/2010 |
| WO | WO 2010/056977 | 5/2010 |
| WO | WO 2010/082872 | 7/2010 |
| WO | WO 2010/089448 | 8/2010 |
| WO | WO 2010/093753 | 8/2010 |
| WO | WO 2010/126444 | 11/2010 |
| WO | WO 2010/139926 | 12/2010 |
| WO | WO 2011/003163 | 1/2011 |
| WO | WO 2011/023650 | 3/2011 |
| WO | WO 2011/068310 | 6/2011 |
| WO | WO 2011/082461 | 7/2011 |
| WO | WO 2011/087871 | 7/2011 |
| WO | WO 2011/097361 | 8/2011 |
| WO | WO 2011/097362 | 8/2011 |
| WO | WO 2011/103890 | 9/2011 |
| WO | WO 2011/130542 | 10/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO 2011/146535 | 11/2011 |
| WO | WO 2011/148188 | 12/2011 |
| WO | WO 2011/150529 | 12/2011 |
| WO | WO 2012/009370 | 1/2012 |
| WO | WO 2012/034238 | 3/2012 |
| WO | WO 2012/048179 | 4/2012 |
| WO | WO 2012/074512 | 6/2012 |
| WO | WO 2012/088572 | 7/2012 |
| WO | WO 2012/095245 | 7/2012 |
| WO | WO 2012/140180 | 10/2012 |
| WO | WO 2012/142002 | 10/2012 |
| WO | WO 2012/143665 | 10/2012 |
| WO | WO 2012/146656 | 11/2012 |
| WO | WO 2012/150235 | 11/2012 |
| WO | WO 2013/006932 | 1/2013 |
| WO | WO 2013/015827 | 1/2013 |
| WO | WO 2013/019017 | 2/2013 |
| WO | WO 2013/064852 | 5/2013 |
| WO | WO 2013/065423 | 5/2013 |
| WO | WO 2013/078214 | 5/2013 |
| WO | WO 2013/090810 | 6/2013 |
| WO | WO 2013/117945 | 8/2013 |
| WO | WO 2013/118447 | 8/2013 |
| WO | WO 2013/119854 | 8/2013 |
| WO | WO 2013/133652 | 9/2013 |
| WO | WO 2013/158897 | 10/2013 |
| WO | WO 2014/008348 | 1/2014 |
| WO | WO 2014/020440 | 2/2014 |
| WO | WO 2014/020443 | 2/2014 |
| WO | WO 2014/022440 | 2/2014 |
| WO | WO 2014/113253 | 7/2014 |
| WO | WO 2014/151930 | 9/2014 |
| WO | WO 2015/022340 | 2/2015 |
| WO | WO 2015/031216 | 3/2015 |
| WO | WO 2016/018448 | 2/2016 |
| WO | WO 2016/103031 | 6/2016 |
| WO | WO 2016/103032 | 6/2016 |
| WO | WO 2016/103033 | 6/2016 |
| WO | WO 2016/103035 | 6/2016 |

OTHER PUBLICATIONS

International Search Report and Written Opinion, re PCT Application No. PCT/IB2015/002536, dated Jul. 22, 2016.
Invitation to Pay Additional Fees and Partial Search Report, re PCT Application No. PCT/IB2015/002542, dated Apr. 22, 2016.
International Search Report and Written Opinion, re PCT Application No. PCT/IB2015/002542, dated Aug. 1, 2016.
International Search Report and Written Opinion, re PCT Application No. PCT/IB2015/002535, dated Apr. 12, 2016.
International Search Report and Written Opinion, re PCT Application No. PCT/IB2015/002532, dated Apr. 22, 2016.
"Technology Watch", May 1989, in 1 page.
Hersle, K. et al., "Uses of Dextranomer Absorbent Pads After Cryosurgery of Cutaneous Malignancies", The Journal of Dermatologic Surgery and Oncology, vol. 8, Jan. 1982, in 4 pages.
Invitation to Pay Additional Fees and Partial International Search Report, re PCT Application No. PCT/IB2013/001513, dated Sep. 30, 2013, in 7 pages.
International Preliminary Report, re PCT Application No. PCT/IB2013/001513, dated Nov. 27, 2014.
International Search Report and Written Opinion, re PCT Application No. PCT/EP2015/063373, dated Sep. 2, 2015.
International Search Report and Written Opinion, re PCT Application No. PCT/GB2014/050786, dated Jun. 12, 2014.
International Preliminary Report on Patentability, re PCT Application No. PCT/IB2015/002535, dated Jul. 6, 2017.
International Search Report, re PCT Application No. PCT/IB2013/001513, dated Feb. 11, 2014.
Kendall ULTEC Hydrocolloid Dressing (4"×4"), product ordering page, web page downloaded Jul. 13, 2014, in 1 page.
Advantec MFS, Inc., "Membrane Filters" (catalog), accessed Jan. 29, 2016 (publication date unknown, but believed to be copyright 2001-2011), in 17 pages. URL: http://www.advantecmfs.com/catalog/filt/membrane.pdf#page=11.
Morcos, A.,"Voice Coil Actuators & Their Use in Advanced Motion Control Systems", Motion, Jul./Aug. 1995, pp. 25-27, in 3 pages.
Park, S. et al., "Design and Analysis of a VCA for Fuel Pump in Automobile," World of Academy of Science, Engineering and Technology; 80 2011; pp. 573-576, in 4 pages.
Protz, K., "Moderne Wundauflagen unterstutzen Heilungsprozess", Wundversorgung: Indikation und Anwendung, Geriatrie Journal, Apr. 2005, pp. 3333-3339, with translation, in 17 pages.

(56) References Cited

OTHER PUBLICATIONS

Smith & Nephew, "PICO Single Use Negative Pressure Wound Therapy System", spiral booklet, Mar. 2011, in 7 pages.

* cited by examiner

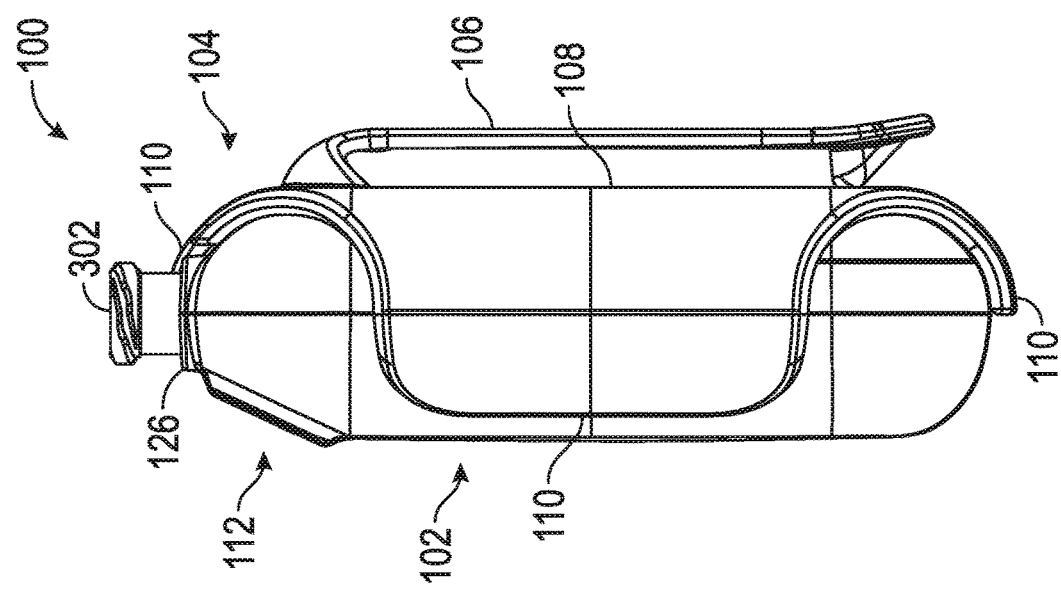
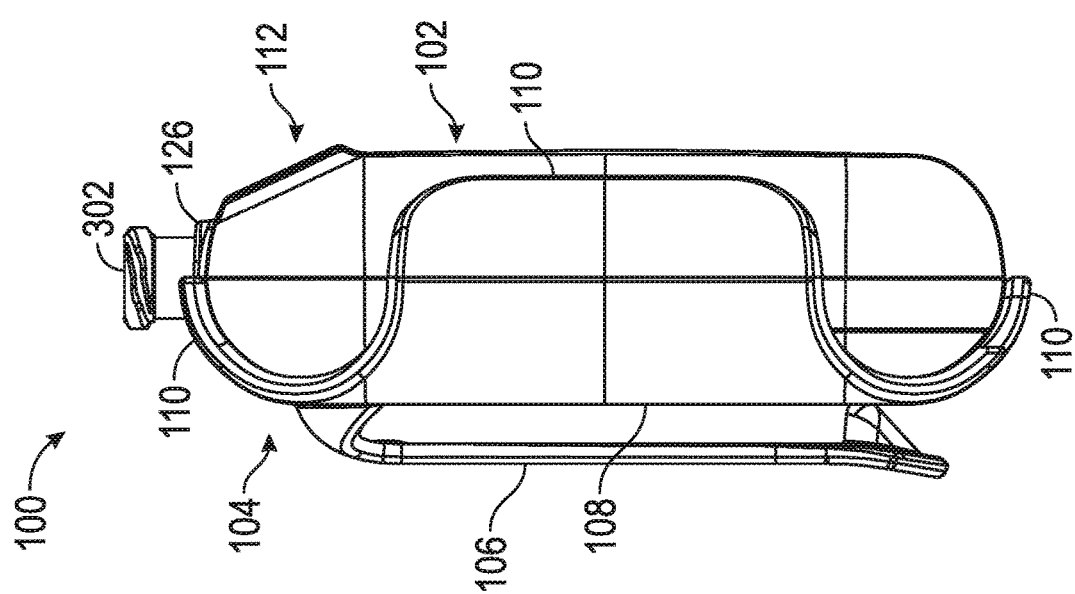

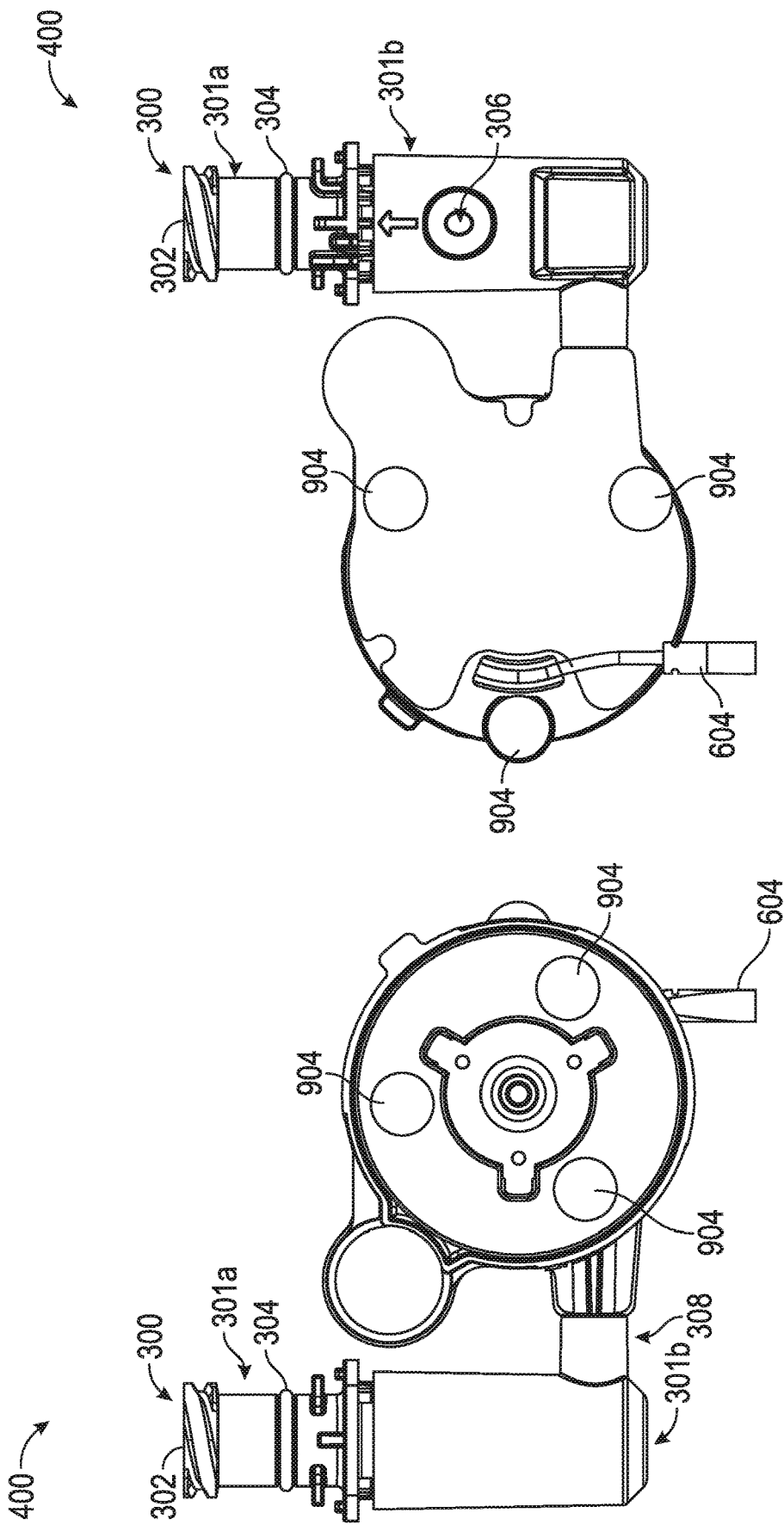

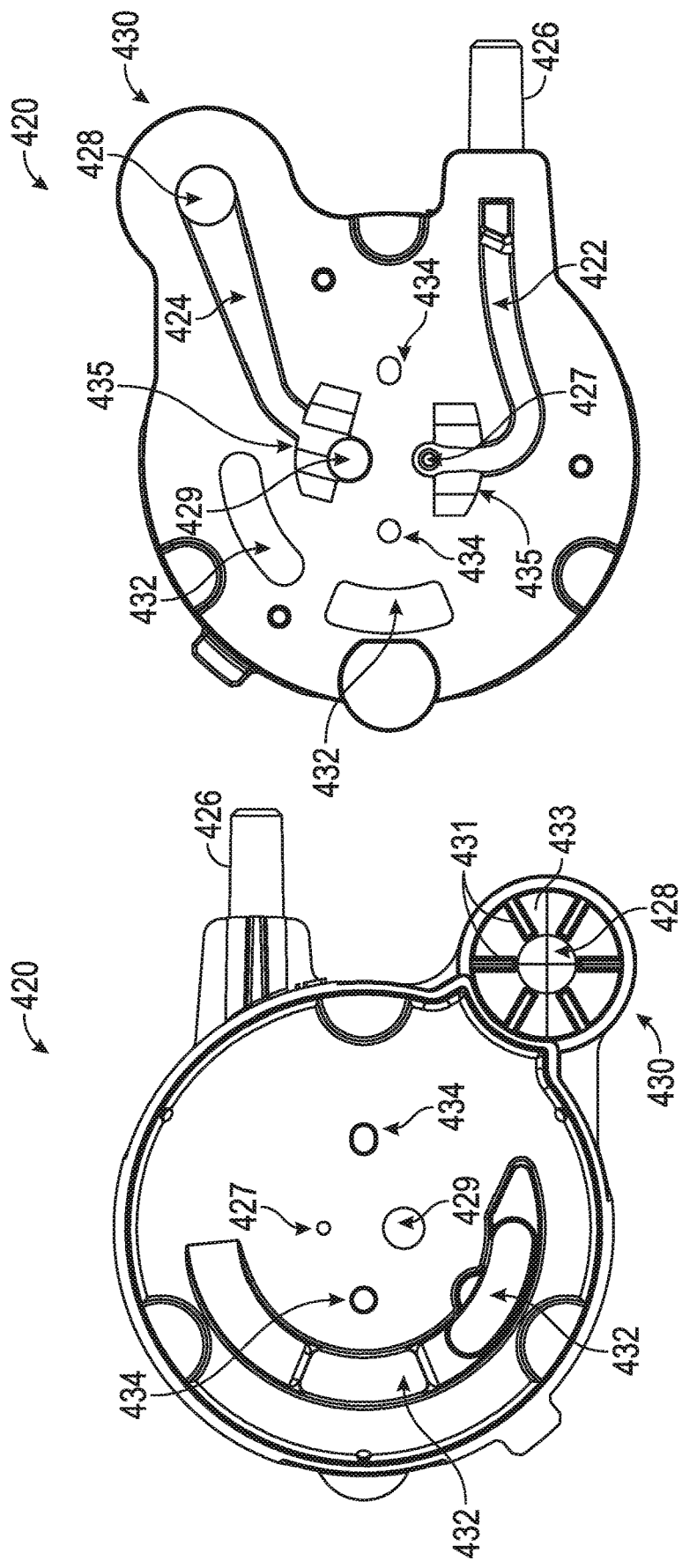

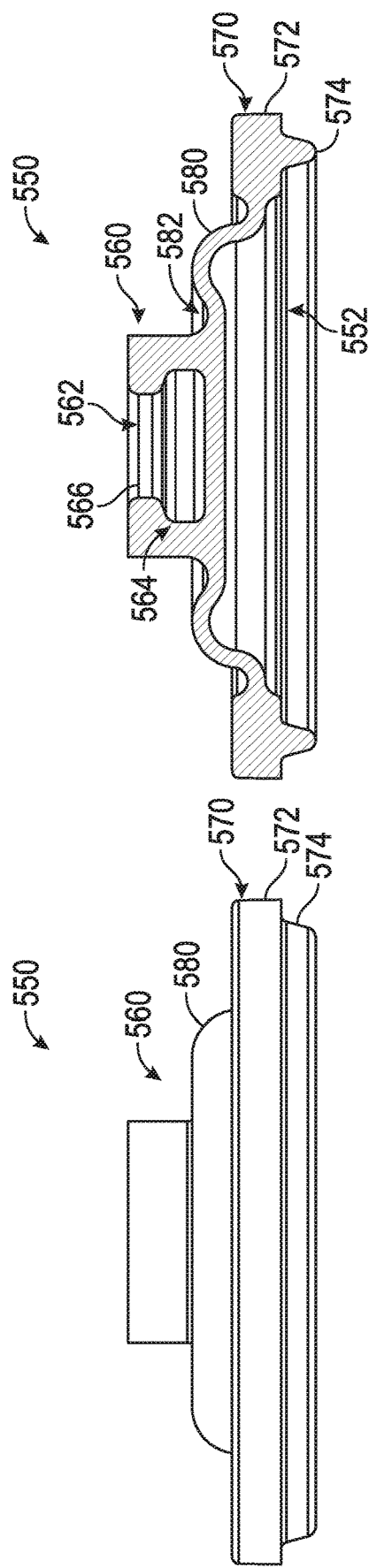

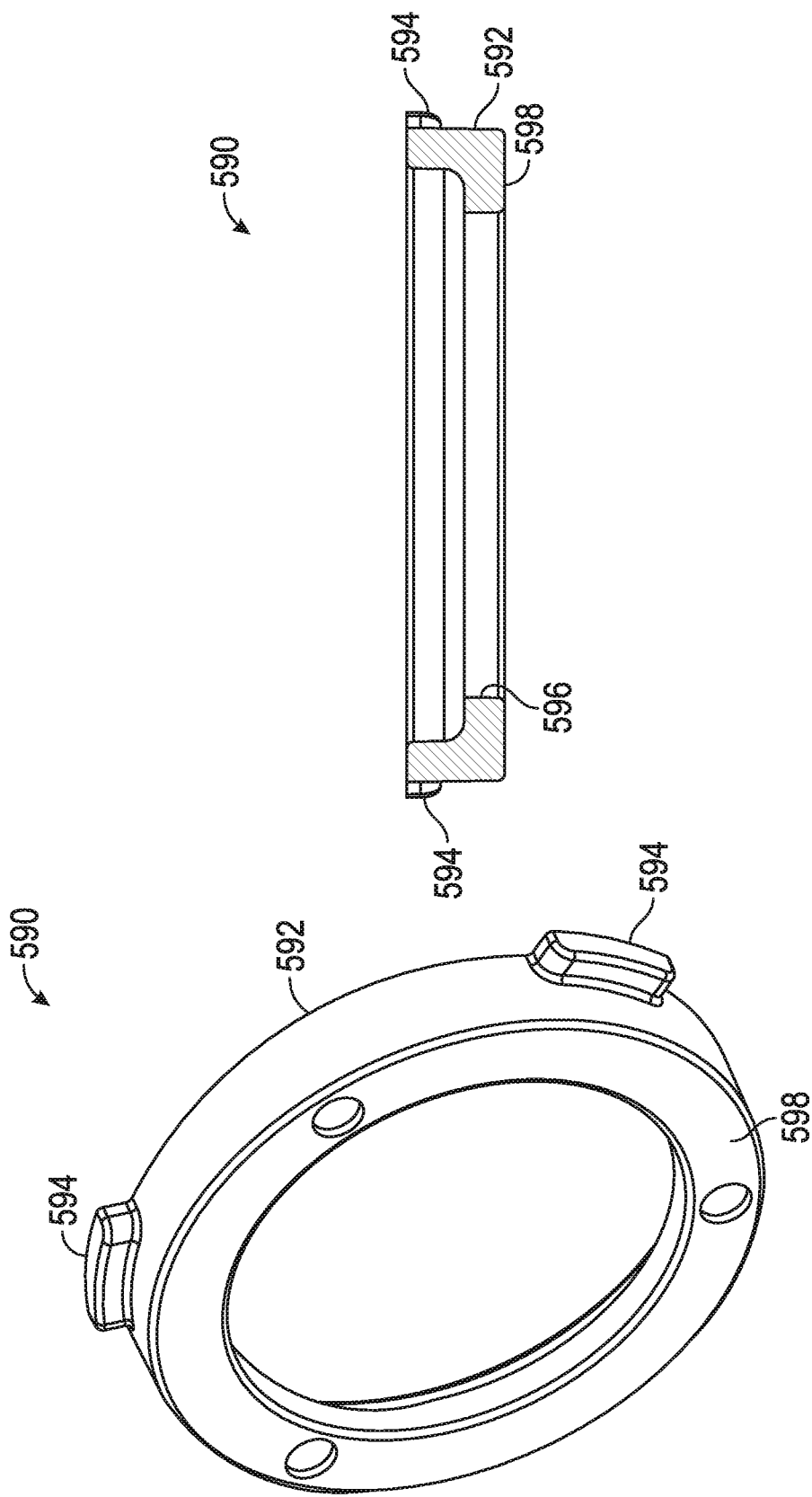

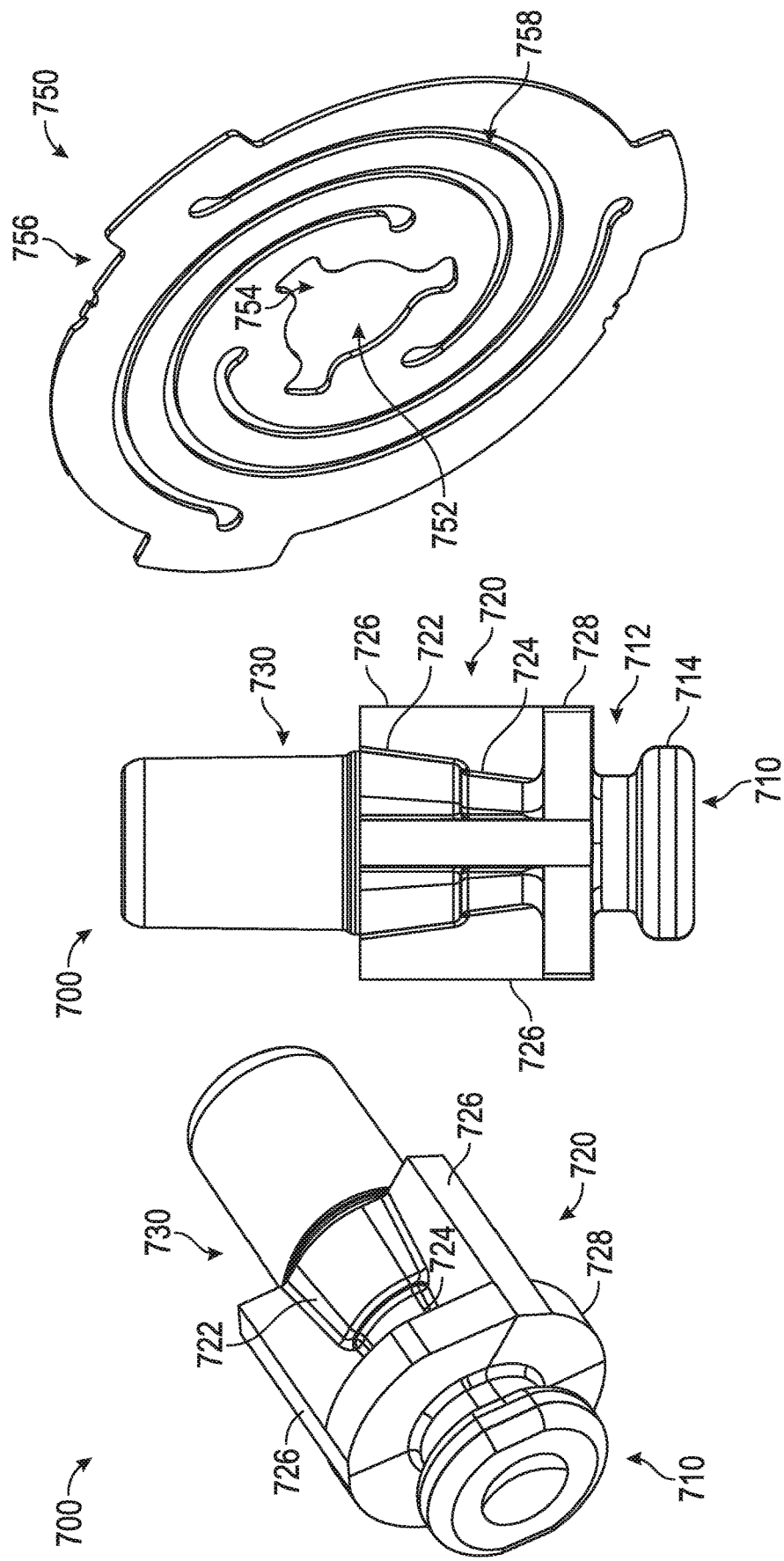

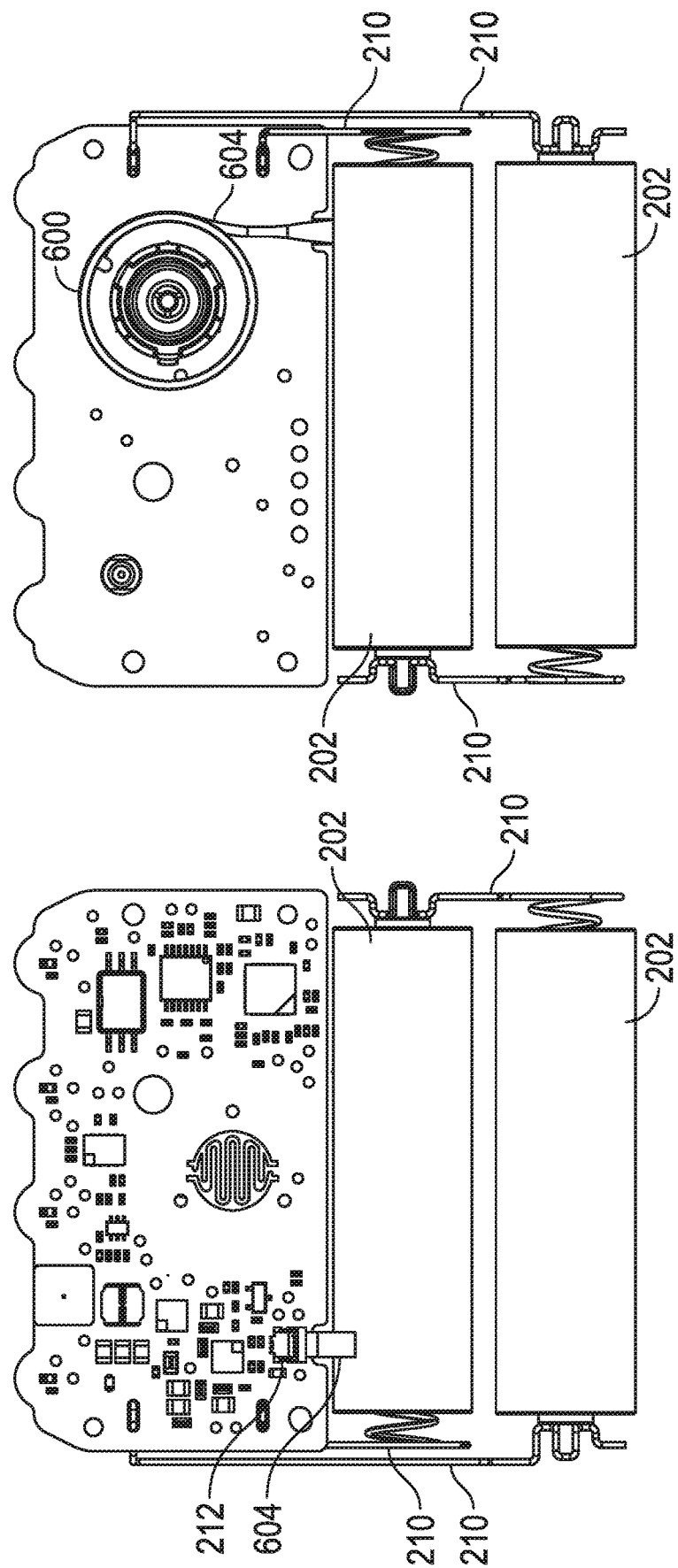

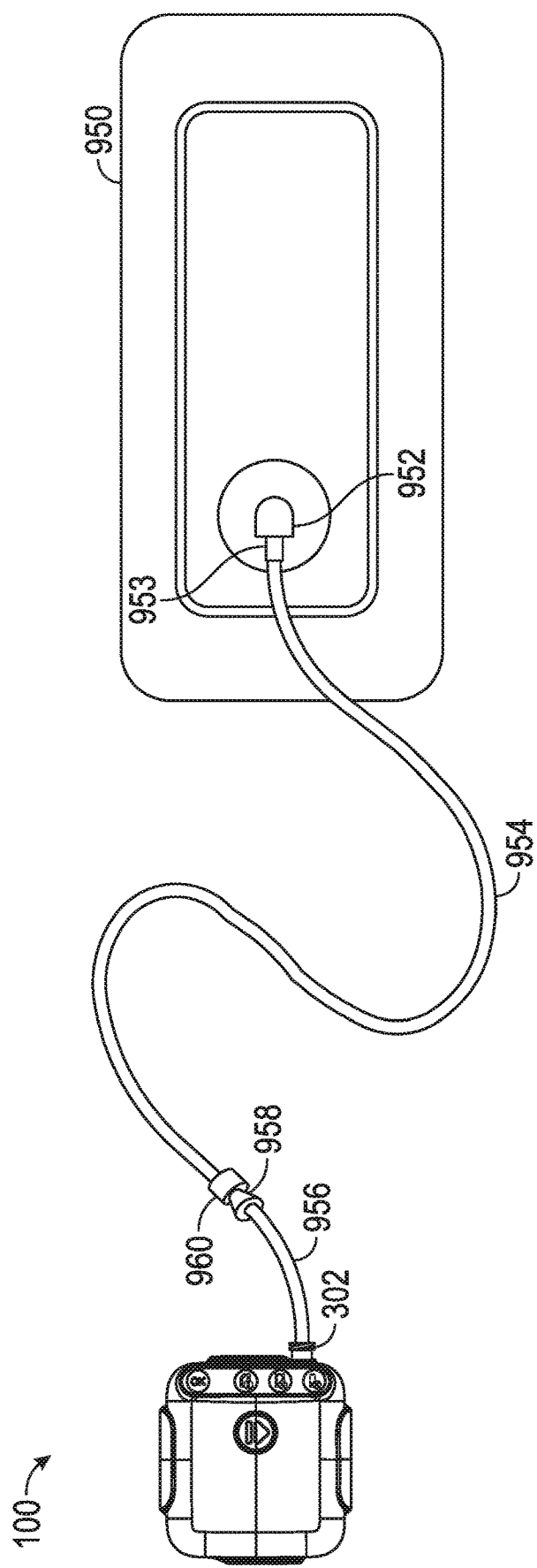

DRESSING STATUS DETECTION FOR NEGATIVE PRESSURE WOUND THERAPY

CROSS-REFERENCE TO RELATED APPLICATIONS

This application is a U.S. National Phase of the PCT Internal Application No. PCT/IB2015/002535, filed on Dec. 21, 2015, which claims the benefit of U.S. Provisional Application No. 62/095,721, filed Dec. 22, 2014, titled "NEGATIVE PRESSURE WOUND THERAPY APPARATUS AND METHODS," the disclosure of which is hereby incorporated by reference in its entirety herein.

INCORPORATION BY REFERENCE

Further components, features, and details of pump assemblies, wound dressings, wound treatment apparatuses and kits, and negative pressure wound treatment methods that may be used with any of the embodiments disclosed in this application are found in the following applications and/or publications, which are hereby incorporated by reference in their entireties herein.

U.S. patent application Ser. No. 14/715,527, filed May 18, 2015, titled "FLUIDIC CONNECTOR FOR NEGATIVE PRESSURE WOUND THERAPY."

U.S. patent application Ser. No. 14/418,908 (U.S. Patent Publication No. 2015/0190286), filed Jan. 30, 2015, titled "WOUND DRESSING AND METHOD OF TREATMENT."

U.S. patent application Ser. No. 14/403,036 (U.S. Patent Publication No. 2015/0141941), filed Nov. 21, 2014, titled "APPARATUSES AND METHODS FOR NEGATIVE PRESSURE WOUND THERAPY."

PCT International Application No. PCT/IB2013/001513 (International Publication No. WO/2013/171585), filed May 15, 2013, titled "NEGATIVE PRESSURE WOUND THERAPY APPARATUS."

PCT International Application No. PCT/IB2013/000847 (International Publication No. WO/2013/136181), filed Mar. 12, 2013, titled "REDUCED PRESSURE APPARATUS AND METHODS."

U.S. patent application Ser. No. 13/092,042 (U.S. Patent Publication No. 2011/0282309), filed Apr. 21, 2011, titled "WOUND DRESSING AND METHOD OF USE."

Each and all of the foregoing patent applications are hereby incorporated by reference in their entireties and made part of this disclosure.

BACKGROUND OF THE DISCLOSURE

Field of the Disclosure

Embodiments or arrangements disclosed herein relate to methods and apparatuses for dressing and treating a wound with topical negative pressure (TNP) therapy. For example but without limitation, any embodiments disclosed herein relate to treating a wound with reduced pressure provided from a pump kit. Although not required, any embodiments of the pump kit can be sterile. As another non-limiting example, any embodiments disclosed herein relate to apparatuses and methods for controlling the operation of a TNP system.

Description of the Related Art

Many different types of wound dressings are known for aiding in the healing process of a human or animal. These different types of wound dressings include many different types of materials and layers, for example, pads such as gauze pads and/or foam pads. Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema; encouraging blood flow; stimulating the formation of granulation tissue; removing excess exudates, and may reduce bacterial load and thus reduce the potential for infection of the wound. Furthermore, TNP therapy permits less outside disturbance of the wound and promotes more rapid healing.

SUMMARY OF SOME EMBODIMENTS

Embodiments of the present disclosure relate to apparatuses and methods for wound treatment. Some of the wound treatment apparatuses described herein comprise a pump system for providing negative pressure to a wound site. Wound treatment apparatuses may also comprise wound dressings that may be used in combination with the pump assemblies described herein, and connectors for connecting the wound dressings to the pump assemblies.

In some embodiments, an apparatus for use in negative pressure wound therapy comprises a pump assembly, comprising an electrically conductive coil, a magnet, a diaphragm, and a dampener. The coil can be directly or indirectly coupled with the diaphragm and can be configured to move at least a portion of the diaphragm to pump a fluid through the pump assembly in response to a drive signal applied to the coil.

The apparatus, which may be or include a pump apparatus, may be arranged such that the pump assembly includes an electrically conductive upper pole, an electrically conductive lower pole, and one or more valves, wherein the magnet is positioned between at least a portion of the upper pole and the lower pole, and wherein the coil is positioned between at least a portion of the upper pole and the lower pole. The pump apparatus may be arranged such that the pump housing includes a chamber within which the dampener can be positioned. The pump apparatus may be arranged such that the dampener is retained within the chamber via an interference fit. The pump apparatus may be arranged such that the pump housing includes an exhaust channel designed to communicate fluid flow out of the pump assembly, the chamber being in communication with the exhaust channel. The pump apparatus may be arranged such that the chamber includes an opening. The pump apparatus may be arranged such that the chamber includes one or more ribs, the ribs spacing the dampener from the opening. The pump apparatus may be arranged such that the opening is positioned at an end of the exhaust channel.

The pump apparatus may be arranged such that it includes a manifold positioned between the pump assembly and a wound dressing. The pump apparatus may be arranged such that it includes a second dampener within the manifold. The pump apparatus may be arranged such that it includes a control board. The pump apparatus may be arranged such that it includes an electrical conduit for connecting the control board to the electrically conductive coil. The pump apparatus may be arranged such that it includes a wound dressing designed to sealingly surround a wound. The pump apparatus may be arranged such that it includes a spring member wherein a periphery of the spring member is supported within the pump assembly so as to be in a fixed position relative to the diaphragm and a middle portion of the spring member is designed to deflect relative to the periphery of the spring member when a middle portion of the diaphragm axially deflects.

In some embodiments disclosed herein, the pump system can optionally form part of a wound treatment apparatus that also includes a wound dressing. In some embodiments, the pump system and/or a wound dressing can optionally have one or more sensors therein. For example, in some embodiments disclosed herein, the pump system and/or dressing can have a pressure monitor configured to monitor the pressure within the pump housing, dressing, or conduit or chambers within the pump system or between the pump system and the dressing, or in any combination of such. Additionally, some pump embodiments disclosed herein can use orifices or other features or components to control a flow or rate of flow of fluid through the pump system.

Some embodiments disclosed herein may also relate to a negative pressure therapy kit for reduced pressure wound therapy. The negative pressure therapy kit in some embodiments may include a pump system having an outer housing, a pump assembly supported within the housing, and a controller supported within or by the outer housing. In some embodiments, at least one switch or button may be supported by the outer housing. The at least one switch or button can be in communication with the controller and can be accessible to a user so as to permit a user to control one or more modes of operation of the pump system.

In some embodiments disclosed herein, though not required, a negative pressure therapy system can comprise a dressing configured to form a substantially fluid tight seal over a wound and a conduit coupleable with the dressing and the pump system and configured to provide a substantially or completely enclosed fluid flow pathway from the pump system to the dressing.

In some embodiments, a method for controlling a pump system can include calculating at least one of an amplitude and an offset for a drive signal based at least in part on previously calculated parameters and a negative pressure setting, generating the drive signal with the at least one calculated amplitude and offset, and applying the drive signal to the pump system. In some embodiments, the method can be performed under control of a controller of the pump system.

In some embodiments, the previously calculated parameters can include a plurality of calibrated amplitudes at a plurality of negative pressure settings. In some embodiments, the previously calculated parameters can include a plurality of calibrated offsets at a plurality of negative pressure settings. In some embodiments, the previously calculated parameters can include at least 3 parameters. In some embodiments, the previously calculated parameters can be specific to the pump system. In some embodiments, calculating the at least one of the amplitude and the offset for a drive signal can include calculating both the amplitude and the offset for the drive signal. In some embodiments, calculating the at least one of the amplitude and the offset for the drive signal can include interpolating between at least two previously calculated amplitudes or offsets. In some embodiments, the interpolation can be a linear interpolation. In some embodiments, the pump system can include a voice coil actuator connected to a diaphragm. In some embodiments, the pump system can include a spring which can affect a resonant frequency of the pump system.

In some embodiments, the method can include applying a start up signal when the pump system has been activated after a period of inactivity, the start up signal having at least one of an amplitude and an offset different from at least one of the amplitude and the offset of the drive signal. In some embodiments, the method can include calculating at least one of an amplitude and an offset for the start up signal based at least in part on previously calculated parameters and a negative pressure setting less than the negative pressure setting for calculating the drive signal. In some embodiments, the method can include generating the start up signal with the at least one calculated amplitude and offset.

In some embodiments, a pump system for negative pressure wound therapy can include a pump assembly, having an actuator and a diaphragm, and a controller which can control operation of the pump system. In some embodiments, the controller can calculate at least one of an amplitude and an offset for a drive signal based at least in part on previously calculated parameters and a negative pressure setting, generate the drive signal with the at least one calculated amplitude and offset and apply the drive signal to the pump system.

In some embodiments, the previously calculated parameters can include a plurality of calibrated amplitudes at a plurality of negative pressure settings. In some embodiments, the previously calculated parameters can include a plurality of calibrated offsets at a plurality of negative pressure settings.

In some embodiments, the controller can calculate both the amplitude and the offset for the drive signal. In some embodiments, the controller can interpolate between at least two previously calculated amplitudes or offsets. In some embodiments, the controller can linearly interpolate between at least two previously calculated amplitudes or offsets. In some embodiments, the previously calculated parameters can include at least 3 parameters. In some embodiments, the previously calculated parameters can be specific to the pump system. In some embodiments, the actuator can include a voice coil actuator connected to the diaphragm. In some embodiments, the pump assembly can include a spring which can affect a resonant frequency of the pump assembly.

In some embodiments, the controller can apply a start up signal when the pump system has been activated after a period of inactivity, the start up signal having at least one of an amplitude and an offset different from at least one of the amplitude and the offset of the drive signal. In some embodiments, the controller can calculate at least one of an amplitude and an offset for the start up signal based at least in part on previously calculated parameters and a negative pressure setting less than the negative pressure setting for calculating the drive signal and generate the start up signal with the at least one calculated amplitude and offset.

In some embodiments, a method for calibrating a pump system for negative pressure wound therapy can include generating a drive signal, actuating the pump system with the drive signal, measuring movement of a component of the pump system, calculating a first dimension based on the measured movement of the component and determining whether a convergence condition has been satisfied, wherein the convergence condition comprises a first condition that the first dimension be within a first tolerance of a first target value. In some embodiments, the method can be performed under control of a controller of the pump system.

In some embodiments, the method can include calculating a second dimension based on the measured movement of the component. In some embodiments, the convergence condition can include a second condition that the second dimension be within a second tolerance of a second target value. In some embodiments, the convergence condition can include a third condition that the first condition and the second condition are satisfied substantially simultaneously. In some embodiments, in response to determining that the convergence, the method can include storing a set of parameters associated with the drive signal condition is met. In some embodiments, in response to determining that the convergence condition is not satisfied, the method can include adjusting one or more parameters of the drive signal based at least in part on the measured movement of the component, generating an adjusted drive signal, actuating the pump system with the adjusted drive signal, measuring the movement of the component of the pump assembly, and determining whether the convergence condition has been satisfied.

In some embodiments, generating the drive signal includes selecting an amplitude of the drive signal. In some embodiments, generating the drive signal includes selecting an offset of the drive signal. In some embodiments, at least one of the first and second dimensions includes a travel of the component. In some embodiments, at least one of the first and second dimensions includes an average position of the component. In some embodiments, the component includes a piston connected to a diaphragm.

In some embodiments, a calibration system for calibrating a pump system for negative pressure wound therapy can include a sensor and a controller which can control operation of the calibration system. In some embodiments, the controller can generate a drive signal, actuate the pump system with the drive signal, measure movement of a component of the pump system with the sensor, and calculate a first dimension based on the measured movement of the component, and determine whether a convergence condition has been satisfied, wherein the convergence condition can include a first condition that the first dimension be within a first tolerance of a first target value.

In some embodiments, the controller can calculate a second dimension based on the measured movement of the component. In some embodiments, the convergence condition can include a second condition that the second dimension be within a second tolerance of a second target value. In some embodiments, the convergence condition can include a third condition that the first condition and the second condition are satisfied substantially simultaneously. In some embodiments, upon determining that the convergence condition is met, the controller can store a set of parameters associated with the drive signal. In some embodiments, upon determining that the convergence condition is not satisfied, the controller can adjust one or more parameters of the drive signal based at least in part on the measured movement of the component, generate an adjusted drive signal, actuate the pump system with the adjusted drive signal, measure the movement of the component of the pump assembly with the sensor, and determine whether the convergence condition has been satisfied. In some embodiments, the controller can select an amplitude of the drive signal when generating the drive signal. In some embodiments, the controller can select an offset of the drive signal when generating the drive signal. In some embodiments, at least one of the first and second dimensions can include a travel of the component. In some embodiments, at least one of the first and second dimensions can include an average position of the component. In some embodiments, the component can include a piston connected to a diaphragm.

In some embodiments, a method for controlling a pump system for negative pressure wound therapy can include providing negative pressure, via a flow path, to a wound dressing positioned over a wound, the flow path fluidically connecting the pump system to the wound dressing, measuring a first pressure value in the flow path at a first time, measuring a second pressure value in the flow path at a second time, calculating a first rate of pressure change using the first and second pressure values and in response to determining that the calculated first rate of pressure change satisfies a threshold rate, providing an indication that the wound dressing is full. In some embodiments, the method can be performed under control of a controller of the pump system.

In some embodiments, the method can include measuring a third pressure value in the flow path at a third time, measuring a fourth pressure value within the flow path at a fourth time, calculating a second rate of pressure change using the third and fourth pressure values, and providing the indication that the wound dressing is full in response to determining that the calculated first and second rates of pressure change satisfy the threshold rate. In some embodiments, the pressure in the fluid flow path is between a maximum pressure and a minimum pressure. In some embodiments, the method can include determining whether the second pressure value is less than a minimum pressure.

In some embodiments, a pump system for negative pressure wound therapy can include a pump assembly to provide a negative pressure, via a flow path, to a wound dressing positioned over a wound, the flow path fluidically connecting the pump system to the wound dressing, a sensor which can measure a pressure in the flow path, and a controller which can control operation of the pump system. In some embodiments, the controller can measure a first pressure value in the flow path at a first time, measure a second pressure value in the flow path at a second time, calculate a first rate of pressure change using the first and second pressure values and provide an indication that the wound dressing is full in response to determining that the calculated first rate of pressure change satisfies a threshold rate.

In some embodiments, the controller can measure a third pressure value in the flow path at a third time, measure a fourth pressure value within the flow path at a fourth time, calculate a second rate of pressure change using the third and fourth pressure values and provide the indication that the wound dressing is full in response to determining that the calculated first and second rates of pressure change satisfy the threshold rate. In some embodiments, the pressure in the fluid flow path is between a maximum pressure and a minimum pressure. In some embodiments, the controller can determine whether the second pressure value is less than a minimum pressure.

In some embodiments, a method for controlling a pump system for negative pressure wound therapy can include applying a drive signal to a pump assembly of the pump system, the drive signal alternating between a positive amplitude and a negative amplitude and the drive signal having an offset and sampling a pressure within a fluid flow path connecting the pump system to a wound dressing placed over a wound during one or more time intervals, wherein each of the one or more time intervals occurs when the drive signal is approximately at an amplitude that is substantially at one or more sampling amplitudes. In some embodiments, the method can be performed under control of a controller of the pump system.

In some embodiments, the sampling amplitude can include a local maxima of the amplitude. In some embodiments, the sampling amplitude can include a local minima of the amplitude. In some embodiments, the sampling amplitude can include a zero crossing of the amplitude. In some embodiments, the sampling amplitude can include an offset crossing of the amplitude. In some embodiments, the method can include, during each of the one or more time intervals, sampling the pressure at least twice. In some embodiments, the method can include averaging the pressure samples during each time interval.

In some embodiments, a pump system for negative pressure wound therapy can include a pump assembly, having an actuator and a diaphragm, and a controlled which can control operation of the pump system. In some embodiments, the controller can apply a drive signal to the pump assembly, the drive signal alternating between a positive amplitude and a negative amplitude and the drive signal having an offset and sample a pressure within a fluid flow path connecting the pump assembly to a wound dressing placed over a wound during one or more time intervals, wherein each of the one or more time intervals occurs when the drive signal is approximately at an amplitude that is substantially at one or more sampling amplitudes.

In some embodiments, the sampling amplitude can include a local maxima of the amplitude. In some embodiments, the sampling amplitude can include a local minima of the amplitude. In some embodiments, the sampling amplitude can include a zero crossing of the amplitude. In some embodiments, the sampling amplitude can include an offset crossing of the amplitude. In some embodiments, during each of the one or more time intervals, the controller can sample the pressure at least twice. In some embodiments, the controller can average the pressure samples during each time interval.

In various embodiments, a pump system configured for negative pressure wound therapy is described. The pump system can include a pump assembly configured to provide a negative pressure, via a flow path, to a wound dressing configured to be positioned over a wound, the flow path configured to fluidically connect the pump system to the wound dressing. The pump system can include a sensor configured to measure a pressure in the flow path. The pump system can include a controller configured to control operation of the pump system. The controller can be configured to measure a first pressure value in the flow path at a first time, measure a second pressure value in the flow path at a second time, calculate a first rate of pressure change using the first and second pressure values, and provide an indication that the wound dressing is full in response to determining that the calculated first rate of pressure change satisfies a threshold rate of change.

In various embodiments, a method for controlling a pump system configured for negative pressure wound therapy is described. The method can include causing provision of negative pressure, via a flow path, to a wound dressing configured to be positioned over a wound, the flow path configured to fluidically connect the pump system to the wound dressing. The method can include measuring a first pressure value in the flow path at a first time. The method can include measuring a second pressure value in the flow path at a second time. The method can include calculating a first rate of pressure change using the first and second pressure values. In response to determining that the calculated first rate of pressure change satisfies a threshold rate of change, the method can include providing an indication that the wound dressing is full. The method can be performed under control of a controller of the pump system.

Any of the features, components, or details of any of the arrangements or embodiments disclosed in this application, including without limitation any of the pump embodiments (for example, any of the voice coil pump embodiments) and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which:

FIG. 7 is a right side view of the pump system of FIG. 1.

FIG. 8 is a left side view of the pump system of FIG. 1.

FIG. 15 is a rear view of the pump assembly and intake manifold of FIG. 14.

FIG. 16 is a front view of the pump assembly and intake manifold of FIG. 14.

FIG. 21 is a rear view of an embodiment of a pump housing

FIG. 22 is a front view of the pump housing of FIG. 21.

FIG. 30 is a side view of the diaphragm of FIGS. 28-29.

FIG. 31 is a side, cross-sectional view of the diaphragm of FIGS. 28-29.

FIG. 32 is a perspective view of an embodiment of a spacer.

FIG. 33 is a side, cross-sectional view of the spacer of FIG. 32.

FIG. 36 is a perspective view of an embodiment of a shaft.

FIG. 37 is a side view of the shaft of FIG. 36.

FIG. 38 is a perspective view of an embodiment of a spring.

FIG. 48 is a front view of the circuit board of FIG. 11.

FIG. 49 is a rear view of the circuit board of FIG. 11.

FIG. 57A is a top view of an embodiment of a pump system attached to a wound dressing.

DETAILED DESCRIPTION OF SOME EMBODIMENTS

Figure 2:
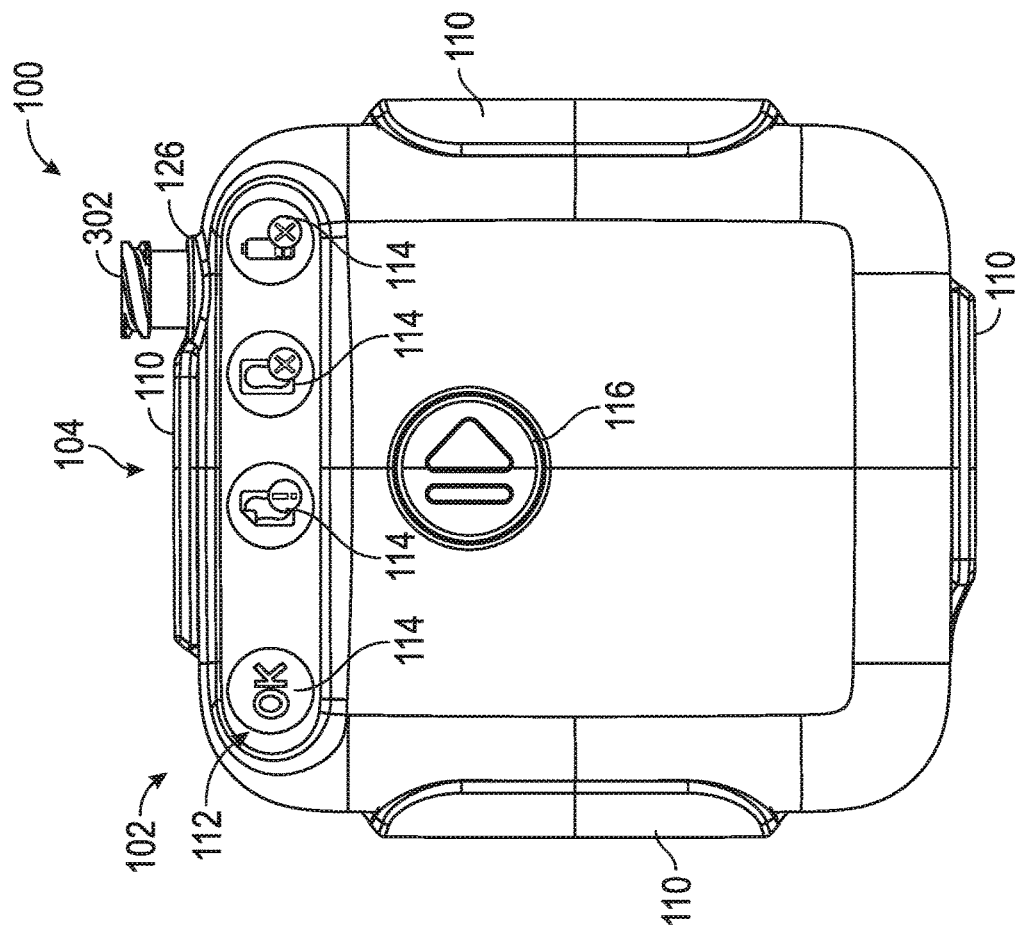
FIG. 2 is a front view of the pump system of FIG. 1.

Embodiments disclosed herein relate to apparatuses and methods of treating a wound with reduced pressure, including pump and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments disclosed herein, the components of the TNP system described herein can be particularly suited for incisional wounds that exude a small amount of wound exudate.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels that are below standard atmospheric pressure, which corresponds to 760 mmHg (or 1 atm, 29.93 mmHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The operating negative pressure range for some embodiments of the present disclosure can be between approximately −20 mmHg and approximately −200 mmHg, between approximately −50 mmHg and approximately −150 mmHg, between approximately −70 mmHg and −90 mmHg, any subrange within these ranges, or any other range as desired. In some embodiments, an operating negative pressure range of up to −70 mmHg, up to −80 mmHg, up to −90 mmHg, up to −100 mmHg, up to −110 mmHg, or up to any other pressure as desired can be used. For example, in some embodiments, the pump system can maintain negative pressure wound therapy at −80 mmHg (nominal)+/−20 mmHg to a wound dressing and/or to a wound surface. Other details regarding the operation of the pump system are set forth in U.S. Publication Nos. 2011/0282309, 2013/0110058 and 2013/0331823 as well as International Patent Publication No. 2013/171585, and all embodiments, configurations, details, and illustrations of these publications are hereby incorporated by reference in their entireties as if made part of this disclosure.

Any of the embodiments disclosed herein can include a pump and/or a pump and dressing kit. However, the pump apparatuses and embodiments of the present disclosure are not limited to use with a dressing or for wound therapy. Any of the pump embodiments disclosed herein can be used independently of the dressing components disclosed herein. Further, any of the pump embodiments disclosed herein can be used, or can be adapted for use, for other purposes outside of negative pressure wound therapy. As such, any of the pump embodiments disclosed herein can be used, or can be adapted for use, to move fluids (gaseous and/or liquid) in any system or application. Any of the embodiments disclosed herein can be used on an exuding wound. For example, in some embodiments, the pump and/or kit can be used on wounds where the level of exudate is low (e.g., 0.6 g (nominal) of liquid exudate/cm$^2$ of wound area per 24 hours), or on wounds where the level of exudate is moderate (e.g., 1.1 g (nominal) of liquid exudate/cm$^2$ of wound area per 24 hours). In some embodiments, exudate from the wound is managed by the dressings disclosed herein through a combination of absorption in the dressing and an evaporation of moisture through the dressing. In some embodiments, exudate from the wound is managed by the dressings disclosed herein through absorption in the dressing or evaporation of moisture through the dressing. In embodiments where evaporation of exudate moisture through the dressing is intended, occlusive materials positioned over the dressing area can impair the intended evaporation.

Overview of the Mechanical Aspects of the Pump System

The pump system embodiments described herein can have a compact, small size. In some embodiments disclosed herein, a pump assembly of the pump system can have a diameter (e.g., equivalent diameter) or lateral size between 15 mm and 35 mm, less than 15 mm, less than 25 mm, less than 35 mm, or less than 50 mm. For example, in some embodiments, the pump system can have a diameter or lateral size of 10 mm, 23 mm, or 40 mm, or can have a diameter or lateral size in the range of approximately 26 mm to approximately 27 mm, between approximately 22 mm or smaller and approximately 28 mm. In some embodiments disclosed herein, the pump assembly can have a thickness or height of approximately 8 mm, between approximately 6 mm and approximately 10 mm, or a thickness or height of less than 20 mm. For example, in some embodiments, the thickness or height of the pump assembly can be 5 mm, 12 mm, or 20 mm. For example and without limitation, in some embodiments the pump assembly can have a volume of approximately 6.2 cubic centimeters, between approximately 5.0 cubic centimeters or less to approximately 7.0 cubic centimeters, or a volume of less than 10.0 cubic centimeters. For example, in some embodiments, the volume of the pump assembly can be 4.0 cubic centimeters, 6.0 cubic centimeters, or 8.0 cubic centimeters. In some embodiments, the housing of can have a lateral size of approximately 60.0 mm, between approximately 40.0 mm and approximately 80.0 mm, or a lateral size of less than 90 mm, and a height of approximately 15.0 mm, between approximately 10.0 mm and approximately 20.0 mm, or a height of less than 30 mm. For example, in some embodiments, the housing can have a Length×Width×Height dimension of 72 mm×66 mm×21 mm, approximately 72 mm×66 mm×21 mm, 70-73 mm×64-67 mm×20-22 mm, or a Length×Width×Height dimension of less than 90 mm×less than 90 mm×less than 30 mm. For example, in some embodiments, the Length×Width×Height dimension of the housing can be 68 mm×62 mm×18 mm, 65 mm×78 mm×21 mm, 65 mm×79 mm×21 mm, or 80 mm×74 mm×25 mm. In some embodiments, the pump system can have a mass of 150 grams, approximately 150 grams, between 100-150 grams, or a mass of less than 200 grams, or a mass of less than 300 grams. For example, in some embodiments, the mass of the pump system can be 90 grams, 125 grams, 150 grams, or 220 grams. Of course, the pump system can be any miniaturized size and have any mass and volume that is manufacturable, and the overall power output and efficiency meet the needed requirements for the desired application, within or outside of wound therapy. As used herein, efficiency can be defined as (fluid power out)/(electrical power in).

The pump system can be produced for a low cost and can operate at high efficiencies, making it beneficial for portable, disposable, and/or single use applications. This pump can optionally be used in an ultra-portable single-use negative-pressure wound therapy (NPWT) device. In some embodiments, the pump system can run for 10 days on a small primary cell without the need for battery replacement or recharging. In some embodiments the pump system can run up to 10 days on a 3V, 2000 mAh cell (e.g., with the pump working for about 20% of the time). In some embodiments, the pump system can be powered by two 1.5 volt, 2500-3000 mAh batteries connected in series. In some embodiments, the pump system can run for a week on a small primary cell such as one or more batteries having a total capacity of 3000 mAh at 3V without the need for battery replacement or recharging. Additionally, in some embodiments, the pump system can be subjected to X-ray scans during its use without interfering with its function. For example, in some embodiments, the pump system can be worn during computed tomography (CT) scans, computerized axial tomography (CAT) scans, and the like.

Figure 1:
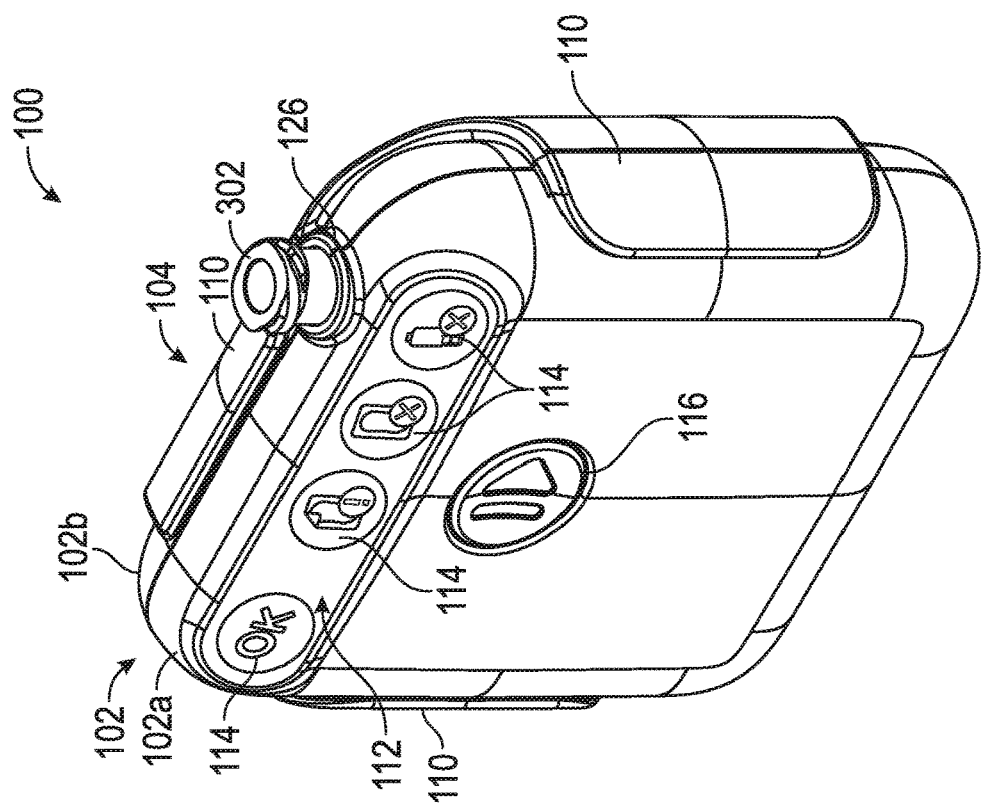
FIG. 1 is a front perspective view of an embodiment of a pump system having an outer housing with an optional mounting component attached thereto.
Figure 4:
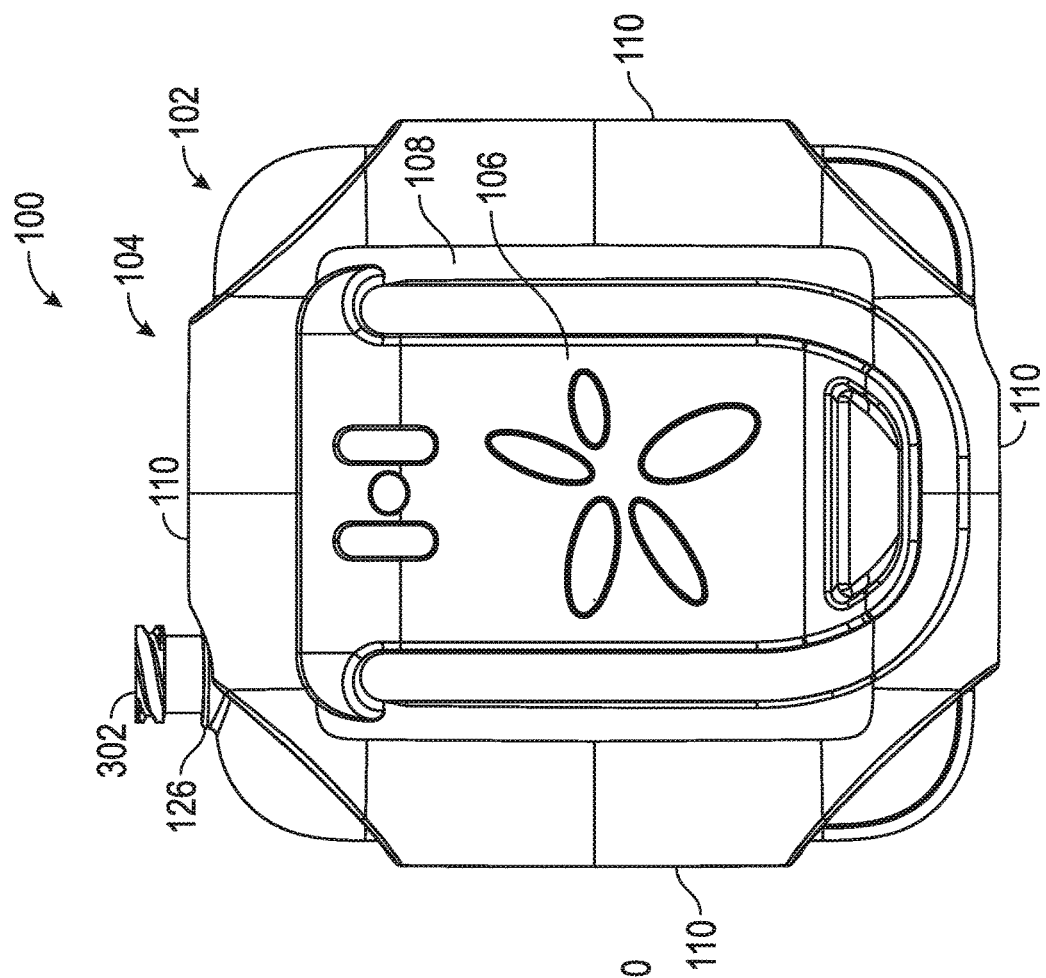
FIG. 4 is a rear view of the pump system of FIG. 1.
Figure 3:
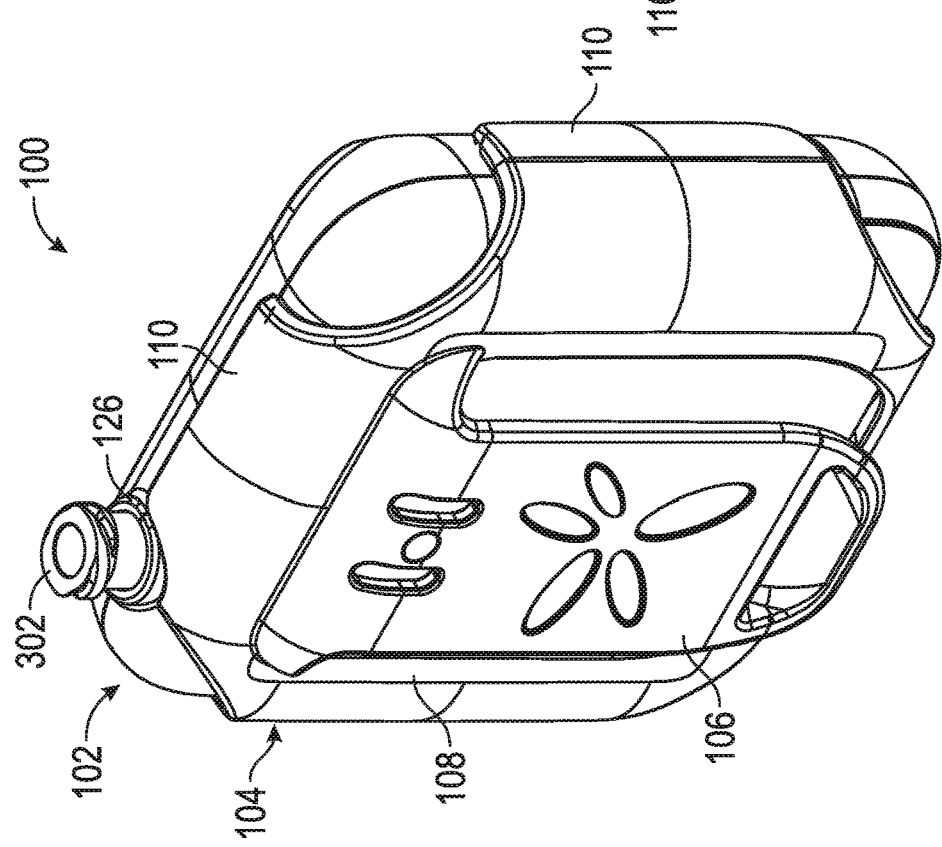
FIG. 3 is a rear perspective view of the pump system of FIG. 1.
Figures 5, 6:
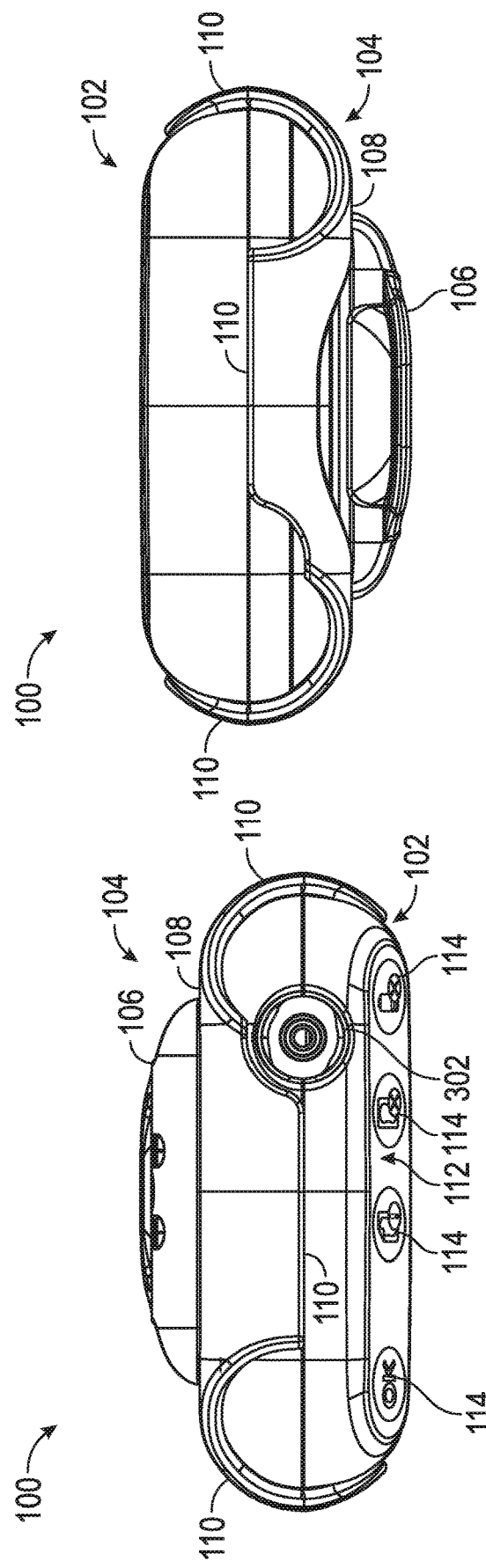
FIG. 5 is a top view of the pump system of FIG. 1.
FIG. 6 is a bottom view of the pump system of FIG. 1.

FIGS. 1-8 illustrate multiple views of an embodiment of a pump system 100 having an outer housing 102 and an optional mounting component 104, and FIGS. 73-80 illustrate additional views of the pump system 100 with the optional mounting component 104 removed. As shown in the illustrated embodiment in FIGS. 1-8, the pump system 100 can include an outer housing 102 for containing and/or supporting components of the pump system 100. The outer housing 102 can be formed from one or more portions, such as a front portion 102a and a rear portion 102b as shown in FIG. 1, which can be removably attached to form the outer housing 102.

In some embodiments, the pump system 100 can optionally include a mounting component 104 which can be designed to advantageously allow the pump system 100 to be mounted on another object such as, but not limited to, a user's person. For example, FIGS. 81-88 illustrate multiple views of an optional mounting component 104 that can be attached to a pump system 100, and which is shown attached to the pump system 100 in FIGS. 1-8. In some embodiments, the mounting component 104 can include a clip 106 (as shown in FIGS. 3-8) designed to retain the mounting component 104 on a user's outerwear, such as on a user's pocket, a pouch, a belt, a flap, or otherwise. The clip 106 can be integrally formed with the base 108 of the mounting component 104 such that the clip 106 can provide a clamping force via resiliency of the material used to form the clip 106. In some embodiments, the clip 106 can be a separate component from the base 108 and can include a biasing component, such as a coil spring, bent spring or the like, to provide a clamping force to retain the clip 106 on the user's person. In some embodiments, the clamping force can be low enough that a user can open the housing from the clamped position, but strong enough so that it will remain clamped about the pocket, flap, or other material.

In some embodiments, the mounting component 104 can be removably attached to the outer housing 102 such that the pump system 100 can be used with or without the mounting component 104. For example, FIGS. 1-8 illustrate the pump system 100 with the optional mounting component 104, and FIGS. 73-80 illustrate the pump system 100 without the optional mounting component 104. As shown in these figures, this can beneficially give the user the option to reduce the overall form factor of the pump system 100 should the user decide to forego use of the optional mounting component 104 as illustrated in FIGS. 73-80. Moreover, this can advantageously allow a user to more easily replace one mounting component with another mounting component should the user decide to do so. As shown in the illustrated embodiment, the mounting component 104 can include one or more retention features, such as clasps 110 extending from the periphery of the base 108, to retain the mounting component 104 on portions of the outer housing 102. In the illustrated embodiment, the mounting component 104 can be retained on the pump system 100 in a snap fit manner via use of the clasps 110. In some embodiments, the retention features can be mechanical fasteners such as screws, nuts, bolts, snap-fit connectors, or the like.

Figure 56:
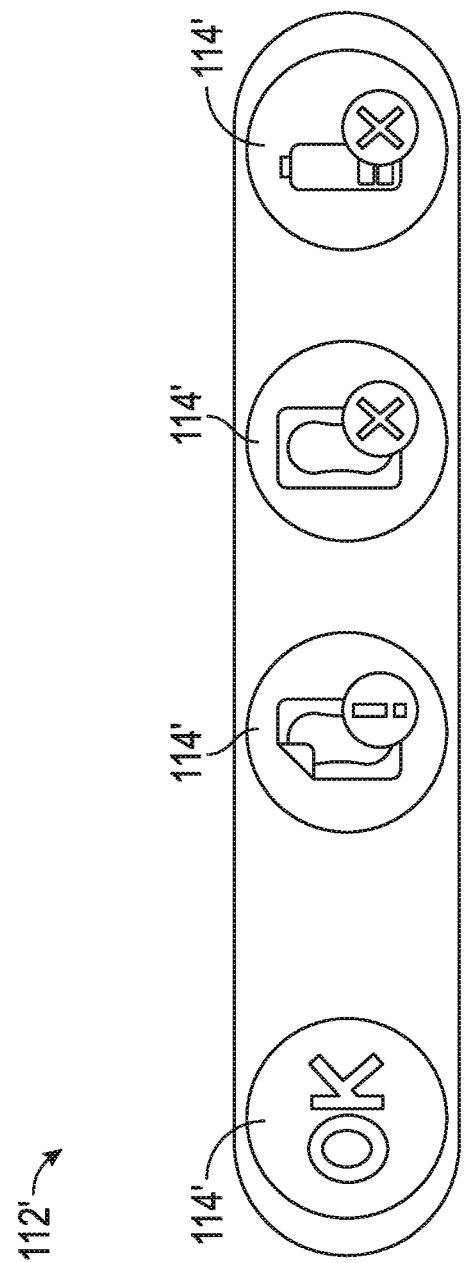
FIG. 56 is an embodiment of an arrangement of icons for a display.

With continued reference to the pump system 100 of FIGS. 1-8, the outer housing 102 can include a display 112 which can be designed to provide a user with information (e.g., information regarding an operational status of the pump system 100). In some embodiments, the display 112 can include one or more indicators, such as icons 114, which can alert the user to one or more operating and/or failure conditions of the pump system 100. For example, the indicators can include icons for alerting the user to normal or proper operating conditions, pump failure, power failure, the condition or voltage level of the batteries, the condition or capacity of a wound dressing, detection of a leak within the dressing or fluid flow pathway between the dressing and the pump assembly, suction blockage, or any other similar or suitable conditions or combinations thereof. An exemplary set of icons 114' of a display 112' is illustrated in FIG. 56 which, from left to right, can include an "OK" indicator which can indicate normal operation of the pump system 100, a "leak" indicator which can indicate the existence of a leak in the pump system 100 or components attached thereto, a "dressing full" indicator which can indicate that a wound dressing is at or near capacity, and a "battery critical" indicator which can indicate that the battery is at or near a critical level. In some embodiments, the icons 114 or 114' can have a green and/or orange color, and/or can be illuminated with a green and/or orange light (e.g., colored LEDs).

In the illustrated embodiment, one or more icons 114 can be printed directly on the display 112 of the outer housing 102. In some embodiments, one or more of the icons 114 can be provided on a label attached to a portion of the outer housing 102. One or more of the icons 114 can be illuminated when the status corresponding to that icon exists in the system. As will be discussed in further detail below, one or more illumination components, such as LEDs, can be positioned within the outer housing 102 to illuminate the icons 114. To enhance illumination of the icons using an illumination component within the outer housing 102, portions of the outer housing 102 proximate and/or underlying one or more of the icons 114 can be reduced in thickness to increase the translucency of the outer housing 102 proximate and/or underlying the icons 114. In some embodiments, portions of the outer housing 102 proximate and/or underlying one or more of the icons 114 can be made from a transparent material. For example, in some embodiments, the display 112 of the outer housing 102 can comprise an illumination panel that is thinned and/or made of transparent and/or translucent material. Thinning portions of the outer housing 102 and/or making portions of the outer housing 102 from a transparent and/or translucent material can allow light from the illumination components to pass through the housing 102 and illuminate the icons 114. Advantageously, as no openings are formed in the outer housing 102 to provide illumination for the one or more icons 114 with a thinner or transparent and/or translucent housing, the potential for leakage around the icons 114 is eliminated or at least significantly reduced.

In some embodiments, the pump housing can include a display integrated with the housing such that the display includes part of the housing. In some embodiments, the display can include one or more indicators configured to be illuminated by one or more corresponding illumination sources positioned within the housing. In some embodiments, the one or more illumination sources can include one or more light emitting diodes (LEDs). In some embodiments, the pump housing can also include a nonhomogeneous thickness, the nonhomogeneous thickness including at least a first thickness and a second thickness such that the first thickness is less than the second thickness. In some embodiments, the first thickness can be proximate (e.g., adjacent) the second thickness. In some embodiments, a portion of the display can include the first thickness and at least a portion of the housing proximate the display can include the second thickness. In some embodiments, a portion of the display can include the one or more indicators. In some embodiments, a portion of the display can include translucent and/or transparent material, wherein the transparent material is contiguous with the portion of the housing proximate the display.

To prevent the illumination of one icon from bleeding into and illuminating another icon, baffles can be positioned on one or more portions of one or more interior surfaces of the outer housing 102 proximate the one or more illumination components positioned within the outer housing 102. The baffles can be attached to and/or formed integrally with interior surfaces of the outer housing 102 and/or with one or more components and/or surfaces of components positioned within the outer housing 102. For example, in some embodiments, the baffles can comprise portions of the outer housing 102 that have not been reduced in thickness. In some embodiments, an integrally formed or separately attached baffle can surround the perimeter of each icon on the inside of the outer housing 102. Of course, any suitable baffle is appreciated and envisioned, such as, for example, baffles integrally formed with the outer housing 102 having a reduced thickness but having a dark or opaque color relative to the transparent material underlying the one or more icons 114. The skilled artisan will also appreciate that any suitable baffle placement is envisioned. In some embodiments, more than one type of baffle can be used and/or combined with one or more different types of baffles. The baffles can inhibit (e.g., prevent) one or more of the illumination components from illuminating one or more of the icons 114 when one or more of the illumination components are illuminated. Advantageously, the baffles can help reduce the potential of users misreading the icons by preventing light that was intended for one icon from erroneously illuminating another icon. For example, with reference to the exemplary set of icons 114' of display 112' shown in FIG. 56, the baffles can be positioned under the display 112' so that each of the four icons can be separately illuminated without bleeding light into one of the three other icons.

With continued reference to the pump system 100 illustrated in FIGS. 1-8, the pump system 100 can include one or more user input features, such as button 116, designed to receive an input from the user for controlling the operation of the pump system 100. In the embodiment shown, a single button is present which can be used to activate and deactivate the pump system 100 and/or control other operating parameters of the pump system 100. For example, in some embodiments, the button 116 can be used to activate the pump system 100, pause the pump system 100, clear indicators such as icons 114, and/or be used for any other suitable purpose for controlling an operation of the pump system 100 (e.g., by sequentially pushing on the button 116). The button can be a push style button that can be positioned on an outside, front surface of the housing. In other embodiments, multiple input features (e.g., multiple buttons) can be provided on the pump system 100.

In some embodiments, the button 116 can be designed to eliminate or at least reduce the potential for leakage around the button 116. In some embodiments, a peripheral portion of the button 116 can be placed in an interference fit with a surrounding lip of the outer housing 102. In some embodiments, the entirety or portions of the button 116 can be formed of a deformable material capable of forming a relatively hermetic seal when abutted against a surface, such as rubber, silicon, or any other suitable material.

Figure 57B:
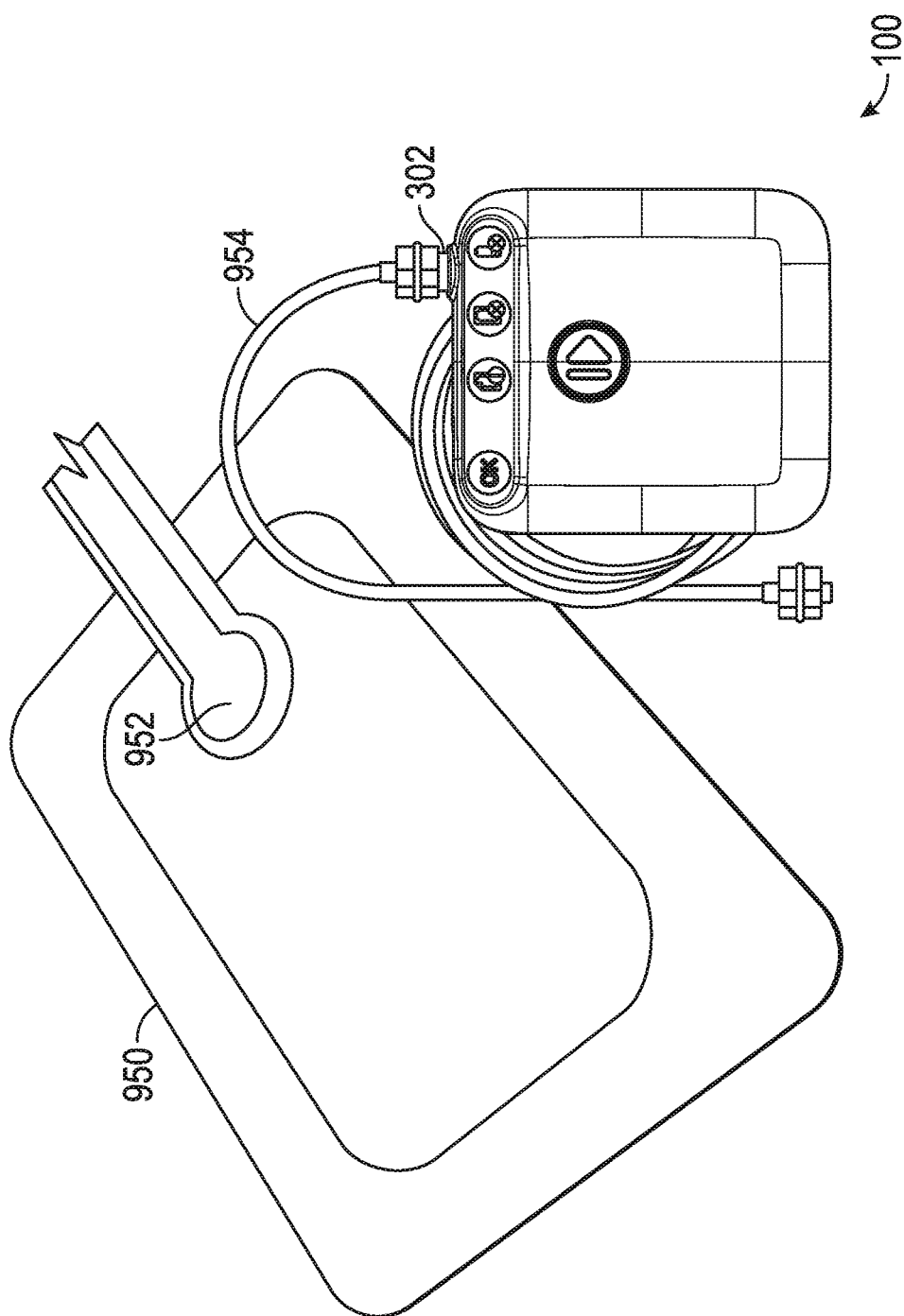
FIG. 57B is a view of an embodiment of a pump system configured to be attached to a wound dressing.

In some embodiments, the pump system 100 can include a connector 302 for connecting a tube or conduit to the pump system 100. For example, as shown in FIGS. 57A and 57B, the connector 302 can be used to connect the pump system 100 to a dressing 950. As shown in the illustrated embodiment, the wound dressing 950 can include a port 952 for receiving an end of the conduit 954. In some embodiments, the port 952 can include a connector portion 953 for receiving the conduit 954. In some embodiments, the conduit 954 can be connected directly to the connector 302 of the pump system 100. In some embodiments, such as that shown in FIG. 57A, an intermediate conduit 956 can be used and attached to conduit 954 via a connector, such as a quick release connector 958, 960.

In some embodiments, the pump system can be configured to operate in a canisterless system, in which the wound dressing, such as wound dressing 950, retains exudate aspirated from the wound. Such a dressing can include a filter, such as a hydrophobic filter, that prevents passage of liquids downstream of the dressing (toward the pump system). In other embodiments, the pump system can be configured to operate in a system having a canister for storing at least part of exudate aspirated from the wound. Such canister can include a filter, such as a hydrophobic filter, that prevents passage of liquids downstream of the dressing (toward the pump system). In yet other embodiments, both the dressing and the canister can include filters that prevent passage of liquids downstream of the dressing and the canister.

As will be described in further detail below in connection with FIGS. 13-17B, the connector 302 can be part of an intake manifold 300 of the pump system 100 which can form an initial fluid flow pathway through the pump system 100. As shown in the illustrated embodiment, the connector 302 can include one or more retention features, such as threading, snap-fit mounts such as clips, bayonet mounts, or the like to more securely retain a connected component to the connector 302.

Figure 10:
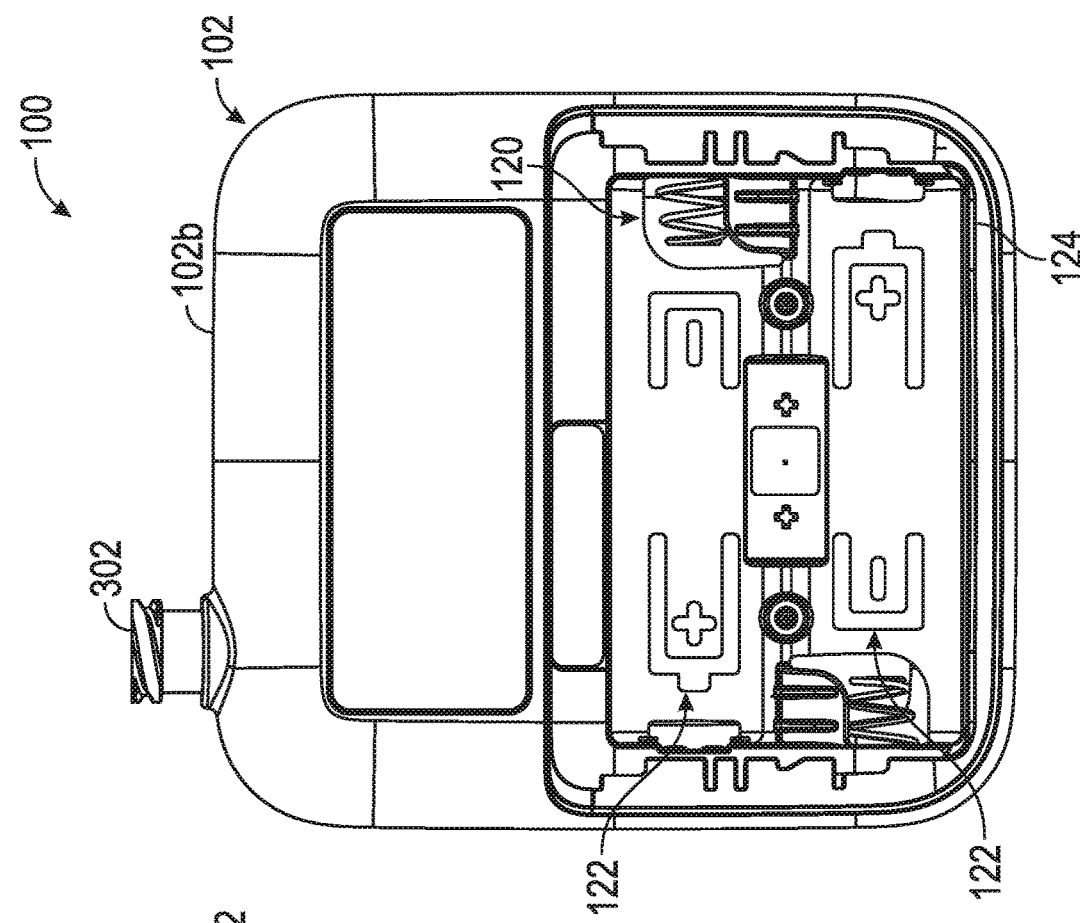
FIG. 10 is a rear view of the outer housing of FIG. 9, with a cover removed to expose cavity within the outer housing.
Figure 9:
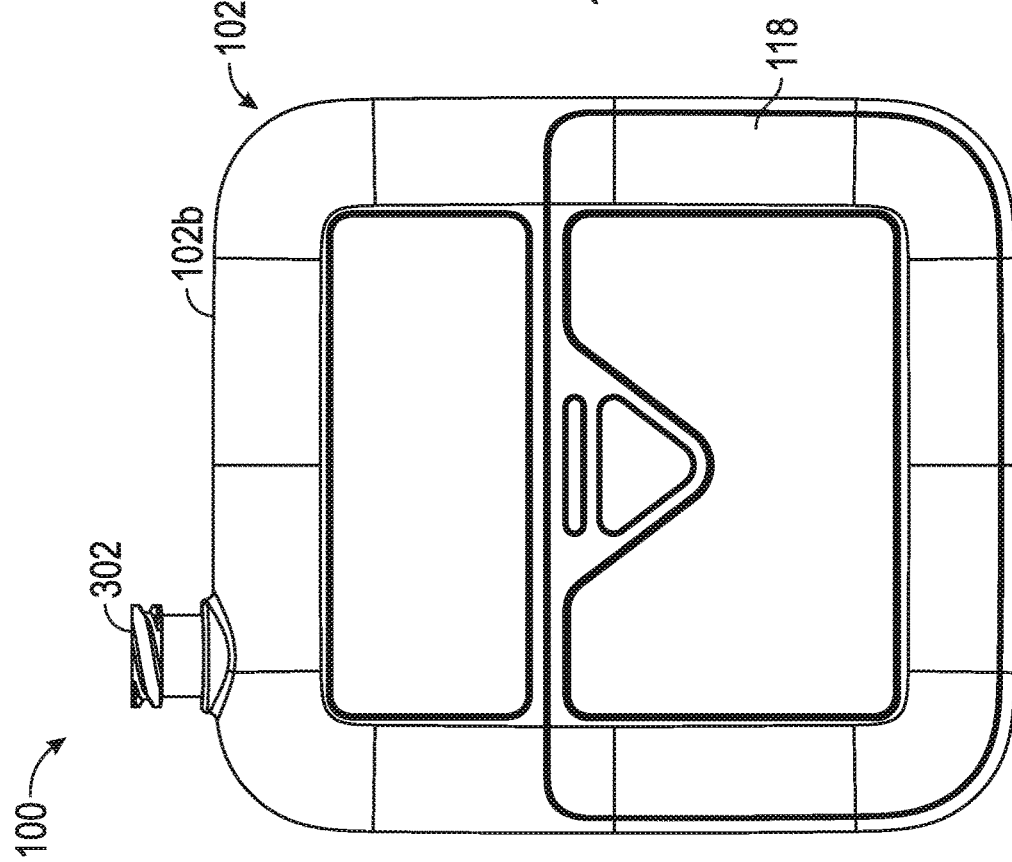
FIG. 9 is a rear view of the outer housing of FIG. 1, without the optional mounting component.

FIGS. 9-10 illustrate rear elevation views of an embodiment of the pump system 100 without the optional mounting component 104 attached to the outer housing 102. As shown in the illustrated embodiment, the rear portion 102b of the outer housing 102 can include a removable cover 118 for placement over a cavity 120. The cavity 120 can include one or more recesses 122 designed to receive one or more power sources, such as batteries, for powering the device. In some embodiments, an outer periphery 124 of the cavity 120 can include features which can cooperate with respective features of the cover 118 to reduce the likelihood that moisture will enter the cavity 120. For example, in some embodiments, the outer periphery 124 can include a rib along the bottom periphery, a side periphery, a top periphery, and/or a combination of one or more peripheries to reduce the likelihood of moisture ingress into the cavity 120. In some embodiments, the outer periphery 124 can include a recess along the bottom periphery, a side periphery, a top periphery, and/or a combination of one or more peripheries to redirect moisture, such as water droplets, away from the cavity 120.

Figure 12:
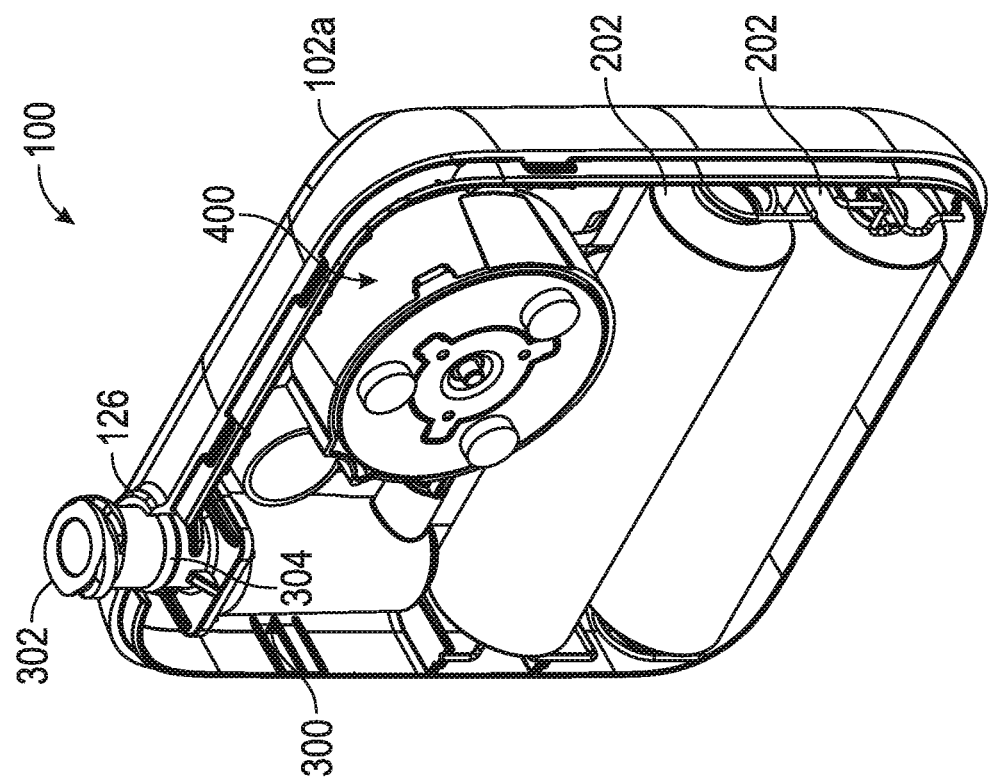
FIG. 12 is a rear perspective view of the outer housing of FIG. 1, with a rear portion of the outer housing removed to expose an embodiment of a circuit board and pump assembly.
Figure 11:
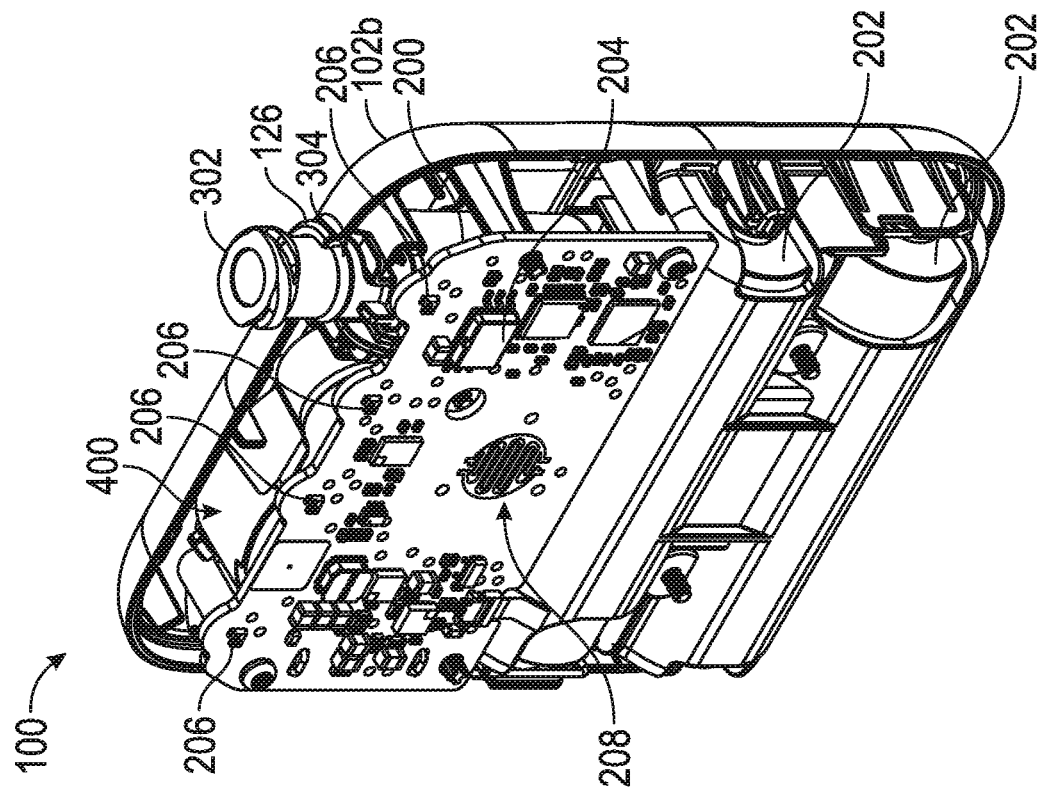
FIG. 11 is a front perspective view of the outer housing of FIG. 1, with a front portion of the outer housing removed to expose an embodiment of a circuit board and pump assembly.
Figure 13:
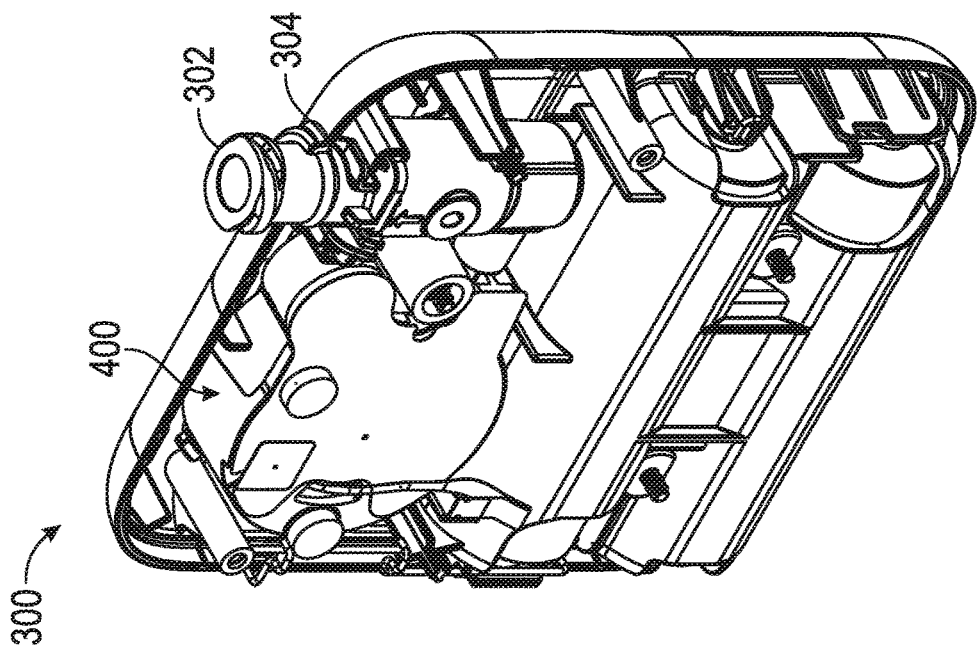
FIG. 13 is a front perspective view of the outer housing of FIG. 1, with a front portion of the outer housing and the circuit board removed to expose the pump assembly.

FIGS. 11-12 illustrate perspective views of an embodiment of a pump system 100 with portions of the outer housing 102 removed to expose an embodiment of a circuit board 200, an intake manifold 300, and a source of negative pressure such as a pump assembly 400. FIG. 13 illustrates a perspective view of an embodiment of pump system 100 with a front portion of the outer housing 102 removed as well as the circuit board 200 to expose the intake manifold 300 and pump assembly 400. As shown in the illustrated embodiment, the circuit board 200, the intake manifold 300, and/or the pump assembly 400 can be positioned within and/or supported by the outer housing 102.

The control board 200 can be designed to control the function of the pump system 100 such as the pump assembly 400. The control board 200, such as a printed circuit board assembly (PCBA), can be designed to mechanically support and electrically connect various electrical/electronic components of the pump system 100. For example, in some embodiments, the control board 200 can connect one or more batteries 202 to the pump assembly 400 to provide power to operate the pump assembly 400. In some embodiments, the control board 200 can include a pressure monitor 204. The pressure monitor 204 can be supported by the control board 200 and can be designed to monitor a level of pressure in a fluid flow passageway. The control board 200, in conjunction with the pressure monitor 204, can be designed to protect the pump assembly 400 from exceeding a predefined threshold pressure and/or can be designed to maintain a target pressure at the wound.

The circuit board 200 can be designed to cut power to the pump assembly 400 if the pressure reading reaches a predetermined value, and be designed to resume when the pressure level drops below the predetermined value or a second predetermined value that can be higher or lower than the first predetermined value. Additionally, the control board 200 can be programmed to prevent such over-pressurization.

In some embodiments, the control board 200 can include indicator lights, audible alarms, and/or a combination of such features. For example, in some embodiments, the control board 200 can include indicator lights in the form of one or more LEDs 206. As discussed above in connection with FIGS. 1-8, the one or more LEDs 206 can be used to illuminate one or more icons 114 of the display 112 on the outer housing 102. In some embodiments, each LED 206 can correspond to one or more icons 114. In some embodiments, the control board 200 can have one or more features 208 (e.g., pressure sensitive switch(es)) to receive an input from the control button 116.

FIG. 13 illustrates a front perspective view of a pump system 100 with a front portion of the outer housing 102 removed as well as the control board 200, to expose the intake manifold 300 and the pump assembly 400. As shown in the illustrated embodiment, the manifold 300 and the pump assembly 400 can be positioned within and/or supported by one or more portions of the outer housing 102.

Figure 17A:
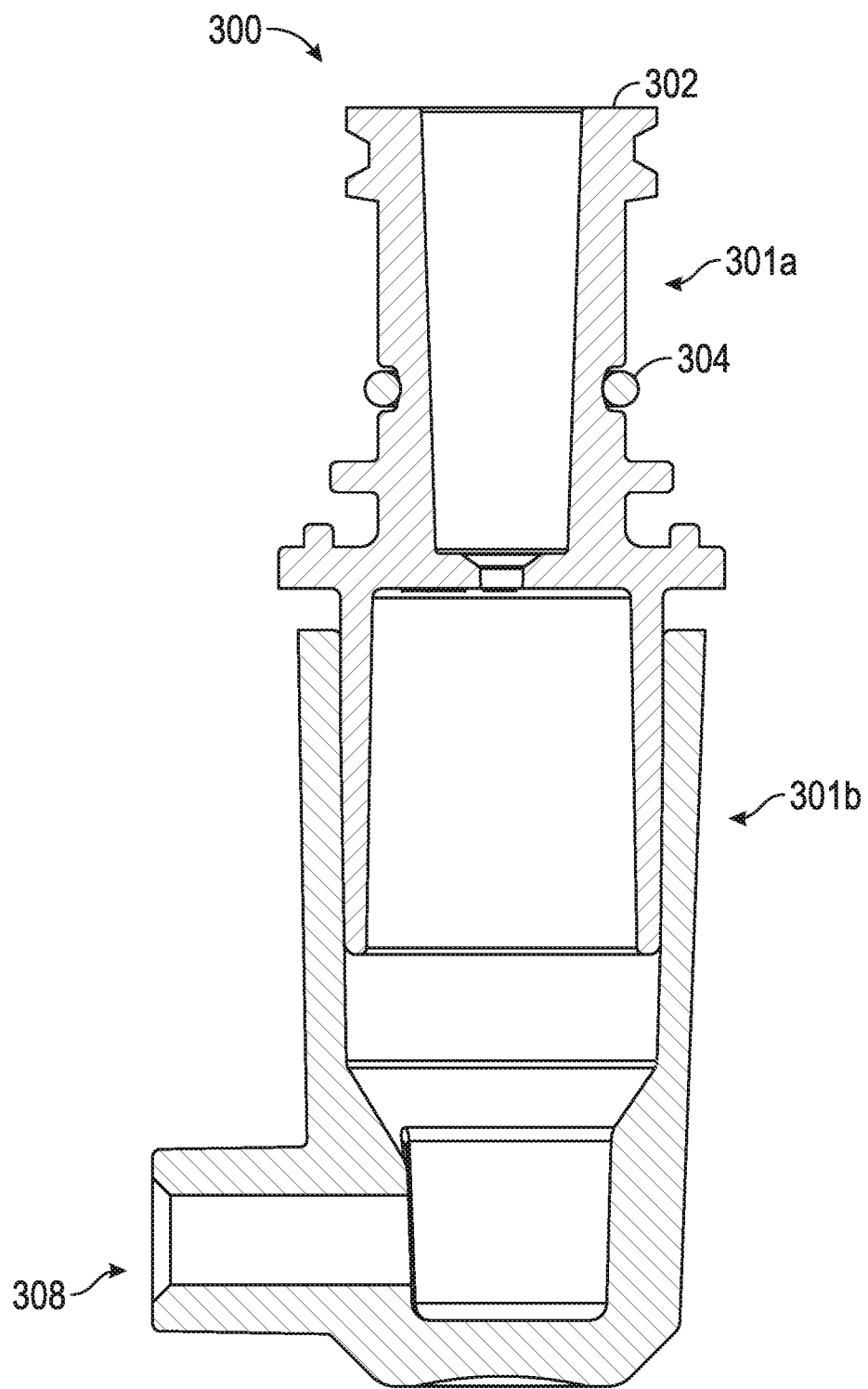
FIG. 17A is a cross sectional view of the intake manifold of FIG. 14.
Figure 17B:
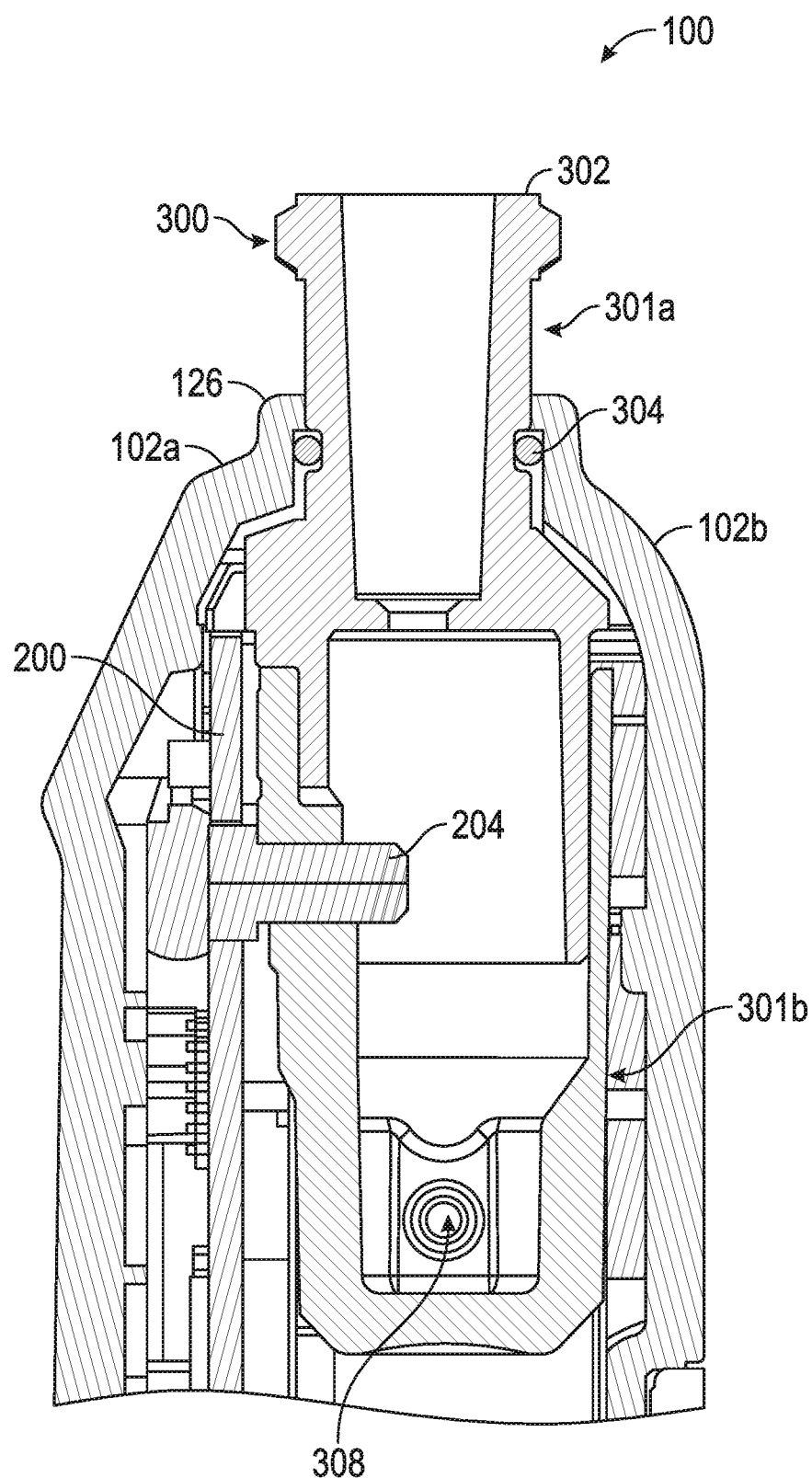
FIG. 17B is a cross sectional view of the intake manifold with an outer housing and a control board.

FIGS. 14-17B illustrate various views of the intake manifold 300 and the pump assembly 400. As shown in the illustrated embodiment, the intake manifold 300 can be in fluid communication with an intake port 426 (shown in FIGS. 21-22) of the pump assembly 400. The intake manifold 300 can be formed from one or more portions, such as a top portion 301a and a bottom portion 301b, which can be removably attached to form the intake manifold 300. For example, as shown most clearly in FIG. 17A, the top portion 301a can be received within the bottom portion 301b in a friction and/or interference fit. In some embodiments, the top portion 301a and the bottom portion 301b can be a monolithic structure. In some embodiments, the intake manifold 300 can include a connector 302 at an end of the top portion 301a which can protrude from the outer housing 102 to connect a tube or conduit to the intake manifold 300. As discussed above, the connector 302 can include one or more retention features, such as the illustrated threading, to secure the tube or conduit to the connector 302 and reduce the likelihood of accidental detachment. The intake manifold 300 can include a sealing member 304, such as an O-ring, positioned around a top portion 301a of the intake manifold 300. The sealing member 304 can advantageously be positioned between the intake manifold 300 and the outer housing 102 to eliminate or reduce the potential for leakage around the intake manifold 300. For example, the sealing member 304 can be positioned within an extension 126 of the outer housing 102 as shown in FIG. 17B. In some embodiments, the sealing member 304 can be made from silicon.

The intake manifold 300 can include a port 306 designed to be in fluid communication with the pressure monitor 204. For example, as shown in FIG. 17B, the port 306 can directly receive a portion of the pressure monitor 204 within the port 306. This can beneficially reduce the total amount of plumbing through the pump system 100 and/or reduce the potential for leakage. The port 306 can be positioned on the bottom portion 301b of the intake manifold 300 although it can also be positioned along any other portion of the intake manifold 300 as desired. The intake manifold 300 can include an outlet port 308 for connection to the intake port 426 of the pump assembly 400. As shown in the illustrated embodiment, the intake manifold 300 does not include a check valve or one-way valve. In some embodiments, the intake manifold 300 can include a check valve or one-way valve to allow flow into the pump system 100 but inhibit flow out of the pump system 100.

Figure 18:
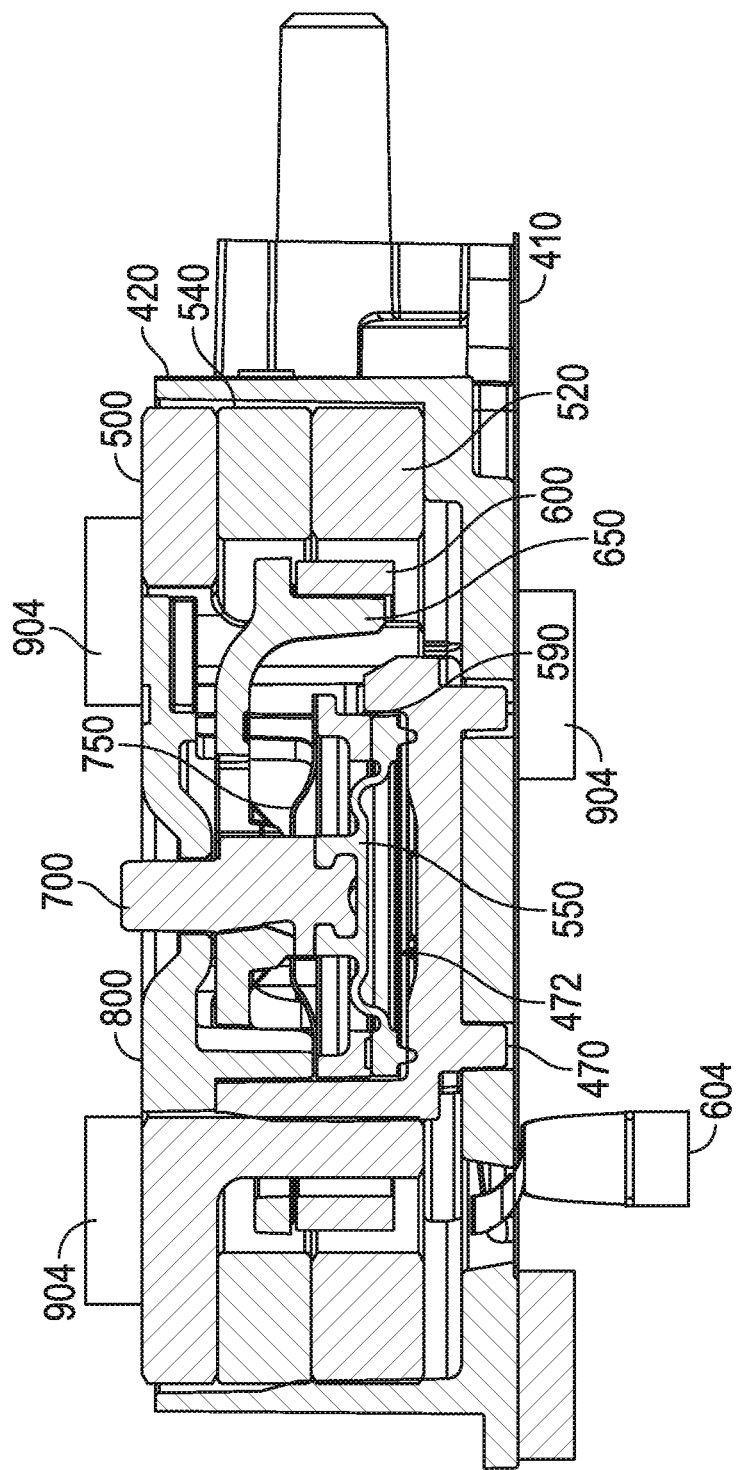
FIG. 18 is a cross sectional view of the pump assembly of FIG. 14.
Figure 19:
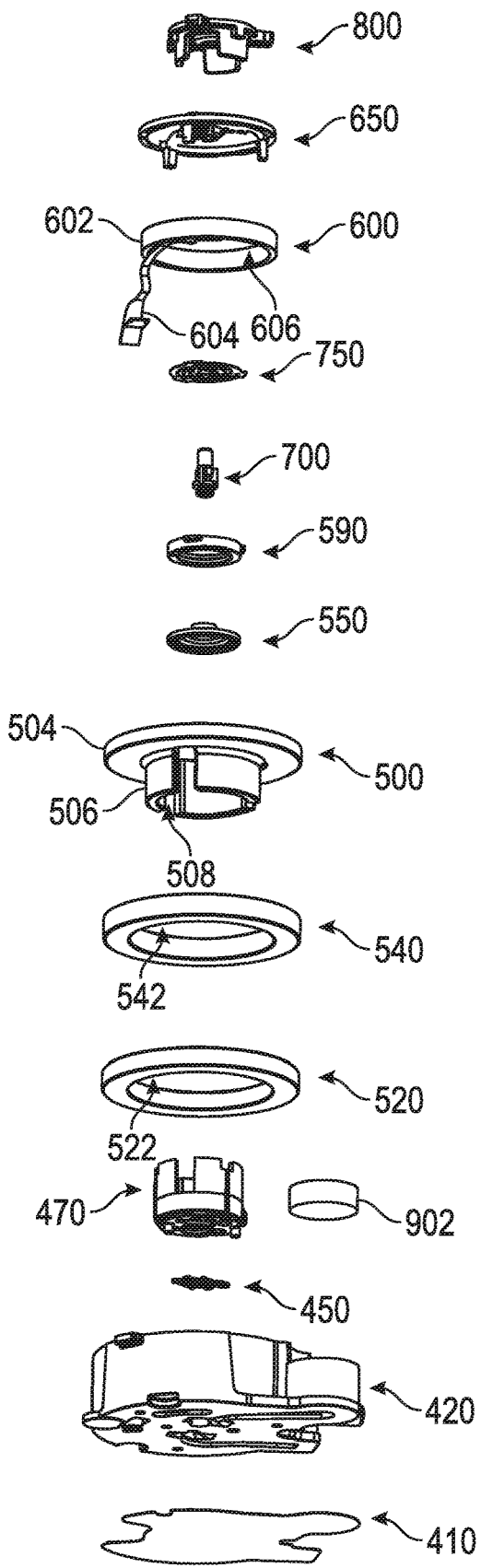
FIGS. 19-20 are exploded views of the pump assembly of FIG. 14
Figure 20:
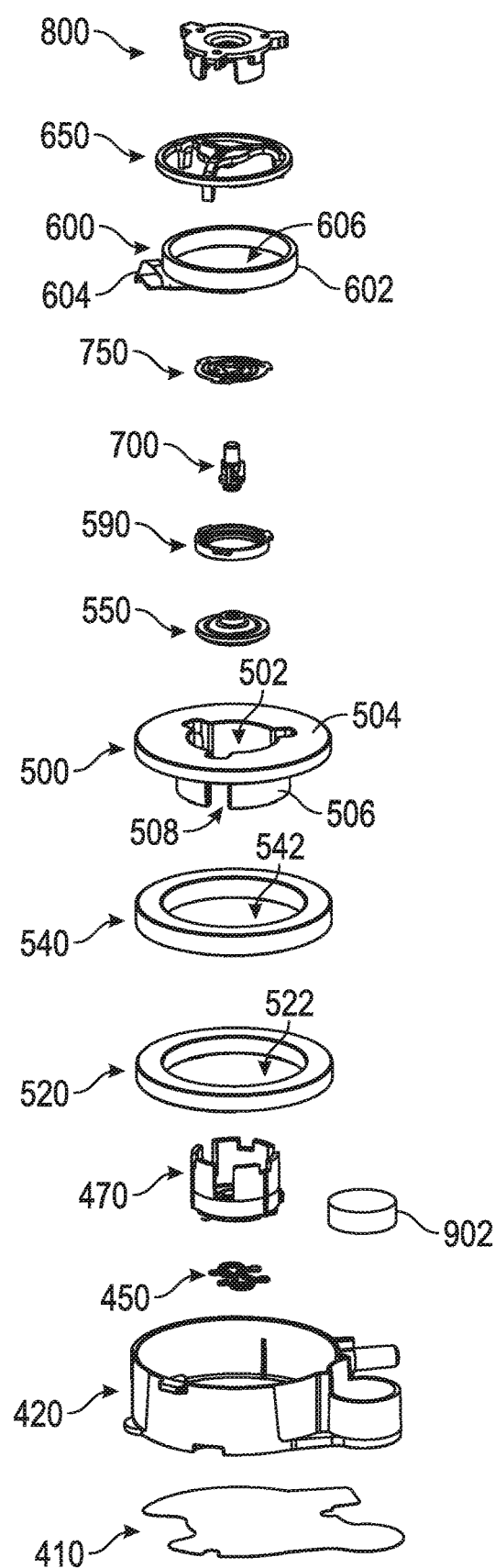

FIG. 18 illustrates a cross-section of an embodiment of a pump assembly 400 in an assembled configuration. FIGS. 19-20 illustrate an exploded view of the pump assembly 400 illustrating these various components. As shown in the illustrated embodiment, the pump assembly 400 can include a cover 410, a pump housing 420, one or more valves 450, and a pump chamber body 470. The one or more valves 450 can be used to control the flow of fluids through a diaphragm chamber 472 which can be defined between the pump chamber body 470 and a diaphragm 550. As will be discussed in further detail below, the diaphragm 550 can move relative to the pump chamber body 470 to alter the volume of the diaphragm chamber 472. This change in volume can result in changes in pressure within the diaphragm chamber 472 which can generate fluid flow into and out of the diaphragm chamber 472. For example, the one or more valves 450 can be designed to alternately open and close in response to the changes in pressure within the diaphragm chamber 472. The one or more valves 450 can be designed to control the fluid flow through the diaphragm chamber 472 such that fluid enters from one or more intake openings and fluid is expelled from one or more exhaust openings which can be different from the intake openings.

As shown in the illustrated embodiment, the pump assembly 400 can include an upper pole 500, a lower pole 520, and a magnet 540. The magnet 540 can provide a permanent magnetic field through at least a portion of the pump assembly 400. In some embodiments, the upper pole 500 and/or the lower pole 520 can support the magnet 540. In some embodiments, the upper pole 500 and/or the lower pole 520 can be arranged to more effectively align the magnetic field with respect to one or more components of the pump assembly 400, such as a coil 600. For example, in some embodiments, the upper pole 500 and/or the lower pole 520 can be arranged to shape the magnetic field of the magnet 540 so that it is normal to any current that flows through the coil. In so doing, the efficiency of the pump assembly 400 can advantageously be increased. In some embodiments, the upper pole 500 and/or the lower pole 520 can optionally include magnetic material.

As shown in the illustrated embodiment, the pump assembly 400 can include a voice coil actuator (VCA). The pump assembly 400 can include a coil 600 attached to a piston sub-assembly which can include a support member 650 designed to support the coil 600, a shaft 700, and/or a spring member 750. The pump assembly 400 can also include a bearing or bushing 800. The VCA can be used to generate vertical harmonic movements of the shaft 700 by passing a current inside a wire fully absorbed in the permanent magnetic field of the magnet 540. An electric current can flow through the coil 600 to generate a magnetic field such that a magnetic force can be applied to the coil 600 by virtue of the permanent magnetic field provided by magnet 540. In some embodiments, the magnetic forces applied to the coil 600 can be transferred to the support member 650 and then to the diaphragm 550 through a mechanical connection between the coil 600 and the support member 650. For example, the support member 650 and the spring member 750 can be designed to transmit forces applied to the coil 600 to the shaft 700, which can be connected to the diaphragm 550, such that forces applied to the coil 600 are ultimately transmitted to the diaphragm 550. By controlling the current flow through the coil 600, movement of the diaphragm 550 can ultimately be controlled. In some embodiments, the spring member 750 can be attached to the shaft 700 to alter a resonance frequency for the pump assembly 400 thereby enhancing efficiency around that frequency. In some embodiments, the bushing 800 can be used to help maintain alignment of the pump assembly 400 components during operation.

As noted above, FIGS. 19-20 illustrate an exploded view of the pump assembly 400 illustrating various components such as a cover 410 and a pump housing 420. In some embodiments, the pump housing 420 can be adapted to support and protect many of the components of the pump assembly 400. The pump housing 420 can have one or more air channels, such as intake channel 422 and exhaust channel 424, formed in and/or along an outer surface of the pump housing 420 as shown most clearly in FIG. 22.

The intake channel 422 can be used to channel or communicate fluid, such as air, from an intake port 426 which can be in communication with a wound dressing via the connector 302 towards an inlet opening 427 for an intake valve chamber formed between the pump housing 420 and the pump chamber body 470 and in which the intake valve resides. The exhaust channel 424 can be used to channel or communicate fluid, such as air, from an outlet opening 429 for an exhaust valve chamber formed between the pump housing 420 and the pump chamber body 470 and in which the exhaust valve resides. The exhaust channel 422 can channel or communicate such fluid towards an exhaust port 428 and into an interior of a chamber 430 where it can eventually be exhausted into the atmosphere within the outer housing 102. As will be discussed in further detail below, chamber 430 can form part of a noise reduction system for the pump assembly 400 to reduce the amount of noise generated by the pump assembly 400 during operation. As shown in the illustrated embodiment, the chamber 430 can include one or more ribs 431.

The cover 410 can be positioned over the outer surface of the pump housing 420. The cover 410 can be an adhesive backed foil, film, paper, plastic sheet or label, or other similar object. In some embodiments, the cover 410 can be a thermal transfer polyester such as 3M's 7815 with a topcoat such as FLEXcon's Compucal Excel 10442. In some embodiments, the cover 410 can be a plate made from plastic, metal, or the like and can include a gasket for positioning between the cover 410 and the outer surface of the pump housing 420 to enhance the seal between the cover 410 and the outer surface of the pump housing 420. The cover 410, when positioned over the outer surface of the pump housing 420, can cooperate with intake and exhaust channels 422, 424 to form enclosed air passageways. For example, in some embodiments, the cover 410 can be designed to prevent an air short-circuit between the intake and exhaust channels 422, 424. In some embodiments, the cover 410 can be monolithically formed with the outer surface of the pump housing 420.

Figure 14:
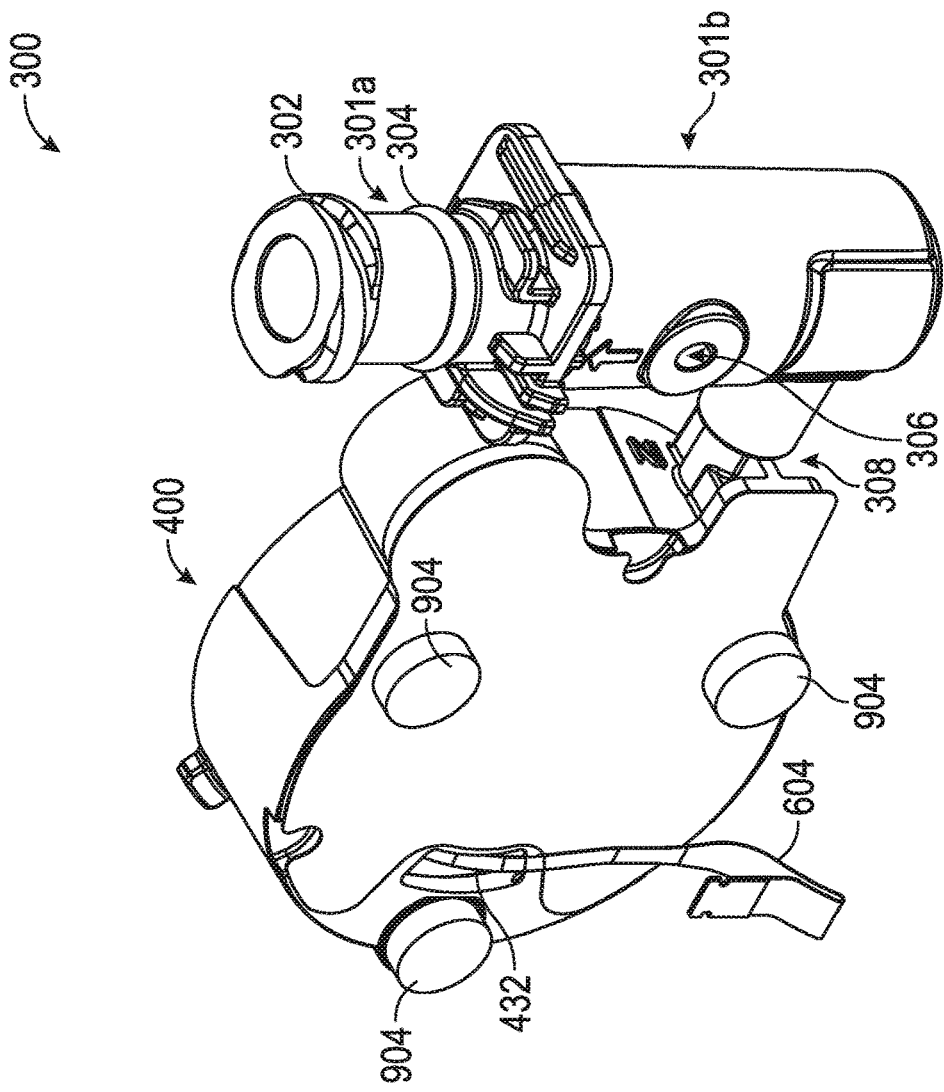
FIG. 14 is a front perspective view of an embodiment of a pump assembly and an intake manifold.

With reference to FIG. 21, the pump housing 420 can include one or more additional openings 432 to allow for components to pass from one side to another. For example, as will be discussed in further detail below, the one or more openings 432 can be used to allow an electrical conduit 604 to connect the coil 600 to the circuit board 200. The openings 432 can also be used to allow for additional clearance for pump assembly 400 plumbing, electronics such as wiring, and the like. For example, in some embodiments, the openings 432 can be used to allow a flexible circuit board to connect to a main circuit board by allowing the flexible circuit board to extend through the openings 432. For example, as shown in FIG. 14, an electrical conduit 604 can extend from an additional opening 432 so that the electronics inside the pump assembly can be electrically connected to the main circuit board 200 (shown in FIG. 11) of the pump system 100 (shown in FIG. 11). In this and other ways, as will be appreciated by the skilled artisan, the openings 432 can advantageously facilitate the management of wires within and around the pump housing 420. In some embodiments, the pump housing 420 can include one or more indexing features, such as the illustrated cutouts 434, which can be designed to facilitate assembly and ensure that components are properly oriented when assembled. In some embodiments, the pump housing 420 can be made from plastics such as polycarbonate, metals, composites, or the like, or a combination of materials.

Figure 24:
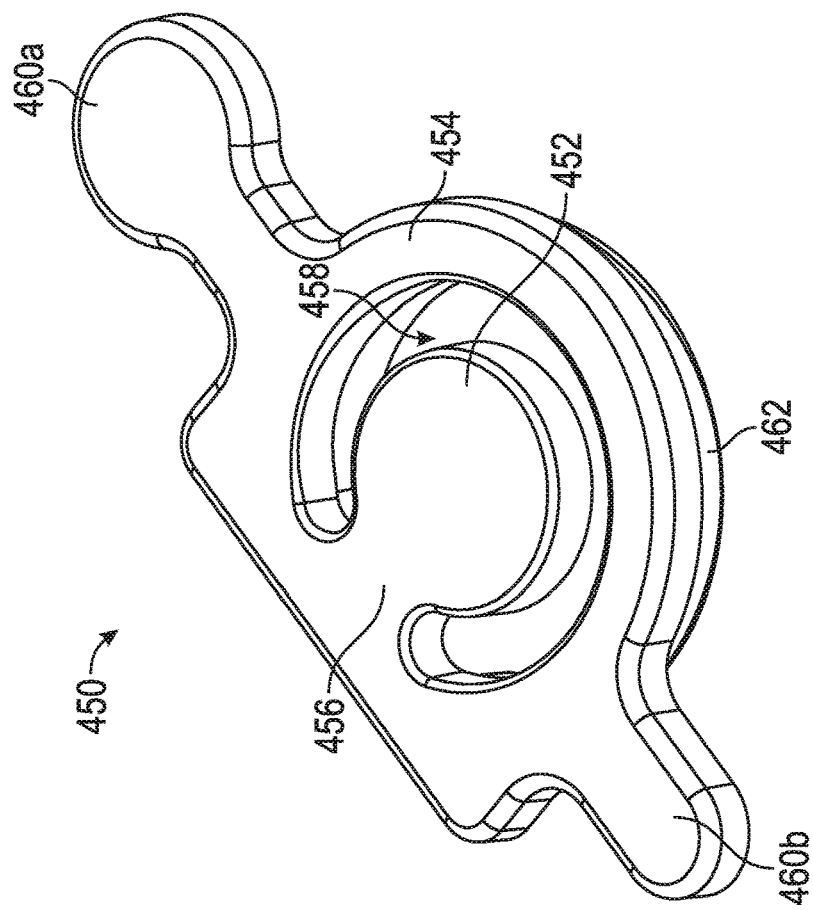
FIGS. 23-24 are perspective views of an embodiment of a valve.
Figure 23:
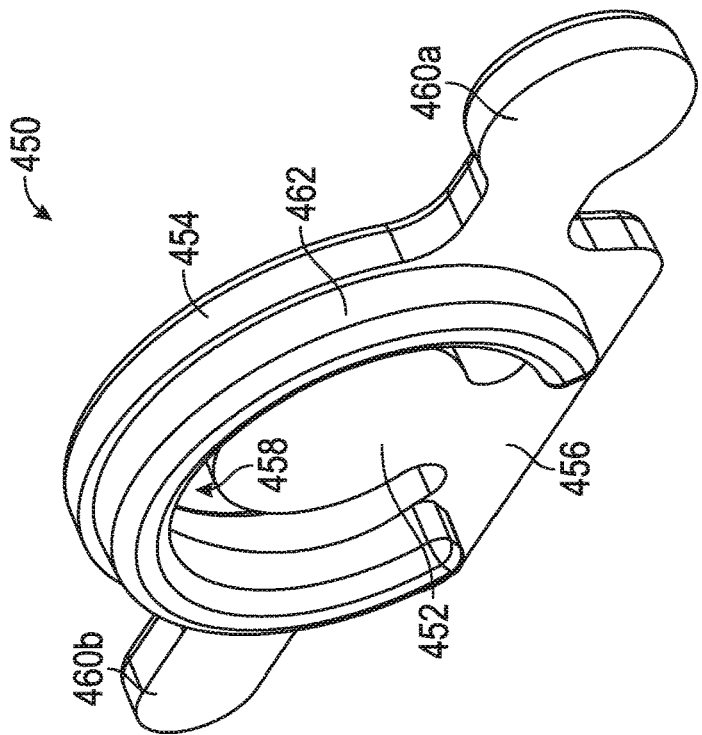

FIGS. 23-24 illustrate various views of an embodiment of a valve 450 which can be used with the pump assembly 400. The valve 450 can have a flexible and/or deflectable tab portion or member 452 supported in a middle portion of the valve 450. The tab portion 452 can be surrounded along its periphery by a frame portion 454 and can be attached to the frame portion 454 via a neck 456 extending from the tab portion 452. As shown in the illustrated embodiment, an opening or gap 458 can exist between the tab portion 452 and the frame portion 454 to facilitate the passage of fluid around the tab portion 452 and past the valve 450. In some embodiments, the opening or gap 458 can have a width of approximately 0.4 mm, or from approximately 0.3 mm to approximately 0.5 mm, and can surround approximately 80% of a perimeter of the tab portion 452.

As shown in the illustrated embodiment, the tab portion 452 can be supported in cantilever fashion via the neck portion 456, such that the tab portion 452 can bend or deflect away from a relaxed or closed position as shown in FIGS. 23-24. In some embodiments, the valve 450 can have one or more hinges, joints, articulations, or curves therein at or adjacent to the neck portion 456 of the tab portion 452 to improve the ability of the tab portion 452 to bend and deflect, thereby potentially improving the efficiency of the valves. In some embodiments, the valves and valve supports can be configured such that the valves are biased against the intake side of the valve or valve supports for improved seal and pump efficiency. As discussed above, movement of the diaphragm 550 can cause the valves to move in opposite directions away from their respective bias. In some embodiments, the valves can be designed such that some degree of leakage past the valve occurs under low pressure conditions. For example, in some embodiments, the valves 450 can be designed to leak at a rate of between about 0.1 mL/min to about 10 mL/min, or a leak rate of less than 10 mL/min, at low pressure conditions, between about 0.1 mL/min to about 5 mL/min, or a leak rate of less than 5 mL/min, at low pressure conditions, between about 0.1 mL/min to about 2 mL/min, or a leak rate of less than 2 mL/min, at low pressure conditions, any subrange within these ranges, or any other leakage rate as desired. Such leakage can facilitate sterilization of the device.

As shown in the illustrated embodiment, the valve 450 can include one or more indexing features, such as alignment tabs 460a, 460b, which can be matched to corresponding indexing features on another component, such as the pump chamber body 470. This can advantageously facilitate the placement, securement, and alignment of the valve 450 relative to the component. As shown in the illustrated embodiment, the alignment tabs 460a, 460b can extend from a periphery of the frame portion 454 and can have different shapes to reduce the likelihood of improper installation. In some embodiments, the valve member 450 can have just one alignment tab, such as alignment tab 460a or 460b.

As shown in the illustrated embodiment, the valve 450 can have a raised surface or rib 462 (also referred to as a compression ring) extending away from a surface of the valve 450. As shown in the illustrated embodiment, the rib 462 can be positioned along a periphery of the frame portion 454. The rib 462 can advantageously function as a spacer to ensure that a gap exists between the tab portion 452 and an exhaust side of the valve 450 such that the tab portion 452 has adequate space to bend or deflect to an open position. The rib 462 can also advantageously function to create a preload (also referred to as bias) against an inlet or exhaust nozzle to increase the seal between the valve and the nozzle. As discussed above, in some embodiments, the valve 450 can be secured (also referred to as sandwiched) between a pump chamber body and the pump housing such that the valve is compressed between the pump chamber body and the pump housing. In some embodiments, as will be described in further detail below, the pump chamber body can be laser welded to the pump housing. When the valve 450 is secured, the rib 462 can compress. In some embodiments, compression of the rib 462 allows the preload to form against the inlet and exhaust nozzles.

For example, in some embodiments, compression of the rib 462 preloads the tab portion 452 in a direction away from the rib, such as, for example, toward the intake sides of the inlet or exhaust nozzle openings. The tab portion 452 can be designed to inflect (also referred to as flex) itself until it contacts the nozzle planes of the inlet exhaust openings when the rib 462 is compressed. For example, with reference to FIGS. 23, 25, and 26, the valve 450 can be placed in the intake and exhaust recesses 476a, 476b such that the rib 462 faces toward the surface of the intake recess 476a and faces away from the surface of the exhaust recess 476b. When the rib 462 is compressed, the tab portion 452 of the valve 450 in the intake recess 476a is forced toward the inlet opening in the pump housing, and the tab portion 452 of the valve 450 in the exhaust recess 476b is forced toward the exhaust opening in the pump chamber body 470. In this way, the tab portion 452 of the one or more valves 450 can interfere with the inlet and exhaust nozzles such that the tab portion is biased across the planes of the inlet and exhaust nozzles.

In some embodiments, the valve 450 can be made from polymers such as rubbers, silicon, or the like, or a combination of materials. In some embodiments, the valve 450 can be dimensioned to meet a desired initial preload and total stiffness. The initial preload can be designed so as to provide a seal against the nozzles. For example, in some embodiments, the valve 450 can have an initial preload against the inlet or exhaust nozzle of approximately 0.03 millimeters and can have a total stiffness of about 12 Newtons/meter, although any suitable initial preload and total stiffness is envisioned.

Figures 25, 26, 27:
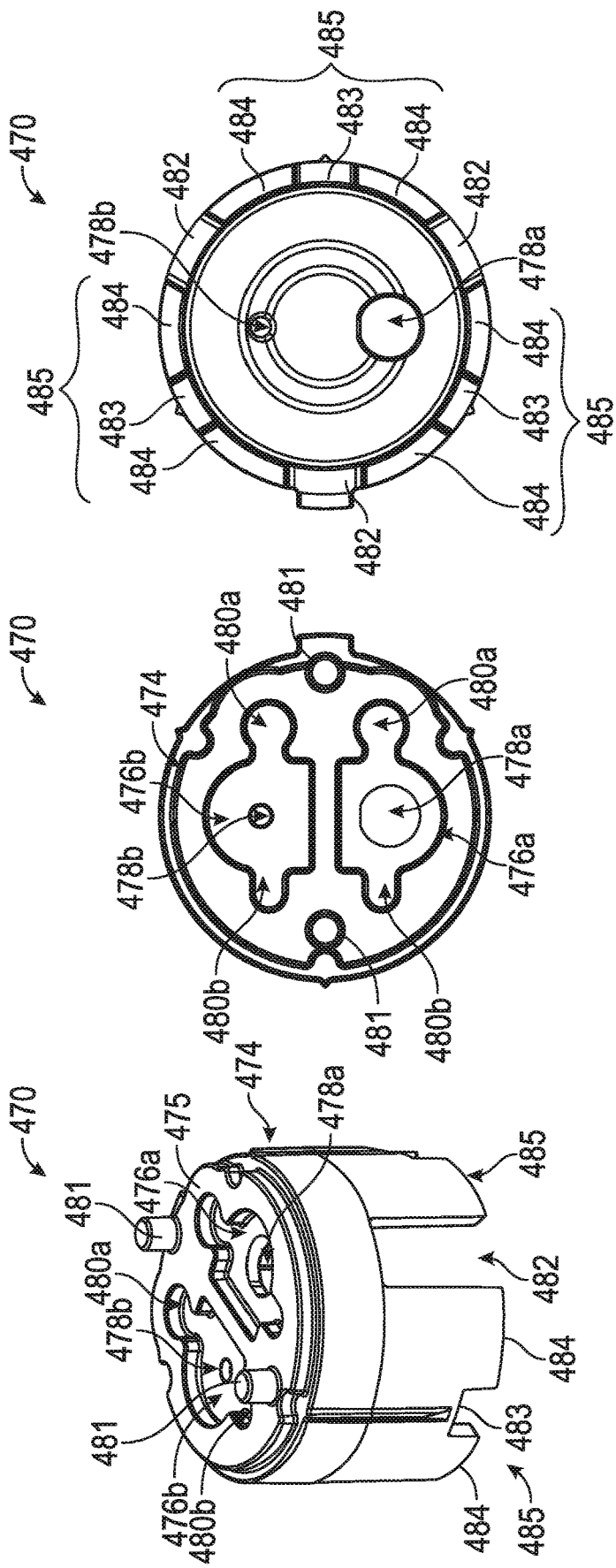
FIG. 25 is a perspective view of an embodiment of a pump chamber body.
FIG. 26 is a front view of the pump chamber body of FIG. 25.
FIG. 27 is a rear view of the pump chamber body of FIG. 25.
Figure 29:
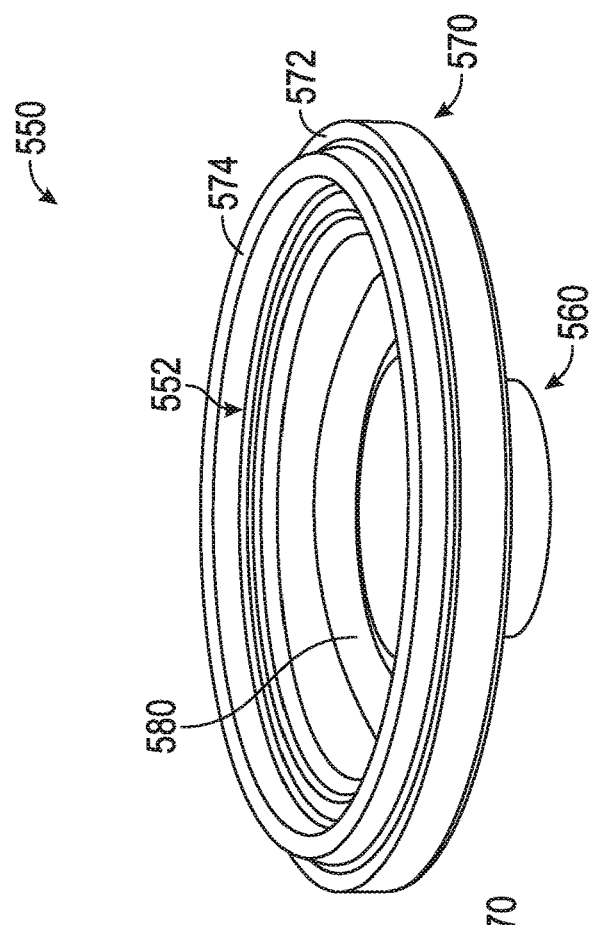
FIGS. 28-29 are perspective view of an embodiment of a diaphragm.
Figure 28:
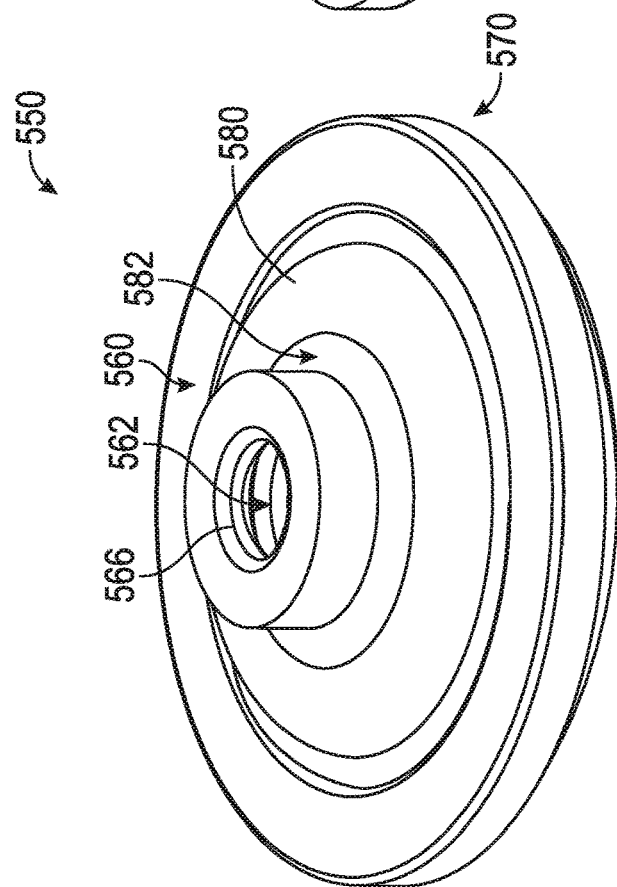

FIGS. 25-27 illustrate various views of an embodiment of a pump chamber body 470 which can form part of the pump assembly 400. The pump chamber body 470 can cooperate with the diaphragm 550 to form a diaphragm chamber 472 (shown in FIG. 18). Via movement of the diaphragm 550 relative to the pump chamber body 470, the diaphragm 550 can effectively alter the volume of the diaphragm chamber 472 to generate fluid flow into and out of the diaphragm chamber 472.

As discussed above, the fluid flow into and out of the diaphragm chamber 472 can be controlled by the one or more valves 450, which can be designed to passively move in response to the volume and pressure changes within the diaphragm chamber. For example, in some embodiments, the tab portions 452 of the one or more valves 450 can passively move in response to the volume and pressure changes within the diaphragm chamber. In some embodiments, the volume inside the diaphragm chamber 472 can increase when the shaft 700 moves the diaphragm 550 (e.g., by deforming it) away from the pump chamber body 470 (e.g., toward the bushing 800). This increase in volume can generate a vacuum condition by reducing the pressure inside of the diaphragm chamber 472 below the surrounding atmospheric pressure. When the shaft 700 moves to create a vacuum condition, it can be said to be in suction travel. For example, during suction travel, the shaft 700 can move the diaphragm 550 downward and/or away from the inlet and exhaust nozzles of the pump chamber body 470 and/or toward a bottom dead center (BDC) of the pump assembly 400. When a vacuum condition forms in the diaphragm chamber 472 as a result of suction travel of the shaft 700, the inlet valve can open and the outlet valve can close. For example, the vacuum condition can cause the tab portion of the inlet valve to move away from the nozzle plane of the inlet nozzle, thereby opening the inlet valve, and can cause the tab portion of the outlet valve to be pushed against the nozzle plane of the exhaust nozzle, thereby closing the outlet valve. Similarly, in some embodiments, the volume inside the diaphragm chamber 472 can decrease when the shaft 700 moves the diaphragm 550 (e.g., by deforming it) toward the pump chamber body 470 (e.g., away from the bushing 800). This decrease in volume can generate an overpressure condition by increasing the pressure inside of the diaphragm chamber 472 above the surrounding atmospheric pressure. When the shaft 700 moves to create an overpressure condition, it can be said to be in pumping travel. For example, during pumping travel, the shaft 700 can move the diaphragm 550 upward and/or toward the inlet and exhaust nozzles of the pump chamber body 470 and/or toward a top dead center (TDC) of the pump assembly 400. When an overpressure condition forms in the diaphragm chamber 472 as a result of pumping travel of the shaft 700, the outlet valve can open and the inlet valve can close. For example, the overpressure condition can cause the cause the tab portion of the outlet valve to move away from the nozzle plane of the exhaust nozzle, thereby opening the outlet valve, and can cause the tab portion of the inlet valve to be pushed against the nozzle plane of the inlet nozzle, thereby closing the inlet valve.

As a result of pressure changes within the diaphragm chamber 472 caused by the suction and pumping travel of the shaft 700, in some embodiments, the inlet and exhaust valves can synchronously move in opposite directions with respect to each other when they open and close (e.g., when the inlet and outlet valves are both positioned on the inside or outside of a diaphragm chamber defined between the diaphragm and the pump chamber body), or can synchronously move in the same direction with respect to each other when they open and close (e.g., when the inlet and outlet valves are positioned such that one is on the inside of the diaphragm chamber and one is positioned on the outside of the diaphragm chamber defined between the diaphragm and the pump chamber body).

In some embodiments, the inlet and exhaust valves can have near synchronous movement in which the inlet or outlet valve closes before the other valve opens. This asynchronous movement (also referred to as near synchronous movement) can be the result of the preload of the tab portion 452 of the one or move valves 450 against the intake sides of the inlet and exhaust nozzle openings of the pump chamber body 470 as described above. The amount of preload can be the same or different for the inlet and outlet valves. In some embodiments, the preload can represent the amount of force that the pressure in the diaphragm chamber must overcome to open the inlet and outlet valves. For example, the forces associated with the preloads of the tab portions of inlet and outlet valves can correspond to the threshold pressures that are required to open the inlet and outlet valves, respectively. The threshold pressures can be any suitable pressure differential relative to any suitable reference pressure, such as, for example, −10 mmHg for the inlet valve and 10 mmHg for the outlet valve, where 0 mmHg is the reference atmospheric pressure.

For example, during suction travel of the shaft 700, an inlet valve 450 can open under a specific change in pressure (e.g., −10 mmHg) while an outlet valve 450 is pushed against the nozzle plane of the outlet nozzle to seal (also referred to as close) the outlet, and during pumping travel of the shaft 700, an outlet valve 450 can open under a specific change in pressure (e.g., 10 mmHg) while an inlet valve is pushed against the nozzle plane of the inlet nozzle to seal (also referred to as close) the inlet. When a vacuum condition is caused by suction travel of the shaft 700, the outlet valve can close before the inlet valve opens because it takes a short amount of time for the vacuum condition to form within the diaphragm chamber to overcome the preload of the inlet valve following an overpressure condition. Similarly, when an overpressure condition is caused by pump travel of the shaft 700, the inlet valve can close before the outlet valve opens because it takes a short amount of time for the overpressure condition to form within the diaphragm chamber to overcome the preload of the outlet valve following a vacuum condition. As discussed, when vacuum and overpressure conditions generated by diaphragm movement exceed the amount of the preload, the tab portions 452 of the inlet and exhaust valves 450 can open. This can allow fluid to flow into and out of the diaphragm chamber 472. In addition to the preload against the inlet and exhaust nozzle openings helping to seal the valve against the nozzles, the valves 450 can also be designed such that the vacuum and overpressure conditions generated within the diaphragm chamber 472 during pumping action helps push the tab portions 452 of the inlet and exhaust valves against the inlet and exhaust nozzles.

In some embodiments, to control the flow of fluid into and out of the diaphragm chamber 472, the pump assembly 400 can include one or more valves, such as valves 450. In some embodiments, the pump chamber body 470 can include a valve support portion 474 designed to receive and support one or more valves of the pump assembly 400. As discussed above, in some embodiments, the one or more valves 450 can be secured between the pump chamber body 470 and the pump housing 420. In some embodiments, the placement of the one or more valves between the pump chamber body 470 and the pump housing 420 can define one or more corresponding pre-chambers adjacent the diaphragm chamber 472 between the pump chamber body 470 and the pump housing 420. In some embodiments, the pre-chambers can be sealed to avoid short-circuits of air between them by a laser welding process that can connect the pump chamber body 470 to the inside of the pump housing 420.

As shown in the illustrated embodiment, the valve support portion 474 can include one or more recesses, such as an intake or inlet recess 476a and exhaust or outlet recess 476b, formed along a surface 475 of the valve support portion 474. The recesses 476a, 476b can be designed to receive and support one or more valves. In some embodiments, the recesses 476a, 476b are larger than the valves that they are designed to receive. The larger recesses can advantageously function to accommodate for the material deformation that can occur when the valve is compressed. The inlet recess 476a can include an inlet opening 478a which can be in fluid communication with the diaphragm chamber 472. The inlet recess 476a can cooperate with an intake valve to allow fluid passage into the diaphragm chamber 472 during an intake phase of the pump assembly 400. The outlet recess 476b can include an outlet opening 478b which can be in fluid communication with the diaphragm chamber 472. The outlet recess 476b can cooperate with an exhaust valve to allow fluid passage into the diaphragm chamber 472 during an exhaust phase of the pump assembly 400. In some embodiments, surface 475 can be designed to be positioned proximate or adjacent an inner surface of the pump housing 420. Accordingly, the inner surface of the pump housing 420 can cooperate with inlet recess 476a to form an intake valve chamber and an exhaust valve chamber via outlet recess 476b. In some embodiments, a sealant or gasket can be positioned between the surface 475 and an inner surface of the pump housing 420 to enhance the seal between the two components.

Figure 58:
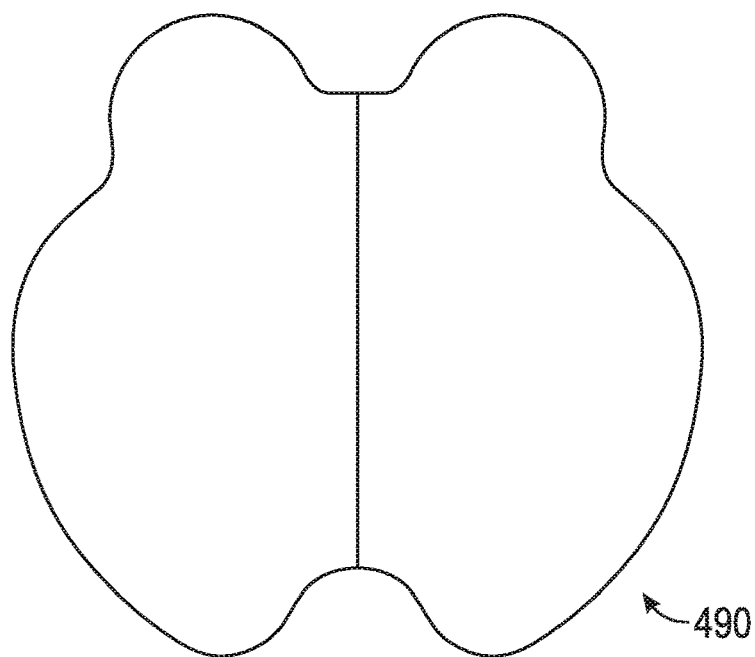
FIG. 58 is a top view of an embodiment of a weld contour between a pump housing and a pump chamber body.

In some embodiments, the pump chamber body 470 can be welded, such as laser welded, to the pump housing 420. For example, a laser beam can be used to weld an absorber material of the pump chamber body 470 to a transparent material of the pump housing 420 by heating up the absorber material to its melting point after passing through the transparent material. The transparent material can allow the laser to pass through the pump housing and heat the absorber material on and/or within the pump chamber body. Similarly, the absorber material can include any suitable laser absorbing pigment that facilitates the absorption of light from the laser such that the temperature of the absorber material can be increased to its melting point. Whereas the transparent material can allow the laser to pass through, the absorber material can allow the laser to be absorbed. To facilitate absorption of energy from the laser, and to in turn increase the temperature of the absorber material to its melting point, the absorber material can include a pigment that absorbs the wavelength(s) of light emitted by the laser. In some embodiments, the pigment of the absorber material can be darker relative to the transparent material. For example, in some embodiments, the absorber material can have a well-defined percentage of black pigment, such as, for example, between 1%-10% black pigment, between 1%-100% black pigment, between 5%-100% black pigment, between 50%-100% black pigment, between 80%-100% black pigment, between 90%-100% black pigment, or between any other suitable percentages, or less than 100% black pigment, less than 90% black pigment, less than 50% black pigment, less than 15% black pigment, or less than any other suitable percentage. For example, in some embodiments, the percentage of black pigment in the absorber material can be 1%, 30%, 80%, 95%, 100%, or any other suitable percentage. In some embodiments, the higher the percentage of laser absorbing pigment that the absorber material has, the faster the absorber material will melt for any given laser intensity. In some embodiments, only the portion of the pump chamber body 470 that is to be welded to the pump housing 420 is black. During the welding process, the pump housing 420 and the pump chamber body 470 can be held together with a constant, increasing, or decreasing pressure to prevent the two components from moving in any dimension relative to one another using, for example, a clamp. For example, in some embodiments, a spring clamp or an air-operated clamp can be used, although any suitable tension providing clamp is envisioned. While the pump housing 420 and the pump chamber body 470 are held together, a laser beam can be guided along a designed melt contour. For example, in some embodiments, the pump chamber body 470 can have a laser absorbing pigment along the melt contour. The resultant melt contour represents the laser weld between the pump housing and the pump chamber body. In some embodiments, the melt contour 490 that connects the pump housing and the pump chamber body together can be designed as shown in FIG. 58. Of course, any other suitably shaped contour is envisioned. Once the melt contour solidifies, a strong connection between the pump chamber 470 and pump housing 420 is created. In some embodiments, the transparent and absorbent materials can be chosen such that they are chemically compatible. For example, the transparent and absorbent materials can be different pigments of the same molecules. With reference to FIG. 19, the pump chamber body 470 can be laser welded to the pump housing 420 from the underside of the pump housing 420. In some embodiments, the intake and outtake channels on the surface of the pump housing 420 can be sloped (as shown in FIG. 22) to prevent sudden changes in laser diffraction when the laser passes over the channels during the welding process. For example, the intake and exhaust channels 422, 424 can have one or more sloped portions 435 as shown in FIG. 22. In some embodiments, the one or more sloped portions 435 can have straight and/or curved profiles.

As shown in the illustrated embodiment, the recesses 476a, 476b can have one or more indexing features, such as the recesses 480a, 480b, sized and shaped to receive corresponding indexing features of the valve, such as alignment tabs 460a, 460b of the valve member 450. The positioning of the alignment tabs 460a, 460b and the recesses 480a, 480b can ensure that the valve members 450 will be in the proper orientation and alignment when positioned in the recesses 476a, 476b. As should be noted, in some embodiments, the same valve 450 can function as either an intake valve or an exhaust valve depending on the orientation of the valve 450. Accordingly, the position of the alignment tabs 460a, 460b and recesses 480a, 480b can ensure that the valve 450 is properly oriented to function as an intake valve or an exhaust valve depending on the recess, such as inlet recess 476a or outlet recess 476b, in which the valve 450 is placed. Proper placement of the valve 450 can ensure that the rib 462 will be facing in a desired direction and that the tab portion 452 will cover an appropriate opening when in a relaxed or closed state such as the inlet opening of the pump housing 420 outlet opening 478b of the pump chamber body.

Moreover, as shown in the illustrated embodiment, the pump chamber body 470 can include one or more indexing features, such as bosses 481, which can be matched to corresponding indexing features on another component, such as the cutouts 434 of the pump housing 420. In some embodiments, the pump chamber body 470 can be made from plastics such as polycarbonate, metals, composites, or the like, or a combination of materials.

FIGS. 28-31 illustrate various views of an embodiment of a diaphragm 550 which can form part of the pump assembly 400. As shown in the illustrated embodiment, the diaphragm 550 can include a connection portion 560 and a peripheral portion 570. In some embodiments, the connection portion 560 can be positioned generally along an axial centerline of the diaphragm 550 such that the connection portion 560 is generally centered on the diaphragm 550. The connection portion 560 can include a recess 562 into which another component, such as the shaft 700, can be inserted. In some embodiments, diaphragm 550 can be designed to help maintain the radial alignment of the shaft 700 with the remainder of the pump assembly 400. The recess 562 can include an undercut portion 564 thereby forming a lip 566 around at least a periphery of the recess 562. In some embodiments, the undercut portion 564 can have a radius that is configured to reduce the amount of stress that is applied to the diaphragm. The lip 566 can advantageously releasably secure the other component, such as the shaft 700, to the diaphragm 550 such that movement of the other component can result in movement of the diaphragm 550. As shown in the illustrated embodiment, the lip can include filleted and/or chamfered edges which can enhance the lifespan of the diaphragm 550. For example, the filleted edges and/or chamfered edges can reduce the amount of stress applied to the connection portion 560 as the diaphragm 550 is removed from a production tool.

As shown in the illustrated embodiment, the peripheral portion 570 can include a body portion 572, in the form of an annular ring, and a lip 574 extending from a bottom surface of the body portion 572. The lip 574 can be formed integrally with the body portion 572. The increased thickness that results from the lip 574 can improve the sealability of the peripheral portion 570 of the diaphragm and hence improve the sealability of the diaphragm 550.

As shown in the illustrated embodiment, the connection portion 560 can be attached to the peripheral portion 570 via a web 580. The web 580 can be sized and shaped to allow the connection portion 560 to move relative to the peripheral portion 570 to allow an interior volume 552 of the diaphragm 550 to be altered. In some embodiments, the web 580 can be made out of a resilient material having a suitable modulus of elasticity. This can allow the web 580 to temporarily deform in response to forces exerted on the web 580. In some embodiments, the web 580 can be designed with excess material to allow for relative movement between the connection portion 560 and the peripheral portion 570. For example, as shown in the illustrated embodiment, the web 580 has excess material such that the web 580 has some slack and takes on a curved shape in an initial configuration. Should the connection portion 560 be moved away from the peripheral portion 570, the web 580 can straighten to some degree via loss of slack in the web 580. In some embodiments, it can be advantageous to reduce the radius of the connection portion 560 relative to the peripheral portion 570 to increase total length of the web 580. This can beneficially enhance the longevity of the diaphragm 550 which can be subjected to constant and cyclical motion. In some embodiments, it can be advantageous to increase the radius 582 of the web 580 proximate the connection portion 560 where the web 580 is in an initial configuration such as is shown in FIGS. 28-31. For example, the radius 582 can be increased so that the junction between the web 580 and the connection portion 560 is thicker. This can reduce the strain at the junction between the web 580 and the connection portion 560, which can in turn reduce fatigue and decrease the likelihood of the diaphragm 550 breaking near or around the radius 582. In some embodiment, the radius 582 can be uniform or can get progressively larger closer to the connection portion 560. In some embodiments, it can be advantageous to decrease the diameter of the connection portion 560 so that the length of the web 580 can be increased. Similarly, in some embodiments, it can be advantageous to increase the thickness and/or radius of the web 580 between the connection portion 560 and the peripheral portion 570. This can reduce the strain of the web 580 between the connection portion 560 and the peripheral portion 570, which can in turn reduce fatigue and decrease the likelihood of the diaphragm 550 breaking between the connection portion 560 and the peripheral portion 570 of the web 580. In some embodiments, the diaphragm 550 can be made from polymers such as rubbers, silicon, or the like, or a combination of materials.

FIGS. 32-33 illustrate various views of an embodiment of a spacer 590 which can form part of the pump assembly 400. In some embodiments, the spacer 590 can be positioned above diaphragm 550 when in an assembled state to maintain the diaphragm 550 in position relative to the pump chamber body 470. For example, the spacer 590 can be positioned such that the spacer 590 maintains the diaphragm 550 in compression against the pump chamber body 470 thereby maintaining sealing engagement between the diaphragm 550 and the pump chamber body 470.

As shown in the illustrated embodiment, the spacer 590 can include a body portion 592 such as the illustrated ring. The body portion 592 can include one or more alignment tabs 594 extending from the body portion 592 which can facilitate positioning and orientation of the spacer 590 within the pump assembly 400. For example, the alignment tabs 594 can correspond to slots 482 formed on the pump chamber body 470 (as shown in FIG. 25). In some embodiments, the body portion 592 can include a radially inward protrusion 596 to increase the surface area of the contact surface 598 between the body portion 592 and the diaphragm 550. This can reduce the localized stress applied to the diaphragm 550 along the contact surface 598 and reduce the likelihood of failure of the diaphragm 550. In some embodiments, the spacer 590 can be made from materials such as plastics, metals, composites, or the like, or a combination of materials. In some embodiments, the spacer 590 can be made from polyphenylene ether (PPE).

With reference back to FIGS. 18-20, the pump assembly 400 can include a magnetic assembly which can include an upper pole 500, a lower pole 520, and a magnet 540. One or both of the upper pole 500 and lower pole 520 can support the magnet 540. In some embodiments, the arrangement and/or placement of the upper pole 500 and/or lower pole 520 beneficially align the magnetic field of the magnet 540 to enhance the efficiency of the pump assembly 400. Such alignment of the magnetic field can improve efficiency of the pump assembly 400. Details regarding the alignment of the magnetic field are described in greater detail in U.S. Publication Nos. 2013/0331823 and International Patent Publication No. 2013/171585, both of which have been hereby incorporated by reference in their entireties as if made part of this disclosure.

The upper pole 500 can have an opening 502 formed through an axial centerline of the upper pole 500. The bushing 800 can be positioned within the opening 502 and/or supported by the upper pole 500. In some embodiments, the upper pole 500 can include a first portion 504 and a second portion 506 extending transverse to the first portion. As shown in the illustrated embodiment, the first portion 504 can be generally planar and extend in a direction generally perpendicular to the axial centerline of the upper pole 500. The second portion 506 can extend away from the first portion 504 in a direction generally parallel to the axial centerline at approximately a 90 degree angle relative to the first portion 504. In some embodiments, the second portion 506 can extend away from the first portion 504 at an angle greater than or less than a 90 degree angle relative to the first portion 504, such as, but not limited to, between about 10 degrees to about 170 degrees, between about 30 degrees to about 150 degrees, between about 45 degrees to about 135 degrees, between about 60 degrees to above 120 degrees, any subranges within these ranges, or any other degree relative to the first portion 504 as desired. In some embodiments, the upper pole 500 can be made from materials such as mild steel, a sintered soft magnetic metal such as GKN 72-IBP2 (S-FeP-130), or sintered steel (or any suitable magnetic or ferromagnetic material).

The lower pole 520 can include an opening 522 formed through an axial centerline of the lower pole 520. The opening 522 can be sized and shaped such that the second portion 506 of the upper pole 500 can pass therethrough. As shown in the illustrated embodiment, the lower pole 520 can be spaced apart from the upper pole 500 and can be supported by the pump housing 420. The lower pole 520 can be made from mild steel, a sintered soft magnetic metal such as GKN 72-IBP2 (S-FeP-130), or sintered steel (or any suitable magnetic or ferromagnetic material).

The magnet 540 can be positioned between the upper pole 500 and the lower pole 520. The magnet 540 can have an opening 542 formed through an axial centerline of the magnet 540. In some embodiments, a top surface of the magnet 540 can be positioned proximate or adjacent a bottom surface of the first portion 504 of the upper pole 500. In some embodiments, a bottom surface of the magnet 540 can be positioned proximate or adjacent a top surface of the lower pole 520. In some embodiments, the magnet 540 can be positioned such that the second portion 506 of the upper pole 500 extends through the opening 542 of the magnet 540. In such an arrangement, the magnetic field can be shifted away from the first portion 502 of the upper pole 500 and closer to the center of the coil 600. The magnet 540 can be made from Neodymium—Iron—Boron (NdFeB)—N 45 M, Neodymium N33, or any other suitable material magnetic material. This material can be used to maximize field strength and minimize losses, thereby increasing the efficiency of the pump assembly 400.

With continued reference to FIGS. 18-20, the pump assembly 400 can include a coil 600. The coil 600 can have a body 602 formed from a length of wound conductive wire, such as without limitation copper wire or any other electrically conductive material. Accordingly, upon application of a current through the body 602, a magnetic field can be generated generally directed along a direction parallel to an axial centerline for the coil 600. As should be understood, the direction of the magnetic field can be reversed by reversing the direction of current flow through the coil 600. To provide current to the coil 600, an electrical conduit 604 can be connected to both ends of the coil 600. In some embodiments, the electrical conduit 604 can be a flexible printed circuit (FPC) attached to the circuit board 200. Other types of electrical conduits 604, such as elongate wires, can also be used.

As shown in the illustrated embodiment, the coil 600 can have an opening 606 which can be sized and shaped to allow the second portion 506 of the upper pole 500 to pass therethrough. As shown FIG. 18, the coil 600 can be positioned between the upper pole 500 and the lower pole 520 and positioned proximate the magnet 540. Accordingly, as the voltage supplied to the coil 600 oscillates between a positive voltage and a negative voltage, the coil 600 can oscillate up and down in the pump assembly 400 between the two poles 500, 520.

Figure 35:
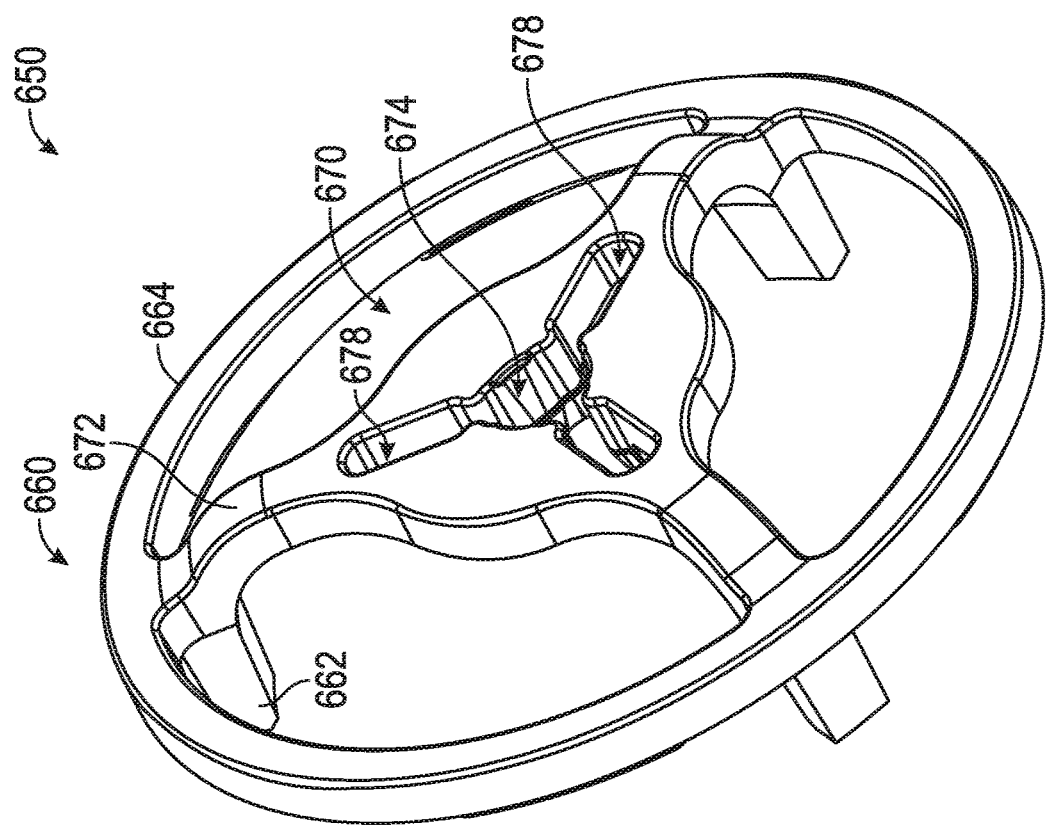
FIGS. 34-35 are perspective views of an embodiment of a support member.
Figure 34:
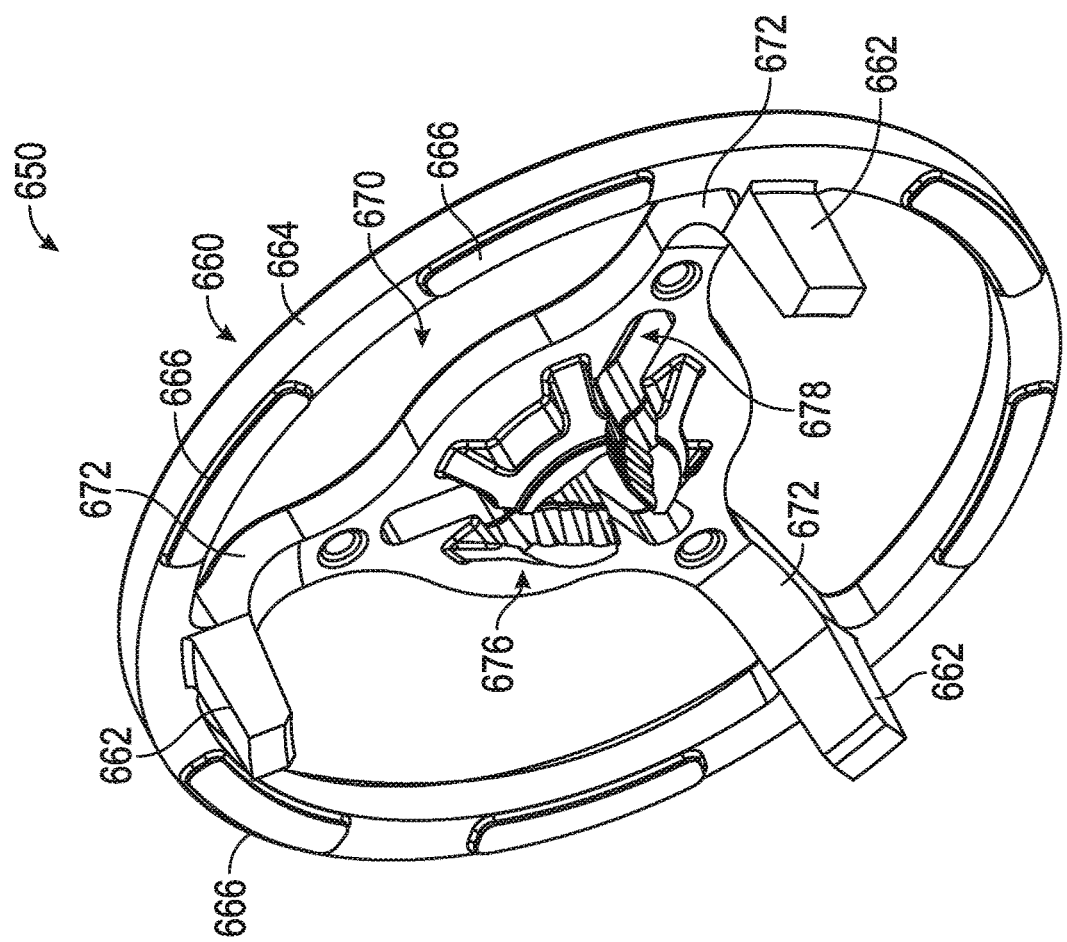

In some embodiments, the coil 600 can be formed by winding approximately 160 turns of wire, or from approximately 100 turns or less to 200 turns or more of wire, which can be but is not required to be, 42 gauge (approximately 0.102 mm diameter) wire. For example, in some embodiments, the coil 600 can be formed by winding approximately 144 turns of wire. In some embodiments, Lorentz's law can be used to determine the appropriate number of turns of wire that are needed so that the desired level of force is applied to the coil 600 when current passes through the coil 600. The wire used can be self-bonding wire that bonds to adjacent sections of wire upon application of heat. The wire can also be non-self-bonding wire. In some embodiments, approximately 200 turns of wire, or up to approximately 260 turns of wire, can be used to form the coil. Increasing the number of turns of wire can potentially reduce ohmic losses and improve the overall efficiency of the pump assembly 400 by between approximately 22% and approximately 24%. As the number of turns of wire is increased, thereby increasing the efficiency of the pump, the size or thickness of the magnet can be decreased, thereby reducing the magnetic field outside of the pump assembly 400 that can potentially interfere with the function of pacemakers and other implanted cardiac devices (ICDs). [0178] FIGS. 34-35 illustrate an embodiment of a support member 650, such as a spider, which can be designed to support the coil 600 and connect the coil 600 to other components of the pump assembly 400 such as the diaphragm 550. As shown in the illustrated embodiment, the support member 650 can include a peripheral portion 660 with longitudinally extending fingers 662. The fingers 662 can be received within the opening 606 of the coil 600. In some embodiments, the protrusions 662 can be sized and positioned such that the protrusions 662 are received within the opening 606 in a friction and/or interference fit to maintain the coil 600 in a desired position relative to the support member 650. In some embodiments, the coil 600 can be affixed to the support member 650 via a mechanical fastener and/or chemical fastener, such as an adhesive. The peripheral portion 660 can include a ring 664 which can have one or more raised platforms 666 extending from a surface of the annular ring 664. The raised platforms 666 can be designed to space the coil 600 from the annular ring 664.

As shown in the illustrated embodiment, the support member 650 can include a base portion 670 attached to the peripheral portion 660 via one or more arms 672. The arms 672 can be aligned with the slots 482 of the pump chamber body 470, the slots 508 of the upper pole 500, and/or slots between wall members 804 on the bushing 760. In some embodiments, the arms 672 can be sized and/or shaped with respect to such slots to limit rotation along an axial centerline of the support member 650 during operation of the pump assembly 400. The arms 672 can be designed to be relatively rigid to limit the amount of flex in the arms 672 when the peripheral portion 660 is moved relative to the base portion 670 and vice versa.

The base portion 670 can include an opening 674 for allowing another component of the pump assembly 400, such as the shaft 700, to pass therethrough. As shown in the illustrated embodiment, the opening 674 can include a collet 676, or other form of clamping member, to more securely fasten the component to the base portion 670 in an interference and/or friction fit. The base portion 670 can include one or more indexing features, such as openings 678, to facilitate positioning and alignment of the base portion 670 relative to other components of the pump assembly 400, such as the shaft 700.

FIGS. 36-37 illustrate various views of an embodiment of a shaft 700 which can form part of the pump assembly 400. The shaft 700 can include a first end portion 710, an intermediate portion 720, and a second end portion 730. In some embodiments, the shaft 700 can be used to connect the diaphragm 550 to the support member 650. In this manner, the shaft 700 can transmit motion from the coil 600 to the diaphragm 550.

As shown in the illustrated embodiment, the first end portion 710 of the shaft 700 can be received within the recess 562 formed in the connection portion 560 of the diaphragm 560. The end portion 710 can include an undercut portion 712 and an annular lip 714 for securing the shaft 700 to the connection portion 560 of the diaphragm 550. The edges of the annular lip 714 can include fillets and/or chamfers similar to those of the undercut portion 564 of the recess 562. The end portion 710 can be retained on the connection portion 560 of the diaphragm 550 in an interference fit. This can beneficially reduce the amount of play between the shaft 700 and the connection portion 560 of the diaphragm 550. In some embodiments, the shaft 700 can be further secured to the connection portion 560 of the diaphragm 550 with an adhesive The intermediate portion 720 can include features for connection to the support member 650. For example, as shown in the illustrated embodiment, the intermediate portion 720 can include one or more tapered features 722, 724 which can cooperate with the collet 676. The shaft 700 can include one or more indexing features, such as longitudinally extending ribs 726, which can cooperate with the indexing features of one or more components of the pump assembly 400, such as the openings 678 of the support member 650. In some embodiments, the shaft 700 can be made from materials such as plastics, metals, composites, or the like, or a combination of materials. In some embodiments, the shaft 700 can be made from polybutylene terephthalate (PBT).

FIG. 38 illustrates a perspective view of an embodiment of a spring 750 which can form part of the pump assembly 400. The spring 750 can include an opening 752 through which a component of the pump assembly 400 can pass through, such as the shaft 700. As shown in FIG. 18, the spring 750 can be positioned between a platform 728 of the shaft 700 and the collet 676 of the support member 650. The spring 750 can include one or more indexing features, such as cutouts 754, which can correspond to indexing features on the shaft 700 to facilitate alignment and orientation of the spring 750 with respect to the shaft 700. In some embodiments, an outer periphery of the spring 750 can be positioned between the spacer 590 and the bushing 800. Accordingly, as the shaft 700 is moved relative to the bushing 800, the force applied to the shaft 700 by the spring 750 can vary. In some embodiments, the spring 750 can include one or more cutouts 758 to allow deformation of the middle portion of the spring 750 relative to an outer periphery of the spring 750. The length and width of these cutouts 758 can be changed to alter the spring constant of the spring 750. In some embodiments, the width of the cutouts can be chosen to avoid potential interference between portions of the spring 750 during operation of the pump assembly 400.

In some embodiments, the spring member 750 can be sized and designed to provide frequency tuning or adjustment to the resonance frequency of the diaphragm 550 and/or other oscillating components pump assembly 400. In some embodiments, the spring member 750 can be designed to help maintain the radial alignment of the diaphragm 550, coil 600, support member 650, and/or shaft 700 with the remainder of the pump assembly 400. In some embodiments, the spring can provide both functions. The spring member 750 can be made from stainless steel such as AISI 301 H03 ¾ hard—stainless steel, spring steel, bronze, or any other suitable material.

Figure 40:
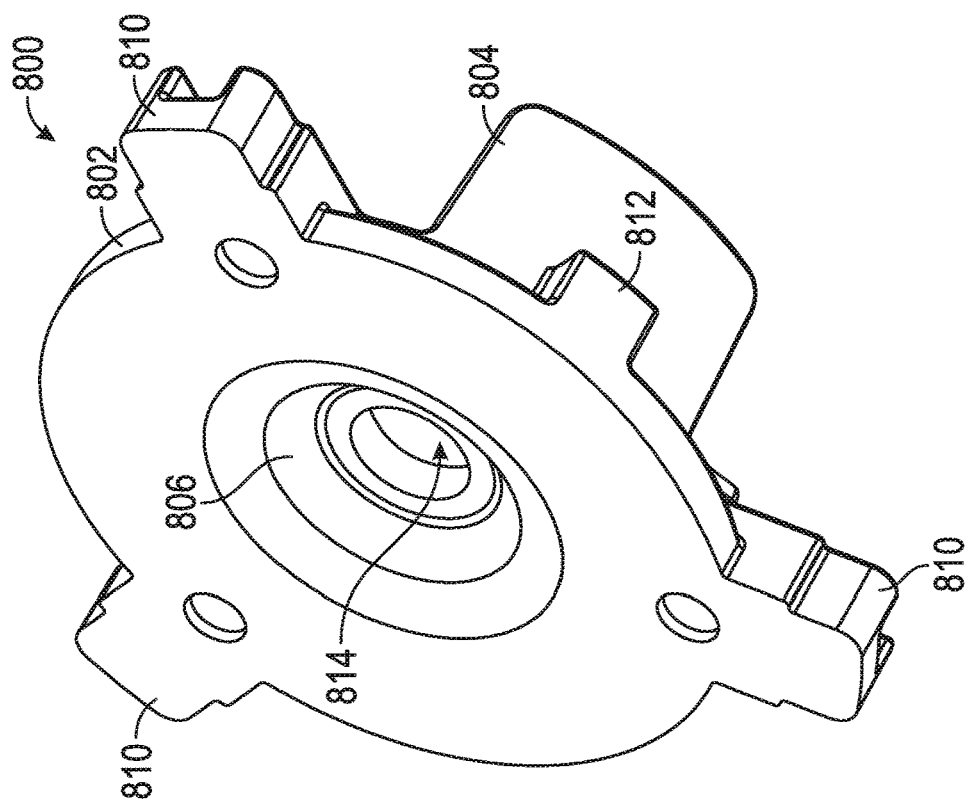
FIGS. 39-40 are perspective views of an embodiment of a bushing.
Figure 39:
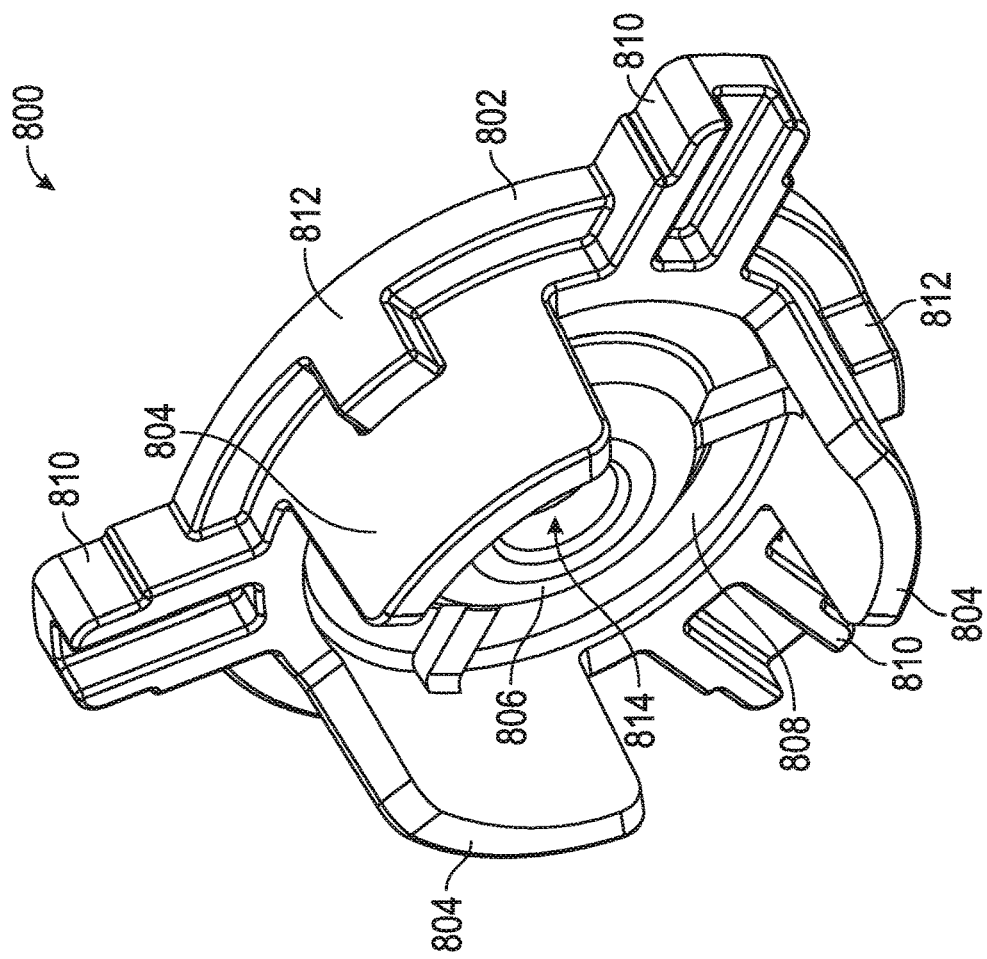
Figure 43:
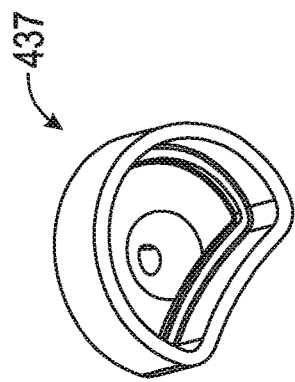
FIG. 43 is a perspective view of an embodiment of a detachable chamber.
Figure 41:
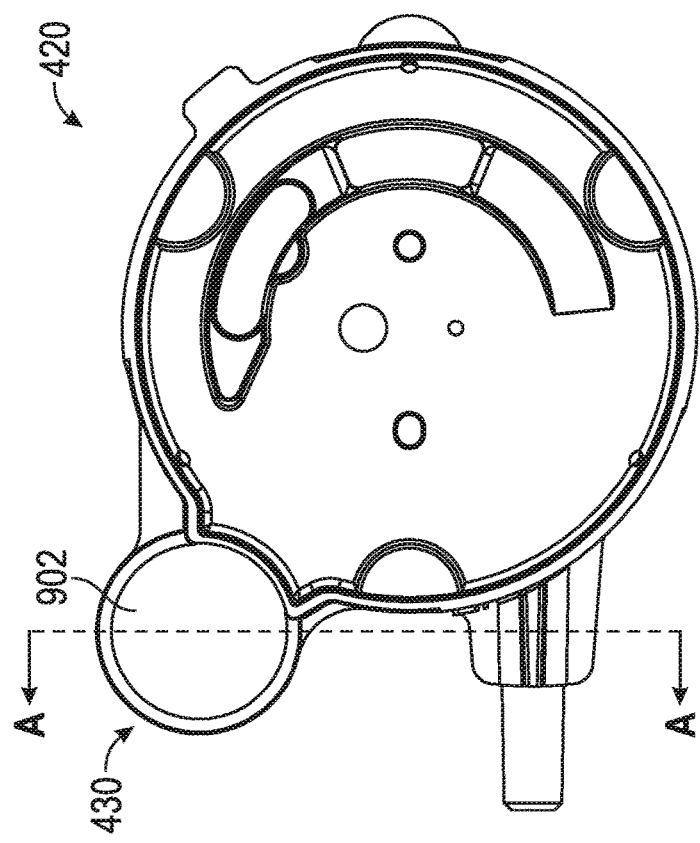
FIG. 41 is a rear view of an embodiment of the pump housing of FIG. 21 with a dampening element.
Figure 42:
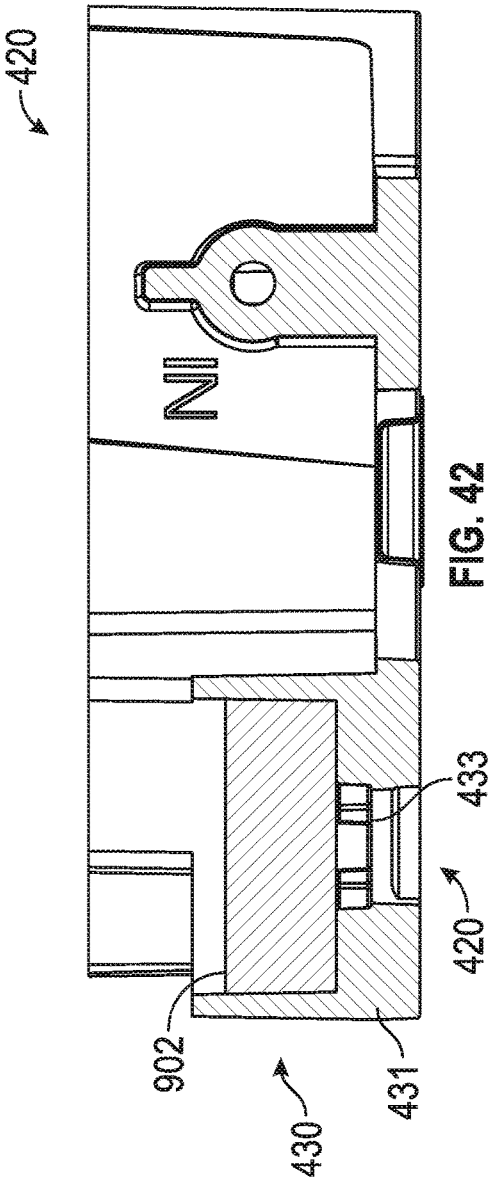
FIG. 42 is a side, cross-sectional view of the pump housing and dampening element of FIG. 41.

FIGS. 39-40 are various views of an embodiment of a bushing 800 which can form part of the pump assembly 400. The bushing 800 can be designed to help maintain the radial alignment of the diaphragm 550, coil 600, support member 650, and/or shaft 700 with the remainder of the pump assembly 400. The bushing 800 can also be used to limit the movement of components of the pump assembly 400, such as the support member 650, to avoid damage to other components of the pump assembly 400, such as the diaphragm 550.

As shown in the illustrated embodiment, the bushing 800 can include a base 802 which can extend in a direction generally radially outward from an axial centerline of the bushing 800. The base 802 can include one or more wall members 804 which can extend generally transverse to the base 802. In the illustrated embodiment, the one or more wall members 804 extend in a direction generally parallel with the axial centerline of the bushing 800. For example, as shown in FIG. 39, the base 802 can have three wall members 804. The wall members 804 of bushing 800 can be designed to push the spring 750 and the spacer 590 against the peripheral portion 570 of the diaphragm 550 such that the lip 574 of the diaphragm 550 is compressed against the pump chamber body 470. As discussed above, compressing the lip 574 of the diaphragm 550 against the pump chamber body 470 can improve the sealability of the diaphragm 550. For example, in some embodiments, compressing the lip 574 against the pump chamber body 470 can help seal the diaphragm chamber 472. The base 802 can include a protrusion 806 extending from a surface 808 of the base 802. The protrusion 806 can be generally centered on the base 802 and can be designed to serve as a stop for the support member 650 as shown more clearly in FIG. 18. For example, the protrusion 806 can contact the support member 650 at top dead center ("TDC") for the pump assembly. In this manner, the support member 650 can be prevented from over-extending the diaphragm 550 thereby reducing the likelihood of damage to the diaphragm 550. As will be described in further detail below, the pump chamber body 470 and the bushing 800 can be designed so that they can be laser welded together. In this way, the bushing 800 and the pump chamber body 470 are designed so that they do not move with respect to the oscillating components of the pump, such as for example, the shaft 700, the support member 650, and the diaphragm 550.

In some embodiments, the radial dimension of the protrusion 806, as measured from the axial centerline of the bushing 800, can be less than the radial dimension of the base 802, such as less than about 75% of the radial dimension of the base 802, less than about 50% of the radial dimension of the base 802, less than about 25% of the radial dimension of the base 802, between about 25% to about 75% the radial dimension of the base 802, between about 40% to about 60% of the radial dimension of the base 802, about 50% of the radial dimension of the base, any subrange within these ranges, or any other percentage as desired. In some embodiments, the depth of the protrusion 806 relative to the base 802 in addition to the radial dimension of the protrusion 806 relative to the base 802 can be chosen to account for flex in the arms 672 of the support portion 650 such that the arms 672 do not contact the base 802 during operation of the pump assembly 400.

As shown in the illustrated embodiment, the bushing 800 can include indexing features, such as the illustrated fingers 810 and ribs 812, which can facilitate in orienting and aligning the bushing 800 with respect to other components in the pump assembly 400. Moreover, the fingers 810 and ribs 812 can be used to maintain radial alignment of the bushing 800 with respect to other components of the pump assembly 400. In some embodiments, the bushing 800 can include an opening 814 for receiving a component therein, such as a second end portion 730 of the shaft 700. The opening 814 can be formed through an axial centerline of the bushing 800. The diameter of the opening 814 can be designed to reduce wobble in the shaft 700 without applying a significant degree of friction to the shaft 700. The bushing 800 can be formed from a low friction material (polymeric or otherwise) or any other suitable material. For example the bushing 800 can be made from polycarbonate, phosphor bronze, oilite, PTFE, acetal, nylon, PTFE, or the like, or a combination of materials.

In some embodiments, the bushing 800 can be laser welded to the pump chamber body 470. For example, as discussed above with respect to laser welding the pump housing 420 to the pump chamber body 470, a laser beam can be used to weld an absorber material of the pump chamber body 470 to a transparent material of the bushing 800 by heating up the absorber material to its melting point after passing through the transparent material. The transparent material can allow the laser to pass through the bushing and heat the absorber material on and/or within the pump chamber body. Similarly, the absorber material can include any suitable laser absorbing pigment that facilitates the absorption of light from the laser such that the temperature of the absorber material can be increased to its melting point.

Whereas the transparent material can allow the laser to pass through, the absorber material can allow the laser to be absorbed. To facilitate absorption of energy from the laser, and to in turn increase the temperature of the absorber material to its melting point, the absorber material can include a pigment that absorbs the wavelength(s) of light emitted by the laser. In some embodiments, the pigment of the absorber material can be darker relative to the transparent material. For example, in some embodiments, the absorber material can have a well-defined percentage of black pigment, such as, for example, between 1%-10% black pigment, between 1%-100% black pigment, between 5%-100% black pigment, between 50%-100% black pigment, between 80%-100% black pigment, between 90%-100% black pigment, or between any other suitable percentages, or less than 100% black pigment, less than 90% black pigment, less than 50% black pigment, less than 15% black pigment, or less than any other suitable percentage. For example, in some embodiments, the percentage of black pigment in the absorber material can be 1%, 30%, 80%, 95%, 100%, or any other suitable percentage. In some embodiments, the higher the percentage of laser absorbing pigment that the absorber material has, the faster the absorber material will melt for any given laser intensity. In some embodiments, only the portion of the pump chamber body 470 that is to be welded to the bushing 800 is black. For example, as shown in FIGS. 25 and 27, the pump chamber body 470 can include three vertical flanges 485 each having a mechanical stop 483 and two circumferential weld surfaces 484. In some embodiments, only the weld surfaces 484 are black. The mechanical stops 483 can be designed to control the penetration of the bushing 800 into the pump chamber body 470 during welding. As shown in FIGS. 25 and 27, the three vertical flanges 485 can be separated by the three slots 482 described above with reference to spacer 590. In some embodiments, the bushing 800 can have three ribs 812. The ribs 812 can advantageously function to stop penetration of the bushing 800 into the pump chamber body 470 during welding at the desired amount of penetration. For example, the ribs 812 can be designed such that a bottom surface comes into contact with the mechanical stops 483 of the pump chamber body 470. In this way, the extent of the bushing 800 penetration can be controlled.

Figure 59:
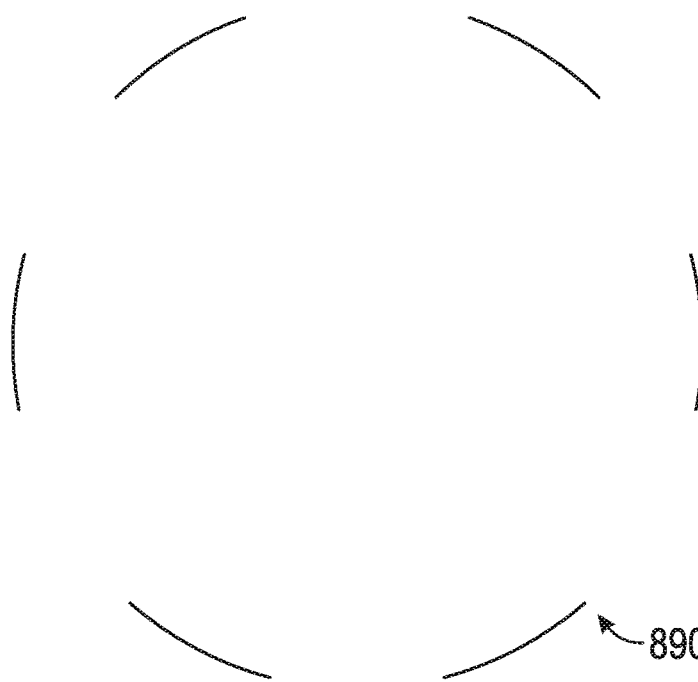
FIG. 59 is a top view of an embodiment of a weld contour between a pump chamber body and a bushing.

During the welding process, the pump chamber body 470 and the bushing 800 can be held together with a constant, increasing, or decreasing pressure to prevent the two components from moving in any dimension relative to one another using, for example, a clamp. For example, in some embodiments, a spring clamp or an air-operated clamp can be used, although any suitable tension providing clamp is envisioned. While the pump chamber body 470 and the bushing 800 are held together, a laser beam can be guided along a designed melt contour. For example, in some embodiments, the pump chamber body 470 can have a laser absorbing pigment along the melt contour. The resultant melt contour represents the laser weld between the pump chamber body 470 and the bushing 800. In some embodiments, the melt contour 890 that connects the pump chamber body and the bushing together can be designed as shown in FIG. 59. Of course, any other suitably shaped contour congruent with a weld surface 484 of the vertical flange 485 is envisioned. Once the melt contour solidifies, a strong connection between the pump chamber body 470 and bushing 800 is created. In some embodiments, the transparent and absorbent materials can be chosen such that they are chemically compatible. For example, the transparent and absorbent materials can be different pigments of the same molecules. With reference to FIG. 19, the pump chamber body 470 can be laser welded to the bushing from the topside of the bushing 800.

Figure 45:
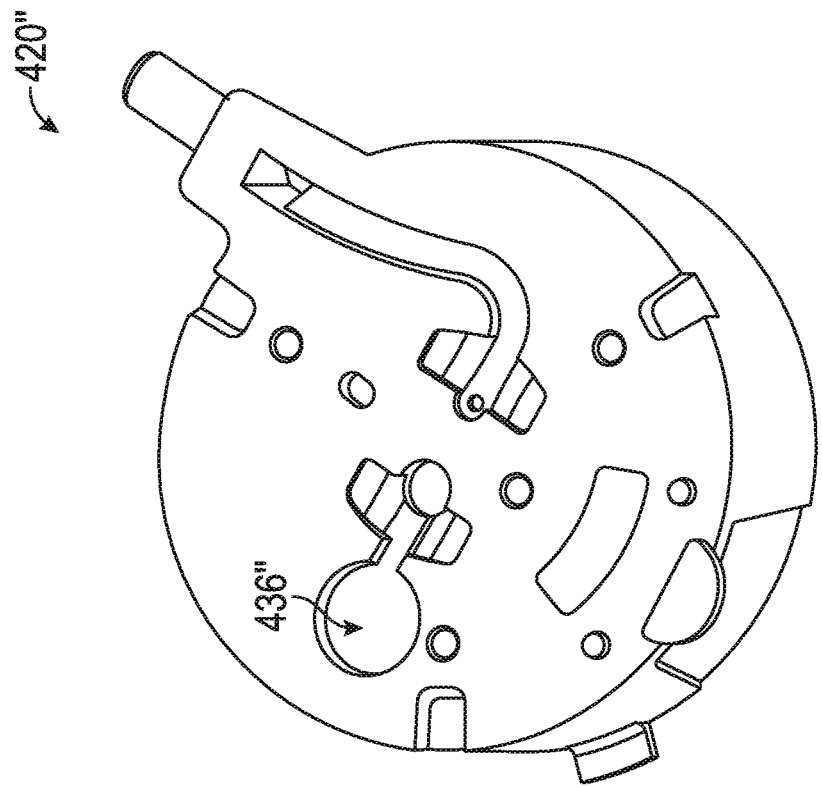
FIG. 45 is a perspective view of another embodiment of a pump housing.
Figure 44:
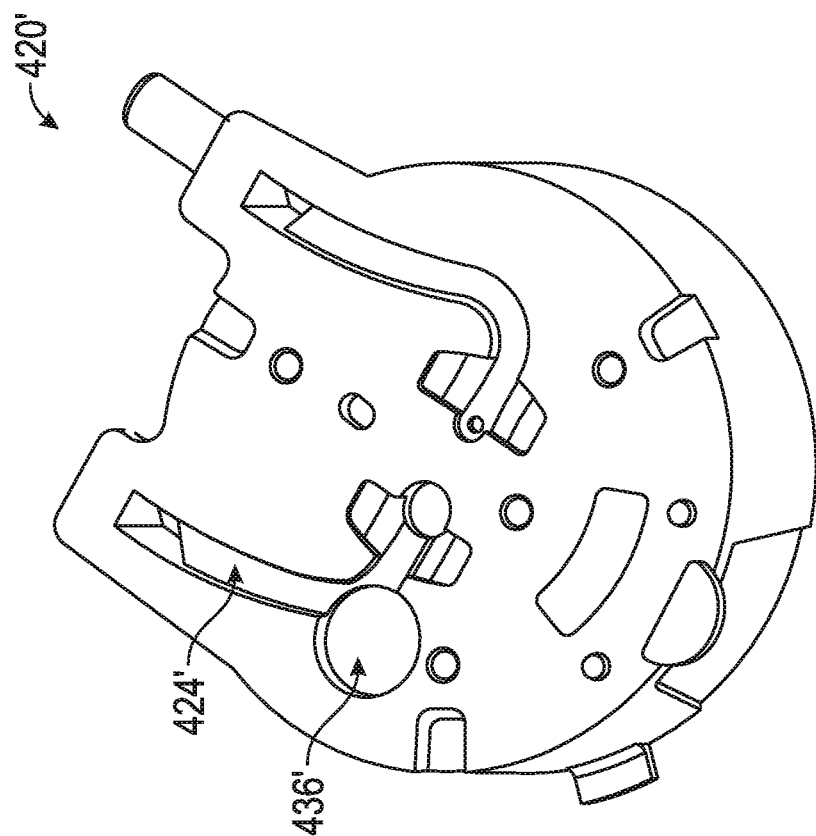
FIG. 44 is a perspective view of another embodiment of a pump housing.

FIGS. 41-46 illustrate embodiments of noise reduction systems. As shown in the illustrated embodiment in FIG. 41, the noise reduction system can include a chamber 430 formed integrally with the pump housing 420. For example, in some embodiments, the chamber 430 can be integrally formed with the pump housing 420 as shown FIG. 42, which is a side cross-sectional view of the pump housing of FIG. 41 along line AA. FIGS. 21 and 22 also show embodiments having a chamber 430 integrally formed with a pump housing 420. Of course, the chamber 430 shown in FIGS. 41, 42, 21, and 22 is exemplary and non-limiting and the skilled artisan will appreciate that any other suitable integrally formed chamber is envisioned. In some embodiments, the chamber 430 can be separate from the pump housing 420 and can be attached to the pump housing 420. For example, FIGS. 44 and 45 show a pump housing 420', 420" in which the chamber 430 has been separated from the pump housing 420', 420". It will be appreciated that the chamber 430 can be attached to the pump housing 420 in FIGS. 44 and 45 at any suitable location along the fluid flow path, such as, for example, somewhere along the exhaust channel 424' in FIG. 44 or somewhere around the opening 436" in FIG. 45.

Figure 47:
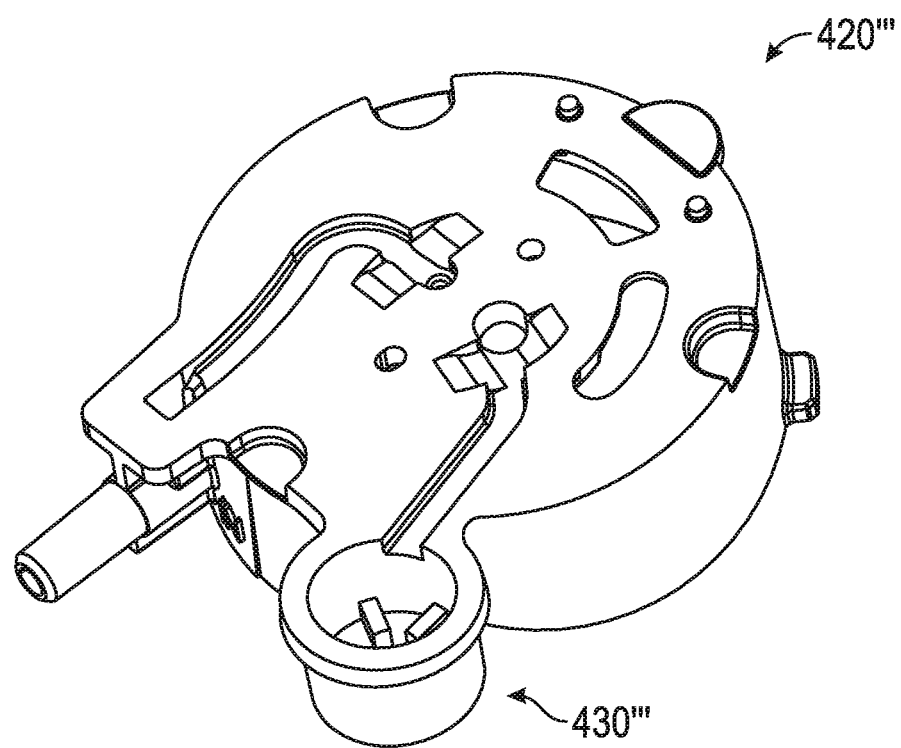
FIG. 47 is a perspective view of another embodiment of a pump housing.

The chamber 430 can be designed to receive a dampening component 902 (also referred to as a silencer). The dampening component can reduce noise emissions from the pump. For example, in some embodiments, the outtake flow of the pump can be passed through the dampening component such that frequencies and/or amplitudes of the pressure waves in the outtake flow are reduced, which in turn dampens the noise emitted by the pump. The dampening component 902 can be integrated into a pump housing by being placed in the pump chamber 430. As described above, in some embodiments, the pump chamber 430 can be integrally formed with the pump housing 420, and in other embodiments, the pump chamber 430 can be separately attached to the pump housing 420'. For example, as shown in FIGS. 41, 42, 21, and 22, the dampening component 902 can be integrated with the pump housing 420 by being placed within the chamber 430. In other embodiments, the dampening component can be placed within a chamber 430 that is separately attached to the pump housing 420. As shown in the illustrated embodiments, the dampening component 902 can be received within (also referred to as integrated with) the chamber 430 in a friction and/or interference fit, although any suitable connection between the dampening component 902 and the chamber 430 is appreciated and envisioned. In some embodiments, the dampening component 902 can be prevented from exiting the chamber 430 via one or more features of the outer housing 102. In some embodiments, the orientation of the chamber 430 shown in FIGS. 41, 42, 21, and 22 can be flipped as is shown in FIG. 47 which illustrates a pump housing 420''' and chamber 430'''. In some embodiments, the chamber 430''' can be integrally formed with the pump housing 420'''. In addition, as discussed above with reference to FIG. 22 and other related figures, in some embodiments, the exhaust channel 422 can channel or communicate fluid towards an exhaust port 428 and into an interior of a chamber 430 where it can eventually be exhausted into the atmosphere within the outer housing 102 after being channeled or communicated through a silencer 902.

The dampening component 902 can be made from any material capable of allowing fluid passage, such as air, through the dampening component 902 while reducing noise. For example, in some embodiments, the dampening component 902 can be formed from a porous material such as foam, including but not limited to urethane foam, which can advantageously allow fluid flow through the foam while reducing noise generated. In some embodiments, the material of the dampening component 902 can be medical grade. The thickness of the dampening component 902 can be chosen based on numerous factors including the type of material used, the desired fluid flow out of the dampening component 902, and the amount of noise reduction desired. In some embodiments, the dampening component 902 can also serve as a filter which can reduce undesirable components in the fluid as the fluid flows through the dampening component 902. For example, in some embodiments, the dampening component can be a foam insert 3 millimeters thick. The skilled artisan will appreciate that the foam insert can take on any suitable shape capable of fitting into the chamber 430, such as, for example, cylindrical or polygonal. Of course, other shapes and sizes are also envisioned. For example, in some embodiments, the foam insert can range in thickness from approximately 1 millimeter to approximately 5 millimeters.

As shown in the illustrated embodiment, the chamber 430 can include one or more ribs 431 extending from an inner surface 433 of the chamber 430. The ribs 431 can beneficially space the dampening component 902 from the inner surface 433 such that a gap is formed between the dampening component 902 and the inner surface 433. This gap can allow for fluid flow from the exhaust port 428 to expand into the gap prior to flowing through the dampening component 902. This can beneficially reduce the likelihood of choking the exhaust flow. In some embodiments, the exhaust port 428 can be designed to have a diffuser 437 shape similar to that illustrated in FIG. 43 to further control expansion of the fluid as the fluid passes through the exhaust port 428 and into the chamber 430.

In some embodiments, the noise reduction system can involve redirecting at least some portion of the exhaust gases back into the pump housing 420. For example, as shown in FIG. 44, a pump housing 420' can include an opening 436' positioned along the exhaust channel 424' for redirecting at least some of the exhaust flow back into an internal volume of the pump housing. This can separate flow between the channel 424' and the internal volume of a pump assembly where the sound-wave encounters different geometries and may thereby be dampened. In some embodiments, such as that illustrated in FIG. 45, the entirety of the exhaust flow can be directed back into the internal volume of the pump housing 420" via opening 436".

Figure 46:
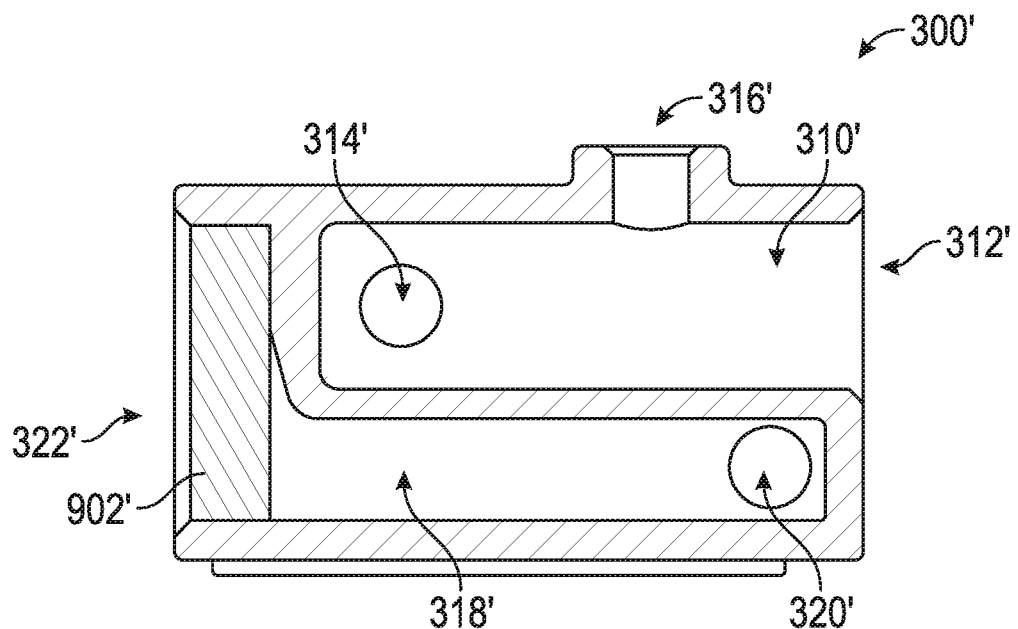
FIG. 46 is a side, cross-sectional view of another embodiment of a manifold.

With reference to FIG. 46, in some embodiments, a manifold 300' of the pump system 100 can incorporate noise reducing features. For example, as shown in the illustrated embodiment, the manifold 300' can include an inlet passageway 310' having an inlet opening 312' designed to be in fluid communication with a wound dressing and an outlet opening 314' which can be in fluid communication with an intake of the pump assembly, such as intake port 426 of the pump housing 420. The inlet passageway 310' can include one or more additional ports, such as port 316', designed to be in fluid communication with other components of the pump system 100, such as the pressure monitor 204. The manifold 300' can include an outlet passageway 318' having an inlet opening 320' designed to be in fluid communication with an exhaust of the pump assembly, such as exhaust port 428 of the pump housing 420, and an outlet opening 322' designed to exhaust the fluid into the atmosphere such as within the outer housing 102. In some embodiments, the manifold 300' can be used to attenuate the noise produced by the pump assembly. For example, the inlet passageway 310' and/or the outlet passageway 318' can be designed to receive a dampening component 902' to reduce noise generated by the pump assembly. In some embodiments, the dampening component 902' can be used to help stabilize the air volume in the manifold so that the pressure monitor 204 can return more accurate readings. For example, in some embodiments, the dampening component 902' can be used to attenuate the noise generated from the harmonic dynamics (also referred to as the resonance) of the pump. In some embodiments, the inlet opening 312', the outlet opening 314', the inlet opening 320', and/or the outlet opening 322' can be designed to have a diffuser shape and/or nozzle shape to help control the expansion or compression of fluid. In some embodiments, the manifold can have an internal volume of approximately 870 mm$^3$.

With reference back to FIGS. 14-16, in some embodiments, the pump assembly 400 can have one or more dampening components 904 attached to a surface of the device. The dampening components 904 can be designed to reduce noise and/or vibration generated by movement of the pump assembly 400 within the outer housing 102. In some embodiments, one or more dampening components 904 can be attached to the front and rear surfaces of the pump assembly 400. For example, as shown in FIGS. 14-16, the pump assembly 400 can have six dampening components 904, three on a rear side of the pump assembly as shown in FIG. 15, and three on a front side of the pump assembly as shown in FIGS. 14 and 16. Advantageously, the one or more dampening components 904 can be used to decouple and/or cushion the pump assembly 400 from one or more of the hard components that surround the pump assembly and/or from the main circuit board of the pump system. For example, in some embodiments, the one or more dampening components 904 on the front side of the pump assembly 400 can be designed to be placed between the front side of the pump assembly and the circuit board 200 (shown in FIG. 13), and the one or more dampening components 904 on the rear side of the pump assembly 400 can be designed to be placed between the rear side of the pump assembly and the rear portion of the outer housing 102b (shown in FIG. 11). In some embodiments, the dampening components 904 can be made from any material having noise and/or vibration dampening characteristics such as foam. For example, the one or more dampening components can be foam cylinders, although any suitable shape is envisioned. In some embodiments, a layer of open foam or other material can be wrapped at least partially around an outside surface of the pump assembly 400 to reduce noise and/or vibration produced by the pump assembly 400. Additionally, in some embodiments, the pump assembly 400 can have one or more weights, cushions, foam (such as a viscoelastic foam), plastic (such as ABS, polyurethane, urethane, or otherwise), or other pads, panels, sheets, or segments supported by the pump or positioned adjacent to one or more outside surfaces of the pump. In some embodiments, the pump assembly 400 can have mass based or compliant damping materials. Such components or materials (not illustrated) can damp vibration and/or attenuate noise produced by the pump.

FIGS. 48-49 are various views illustrating wiring of the pump system 100 within the outer housing 102. As shown in the illustrated embodiment, the pump system 100 can include terminals 210 for connecting the circuit board 200 to a power source, such as batteries 202. The circuit board 200 can route power from the power source to the coil 600 via an electrical conduit 604 attached to a connector 212 of the circuit board 200. In some embodiments, the electrical conduit 604 can be a flexible printed circuit (FPC) to facilitate assembly. In some embodiments, the electrical conduit 604 can be connected directly to the coil 600. For example, the ends of the FPC corresponding to a positive and negative terminal can be attached, such as via soldering and/or via adhesives, to ends or terminals of the coil 600. For example, the coil 600 can have two terminals that can be soldered to two corresponding solder pads of the FPC. However, the wire used to manufacture the coil can be protected by an insulation layer and a self-bonding coating layer that can make manual soldering difficult and/or unreliable since manual soldering can expose the FPC to temperatures of 400 degrees Celsius for too long a time, which can damage the FPC substrate. To mitigate this problem, in some embodiments, a micro welding process can be used to electrically connect the FPC to the two terminals of the coil 600. In micro welding, a high current spike can be generated for a few milliseconds between the terminals of the coil and the pads of the FPC. The current spike can result in a localized temperature spike that can vaporize the insulating and self-bonding layers so that the wire of the coil can be bonded to the pads of the FPC. For example, the temperature spike can be 400 degrees Celsius or higher. However, since the temperature spike is limited to a few milliseconds using the micro welding process, the FPC substrate is not damaged.

Figure 50:
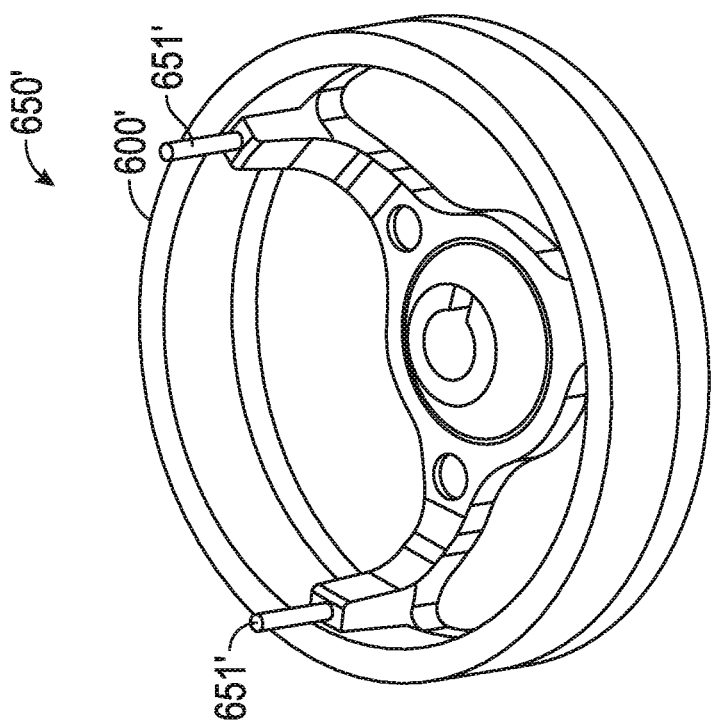
FIG. 50 is a perspective view of another embodiment of a support member and coil.

FIG. 50 illustrates an embodiment of a coil 600' and a support member 650'. The support member 650' can incorporate electrically conductive pins 651' which can connect terminals of the coil 600' to a power source, such as control board 200. As shown in the illustrated embodiment, the terminals of the coil 600' can be attached to the pins 651' via soldering and/or adhesives.

Figure 51:
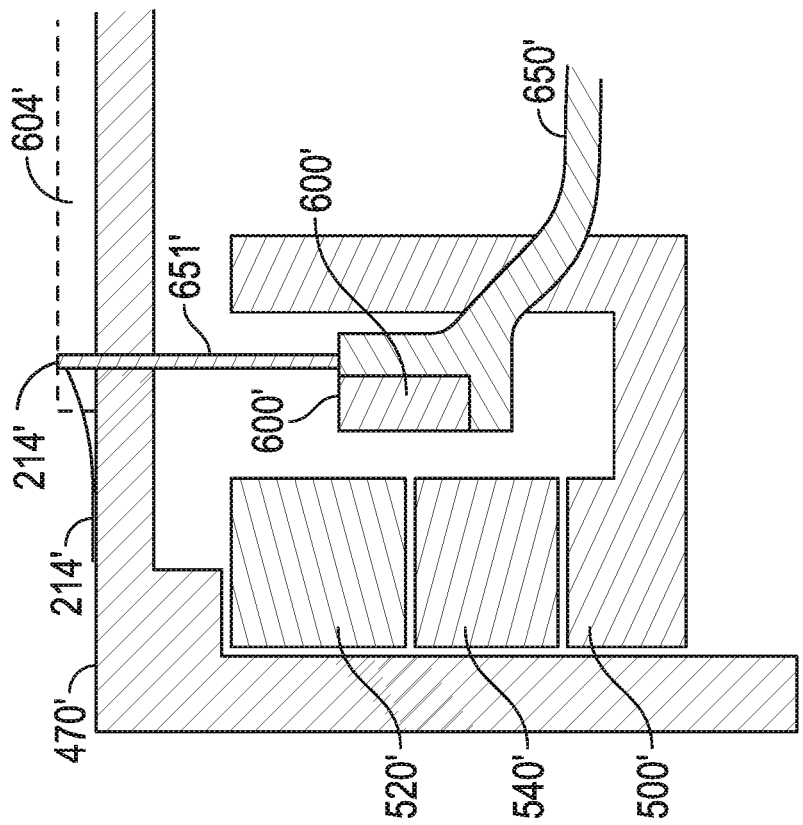
FIG. 51 is a schematic, cross-sectional view of an embodiment of wiring for the coil and support member of FIG. 50.

FIG. 51 illustrates one example of a connection mechanism for connecting the coil 600 to the power source. As shown in the illustrated embodiment, the pins 651' can extend past the pump chamber body 470' and into contact with a leaf spring 214'. The leaf spring 214' can be connected to terminal ends of an electrical conduit 604' for a power source, such as terminal ends of an FPC. Accordingly, as the support member 650'' moves in the vertical direction, the leaf spring 214' can maintain contact with the pins 651'.

Figure 52:
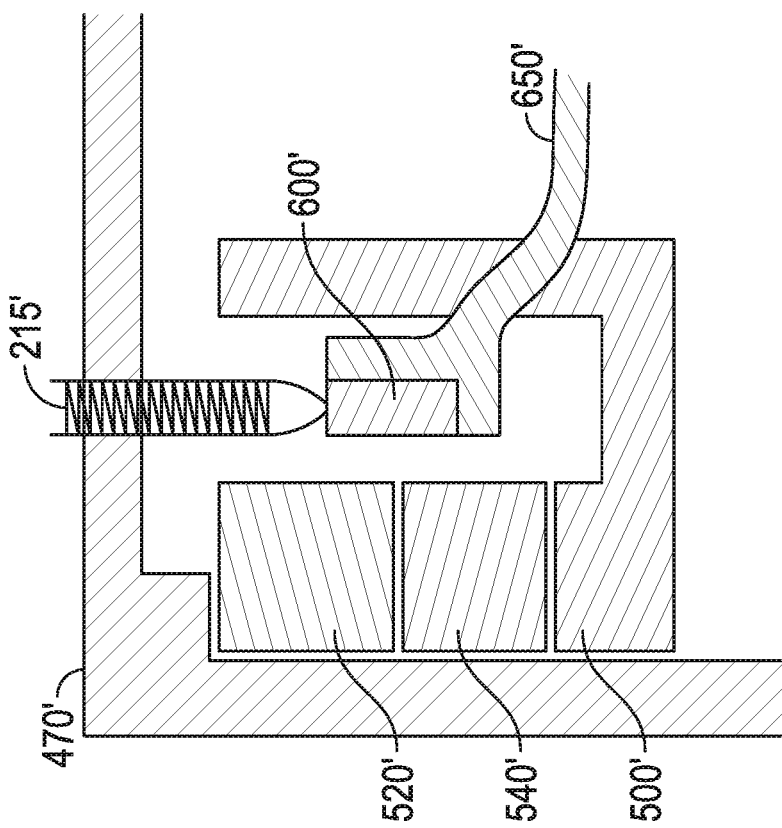
FIG. 52 is a schematic, cross-sectional view of another embodiment of wiring for the coil and support member of FIG. 50.

FIG. 52 illustrates another example of a connection mechanism for connecting coil 600' to the power source. As shown in the illustrated embodiment, an electrically conductive coil spring 215' can extend into the pump chamber body 470' and into contact with one or more terminals of the coil 600'. Accordingly, as the coil 600' moves in the vertical direction, the coil spring 215' can compress and/or expand. In some embodiments, the electrically conductive coil spring 215' can be in contact with pins (not shown) on the support member 650'. The coil spring 215' can be connected to terminal ends of an electrical conduit for a power source, such as terminal ends of an FPC.

Figure 53:
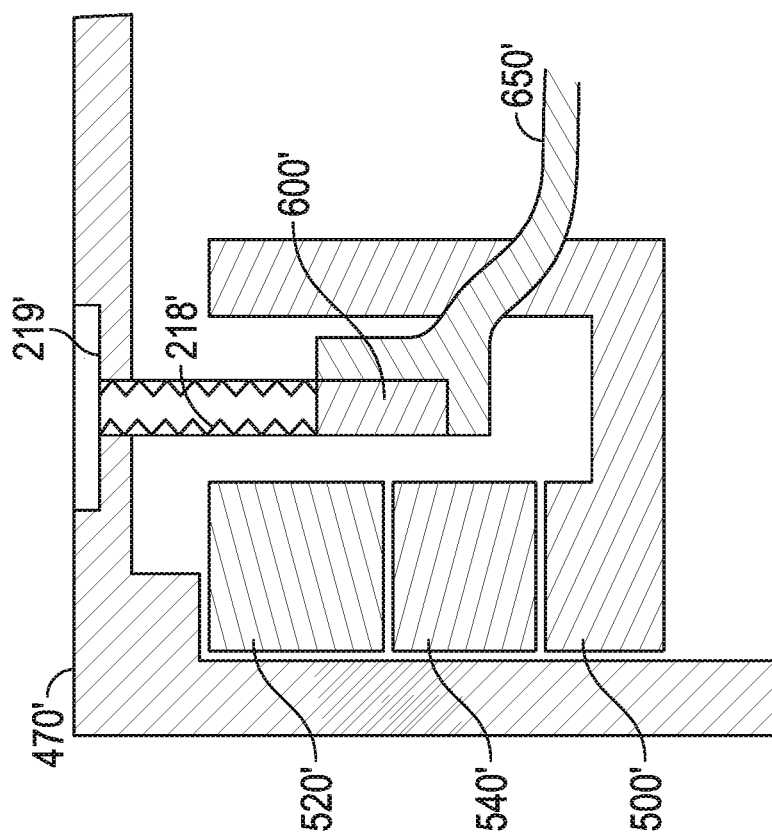
FIG. 53 is a schematic, cross-sectional view of another embodiment of wiring for the coil and support member of FIG. 50.

FIG. 53 illustrates another example of a connection mechanism for connecting coil 600' to the power source. As shown in the illustrated embodiment, an electrically conductive zebra connector 218' can extend into the pump chamber body 470' and into contact with one or more terminals of the coil 600'. Accordingly, as the coil 600' moves in the vertical direction, the zebra connector 218' can maintain contact with terminals of the coil 600'. In some embodiments, the zebra connector 218' can be in contact with pins (not shown) on the support member 650'. The zebra connector 218' can be connected to terminal ends of an electrical conduit for a power source, such as terminal ends of an FPC, or contacts 219'.

Figure 54:
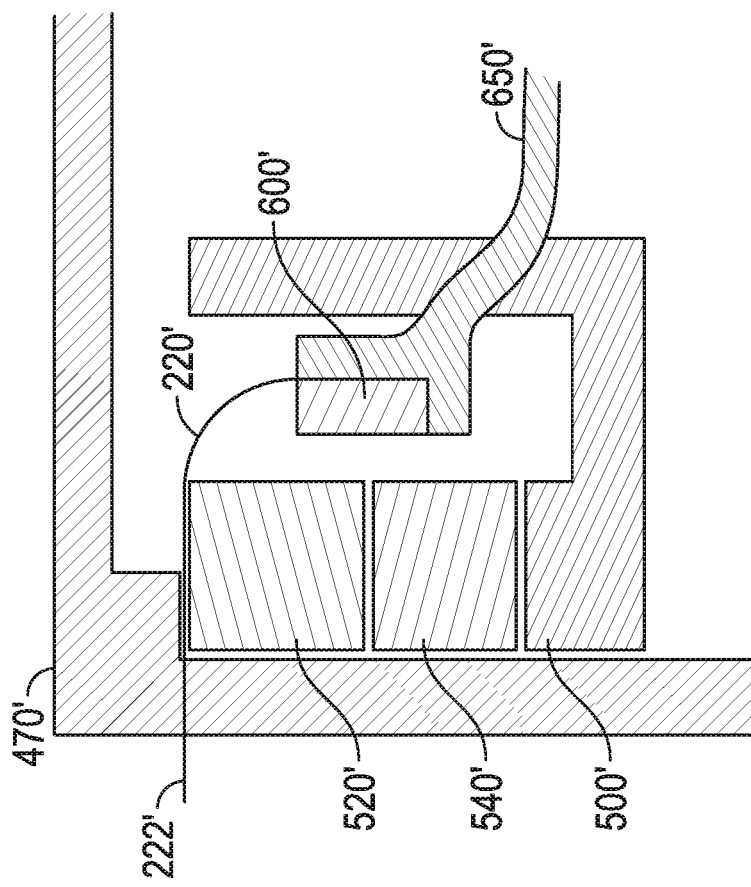
FIG. 54 is a schematic, cross-sectional view of another embodiment of wiring for the coil and support member of FIG. 50.

FIG. 54 illustrates another example of a connection mechanism for connecting coil 600' to the power source. As shown in the illustrated embodiment, one or more individual terminals of the coil 600' can be encased together in a membrane 220' which extends out of pump chamber body 470'. The membrane 220' can be made from any suitable material, such as silicone. The individual terminals can then be attached, via soldering and/or adhesives, to more robust wiring 222' for routing towards the power source.

Figure 55:
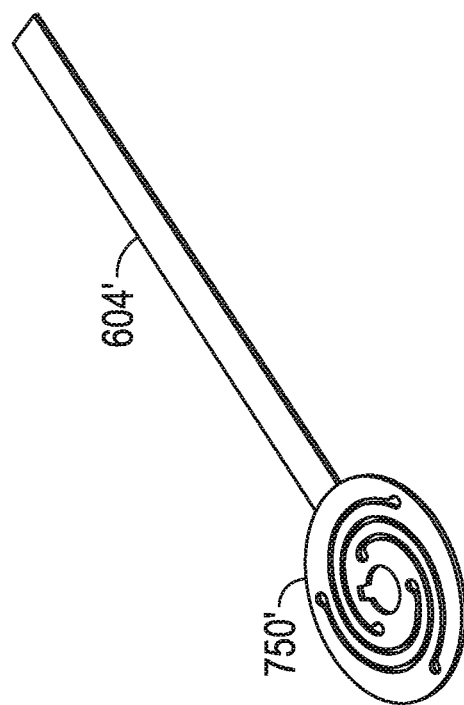
FIG. 55 is a perspective view of an embodiment of a combined spring and electrical conduit.

FIG. 55 illustrates another example of a connection mechanism for connecting coil 600' to the power source. As shown in the illustrated embodiment, the electrical conduit 604' can be integrated with the spring 750'.

In some embodiments, the pump system 100 can be configured such that the battery connections or terminals have polarity protection. For example and without limitation, one or more of the battery contacts can be designed to have plastic or other non-conductive protrusions adjacent to the battery terminal contacts to inhibit the contact between the battery contact and the incorrect side of a battery that is inserted into the battery compartment in the incorrect orientation. In some embodiments, the one or more protrusions can be sized and designed to prevent the negative side of a standard cylindrical battery from contacting the battery contact adjacent to the one or more protrusions, while permitting a positive side of such battery to contact the battery contact. Generally, with this configuration, the battery can generally only make contact with the contact if the battery is inserted in the battery compartment in the correct orientation, thereby providing polarity protection to the pump assembly. Alternatively or additionally, a control board of the pump assembly can be designed to have polarity protective features or components. Additionally, a control board of the pump assembly can have one or more fuses to protect against overpower conditions or surge power conditions.

In any of the embodiments disclosed herein, the control board 200 can be a flexible circuit board and/or can have one or more flexible components. A flexible circuit board is generally a patterned arrangement of printed circuitry and components that utilizes flexible based material with or without flexible overlay. These flexible electronic assemblies can be fabricated using the same components used for rigid printed circuit boards, but allowing the board to conform to a desired shape (flex) during its application. In their simplest form, flexible circuits are PCBs made of materials that allow for a non-planar positioning within the end product. Typical materials a polyimide-based, and can go under trade names such as Kapton (DuPont). Additionally, any of the control boards or controllers disclosed herein can have a combination of flexible and rigid substrates laminated into a single package.

Overview of the Electrical Aspects of the Pump System

Figure 60:
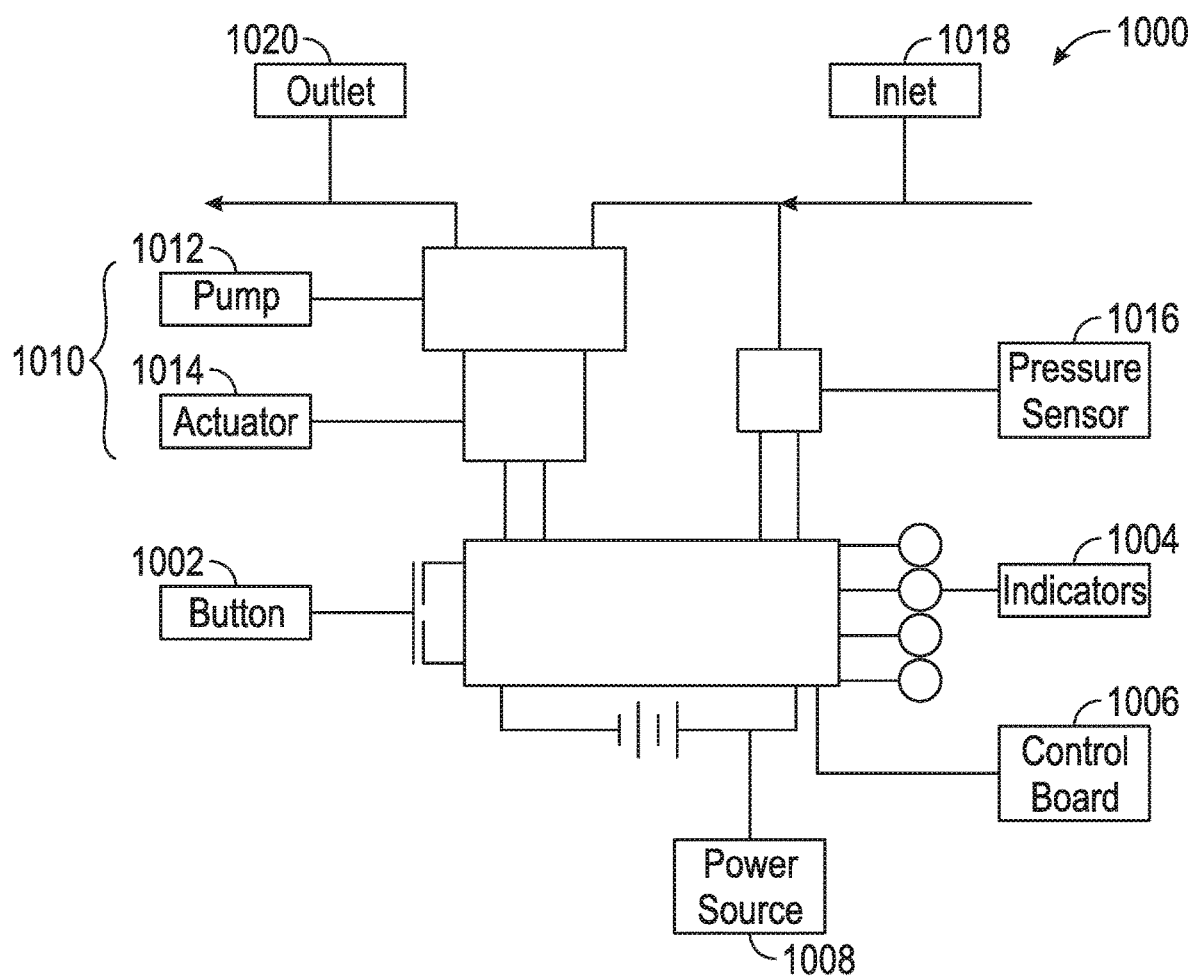
FIG. 60 is a schematic of an embodiment of a pump system.

FIG. 60 illustrates a schematic of an embodiment of a pump system 1000. In some embodiments, the pump system 1000 can have any of the same or similar components, features, materials, sizes, configurations, and other details of any other pump system embodiments disclosed or incorporated by reference herein, including the embodiment of the pump system 100 described above. In some embodiments, the pump system 1000 can be miniaturized and portable, although larger conventional portable or non-portable (e.g., wall suction) pumps can also be used.

As shown in the illustrated embodiment, the pump system 1000 can include a switch or a button 1002, one or more indicators 1004, and a control board 1006. The button 1002 and/or the one or more indicators 1004 can be in electrical communication with the control board 1006. As is explained in further detail below, in some embodiments the button 1002 can be used for any suitable purpose for controlling an operation of the pump system 1000. For example, button 1002 can be used to activate the pump system 1000, pause the pump system 1000, clear system indicators 1004, and/or be used for any other suitable purpose for controlling an operation of the pump system 1000. Button 1002 can by any type of switch or button, such as a touchpad, touch screen, keyboard, and so on. In some embodiments, the button 1002 can be a press button. For example, the button 1002 can be similar to button 116 of pump system 100.

In some embodiments, the one or more indicators 1004 can indicate one or more operating and/or failure conditions of the pump system 1000. In some embodiments, each of the one or more indicators 1004 can provide an indication regarding a different operating and/or failure condition. For example, an active (e.g., lit) indicator 1004 can represent normal operation. Another indicator 1004, for example a dressing indicator, can provide an indication as to presence of leaks in the system. For example, an active (e.g., lit) dressing indicator can represent a leak. Another indicator 1004, for example a dressing capacity indicator, can provide an indication as to the remaining fluid capacity of a dressing. For example, an active (e.g., lit) dressing capacity indicator can represent that the dressing is at or nearing capacity. Another indicator 1004, such as a battery indicator, can provide an indication as to remaining capacity or life of a power source, such as batteries. For example, an active (e.g., lit) battery indicator can represent a low capacity. In some embodiments, an indicator 1004 can represent a combination of the above operating and/or failure conditions of the pump system 1000 and/or other operating and/or failure conditions.

With continued reference to the embodiment of pump system 1000 illustrated in FIG. 60, in some embodiments, the one or more indicators 1004 can be icons. For example, the one or more indicators 1004 can be similar to the icons 114 of pump system 1004 and can be activated (e.g., lit) via an illumination source such as LEDs 206 of pump system 100. In some embodiments, the one or more indicators 1004 can be of a different color, two different colors (e.g., two indicators can share the same color), or the same color. Although the pump system 1000 can include four icons and a push play/pause button, other configurations, locations, and types of indicators, alarms, and switches can alternatively be used. In some embodiments, the pump system 1000 can include visual, audible, tactile, and other types of indicators or alarms configured to signal to the user various operating conditions. Such conditions include system on/off, standby, pause, normal operation, dressing problem, leak, error, and the like. The indicators can include speakers, displays, light sources, etc., and/or combinations thereof.

As shown in the illustrated embodiment, the pump system 1000 can be powered by a power source 1008 such as a battery power cell. The pump system 1000 can also include a source of negative pressure 1010, such as a pump assembly having a pump 1012 powered by an electric motor 1014, and a pressure sensor 1016, such as pressure monitor 204 of pump system 100. In some embodiments, the pump system 1000 can include an inlet 1018 to connect the pump system 1000 to a wound dressing. For example, in some embodiments, the inlet 1018 can be a connector for connecting the inlet 1018 to a conduit which is in fluid communication with a wound dressing. The connector can be similar to connector 302 of pump system 100. The pump 1012 can be connected to an outlet 1020. In some embodiments, the outlet 1020 can vent air to the atmosphere. In some embodiments, a filter (not shown) can be interposed between the outlet and the atmosphere. The filter can provide filtration of the air prior to venting to the atmosphere. In some embodiments, the filter can be a bacterial filter, odor filter, etc. or any combination thereof. In some embodiments, a dampening component (not shown), such as a noise dampening component, can be interposed between the outlet and the atmosphere. The dampening component can reduce the noise generated by the pump system 1000 during operation. In some embodiments, the dampening component can be similar to dampening component 902 of pump system 100.

In some embodiments, the pump system 1000 can include a valve (not shown), such as a one-way valve, in a flow passage between the wound dressing and an inlet of the pump 1012. The valve can help maintain a level of negative pressure when the pump 1012 is not active. In some embodiments, the valve can help avoid leaks. The valve can also help prevent fluids and/or exudate aspirated or removed from the wound from entering the pump system 1000.

Figure 61:
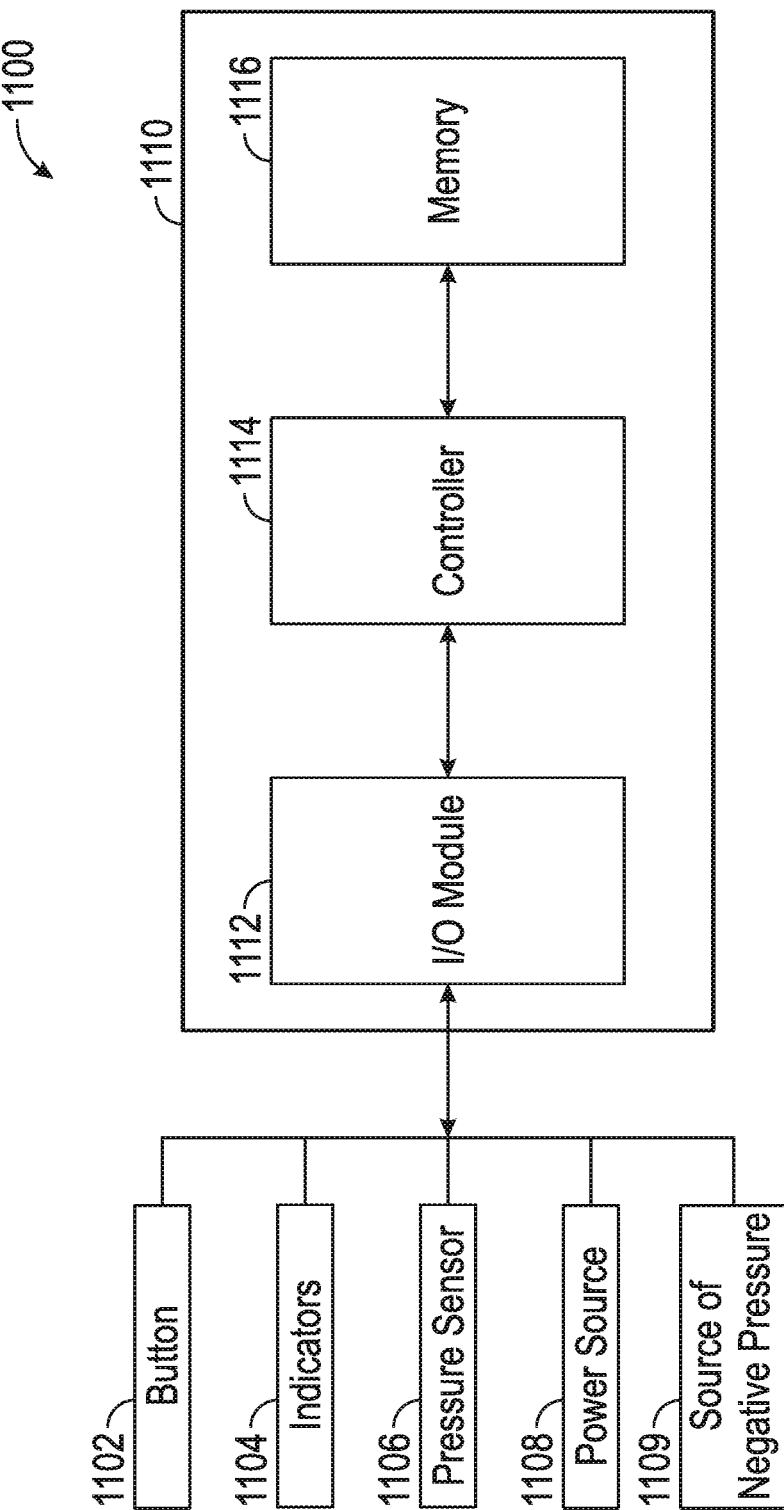
FIG. 61 is a schematic of another embodiment of a pump system.

FIG. 61 illustrates an electrical component schematic of a pump system 1100 according to an embodiment. In some embodiments, the pump system 1100 can have any of the same or similar components, features, materials, sizes, configurations, and other details of any other pump system embodiments disclosed or incorporated by reference herein, including the embodiment of the pump system 100, 1000 described above. Pump system 1100 can include one or more buttons 1102, one or more indicators 1104, one or more pressure sensors 1106, power source 1108, a source of negative pressure 1109, and/or a module 1110. In some embodiments, the one or more buttons 1102, one or more indicators 1104, one or more pressure sensors 1106, power source 1108, and/or source of negative pressure 1109 can be similar to button 1002, indicators 1004, pressure sensor 1016, power source 1008, and/or source of negative pressure 1010 of pump system 1000. Module 1110, which can be a control board (e.g., PCBA), can include an input/output (I/O) module 1112, controller 1114, and memory 1116. In some embodiments, module 1110 can include additional electric/electronic components, for example, fuse or fuses, or external memory (such as flash-memory). The controller 1114 can be a microcontroller, processor, microprocessor, etc. or any combination thereof. For example, the controller 1114 can be of the STM8L MCU family type from ST Microelectronics, such as STM8L 151G4U6 or STM8L 151K6U6TR, or of MC9S08QE4/8 series type from Freescale, such as MC9S08QE4CWJ. Preferably, the controller 1114 is a low power or ultra low power device, but other types of devices can alternatively be used. Memory 1116 can include one or more of volatile and/or nonvolatile memory modules, such as one or more of read-only memory (ROM), write once read many memory (WORM), random access memory (e.g., SRAM, DRAM. SDRAM, DDR, etc.), solid-state memory, flash memory, Magnetoresistive random-access memory (MRAM), magnetic storage, etc. or any combination thereof. Memory 1116 can be configured to store program code or instructions (executed by the controller), system parameters, operational data, user data, etc. or any combination thereof. In some embodiments, one or more components of the pump system 1100 can form part of a monolithic unit. In some embodiments, the memory 1116 can be 16 megabits, 32 megabits, or of another suitable size depending on the amount of data configured to be logged during operation of the pump system 1100. In some embodiments, the logged data can be stored to advantageously gather information that is relevant to clinical trial(s). In some embodiments, one or more components of the pump system 1100 can be removable from other components. For example, in some embodiments, memory 1116 can be removable flash memory.

Figure 62:
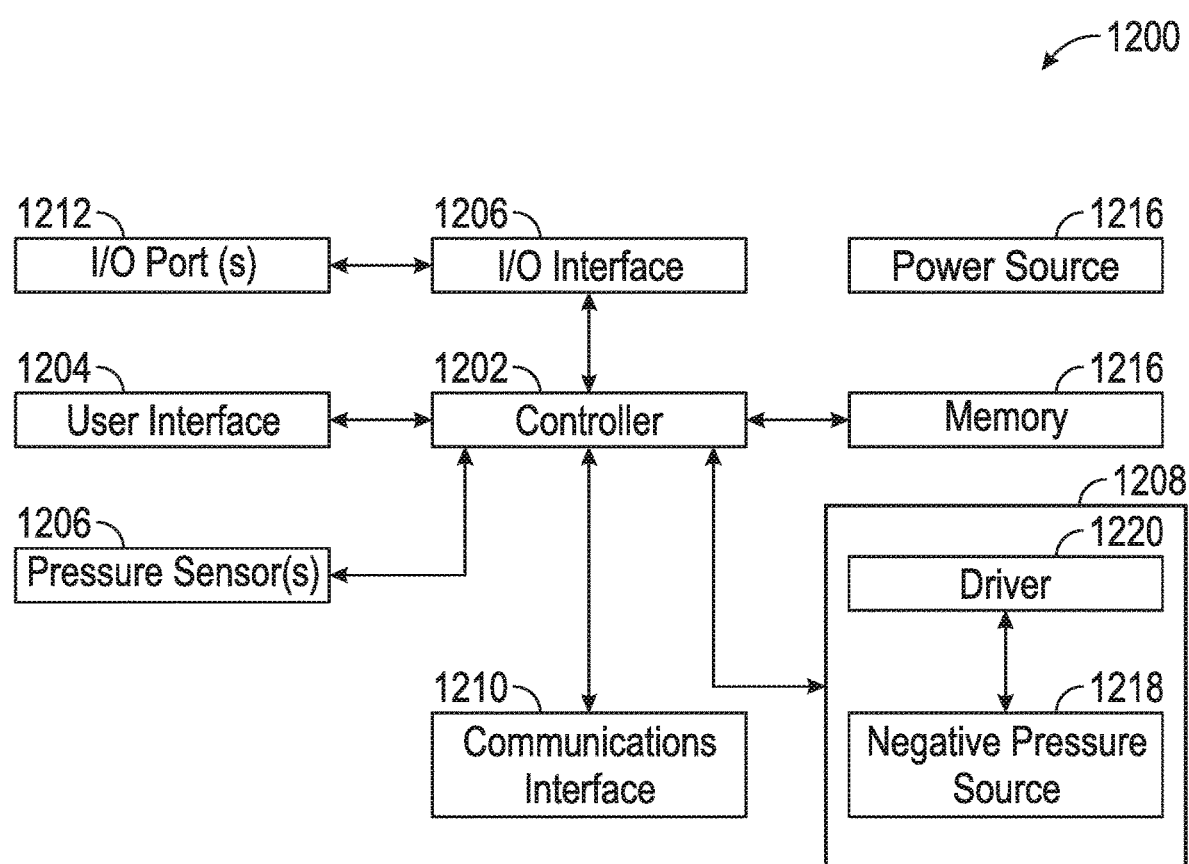
FIG. 62 is a schematic of another embodiment of a pump system.

FIG. 62 illustrates an electrical component schematic of a pump system 1200 according to an embodiment. In some embodiments, the pump system 1200 can have any of the same or similar components, features, materials, sizes, configurations, and other details of any other pump system embodiments disclosed or incorporated by reference herein, including the embodiment of the pump system 100, 1000, 1100 described above. Electrical components can operate to accept user input, provide output to the user, operate the pump system and the source of negative pressure, provide network connectivity, and so on. Electrical components can be mounted on one or more PCBs (not shown). The pump system can include a controller or processor 1202. In any embodiments disclosed herein, the controller 1202 can be a general purpose processor, such as a low-power processor. In other embodiments, the controller 1202 can be an application specific processor. In any embodiments disclosed herein, the controller 1202 can be configured as a "central" processor in the electronic architecture of the pump system, and the controller 1202 can coordinate the activity of other controllers, such as a user interface controller 1204, I/O interface controller 1206, negative pressure control module 1208, communications interface controller 1210, and the like.

The pump system 1200 can also include a user interface controller or processor 1204 which can operate one or more components for accepting user input and providing output to the user, such as buttons, indicators (e.g., LEDs), displays, etc. Input to the pump system 1200 and output from the pump system 1200 can be controlled via one or more input/output (I/O) ports 1212 controlled by a I/O interface module or controller 1206. For example, the I/O module 1206 can receive data from one or more I/O ports 1212, such as serial, parallel, hybrid ports, expansion ports, and the like. In any embodiments disclosed herein, I/O ports 1212 include one or more USB ports, SD ports, Compact Disc (CD) drives, DVD drives, FireWire ports, Thunderbolt ports, PCI Express ports, and the like. The controller 1202, along with other controller or processors, can store data in one or more memory modules 1214, which can be internal and/or external to the system 1200. Any suitable type of memory can be used, including volatile and/or non-volatile memory, such as RAM, ROM, WORM, magnetic memory, solid-state memory, MRAM, and the like or any combination thereof. The pump system 1200 can be powered by a power source 1216, which can comprise one or more disposable or rechargeable batteries, power from mains, etc. The power source 1216 can be internal or external to the system 1200.

With continued reference to the embodiment of pump system 1200 illustrated in FIG. 62, in some embodiments, a negative pressure or pump control module 1208 can be configured to control the operation of a negative pressure source 1218. The negative pressure source 1218 can be a voice coil pump. Other suitable pumps include diaphragm pumps, peristaltic pumps, rotary pumps, rotary vane pumps, scroll pumps, screw pumps, liquid ring pumps, diaphragm pumps operated by a piezoelectric transducer, and the like. The pump control module 1208 can include a driver module 1220 configured to control the operation of the negative pressure source 1218. For example, the driver module 1220 can provide power to the negative pressure source 1218. Power can be provided in a form of a voltage and/or current signal. In any embodiments disclosed herein, the driver module 1220 can control the negative pressure source 1218 using pulse-width modulation (PWM). A control signal for driving the negative pressure source 1218 (or pump drive signal) can be a 0-100% duty cycle PWM signal. The drive module 1220 can control the negative pressure source 1218 using any other suitable control, such as proportional-integral-derivative (PID).

The controller 1202 can receive information from one or more sensors, such as pressure sensors 1206, placed in a suitable location in a fluid flow path, such as pressure monitor 204 placed within intake manifold 300 of pump system 100. In any embodiments disclosed herein, the controller 1202 can measure pressure in the fluid flow path, using data received from one or more pressure sensors 1206, calculate the rate of fluid flow, and control the negative pressure source 1218 so that desired level of negative pressure is achieved in a wound cavity or under the dressing. The desired level of negative pressure can be pressure set or selected by a user. Pressure measured by the one or more sensors can be provided to the controller 1202 so that the controller can determine and adjust the pump drive signal to achieve the desired negative pressure level. In any embodiments disclosed herein, the tasks associated with controlling the negative pressure source 1218 can be offloaded to the pump control module 1208, which can include one or more controllers or processors.

In any embodiments disclosed herein, it may be advantageous to utilize multiple processors for performing various tasks. In any embodiments disclosed herein, a first processor can be responsible for user activity and a second processor can be responsible for controlling the negative pressure source. This way, the activity of controlling the negative pressure source, which may necessitate a higher level of responsiveness, can be offloaded to a dedicated processor and, thereby, will not be interrupted by user interface tasks, which may take longer to complete because of interactions with the user.

A communications interface controller or processor 1210 can be configured to provide wired and/or wireless connectivity. The communications processor 1210 can utilize one or more antennas (not shown) for sending and receiving data. In any embodiments disclosed herein, the communications processor 1210 can provide one or more of the following types of connections: Global Positioning System (GPS) technology, cellular or other connectivity, such as 2G, 3G, LTE, 4G, WiFi, Internet connectivity, Bluetooth, zigbee, RFID, and the like. Additionally, any embodiments disclosed herein can be configured to synchronize, upload, or download data to and/or from the pump apparatus to and/or from a portable data device, such as a tablet, smart phone, or other similar devices.

Connectivity can be used for various activities, such as pump system location tracking, asset tracking, compliance monitoring, remote selection, uploading of logs, alarms, and other operational data, and adjustment of therapy settings, upgrading of software and/or firmware, and the like. In any embodiments disclosed herein, the communications processor 1210 can provide dual GPS/cellular functionality. Cellular functionality can, for example, be 3G and/or 4G functionality. In such cases, if the GPS module is not be able to establish satellite connection due to various factors including atmospheric conditions, building or terrain interference, satellite geometry, and so on, the device location can be determined using the 3G and/or 4G network connection, such as by using cell identification, triangulation, forward link timing, and the like. In any embodiments disclosed herein, the pump system 1200 can include a SIM card, and SIM-based positional information can be obtained.

Pump System Control

Figure 63:
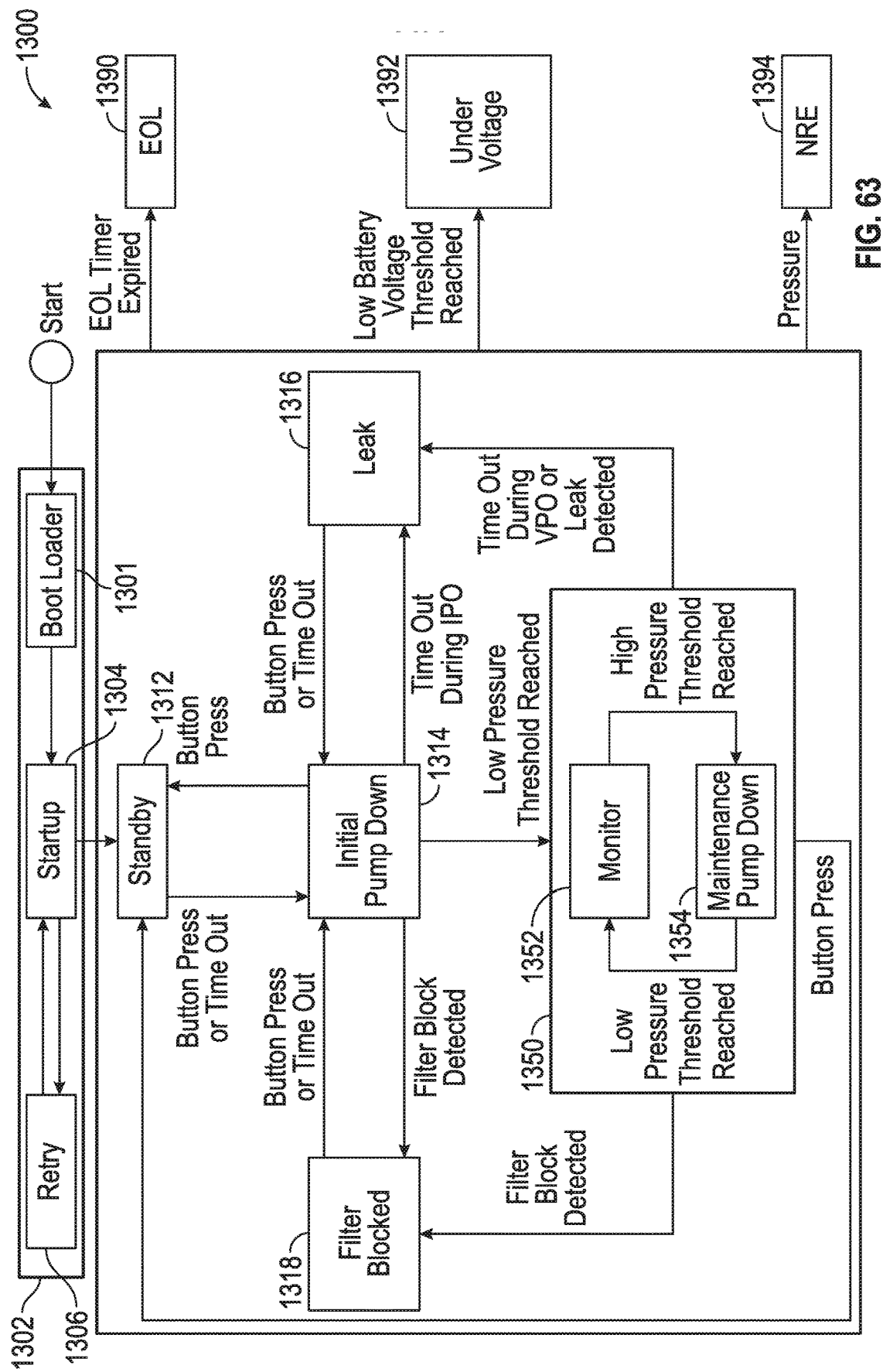
FIG. 63 is a top level state diagram according to some embodiments.

FIG. 63 illustrates a top level state diagram 1300 of operation of the pump system according to some embodiments. In some embodiments, the pump system, such as pump systems 100, 1000, 1100, 1200 and any other embodiments disclosed herein, can control the operation of the system. For example, the pump system can provide a suitable balance between uninterrupted delivery of therapy and/or avoidance of inconveniencing the user by, for example, frequently or needlessly pausing or suspending therapy and a desire to conserve power, limit noise and vibration generated by the negative pressure source, etc. In some embodiments, the controller, such as controllers 1114, 1202, can be configured to implement the flow of the state diagram 1300. As is illustrated in FIG. 63, the operation of the pump system can, in some embodiments, be grouped into three general modes: initialization 1302, operational 1310, which includes maintenance 1350, and end of life 1390. As is illustrated in FIG. 63, categories 1302, 1310, and 1350 can each include multiple states and transitions between states.

In some embodiments, so long as a power source is not connected or removed, or the pump system has not been activated (e.g., by pulling an activation strip, triggering the switch, or the like), the pump system can remain in an inactive state. While remaining in this state, the pump system can remain inactive. When the power source is connected and/or the pump system has been activated from the inactive state, such as being activated for the first time, the pump system can transition to an initialization mode 1302, where a bootloader 1301 can initiate a sequence of startup procedures as shown in block 1304. The bootloader 1301 can be stored on any suitable non-volatile memory such as, for example, read only memory (ROM), erasable programmable read only memory (EPROM), electrically erasable programmable read-only memory (EEPROM), and the like. In some embodiments, controllers 1114 or 1202 can execute the bootloader 1301 upon startup. The startup procedures can include power on selftest(s) (POST) and other tests or procedures that can be performed as shown in startup block 1304. As shown in FIG. 63, the bootloader 1301 can initiate one or more of the POST(s) and/or one or more of the other tests. In some embodiments, the startup procedures can advantageously prepare and/or ensure that the pump system will deliver negative pressure wound therapy safely during operation.

Power on self test(s) can include performing various checks to ensure proper functionality of the system, such as testing one or more components of the system including, but not limited to, memory such as memory 1116, 1214 (e.g., performing a check, such as a cyclic redundancy check (CRC check), of the program code to determine its integrity, testing the random access memory, etc.), reading the pressure sensor such as pressure sensors or monitors 204, 1016, 1106, 1206, to determine whether the pressure values are within suitable limits, reading the remaining capacity or life of the power source (e.g., battery voltage, current, etc.) to determine whether it is within suitable limits, testing the negative pressure source, and the like. Other tests or procedures can include waiting for automatic test equipment (ATE), initializing a watch dog timer (WDT), checking whether the pump system has previously entered a non-recoverable error (NRE), and determining whether the pump system has reached the end of its allotted operational lifespan (also referred to as its end of life (EOL)), and the like. For example, in some embodiments, the WDT can advantageously be used as a countermeasure to a firmware execution hanging conditions, the check for a previous NRE can advantageously prevent the reuse of a device that has transitioned to an NRE state, and the check of whether the device has reached its end of life can advantageously prevent the reuse of a device that has transitioned to an EOL state.

In some embodiments, the bootloader 1301, which can be executed by the controllers 1114, 1202, can also initiate the operational mode 1310. For example, as shown in FIG. 63, the bootloader can execute initialization of the operational mode 1310 after the initialization mode 1302 has been performed. In some embodiments, one or more indicators (such as icons 114, 114' and/or indicators 1004, 1104) can indicate to the user (e.g., by blinking or flashing once) that the pump system is undergoing POST test(s). In some embodiments, during the initialization mode 1302, all indicators can continuously remain on.

In some embodiments, the one or more indicators can blink or flash intermittently or continuously to indicate to the user that the system has passed the POST(s) and/or other tests and procedures. For example, as discussed above with reference to FIG. 56, in some embodiments, the one or more indicators can include a set of four icons 114' that include an "OK" indicator which can indicate normal operation of the pump system 100, a "leak" indicator which can indicate the existence of a leak in the pump system 100 or components attached thereto, a "dressing full" indicator which can indicate that a wound dressing is at or near capacity, and a "battery critical" indicator which can indicate that the battery is at or near a critical level. In some embodiments, the one or more indicators can be individually or cooperatively illuminated to indicate to the user that the pump system has passed POST(s) and/or other tests and procedures. For example, in some embodiments, the set of four icons 114' can be cooperatively illuminated to indicate that the system has passed the one or more tests such that the "OK" LED flashes once, the "leak" LED flashes once, the "dressing full" LED flashes once, and the "battery critical" LED flashes once. Similarly, if a previous non-recoverable error is discovered during startup or subsequently encountered during pump operation, the set of four icons 114' can be cooperatively illuminated such that the "OK" LED is solid, the "leak" LED is solid, the "dressing full" LED is solid, and the "battery critical" LED is solid. Any suitable individual or cooperative LED arrangement is envisioned in certain embodiments. In various embodiments, in addition to or instead of providing the visual indication using the one or more indicators, other indications can be provided, including audible, tactile, and the like.

In some embodiments, if one or more of the POST test(s) or other tests or procedures fail, the pump system can transition to a retry state 1306. The retry state 1306 can include a delay and/or require user input before retrying the POST test(s) or other tests or procedures. In some embodiments, the retry state 1306 can be executed until each test or procedure that is part of the initialization mode passes or otherwise does not fail. In some embodiments, if one or more of POST test(s) fail after one or more retries, the pump system can transition to a non-recoverable error state. While in this state, the pump system can deactivate therapy, and indicators can indicate to the user that an error was encountered. In some embodiments, all indicators can remain active. Based on the severity of error, in some embodiments, the pump system can recover from the error and continue operation (or transition to the non-recoverable error state 1394). As is illustrated, the pump system can transition to the non-recoverable error state 1394 upon encountering a fatal error during operation. Fatal errors can include program memory errors, program code errors (e.g., encountering an invalid variable value), controller operation errors (e.g., watchdog timer expires without being reset by the controller such as controller 1114, 1202), component failure (e.g., inoperative negative pressure source such as negative pressure sources 1010, 1109, 1218, inoperative pressure sensor such as pressure sensors or monitors 204, 1016, 1106, 1206, etc.), and any combination thereof.

With continued reference to the embodiment discussed in connection with FIG. 63, in some embodiments, when initialization has been successfully completed in state 1304, the pump system can transition to the operational mode 1310. This transition can be indicated to the user by deactivating and/or activating one or more indicators. In some embodiments, when the pump system transitions into the operational mode 1310, the pump system can first enter a standby or paused state 1312. While the pump system remains in the standby state 1312, the user can be provided an indication, such as by deactivating and/or activating indicators (e.g., an OK indicator and/or a dressing indicator). In some embodiments, the user can be provided an indication of the standby state 1312 by deactivating all indicators. In some embodiments, therapy can be suspended while the pump system remains in the standby state 1312. For example, the source of negative pressure such as sources of negative pressure 1010, 1109, 1218, can be deactivated (or turned off). In some embodiments, indication can be provided to the user by deactivating the source of negative pressure.

In some embodiments, the pump system can be configured to make a transition from the standby state 1312 to an initial pump down ("IPD") state 1314 (where the pump system is configured to deliver therapy) in response to receiving a signal from the user. For example, the user can press a button to start, suspend, and/or restart therapy. In some embodiments, the pump system can monitor the duration of time the pump system remains in the standby state 1312. This can be accomplished, for example, by maintaining a timer (in firmware, software, hardware or any combination thereof), which can be reset and started when the pump system transitions into the standby state 1312. The pump system can automatically make the transition from the standby state 1312 to the IPD state 1314 when the time duration exceeds a threshold (e.g., times out). In some embodiments, such threshold can be a preset value, such as between 1 minute or less and 1 hour or more. In some embodiments, the threshold can be set or changed by the user. In some embodiments, the threshold can be varied based on various operating conditions or on any combination thereof. For example, as the pump system nears the end of life (as is explained below), the threshold can be decreased used over the lifespan of the pump system. This can advantageously ensure that the battery is used more efficiently over the lifespan of the pump system by reducing the amount of time spent in the standby state 1312 and utilizing more of the battery by activating the pump sooner. In some embodiments, the pump system can monitor the entire amount of time spent in the standby state and store this information in memory.

During the IPD state 1314, the pump system can activate the source of negative pressure to begin therapy and reduce pressure in the system or some portion thereof, such as a fluid flow path between a source of negative pressure and a wound dressing. In some embodiments, the pump system can reduce pressure in the system to a desired pressure, such as a low pressure threshold. The pump system can intermittently and/or continuously monitor the pressure in the pump system or some portion thereof. For example, the pump system can monitor the pressure in the pump system or some portion thereof at a preset sampling rate of approximately 100 ms. In some embodiments, the sampling rate can be between approximately 20 ms and approximately 500 ms, between approximately 50 ms and 250 ms, between approximately 80 ms and 150 ms, approximately 100 ms, any value and/or subrange with these ranges, or any other sampling rate as desired. In some embodiments, the pump system can also calculate the rate of pressure change to estimate the amount of time until the pump system reaches a desired pressure, such as the low pressure threshold.

In some embodiments, one or more indicators can blink or flash intermittently or continuously to indicate to the user that the pump system is in the IPD state. For example, as discussed above with reference to FIG. 56, in some embodiments, the one or more indicators can include a set of four icons 114' that include an "OK" indicator which can indicate normal operation of the pump system 100, a "leak" indicator which can indicate the existence of a leak in the pump system 100 or components attached thereto, a "dressing full" indicator which can indicate that a wound dressing is at or near capacity, and a "battery critical" indicator which can indicate that the battery is at or near a critical level. In some embodiments, the one or more indicators can be individually or cooperatively illuminated to indicate to the user that the system is in the IPD state. For example, in some embodiments, the set of four icons 114' can be cooperatively illuminated to indicate that the system is in the IPD state such that the "OK" LED is flashing, the "leak" LED is flashing, the "dressing full" LED is off, and the "battery critical" LED does not change (on, off, or flashing). Any suitable individual or cooperative LED arrangement is envisioned in certain embodiments. Once a desired negative pressure is reached during the IPD state, the one or more indicators can be individually or cooperatively illuminated to indicate that the desired negative pressure has been reached. For example, in some embodiments, the set of four icons 114' can be cooperatively illuminated to indicate that the negative pressure has been reached such that the "OK" LED is flashing, the "leak" LED is off, the "dressing full" LED is off, and the "battery critical" LED does not change (on, off, or flashing). In some embodiments, this same illumination pattern can also be used to indicate that the pump system is functioning properly, such as during the IPD state to indicate that the pump system is functioning properly during the IPD state, in addition to flashing to indicate that the negative pressure has been reached during the IPD state. In various embodiments, in addition to or instead of providing the visual indication using the one or more indicators, other indications can be provided, including audible, tactile, and the like.

In some embodiments, the user can pause therapy by activating the switch (e.g., pressing the button), thereby causing the pump system to make a transition from the IPD state 1314 to the standby state 1312. In some embodiments, the pump system can be configured so that the user can only pause therapy, whereas disconnecting the power source (e.g., removing batteries) stops therapy. As such, in some embodiments, the pump system can potentially time out while in the standby state 1312 and resume operation thereby reducing any energy expended while in the standby state 1312. After being paused by the user, the pump system can transition from the standby state 1312 to the IPD state 1314 upon receiving a user input such as a button press. In some embodiments, after being paused by the user, the pump system can automatically make the transition from the standby state 1312 to the IPD state 1314 when the time duration exceeds a threshold. The threshold can be the same or different than the threshold of the standby state 1312 described above when the pump system enters the standby state 1312 after startup 1304.

When the pump system transitions into and remains in the standby state 1312, the user can be provided an indication. For example, in some embodiments, all indicators can be deactivated. In some embodiments, the pump system can deactivate an indicator (e.g., an OK indicator) and cause another indicator (e.g., a dressing indicator) to flash or blink. In some embodiments, one or more indicators can blink or flash intermittently or continuously to indicate to the user that the system is in the standby state. For example, as discussed above with reference to FIG. 56, in some embodiments, the one or more indicators can include a set of four icons 114' that include an "OK" indicator which can indicate normal operation of the pump system 100, a "leak" indicator which can indicate the existence of a leak in the pump system 100 or components attached thereto, a "dressing full" indicator which can indicate that a wound dressing is at or near capacity, and a "battery critical" indicator which can indicate that the battery is at or near a critical level. In some embodiments, the one or more indicators can be individually or cooperatively illuminated to indicate to the user that the system is in the standby state. For example, in some embodiments, the set of four icons 114' can be cooperatively illuminated to indicate that the system is in the standby state such that the "OK" LED is off, the "leak" LED is off, the "dressing full" LED is off, and the "battery critical" LED is off. In some embodiments, this same illumination pattern can also be used to indicate that the pump system has completed its course of negative pressure wound therapy or to indicate that the batteries have been depleted, in addition to indicating that the pump is in the standby state. Any suitable cooperative LED arrangement is envisioned in certain embodiments. In various embodiments, in addition to or instead of providing the visual indication using the one or more indicators, other indications can be provided, including audible, tactile, and the like. In some embodiments, therapy can be suspended while the pump system remains in the standby state 1312. For example, the source of negative pressure can be deactivated (or turned off), which provides the indication to the user that the pump system is in the standby state 1312.

With continued reference to the embodiment discussed in connection with FIG. 63, in some embodiments, the pump system can transition from the initial pump down state 1314 into a leak state 1316 when a number of retry cycles exceeds a retry limit and/or when a duty cycle of the pump (explained below) is determined to exceed a duty cycle limit. In some embodiments, exceeding a retry limit and/or duty cycle limit can reflect the presence of a leak in the system. In some embodiments, the pump system can transition from the IPD state 1314 to the leak state 1316 when a threshold pressure is not reached within a desired amount of time. The inability for the threshold pressure to reach the threshold pressure within a desired amount of time can reflect the presence of a leak in the system. In some embodiments, an indicator (e.g., a leak indicator or dressing indicator) can blink or flash intermittently or continuously to indicate to the user the presence of a leak in the system. In some embodiments, one or more indicators can blink or flash intermittently or continuously to indicate to the user the presence of a leak. For example, as discussed above with reference to FIG. 56, in some embodiments, the one or more indicators can include a set of four icons 114' that include an "OK" indicator which can indicate normal operation of the pump system 100, a "leak" indicator which can indicate the existence of a leak in the pump system 100 or components attached thereto, a "dressing full" indicator which can indicate that a wound dressing is at or near capacity, and a "battery critical" indicator which can indicate that the battery is at or near a critical level. In some embodiments, the one or more indicators can be individually or cooperatively illuminated to indicate to the user the presence of a leak. For example, in some embodiments, the set of four icons 114' can be cooperatively illuminated to indicate the presence of a leak such that the "OK" LED is off, the "leak" LED is flashing, the "dressing full" LED is off, and the "battery critical" LED does not change (on, off, or flashing). Any suitable cooperative LED arrangement is envisioned in certain embodiments. In various embodiments, in addition to or instead of providing the visual indication using the one or more indicators, other indications can be provided, including audible, tactile, and the like.

After entering the leak state 1316, the pump system can transition from the leak state 1316 to the IPD state 1314 upon receiving a user input such as a button press. This can advantageously give the user some time to mitigate or remove the leak, such as by checking the connections of the wound dressing and/or checking the seal of the wound dressing around the wound. In some embodiments, the pump system can monitor the duration of time the pump system remains in the leak state 1316. This can be accomplished, for example, by maintaining a timer (in firmware, software, hardware or any combination thereof), which can be reset and started when the pump system transitions into the leak state 1316. In some embodiments, after entering the leak state 1316, the pump system can automatically make the transition from the leak state 1316 to the IPD state 1314 when the time duration exceeds a threshold. The threshold can be the same or different than the other time thresholds described herein, such as that of the standby state 1312 to the IPD state 1314. The threshold can be the same or different depending on the state or mode prior to transitioning to the leak state 1316 (e.g., the IPD state 1314 or the maintenance mode 1350). In some embodiments, such threshold can be a preset value, such as between 1 minute or less and 1 hour or more. In some embodiments, the threshold can be set or changed by the user. In some embodiments, the threshold can be varied based on various operating conditions or on any combination thereof. For example, as the pump system nears the end of life (as is explained below), the threshold can be decreased provided the battery has sufficient capacity remaining. This can advantageously ensure that the battery is more efficiently used over the lifespan of the pump system by reducing the amount of time spent in the leak state 1316 and utilizing more of the battery by activating the pump sooner. The pump system can transition into other modes or states, such as the maintenance mode 1350, after activating the switch or automatically after exceeding the threshold. In some embodiments, the pump system can transition to the IPD state 1314 or the maintenance mode 1350 depending on operating conditions, such as the pressure at the time of the transition.

As noted above, in some embodiments, the pump system can be configured to operate in a canisterless system, in which the wound dressing retains exudate aspirated from the wound. Such dressing can include a filter, such as a hydrophobic filter, that prevents passage of liquids downstream of the dressing (toward the pump system). In other embodiments, the pump system can be configured to operate in system having a canister for storing at least part of exudate aspirated from the wound. Such canister can include a filter, such as a hydrophobic filter, that prevents passage of liquids downstream of the dressing (toward the pump system). In yet other embodiments, both the dressing and the canister can include filters that prevent passage of liquids downstream of the dressing and the canister.

With continued reference to the embodiment discussed in connection with FIG. 63, in some embodiments, the pump system can be configured to transition from the initial pump down state 1314 into a filter blocked state 1318 when the system determines that the filter, such as a wound dressing filter, has encountered a blockage (e.g., caused by the wound dressing being filled with exudate to capacity or nearly to capacity). Example algorithms for determining that the filter has encountered a blockage will be discussed in further detail below. In some embodiments, an indicator (e.g., a filter blocked indicator) can blink or flash intermittently or continuously to indicate to the user the presence of a blockage. In some embodiments, one or more indicators can blink or flash intermittently or continuously to indicate to the user the presence of a blockage. For example, as discussed above with reference to FIG. 56, in some embodiments, the one or more indicators can include a set of four icons 114' that include an "OK" indicator which can indicate normal operation of the pump system 100, a "leak" indicator which can indicate the existence of a leak in the pump system 100 or components attached thereto, a "dressing full" indicator which can indicate that a wound dressing is at or near capacity, and a "battery critical" indicator which can indicate that the battery is at or near a critical level. In some embodiments, the one or more indicators can be individually or cooperatively illuminated to indicate to the user the presence of a blockage. For example, in some embodiments, the set of four icons 114' can be cooperatively illuminated to indicate the presence of a blockage such that the "OK" LED is off, the "leak" LED is off, the "dressing full" LED is flashing, and the "battery critical" LED does not change (on, off, or flashing). Any suitable cooperative LED arrangement is envisioned in certain embodiments. In various embodiments, in addition to or instead of providing the visual indication using the one or more indicators, other indications can be provided, including audible, tactile, and the like. In some embodiments, the transition to the filter blocked state 1318 can be made when a canister filter is blocked (e.g., caused by the canister being full or nearly full).

After entering the filter blocked state 1316, the pump system can transition from the filter blocked state 1318 to the IPD state 1314 upon receiving a user input such as a button press. This can advantageously give the user an opportunity to mitigate or remove the blockage, such as by changing the wound dressing (and/or the canister). In some embodiments, the pump system can monitor the duration of time the pump system remains in the filter blocked state 1318. This can be accomplished, for example, by maintaining a timer (in firmware, software, hardware or any combination thereof), which can be reset and started when the pump system transitions into the filter blocked state 1318. In some embodiments, after entering the filter blocked state 1318, the pump system can automatically make the transition from the filter blocked state 1318 to the IPD state 1314 when the time duration exceeds a threshold. The threshold can be the same or different than the other time thresholds described herein, such as that of the standby state 1312 to the IPD state 1314 and/or the leak state 1316 to the IPD state 1314. The threshold can be the same or different depending on the state or mode prior to transitioning to the filter blocked state 1318 (e.g., the IPD state 1314 or the maintenance mode 1350). In some embodiments, such threshold can be a preset value, such as between 1 minute or less and 1 hour or more. In some embodiments, the threshold can be set or changed by the user. In some embodiments, the threshold can be varied based on various operating conditions or on any combination thereof. For example, as the pump system nears the end of life (as is explained below), the threshold can be decreased provided the battery has sufficient capacity remaining. This can advantageously ensure that the battery is more efficiently used over the lifespan of the pump system by reducing the amount of time spent in the filter blocked state 1316 and utilizing more of the battery by activating the pump sooner. The pump system can transition into other modes or states, such as the maintenance mode 1350, after activating the switch or automatically after exceeding the threshold. In some embodiments, the pump system can transition to the IPD state 1314 or the maintenance mode 1350 depending on operating conditions, such as the pressure at the time of the transition.

With continued reference to the embodiment discussed in connection with FIG. 63, in some embodiments, during the IPD state 1314, once the pump system has detected that the pressure within the pump system or some portion thereof, such as a fluid flow path between a source of negative pressure and a wound dressing, is at or around the low pressure threshold, the pump system can transition into a maintenance mode 1350 and, in particular, to the monitor state 1352. For example, the low pressure threshold can be approximately −90 mmHg. In some embodiments, the low pressure threshold can be between approximately −50 mmHg and approximately −250 mmHg, between approximately −75 mmHg and approximately −125 mmHg, between approximately −80 mmHg and −115 mmHg, approximately −94 mmHg, any value or subrange within these ranges, or any other value as desired.

During the maintenance mode 1350, the pump system can advantageously monitor and maintain the pressure within the pump system or some portion thereof, such as a fluid flow path between a source of negative pressure and a wound dressing, within a target pressure range (or operating range). For example, in some embodiments, during the maintenance mode 1350, the pump system can maintain the pump system or some portion thereof between a high pressure threshold and a low pressure threshold. For example, the high pressure threshold can be approximately −70 mmHg. In some embodiments, the high pressure threshold can be between approximately −40 mmHg and approximately −200 mmHg, between approximately −60 mmHg and approximately −100 mmHg, between approximately −70 mmHg and −80 mmHg, approximately −71 mmHg, approximately −67 mmHg, any value or subrange within these ranges, or any other value as desired. The low pressure threshold can be approximately −90 mmHg. In some embodiments, the low pressure threshold during the maintenance mode 1350 can be the same as the low pressure threshold during the IPD state 1314. In some embodiments, the low pressure threshold during the maintenance mode 1350 can be different from the low pressure threshold during the IPD state 1314. As shown in the illustrated embodiment, the maintenance mode 1350 can include a monitor state 1352 and a maintenance pump down ("MPD") state 1354.

In some embodiments, one or more indicators can blink or flash intermittently or continuously to indicate to the user that the system is in the MPD state. For example, as discussed above with reference to FIG. 56, in some embodiments, the one or more indicators can include a set of four icons 114' that include an "OK" indicator which can indicate normal operation of the pump system 100, a "leak" indicator which can indicate the existence of a leak in the pump system 100 or components attached thereto, a "dressing full" indicator which can indicate that a wound dressing is at or near capacity, and a "battery critical" indicator which can indicate that the battery is at or near a critical level. In some embodiments, the one or more indicators can be individually or cooperatively illuminated to indicate to the user that the system is in the MPD state. For example, in some embodiments, the set of four icons 114' can be cooperatively illuminated to indicate that the system is in the MPD state such that the "OK" LED is flashing, the "leak" LED is off, the "dressing full" LED is off, and the "battery critical" LED does not change (on, off, or flashing). Any suitable cooperative LED arrangement is envisioned in certain embodiments. Once a desired negative pressure is reached during the MPD state, the one or more indicators can be cooperatively illuminated to indicate that the negative pressure has been reached. For example, in some embodiments, the set of four icons 114' can be cooperatively illuminated to indicate that the negative pressure has been reached such that the "OK" LED is flashing, the "leak" LED is off, the "dressing full" LED is off, and the "battery critical" LED does not change (on, off, or flashing). In some embodiments, this same illumination pattern can also be used to indicate that the pump system is functioning properly, such as during the MPD state to indicate that the pump system is functioning properly during the MPD state, in addition to flashing to indicate that the negative pressure has been reached during the MPD state. In various embodiments, in addition to or instead of providing the visual indication using the one or more indicators, other indications can be provided, including audible, tactile, and the like.

During the monitor state 1352, the pump system can monitor the pressure in the pump system or some portion thereof, such as a fluid flow path between a source of negative pressure and a wound dressing, to ensure that the pressure within the pump system or the monitored portion thereof is maintained between a high pressure threshold and a low pressure threshold. The source of negative pressure can be deactivated during the monitor state 1352. The pump system can intermittently and/or continuously monitor the pressure in the pump system or some portion thereof. For example, the pump system can monitor the pressure in the pump system or some portion thereof at a preset sampling rate of approximately 1 second. In some embodiments, the sampling rate can be between approximately 50 ms and approximately 5 seconds, between approximately 200 ms and 2 seconds, between approximately 500 ms and 2 seconds, approximately 1 second, any value and/or subrange with these ranges, or any other sampling rate as desired. In some embodiments, the sampling rate during the monitor state 1352 can be less than the sampling rate during the IPD state 1314 to advantageously reduce power usage and extend the life of the power source. A lower sampling rate can be used in some embodiments as the rate of pressure change during the monitor state 1352 (e.g., when the source of negative pressure is deactivated) can be less than the rate of pressure change when the source of negative pressure is activated. In some embodiments, the pump system can also calculate the rate of pressure change to estimate the amount of time until the pump system reaches a desired pressure, such as a low pressure threshold.

In some embodiments, one or more indicators can blink or flash intermittently or continuously to indicate to the user that the system is in the monitor state. For example, as discussed above with reference to FIG. 56, in some embodiments, the one or more indicators can include a set of four icons 114' that include an "OK" indicator which can indicate normal operation of the pump system 100, a "leak" indicator which can indicate the existence of a leak in the pump system 100 or components attached thereto, a "dressing full" indicator which can indicate that a wound dressing is at or near capacity, and a "battery critical" indicator which can indicate that the battery is at or near a critical level. In some embodiments, the one or more indicators can be individually or cooperatively illuminated to indicate to the user that the system is in the monitor state. For example, in some embodiments, the set of four icons 114' can be cooperatively illuminated to indicate that the system is in the monitor state such that the "OK" LED is flashing, the "leak" LED is off, the "dressing full" LED is off, and the "battery critical" LED does not change (on, off, or flashing). In some embodiments, this same illumination pattern can also be used to indicate that the pump system is functioning properly during the monitor state, in addition to flashing to indicate that the system is in the monitor state. Any suitable cooperative LED arrangement is envisioned in certain embodiments. In various embodiments, in addition to or instead of providing the visual indication using the one or more indicators, other indications can be provided, including audible, tactile, and the like.

The pump system can stay in the monitor state 1352 until the pump system detects that the pressure in the pump system or some portion thereof, such as a fluid flow path between a source of negative pressure and a wound dressing, is at or around a high pressure threshold. Upon detecting that the pump system or some portion thereof is at or around the high pressure threshold, the pump system can transition to the MPD state 1354. During the MPD state 1354, the pump system can activate the source of negative pressure to begin therapy and reduce pressure in the system or some portion thereof until the pressure is at or near the low pressure threshold. In some embodiments, the low pressure threshold can be the same or similar to the low pressure threshold discussed in connection with the IPD state 1314. In some embodiments, the low pressure threshold can be different from that in the IPD state 1314.

The pump system can continually monitor the pressure in the pump system at a preset sampling rate. In some embodiments, the sampling rate can be the same or similar to the low pressure threshold discussed in connection with the IPD state 1314. In some embodiments, the sampling rate can be different from the sampling rate during the IPD state 1314. In some embodiments, the pump system can also calculate the rate of pressure change to estimate the amount of time until the pump system reaches a desired pressure, such as the low pressure threshold. When the pump system detects that the pressure in the pump system or some portion thereof is at or around the low pressure threshold, the pump system can transition back to the monitor state 1352.

With reference back to the embodiment discussed in connection with FIG. 63, in some embodiments, the user can pause therapy by activating the switch (e.g., pressing the button), thereby causing the pump system to make a transition from the maintenance mode 1350 to the standby state 1312. After being paused by the user, the pump system can transition from the standby state 1312 to the IPD state 1314 upon receiving a user input such as a button press. In some embodiments, after being paused by the user, the pump system can automatically make the transition from the standby state 1312 to the IPD state 1314 when the time duration exceeds a threshold. The threshold can be the same or different than the thresholds discussed above, such as the threshold when the pump system enters the standby state 1312 from the IPD state 1314 from a button press. In some embodiments, such threshold can be a preset value, such as between 1 minute or less and 1 hour or more. In some embodiments, the threshold can be set or changed by the user. In some embodiments, the threshold can be varied based on various operating conditions or on any combination thereof. For example, as the pump system nears the end of life (as is explained below), the threshold can be decreased provided the battery has sufficient capacity remaining. In some embodiments, the pump system can transition into the maintenance mode 1350 after activating the switch or automatically after exceeding the threshold. In some embodiments, the pump system can transition to the IPD state 1314 or the maintenance mode 1350 depending on operating conditions, such as the pressure at the time of the transition.

When the pump system transitions into and remains in the standby state 1312, the user can be provided an indication. For example, in some embodiments, all indicators can be deactivated. In some embodiments, the pump system can deactivate an indicator (e.g., an OK indicator) and cause another indicator (e.g., a dressing indicator) to flash or blink. In some embodiments, therapy can be suspended while the pump system remains in the standby state 1312. For example, the source of negative pressure can be deactivated (or turned off), which provides the indication to the user that the pump system is in the standby state 1312.

With continued reference to the embodiment discussed in connection with FIG. 63, in some embodiments, the pump system can transition from the maintenance mode 1350 into a leak state 1316 when a threshold pressure is not reached within a desired amount of time. The inability for the threshold pressure to reach the threshold pressure within a desired amount of time can reflect the presence of a leak in the system. In some embodiments, the pump system can transition from the maintenance mode 1350 to the leak state 1316 when a number of retry cycles exceeds a retry limit and/or when the duty cycle of the pump is determined to exceed a duty cycle limit. In some embodiments, exceeding a retry limit and/or duty cycle limit can reflect the presence of a leak in the system. In some embodiments, an indicator (e.g., a leak indicator or dressing indicator) can blink or flash intermittently or continuously to indicate to the user the presence of a leak in the system.

With continued reference to the embodiment discussed in connection with FIG. 63, in some embodiments, the pump system can be configured to transition from the maintenance mode 1350 into a filter blocked state 1318 when the system determines that the filter, such as the wound dressing filter (and/or the canister filter), has encountered a blockage (e.g., caused by the wound dressing being filled with exudate to capacity or nearly to capacity). Example algorithms for determining that the filter has encountered a blockage will be discussed in further detail below. In some embodiments, an indicator (e.g., a filter blocked indicator) can blink or flash intermittently or continuously to indicate to the user the presence of a blockage.

With continued reference to the embodiment discussed in connection with FIG. 63, in some embodiments, the pump system can be configured to monitor the remaining capacity or life of the power source (e.g., by periodically reading or sampling the battery voltage, current, etc.). The pump system can be configured to indicate to the user the remaining capacity. For example, if the power source is determined to have a normal remaining capacity (e.g., as a result of comparison to a threshold, such as 2.7V, 2.6V, 2.5V, etc.), an indicator (e.g., a battery indicator) can be deactivated. If the power source is determined to have low remaining capacity, the pump system, can provide an indication to the user by, for example, causing an indicator (e.g., a battery indicator) to blink or flash. In some embodiments, an indicator (e.g., a battery indicator) can be configured to be blinking or flashing intermittently or continuously regardless of the state the pump system is in or only in particular states.

In some embodiments, when the remaining capacity of the power source is determined to be at or near a critical level (e.g., as a result of comparison to a threshold, such as 2.4V, 2.3V, 2.2V, etc.), the pump system can transition into an under voltage or battery critical state 1392. In some embodiments, the pump system can remain in this state until the capacity of the power source is increased, such as by replacing or recharging the power source. The pump system can deactivate therapy while remaining in the battery critical state 1392. In addition, the pump system can be configured to indicate to the user that the power source is at or near the critical level by, for example, deactivating all indicators. In some embodiments, when the pause/resume button is pressed after the pump system has transitioned to the under voltage state 1392, the pump system can be configured to indicate that the device has not yet reached its end of life (EOL) by, for example, flashing a battery indicator LED.

With continued reference to the embodiment discussed in connection with FIG. 63, in some embodiments, the pump system can be configured to provide therapy for a predetermined period of time, such as approximately 1 day, 2-10 days, up to 30 days, etc. following a first activation. In some embodiments, such period of time can be a preset value, changed by the user, and/or varied based on various operating conditions or on any combination thereof. The pump system can be disposed upon the expiration of such period of time. Once the pump system has been activated, the pump system can monitor the duration it has remained active. In some embodiments, the pump system can monitor the cumulative duration the system has remained active. This can be accomplished, for example, by maintaining a timer (in firmware, software, hardware or any combination thereof), that reflects such duration.

When the duration reaches or exceeds a threshold (e.g., 10 days), the pump system can transition to an end of life (EOL) state 1390. The pump system can deactivate therapy while remaining in state 1390 and to indicate to the user that the end of the pump system's usable life has been reached. For example, the pump system can deactivate all indicators and/or deactivate the button. In some embodiments, when the pump system is disposable, transitioning to the end of life state 1390 means that the pump system can be disposed of. The pump system can disable reactivation of the pump system once the end of life has been reached. For example, the pump system can be configured to not allow reactivation even if the power source is disconnected and reconnected later, which can be accomplished by storing an indication, value, flag, etc. in the read only memory.

Figure 64:
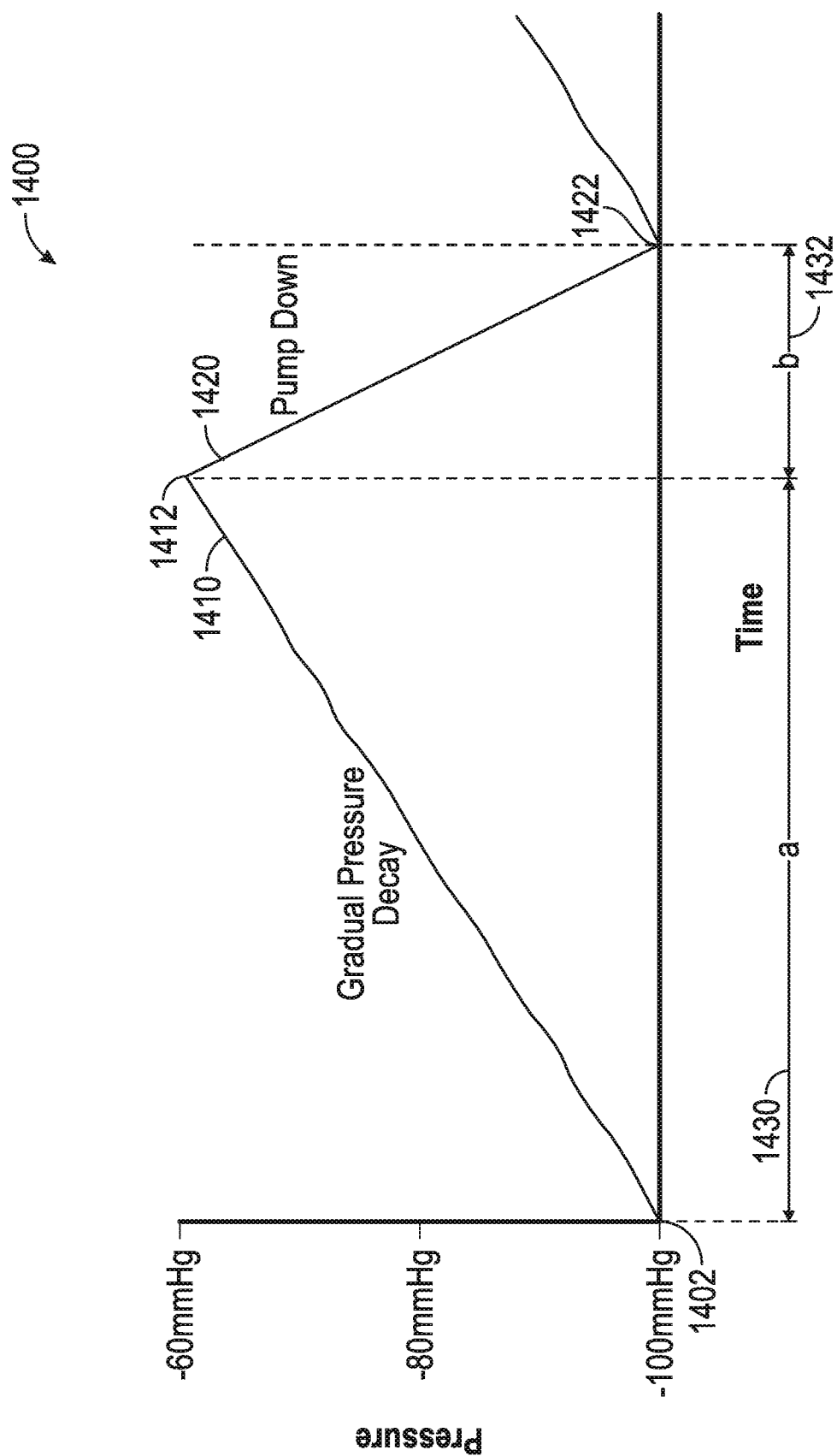
FIG. 64 is an exemplary pressure versus time graph according to some embodiments.

FIG. 64 illustrates an exemplary graph 1400 of pressure versus time when the negative pressure source is active, such as during the maintenance mode 1350, according to some embodiments. As illustrated by line 1410, the system can enter the monitor state 1352 upon detecting that the pressure in the pump system or some portion thereof, such as a fluid flow path between a source of negative pressure and a wound dressing, is at or near a low pressure threshold 1402. In the illustrated embodiment, the low pressure threshold can be approximately −100 mmHg although other low pressure thresholds can be chosen as discussed above. During the monitor state 1352, the pressure in the pump system or some portion thereof may begin to gradually decay due to the source of negative pressure being deactivated and the existence of minor leakages in the system. As is illustrated, the pump system can monitor pressure over the period of time a, as represented by interval 1430. In some embodiments, the pressure can be sampled over the interval 1430 after a transient time period has elapsed. For example, in some embodiments, the transient time period can be measured from when the monitor state 1352 begins. After the transient time period has elapsed, pressure can be sampled in consecutive samples, and two or more of the consecutive samples can be averaged.

When the system detects that the pressure in the pump system or some portion thereof is at or near the high pressure threshold 1412, the system can switch to the MPD state 1354 and reactivate the source of negative pressure to lower the pressure in the pump system or some portion thereof as illustrated by line 1420. In the illustrated embodiment, the high pressure threshold can be approximately −60 mmHg although other high pressure thresholds can be chosen as discussed above. As is illustrated, the pump system can activate the over the period of time b, as represented by interval 1432. When the system detects that the pressure in the pump system or some portion thereof is at or near the low pressure threshold 1422, the system can switch back to the monitor state 1352 and deactivate the source of negative pressure. This process can be repeated as desired.

In some embodiments, the pump assembly can be configured to monitor the duty cycle of the source of negative pressure (e.g., a pump). As is used herein, "duty cycle" reflects the amount of time the source of negative pressure is active or running over a period of time. In other words, the duty cycle can reflect time that the source of negative pressure is in an active state as a fraction of total time under consideration. For example, as described above, in some embodiments, the pump system can transition from the IPD state 1314 or the maintenance mode 1350 to the leak state 1316 when, for example, the duty cycle of the pump is determined to exceed a duty cycle limit. In such a case, exceeding the duty cycle limit can reflect the presence of a leak in the system. In some embodiments, the duty cycle (DC) of the pump over the period illustrated between intervals 1410 and 1420 (i.e., a+b) can be expressed, on percent scale, as:

$$DC = 100\% * [b/(a+b)].$$

In some embodiments, the pump assembly can include a controller, such as controller 1114 or 1202, configured to monitor the duty cycle of the source of negative pressure. Duty cycle measurements can indicate rate of flow through the system and reflect a level of activity of the source of negative pressure. For example, duty cycle can indicate that the source of negative pressure is operating normally, working hard, working extremely hard, etc. Moreover, duty cycle measurements, such as periodic duty cycle measurements, can reflect various operating conditions, such as presence, rate, and/or severity of one or more leaks in the system, rate of flow of fluid (e.g., air, liquid and/or solid exudate, etc.) aspirated from a wound, and the like. Based on the duty cycle measurements, such as by comparing the measured duty cycle to a duty cycle threshold (determined in calibration or at runtime), the controller can execute and/or be programmed to execute algorithms or logic that control the operation of the system in accordance with various system requirements. For example, duty cycle measurements can indicate presence of a high leak in the system, and the controller can be programmed to indicate this condition to a user (e.g., patient, caregiver, physician, etc.) and/or temporarily suspend or pause operation of the source of negative pressure in order to conserve power.

In some embodiments, the pump system 1000, 1100, or 1200 can be configured to periodically monitor the duty cycle, such as once between every 10 seconds or less and 5 minutes or more. In some embodiments, the pump assembly can be configured to monitor the duty cycle once per minute.

For example, in order to determine the duty cycle, the pump system 1000, 1100, 1200 can be configured to monitor the duration of time that the pump has been active (e.g., the pump run time) and/or inactive. In some embodiments, the pump system (e.g., controller 1114, 1202) can be configured to compare the determined duty cycle to a duty cycle threshold, which can be selected from the range between 1% or less and 50% or more. The comparison can, for example, indicate presence of a leak in the system. In other words, if the pump remains active over a period of time so that the duty cycle threshold is reached or exceeded, the source of negative pressure may be working too hard to overcome the leak. In such cases, as explained above, the pump assembly can be configured to suspend or pause the delivery of therapy. The pump assembly can be configured to provide an indication to the user that the pump is working hard (e.g., duty cycle exceeds the duty cycle threshold) by, for example, deactivating the source of negative pressure, activating one or more indicators, and the like. In some embodiments, the duty cycle threshold can be a preset value, set or changed by the user, and/or varied based on various operating conditions or on any combination thereof. In some embodiments, while the duty cycle indicates the level of pump activity, other metrics, such as pump speed, can be used for measuring the level of pump activity. In certain embodiments, the rate of flow of fluid can be measured directly, such as by using a flow meter.

In some embodiments, the pump system 1000, 1100, or 1200 determines and adjusts the duty cycle threshold at run time (or dynamically). For example, the controller 1114 or 1202 can be configured to determine the duty cycle threshold periodically and/or continuously, such as approximately every 1 second or less, 30 seconds or less or more, 1 minute or less or more, 10 minutes or less or more, 30 minutes or less or more, 1 hour or less or more, and so on. The duty cycle threshold can be based at least in part on a capacity of the power source 1108 or 1216 and an operational time of the apparatus (e.g., pump system 100 shown in FIG. 57A, and pump systems 1000, 1100, or 1200 shown in FIGS. 60, 61, and 62). As explained above, the pump system can be configured to provide therapy for a predetermined period of time, and deactivate itself a predetermined period of time after an initial activation. For instance, such predetermined period of time (or lifetime threshold) can be between 1 day or less or 10 days or more, such as 7 days (or 168 hours), 10 days (or 240 hours), etc. The power source 1108 or 1216 can be configured or selected to have sufficient capacity to provide sufficient power to the pump system 100, 1000, 1100, or 1200 to operate for at least an amount of time that equals the lifetime threshold. In some embodiments, the apparatus (e.g., via controller 1114 or 1202) can be configured to determine the operational time based on a total elapsed time since an initial activation of the apparatus and disable activation of the source of negative pressure when the operational time reaches the lifetime threshold.

According to some aspects, adjusting the duty cycle threshold may be beneficial for several reasons. In some embodiments, the duty cycle threshold can represent a balance between the desire to provide therapy to the user with none or fewer interruptions and the need to conserve power. For example, in a situation when there is a leak in the system and leak detection is performed based at least partly on monitoring the duty cycle of the pump and comparing the monitored duty cycle to the duty cycle threshold, the pump system 100, 1000, 1100, or 1200 can be configured to provide therapy for a certain period of time before providing an indication to the user that a leak has been detected, which can include deactivating the delivery of therapy. After the leak has been remedied, delivery of therapy can be restarted. However, increasing the duty cycle threshold can advantageously result in fewer interruptions of the delivery of therapy.

In some embodiments, the duty cycle can be calculated (e.g., by controller 1114 or 1202) periodically and/or dynamically during operation of the pump system. As discussed above, in some embodiments, the duty cycle threshold can be calculated based on an estimation and/or calculation of the remaining or residual battery life of the pump system. Duty cycle estimations and/or calculations that are a function of residual battery life are dynamic because battery life decreases during operation of the pump system (absent any battery charge). As a result, estimated and/or calculated duty cycle thresholds will be adjusted as the residual battery life decreases and end of life is being approached. For example, in some embodiments, the energy (for example, expressed in joules) consumed by the pump system can be tracked over a time period to determine the amount of residual battery life at any given time. In some embodiments, the actual energy consumed by the pump system can be tracked, or the estimated number of joules consumed by the pump system can be tracked.

In some embodiments, the duty cycle threshold can be adjusted based on the determination of the residual battery life. For example, suppose that the pump system is configured to operate for 10 days. During the first day, the duty cycle threshold can be conservatively set to a lower value, such as for example 10%, in order to conserve battery life so that the pump system is able to operate for another 9 days. Now suppose that on day 5 of operation, the residual battery life indicates 75% of remaining battery capacity (not 50% remaining capacity as would be expected half-way through the operational period), and suppose that based on the operational history over the first 5 days of operation, it is estimated that the pump system will consume at most 50% of battery capacity over the last 5 days of operation. The estimated energy consumption of the pump system can be determined in various ways, including taking a conservative estimate of the pump system operating in the presence of one or more leaks, which may be severe. In this example, because the estimated remaining battery capacity on day 5 (or 75%) exceeds the estimated capacity needed for pump operation through the end of life (or 50%), the duty cycle threshold can be increased by 25% (to 12.5%) or by another suitable increment. In another example, the duty cycle threshold can be decreased because the remaining battery capacity is below expected capacity due to, for instance, leaks that had been encountered during operation. In certain embodiments, the duty cycle threshold can be set between minimum and maximum values.

In some embodiments, duty cycle threshold (DC) can be determined as follows. This determination can be performed by a controller (e.g., by controller 1114 or 1202). In the following calculations, $T_{predicted,run}$ is the estimated time during which the pump is expected to be active or running (such as in IPD state, MPD state, etc.), $T_{predicted,wait}$ is the estimated time during which the pump is expected to be inactive or idle (such as in monitor state, pause state, etc.), and $T_{residual}$ is remaining amount of time until end of life is reached. $T_{predicted,run}$ can determined as the amount of residual time ($T_{residual}$) the pump system is expected to be active, which can be expressed in terms of the duty cycle threshold as follows:

$$T_{predicted,run} = T_{residual} * DC \qquad (1)$$

$T_{predicted,wait}$ can be determined as the amount of residual time ($T_{residual}$) the pump system is expected to be idle, which can be expressed in terms of DC as follows:

$$T_{predicted,wait} = T_{residual} * (1-DC) \qquad (2)$$

$P_{run}$ and $P_{wait}$ are estimated power consumptions when the pump is running and idle respectively. These values can be determined using one or more of the following techniques: taking into account historical operation of the device, performing a conservative estimate (which, as explained above, can include expecting the system to operate in presence of one or more severe leaks), performing a less conservative estimate (which can include expecting the system to operate in the presence of one or more manageable leaks), and the like. $E_{residual}$ is the estimated residual capacity of the power source, which can be estimated and/or measured. As is shown in the following equation, $E_{residual}$ can also be expressed as the sum of the estimated energy that will be consumed during periods of activity ($T_{predicted,run}$ multiplied by $P_{run}$) and the estimated energy that will be consumed during periods of inactivity ($T_{predicted,wait}$ multiplied by $P_{wait}$).

$$E_{residual} = (T_{residual}*DC*P_{run}) + (T_{residual}*(1-DC)*P_{wait}) \qquad (3)$$

Simplifying equation (3) yields:

$$E_{residual} = T_{residual}*(DC*P_{run} + (1-DC)*P_{wait}) \qquad (4)$$

Dividing equation (4) by $$\frac{E_{residual}}{T_{residual}} = DC*P_{run} + P_{wait} - DC*P_{wait} \qquad (5)$$

Rearranging equation (5) yields:

$$\frac{E_{residual}}{T_{residual}} - P_{wait} = DC*(P_{run} - P_{wait}) \qquad (6)$$

Solving for the duty cycle (DC) yields:

$$DC = \frac{\frac{E_{residual}}{T_{residual}} - P_{wait}}{P_{run} - P_{wait}} \qquad (7)$$

Accordingly, equation (7) can be used to determine the dynamic duty cycle threshold. This determination can be performed periodically.

Additional details of pump system control are disclosed in U.S. Pat. No. 8,734,425, titled "PRESSURE CONTROL APPARATUS," U.S. Pat. No. 8,905,985, titled "SYSTEMS AND METHODS FOR CONTROLLING OPERATION OF A REDUCED PRESSURE THERAPY SYSTEM," and U.S. Patent Publication No. 2015/0051560, titled "CONTROLLING OPERATION OF A REDUCED PRESSURE THERAPY SYSTEM BASED ON DYNAMIC DUTY CYCLE THRESHOLD DETERMINATION," which are incorporated by reference in their entireties as if made part of this disclosure.

In some embodiments, the pressure during the IPD or MPD state can be sampled after a preset period of time as elapsed from when the IPD or MPD state was initiated. After this time period elapses, the pressure can be sampled in consecutive samples, and two or more of the consecutive samples can be averaged. In some embodiments, sampling of the pressure can be synchronized with the drive signal. For example, sampling of the pressure within the pump system or some portion thereof, such as a fluid flow path between a source of negative pressure and a wound dressing, can be performed when the drive signal is approximately at an amplitude that is substantially at an offset (explained below) and/or at a zero value. In some embodiments, two or more groups of consecutive pressure samples can be averaged to minimize measurement errors due to pressure fluctuations caused by operation of the motor. In some embodiments, averaging two or more groups of consecutive pressure samples can compensate for the time needed to detect the zero value when the pressure samples are synchronized at a zero value. Movement of the pump assembly can highly influence pressure within the pump system, such as a manifold of the pump system. By synchronizing sampling of the pressure with the offset and/or zero value of the drive signal, any measurement errors due to pressure fluctuations caused by operation of the motor can be reduced. In some embodiments, sampling of the pressure can be synchronized with the local maxima and/or local minima of the drive signal. In some embodiments, sampling of the pressure can be synchronized with certain portions of the drive signal, such as portions of the drive signal with a negative rate of change and/or a positive rate of change.

In some embodiments, the pressure can be sampled one or more times at or around the one or more selected sampling amplitudes such as the offset and/or zero value, local maxima, and/or local minima. This can beneficially reduce the likelihood of sampling errors and compensate for the delay elapsed between detection of the one or more selected sampling amplitudes and sampling of the pressure. For example, in some embodiments, the pump system can take 8 consecutive samples at approximately each offset and/or zero value. Accordingly, the pump system can take 16 samples over a single period of the drive signal. In some embodiments, the pump system can average some or all of the samples taken over a period.

Pump Actuation and Control

In any embodiments disclosed herein, the performance and efficiency of the pump can be improved by selecting a suitable signal or waveform for driving the actuator (e.g., coil 600 of the pump system 100). A suitable driving waveform can be applied to the coil by the controller (e.g., controllers 1006, 1114 and/or driver module 1220). In any embodiments disclosed herein, the pressure differential across a diaphragm and the outlet valve of a pump (e.g., diaphragm 550 of pump system 100) when the diaphragm is drawing against vacuum (or removing gas from the fluid flow pathway) can be determined as the sum of the pressure drop across the valves and the vacuum level under the dressing. For example, in any embodiments disclosed herein, the negative pressure range can be approximately −80 mmHg, which means that the vacuum level of up to 80 mmHg can affect the pressure drop across the diaphragm. When the diaphragm is expelling removed fluid (e.g., expelling removed gas to the atmosphere), the pressure differential across the diaphragm and the outlet valve can be determined as the pressure drop across the valves. In other words, when gas is being expelled, the pressure differential across the diaphragm and the outlet valve is substantially equivalent to the pressure drop across the valves.

In any embodiments disclosed herein, the force for expelling removed gas can be smaller than the force for drawing vacuum (e.g., removing gas from the fluid flow pathway). If a symmetric signal, such as a square wave or sine wave of equal positive and negative amplitude is applied to the coil, the diaphragm may oscillate about a point that is not its relaxed center state, which may reduce the total diaphragm travel, thereby reducing efficiency.

Figure 65:
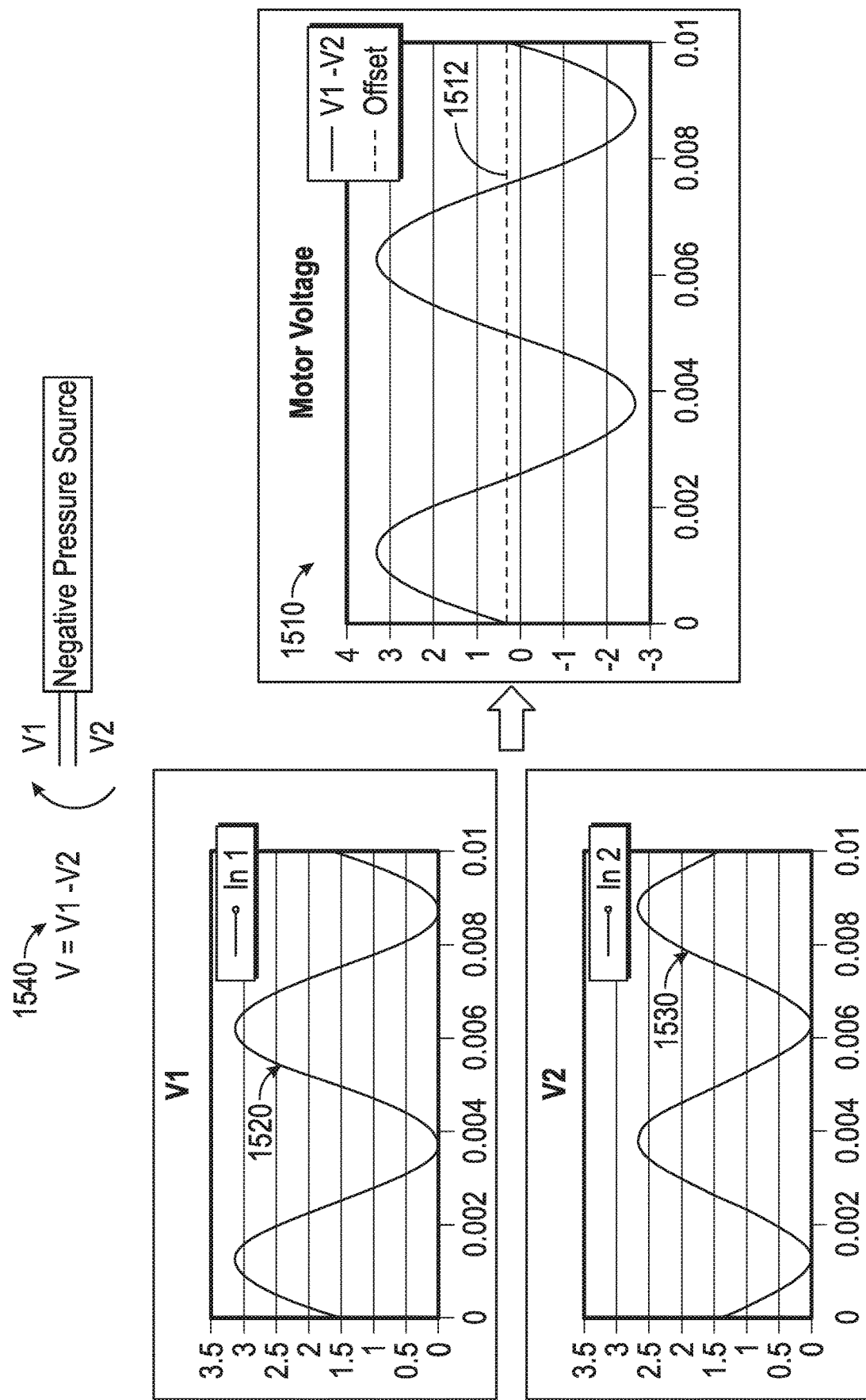
FIG. 65 is an exemplary drive signal for a source of negative pressure according to some embodiments.

FIG. 65 represents an exemplary drive signal for a source of negative pressure according to some embodiments. In any embodiments disclosed herein, a diaphragm can be driven by an offset sinusoidal (or sine) drive signal 1510. For example, the drive signal can be applied to the actuator of the pump, such as coil 600, thereby causing the diaphragm to flex and deflect. FIG. 65 illustrates an offset sine waveform 1510 that can be applied to the actuator according to some embodiments. The x-axis represents time and the y-axis represents amplitude, such as voltage. Although the illustrated amplitude of the sine wave 1510 is the voltage, current can be used for driving the diaphragm.

The sine wave 1510 is offset from 0 V as is shown by line 1512, which is about 0.4 V. Any suitable offset can be used, such as 0.05 V, 0.1 V, 0.65 V, etc. The offset can also be negative. As will be described in further detail below, in some embodiments, the offset can be variable depending on operating conditions of the pump system, such as the current and/or desired pressure in the pump system or some portion thereof. The sine wave 1510 can be a signal of a suitable magnitude, such as between −2.7 V and 3.3 V as illustrated in sine wave 1510. In any embodiments disclosed herein, other suitable magnitudes of voltage can be used, such as between −1.0 V and 1.0V, −2.0 V and 2.0 V, −4.0 V and 4.0 V, and so on. As will be described in further detail below, in some embodiments, the magnitude can be variable depending on operating conditions of the pump system, such as the current and/or desired pressure in the pump system or some portion thereof. In some embodiments, the resonance frequency of the diaphragm and/or other oscillating components of the pump assembly can be matched during operation of the pump system by modifying the offset and/or magnitude of the drive signal during operation. For example, in some embodiments, the drive signal offset and/or magnitude can be continuously modified such that the drive signal oscillates the diaphragm and/or other oscillating components of the pump assembly at the resonant frequencies that are associated with the negative pressure being delivered. For example, in some embodiments, the drive signal can be continuously modified during the IPD state until a target low pressure threshold is satisfied or exceeded. In some embodiments, the drive signal can be similarly continuously modified during the MPD state until a target low pressure is again satisfied or exceeded. By modifying the drive signal offset and/or magnitude during operation, the pump can be advantageously made more efficient and quiet during operation. The sine wave 1510 can be of a suitable frequency, such as approximately 200 Hz as illustrated in sine wave 1510. In some embodiments, other suitable frequencies can be used, such as from approximately 50 Hz to approximately 200 Hz, or from approximately 25 Hz or less to approximately 300 Hz or more. Other frequencies can be used, such as frequencies below 50 Hz and above 200 Hz.

In any embodiments disclosed herein, driving the diaphragm with a sine wave signal, such as the offset sine wave 1510 can increase the efficiency of the negative pressure source. For example, because the sine wave 1510 has a single frequency, that frequency can stimulate a single vibrational or resonance mode of the pump (e.g., the first vibrational mode of the pump is stimulated provided that the other modes have a higher natural or resonant frequency). Efficiency can be optimized if the pump moves or resonates at a single frequency. For instance, the axial spring stiffness of the diaphragm and the offset of the sine wave can be optimized for greater efficiency. In addition, little or no driving energy may be absorbed by components other than the diaphragm, such as rubber components.

In any embodiments disclosed herein, non-offset sine wave drive signals can be used. In various embodiments, other periodic signals such as cosine waves, tangent waves, square, triangular waves, sawtooth waves, pulse duration modulated waveform, and the like can be used to drive the diaphragm. Signals driving the diaphragm can be symmetrical or asymmetrical and/or offset or not offset. In some embodiments, non-periodic driving signals can be used.

With continued reference to the exemplary drive signal of FIG. 65, in some embodiments, the sine wave 1510 can be generated via a combination of one or more other waves. As shown in the illustrated embodiment, two 180 degree phase shifted sine waves 1520 and 1530 can be combined to generate the sine wave 1510. The sine waves 1520 and 1530 can have different amplitudes, such as peak-to-peak amplitudes. In any embodiments disclosed herein, sine wave 1530 can be subtracted from sine wave 1520 and applied to the source of negative pressure, such as an actuator, as illustrated by schematic 1540. In any embodiments disclosed herein, the sine waves 1520 and 1530 can be phase shifted with respect to each other with any suitable phase shift value selected from the range between 0 and 360 degrees. In various embodiments, sine waves 1520 and 1530 can be combined in any linear or non-linear manner.

Figure 66:
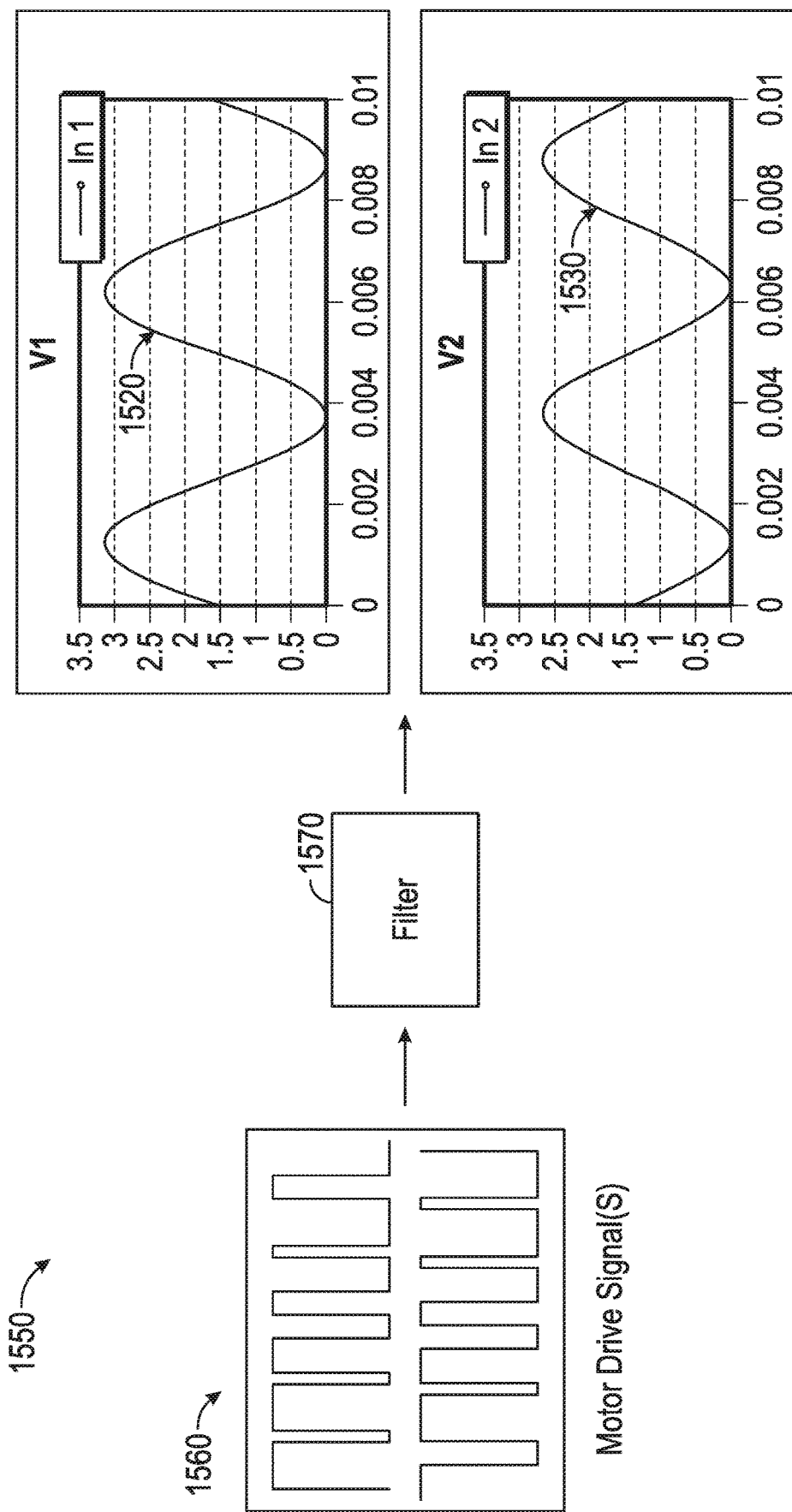
FIG. 66 is a schematic illustrating the generation of a drive signal according to some embodiments.

FIG. 66 illustrates generation of the drive signals, such as the sine waves 1520 and 1530 illustrated in FIG. 65, according to some embodiments. One or more PWM drive signals 1560 can be generated by a controller 1550 (e.g., controllers 1006, 1114 and/or driver module 1220). These PWM drive signals, which can be represented as a combination of square waves at different frequencies, are filtered by a filter 1570, which can be a low-pass filter. The filter 1570 can be configured to filter out all but one frequency component of the PWM drive signals. In any embodiments disclosed herein, filtering the one or more PWM drive signals 1560 can produce the sine waves 1520 and 1530. As shown in the illustrated embodiment, two PWM drive signals 1560 (illustrated as top and bottom signals) can be used to produce the sine waves 1520 and 1530 respectively. Each of the PWM drive signals 1560 can be a signal having appropriate characteristics, such as amplitude, for generating the respective sine wave signal 1520 or 1530.

In any embodiments disclosed herein, the voice coil actuator or motor can be used as the filter 1570. The voice coil motor can behave as a resonant circuit, such as an LC or RLC circuit, that has low-pass filter characteristics. In one embodiment, the motor can have the following characteristics: resistance R=20Ω, inductance L=1 mH, and time constant τ=50 μs. In any embodiments disclosed herein, a suitable separate filter 1570 can be used. In certain embodiments, the filter 1570 can have high pass, band pass, band stop, and/or notch characteristics. In any embodiments disclosed herein, the sine wave 1510 can be generated directly from the one or more PWM signals.

Calibration of Pump Actuation Parameters

In any embodiments disclosed herein, one or more parameters of the drive signal, such as sine wave 1510, can be varied based on the current and/or desired operating conditions of the pump system. For example, in some embodiments, parameters such as the offset and/or amplitude of the drive signal can be varied. Such parameters can be varied based on the current and/or desired pressure for the pump system or some portion thereof, such as a fluid flow path between a source of negative pressure and a wound dressing. As explained below, varying the parameters of the drive signal can increase efficiency of the pump system, reduce power consumption, and reduce noise generated by the components of the negative pressure source.

In some embodiments, the parameters can be varied to reduce the likelihood of or eliminate contact between components of the pump assembly, such as contact between components of a voice coil actuator, such as a support, shaft, or piston, with mechanical stops such as a mechanical stop at top dead center ("TDC"), where the diaphragm chamber can be at or near a minimum volume, and bottom dead center ("BDC"), where the diaphragm chamber can be at or near a maximum volume. As the vacuum increases, the offset can be biased more towards BDC and the amplitude may be increased since the piston will exhibit a lesser degree of movement for a given amplitude at higher vacuum conditions. In some embodiments, the diaphragm can be initially biased towards BDC via components of the pump assembly, such as spring, such that the offset for the drive signal can be towards TDC at ambient or atmospheric pressures and reduce in magnitude as the pressures higher negative pressures. By reducing contact between components of the pump assembly, noise, vibration, and harshness of the pump assembly can also be reduced. Moreover, by varying the parameters of the drive signal, the flow through the pump assembly can be maintained at a desired level.

In some embodiments, the parameters can be varied to alter the rate of pressure decay when the pump assembly is activated. For example, the parameters can be varied such that the rate of pressure decay is generally linear.

In any embodiments disclosed herein, the pump system can determine (using the controller) and store (in memory) one or more parameters for the drive signal. For example, the pump system can determine and store an offset and/or amplitude for one or more target pressures. In some embodiments, the pump system can store an offset and amplitude at three target pressures. For example, the pump system can determine and store an amplitude and offset at or around 0 mmHg, at or around −71 mmHg (−9.5 kPa), and at or around −94 mmHg (−12.5 kPa). In some embodiments, these pressures are selected because 0 mmHg corresponds to the initial pressure in the system, −71 mmHg is around the high pressure threshold in the monitor mode 1350 (as explained above), and −94 mmHg is around the low pressure threshold in the monitor mode 1350 (as explained above).

The pump system can determine and store amplitudes and/or offsets at other target pressures, such as at or around −67 mmHg (−9.0 kPa). In some embodiments, the pump system can determine and store amplitudes and/or offsets for pressures corresponding to at or around ambient pressure and at or around pressure thresholds, such as the low pressure threshold and the high pressure threshold. For example, the pump system can determine and store amplitudes and offsets for pressures corresponding to ambient pressure, a negative pressure less than the high pressure threshold and a negative pressure greater than the low pressure threshold. In some embodiments, the pump system can determine and store amplitudes and/or offsets for pressures outside of the normal operating range during a maintenance mode, such as maintenance mode 1350.

The pump system can determine and store an offset and/or amplitude at fewer or greater target pressures as desired. For example, in some embodiments, the pump system can determine and store an offset and/or amplitude at 5 target pressures. Moreover, the pump system can determine and store an offset and/or amplitude at different pressures from those listed as may be desired. For example, storing an offset and/or amplitude at a greater number of pressures can result in a more efficient pump system.

In some embodiments, the pump system can also determine and store an amplitude and/or offset at a negative pressure value greater than the typical operating range for the pump system. For example, the pump system can determine and store an amplitude and/or offset at or around −218 mmHg (−29 kPa). The stored amplitude and/or offset at or around −218 mmHg can be equal to or less than the stored amplitude and/or offset at the upper operating negative pressure range for the pump system, such as −94 mmHg. In storing such an amplitude and/or offset at a higher negative pressure, the flow through the pump system at higher negative pressures can be reduced and thereby reduce the likelihood of damage to components of the pump system.

In any embodiments disclosed herein, the pump system can determine or calculate one or more parameters of the drive signal based on operating conditions of the pump, such as the current and/or desired negative pressure. For example, the pump system can calculate an offset and/or amplitude for the drive signal. In some embodiments, the pump system can calculate the offset and/or amplitude for the drive signal based at least on part on the stored parameters in the pump system. This can beneficially reduce the total number of parameters stored on the pump system thereby reducing the amount of memory needed in the pump system. Moreover, as will be discussed in further detail below, this can also reduce the time needed to calibrate the pump. In some embodiments, the pump system can interpolate between two or more of the stored parameters. For example, the pump system can interpolate, such as linearly interpolate, between two or more of the stored parameters. Other types of interpolation can also be used, such as polynomial and spline interpolation. The pump system can use other algorithms for calculating one or more parameters for the drive signal. A combination of such techniques can also be used.

Figure 67:
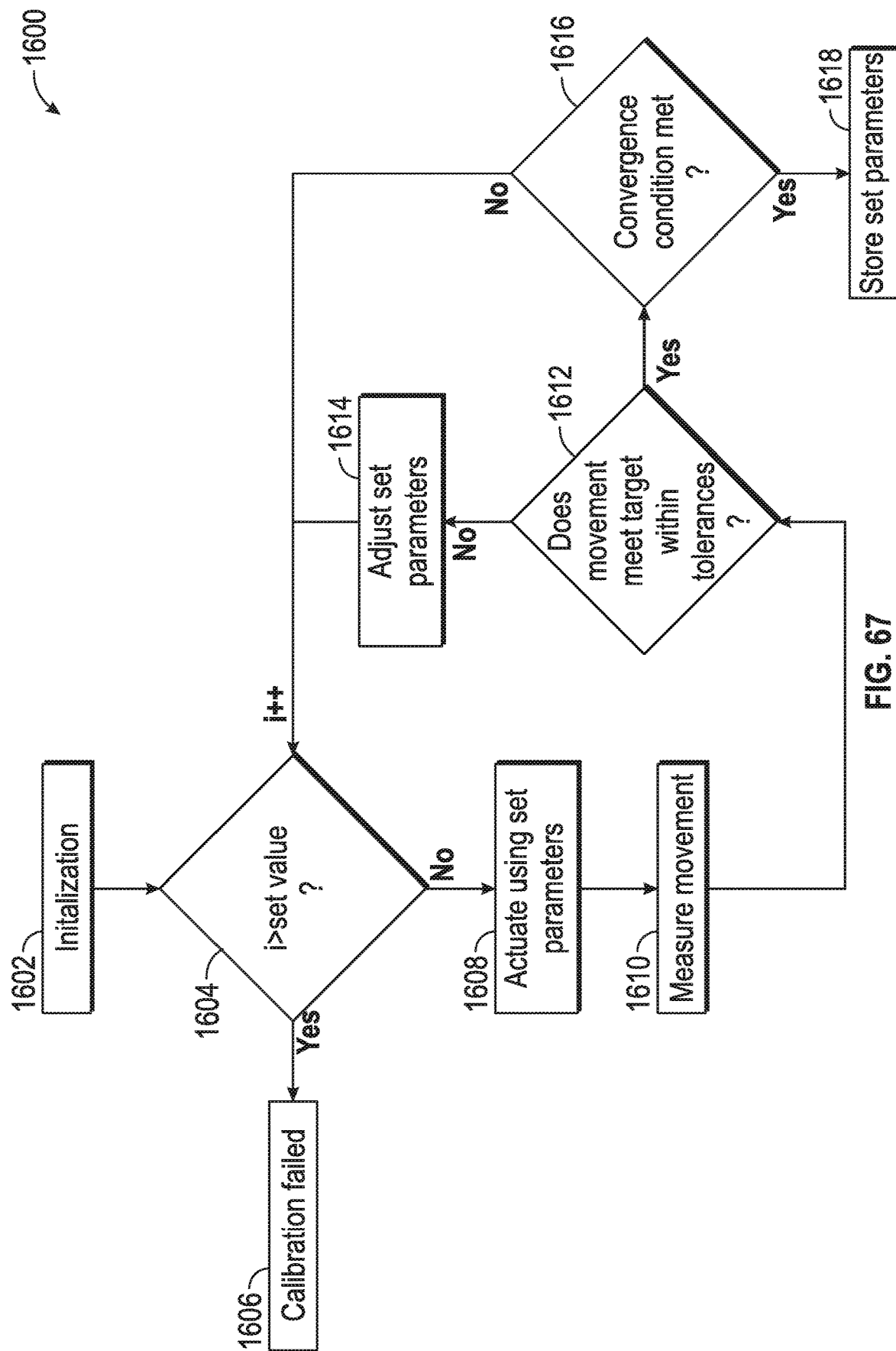
FIG. 67 is an embodiment of a calibration method for generating parameters of a drive signal.

FIG. 67 illustrates a calibration process or method 1600 for obtaining one or more parameters of the drive signal according to some embodiments. In some embodiments, the one or more parameters stored in the pump system can be based on performance of the pump system during such calibration. The calibration can be performed during manufacturing or production after the pump assembly of the pump system has been partially or fully assembled. Calibration can be particularly beneficial for pump assemblies with low manufacturing or assembly tolerances, such as small-scale pumps including small-scale voice coil pumps which are described herein. For example, minor variances during manufacture and installation can potentially significantly alter the optimal parameters between a first pump assembly and a second pump assembly. Accordingly, calibration can significantly enhance the efficiency of such pump systems. The calibration method 1600 can be used to calibrate any of the pump embodiments disclosed herein.

In some embodiments, calibration of the pump system can be performed by a calibration system, which can implement the process 1600. The calibration system (not shown) can include components such as, but not limited to, a pneumatic chamber for applying pressure, one or more sensors for measuring movement of one or more components of the pump system, memory, controller, input and output interfaces, and the like. Calibration can beneficially be used to ensure that a source of negative pressure within the pump system is operating at or near its maximum efficiency for one or more target pressures. Moreover, calibration can also be beneficial for ensuring that components of the source of negative pressure do not contact mechanical stops, thereby preventing wear and tear, malfunction and reducing noise and vibration. With respect to some sources of negative pressure, such as diaphragm pumps having a piston assembly for moving a diaphragm, the force applied to the diaphragm can result in different levels of movement based on the pressure within the pump. Accordingly, the amount of force applied at different pressures should be varied to reduce or eliminate the likelihood that components of the pump, such as the piston assembly, will contact mechanical stops which can cause noise, vibration, and harshness.

As shown in the illustrated embodiment, when the calibration is first performed on the pump system, the calibration system can perform an initialization step 1602. During the initialization step 1602, the calibration system can reset a calibration attempts counter (e.g., setting the counter to a value such as 0, 1, or any other value as desired). During the initialization step 1602, the calibration system can generate an initial set of parameters for a drive signal to apply to a pump assembly of the pump system being calibrated. The initial set of parameters, such as an initial offset, initial amplitude and/or initial frequency, can be based on a preset values for the pressure being calibrated. In some embodiments, the initial set of parameters can also be based on the performance of the pump system for previously calibrated pressures. In some embodiments, the initial set of parameters can also be set by the user. This can advantageously reduce the amount of time needed to calibrate the pump system. In some embodiments, the calibration system can test the polarity of the pump system and adjust the parameters accordingly. This can beneficially account for any reversals in polarity during the assembly process.

In some embodiments, during the initialization step 1602, the calibration system can measure one or more positions of components of the pump including, but not limited to, a piston assembly of the pump assembly. For example, the calibration system can measure one or more positions of a support such as support member 650, a shaft such as shaft 700, a coil such as coil 600, and/or a diaphragm such as diaphragm 550. In some embodiments, such as those involving a pump system having a single translational degree of freedom including, but not limited to, pump systems utilizing a voice coil actuator, the calibration system can measure the position of the one or more components when the pump assembly is inactive ("rest"), the position of the one or more components when at a first end for those components ("top dead center"), and/or the position of the one or more components is at the opposite end for those components ('bottom dead center"). In some embodiments, the calibration system can set the coordinate system such that a zero position is the average point between the top dead center and bottom dead center with the top dead center being a positive value and the bottom dead center being a negative value.

With reference next to step 1604, the calibration system can determine whether the system should attempt to perform the calibration. In some embodiments, the calibration system can be configured such that the system will perform only a certain number of calibration attempts. This can advantageously prevent or reduce the likelihood that the calibration system will expend significant time and resources in attempting to calibrate the pump system. In some embodiments, the number of calibration attempts can be a preset number. In some embodiments, the number of calibration attempts can be set by the user. In some embodiments, the number of calibration attempts can be variable and can be based on performance of the pump system for previously calibrated pressures.

As shown in the illustrated embodiment in FIG. 67, the calibration system can determine whether the counter is greater than a set value of calibration attempts. If the counter is greater than to the set value of calibration attempts, the calibration system can determine that the calibration has failed as shown in step 1606 and the process 1600 terminates. In some embodiments, the calibration can provide a user with an indication that the calibration has failed such as via a visual and/or audio indicator. If the counter is less than or equal to the set value of calibration attempts, the system can transition to step 1608.

With reference to step 1608, in some embodiments, the calibration system can actuate one or more components of the pump system using the set parameters. For example, the calibration system can actuate a coil of a voice coil actuator with a set frequency, offset, and/or amplitude. In some embodiments, the calibration system can continue to actuate one or more components of the pump system for one or more periods or a set duration of time to help ensure that the pump system has reached a relatively steady state.

With reference to step 1610, the calibration system can measure movement of one or more components of the pump system while the pump system is being actuated in accordance with step 1608. For example, the calibration system can measure one or more positions of a support such as support member 650, a shaft such as shaft 700, a coil such as coil 600, and/or a diaphragm such as diaphragm 550. In some embodiments, such as those involving a pump system having a single translational degree of freedom including, but not limited to, pump systems utilizing a voice coil actuator, the calibration system can measure a linear position of the one or more components. In some embodiments, the calibration system can begin to measure movement of the pump system after a set number of periods or a set duration of time. This can beneficially help to ensure that the pump system has reached a relatively steady state prior to taking measurements of the device.

Figure 68:
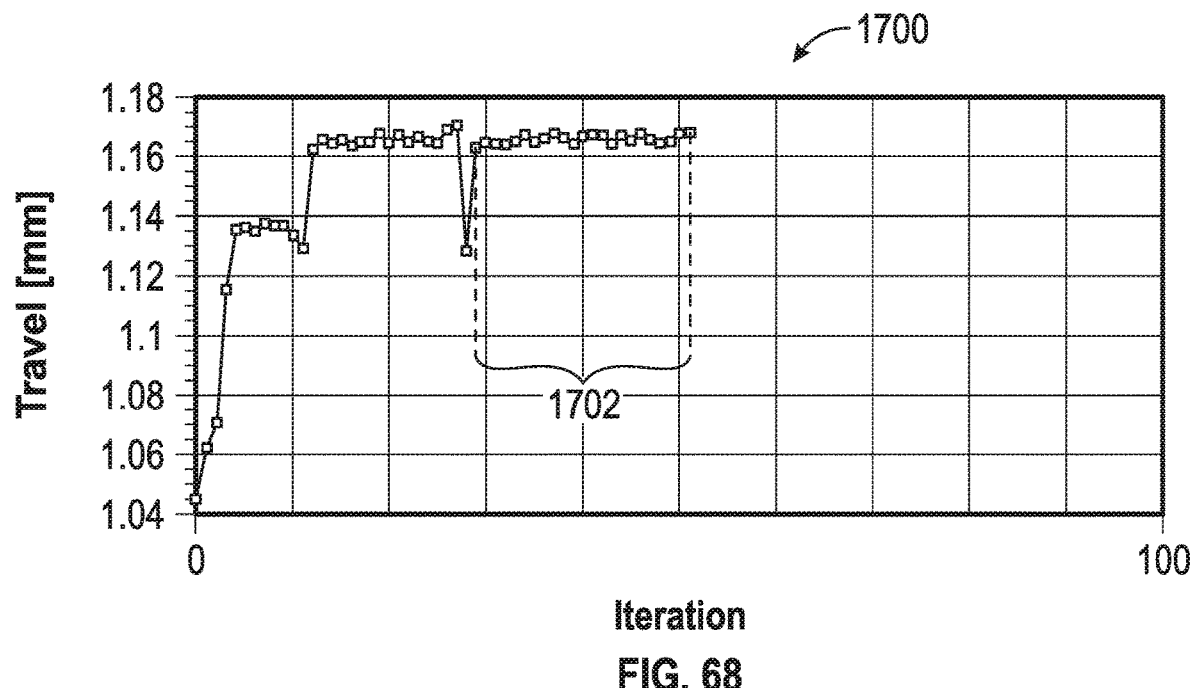
FIG. 68 is an exemplary travel versus iteration graph according to some embodiments.
Figure 69:
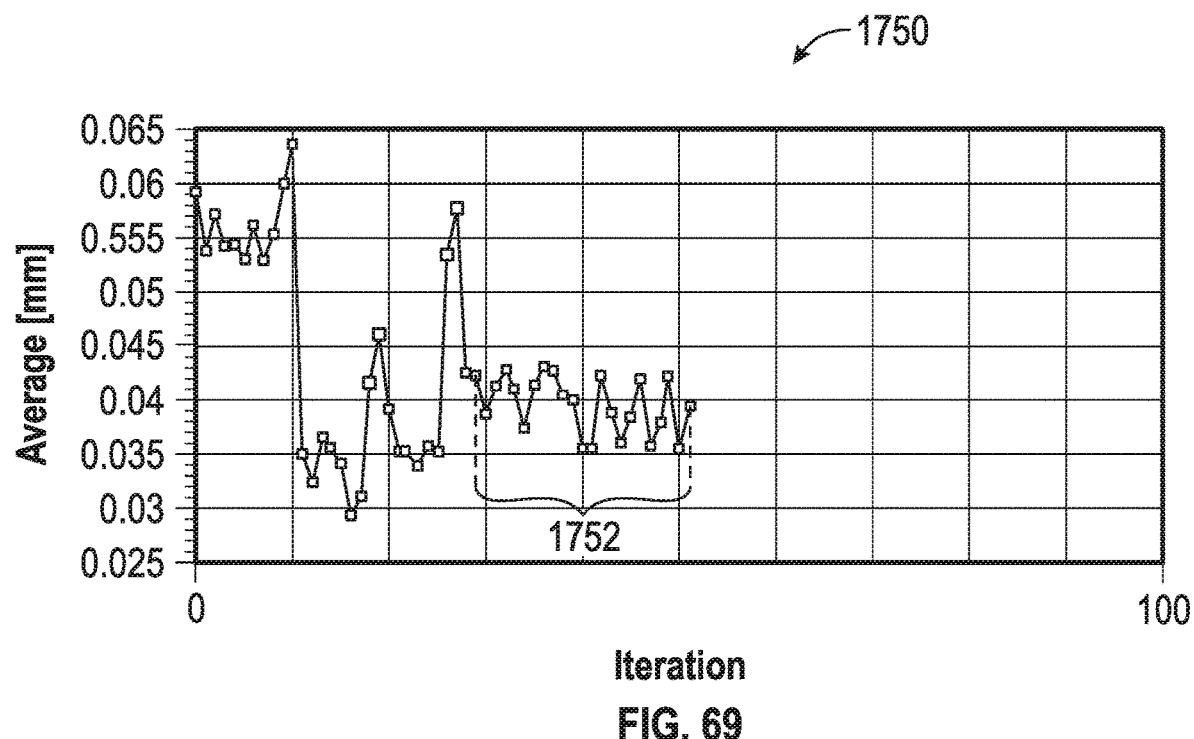
FIG. 69 is an exemplary average position versus iteration graph according to some embodiments.

During step 1610, the calibration system can calculate one or more dimensions based on the measured movement of the one or more components of the pump system. For example, the calibration system can calculate a travel and/or average position of one or more components. In some embodiments, the travel can be based on a linear distance between a high position (i.e., the highest positive position value measured) and a low position (i.e., the highest negative position value measured) of the one or more components. An exemplary graph 1700 of travel over multiple iterations is illustrated in FIG. 68 with the x-axis being the iteration and the y-axis being the calculated travel. The high position and the low position can be an average position values based on two or more periods of calibration or can be the maximum and minimum position values measured. An exemplary graph 1750 of average position over multiple iterations is illustrated in FIG. 69 with the x-axis being the iteration and the y-axis being the calculated average position. In some embodiments, the calibration system can calculate additional or alternative parameters based on the measure movement or some other characteristic of the pump system, such as expelled fluid volume, flow rate, etc.

During step 1612, the calibration system can determine whether the measured movement of the one or more components of the pump system meets a target value within a desired tolerance. For example, the calibration system can determine whether the calculated travel and/or the average position of the one or more components of the pump system meets a target value for travel within a tolerance of 10%. The target value and/or tolerance can be a preset value based on the specific pressure being calibrated. In some embodiments, the tolerance can be between approximately 0.1% to approximately 20%, between approximately 0.5% to approximately 10%, between approximately 1% to approximately 5%, approximately 2%, any sub-range of the following ranges, and/or any other tolerance as desired. In some embodiments, the target value and/or the desired tolerance can be set by the user. In some embodiments, the tolerances can be the same for the travel and average position parameters. In some embodiments, the tolerances can be different.

In some embodiments, such as those involving a pump system having a single translational degree of freedom including, but not limited to, pump systems utilizing a voice coil actuator, the target value and/or tolerances can be chosen such that components of the pump assembly, such as a piston assembly, do not contact the mechanical stops or at least has a reduced likelihood of contacting the mechanical stops.

If the calibration system determines that the measure movement of the one or more components of the pump system do not meet the target value within a desired tolerance, the calibration system can transition to step 1614 and adjust the set parameters, such as the offset and/or amplitude. In some embodiments, the adjustments to the set parameters can be based at least in part on the previous measurements and calculations. The calibration system can then transition back to step 1604. In some embodiments, the calibration system can increase the counter by one.

If the calibration system determines that the measure movement of the one or more components of the pump system meet the target value within a desired tolerance, the calibration system can transition to step 1616 and determine whether a convergence condition has been met. In some embodiments, the convergence condition can include meeting the target value within a desired tolerance for a set number of iterations. In some embodiments, the convergence condition can include a condition that the calculated travel satisfies a target travel within tolerances for one or more iterations as shown, for example, in region 1702 of FIG. 68. In some embodiments, the convergence condition can include a condition that the calculated average position meeting a target average position within tolerances for one or more iterations as shown, for example, in region 1752 of FIG. 69. In some embodiments, the convergence condition can include that two or more conditions be satisfied substantially simultaneously or simultaneously. If the convergence condition has been met, the calibration system can transition to step 1618 and store the set parameters in the pump system, such as in memory. In step 1618, the process 1600 terminates successfully. If the convergence condition has not been met, the calibration system can transition to step 1604. In some embodiments, the calibration system can increase the counter by one.

In some embodiments, the process 1600 can be repeated for each target pressure in the set of target pressures (such as three target pressures as described above). For each target pressure in the set, parameters can be determined and stored. When the pump system is activated by the user to provide negative pressure wound therapy, stored parameters can be utilized in order to determine how to drive the negative pressure source. For example, when an offset sinusoidal signal is used for driving the actuator, such as the voice coil motor, stored parameters are used to determine the offset and amplitude of the sinusoidal signal in order to achieve a target pressure. When a particular target pressure does not coincide with any of the target pressures in set for which parameters have been determined (through calibration) and stored, the pump system can determine parameters for achieving the particular target pressure by interpolation, such as linear interpolation. In some embodiments, the stored parameters can be combined in any suitable linear or non-linear manner in order to calculate parameters for achieving the particular target pressure.

Filter Blocked Determination

Figure 70:
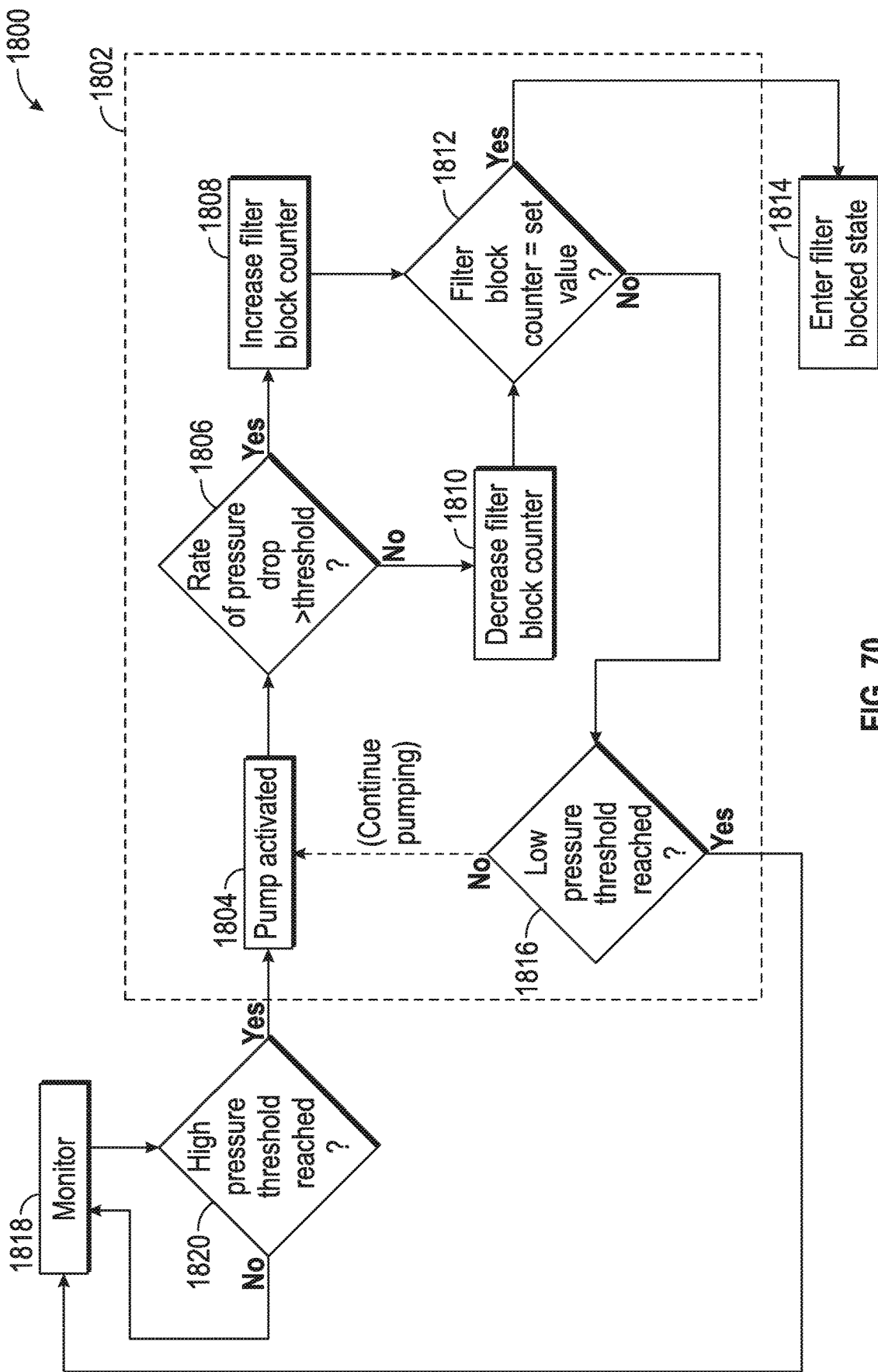
FIG. 70 is an embodiment of a method for determining a filter blockage.

FIG. 70 illustrates a process or method 1800 for determining whether a filter blockage is present in a pump system according to some embodiments. The process 1800 can be implemented by the controller of a pump system, such as controllers 1114, 1202, and the process 1800 can be implemented as part of executing the state diagram 1300. The method 1800 can be used to determine the existence of a filter blockage for any of the pump embodiments disclosed herein. In some embodiments, it can be advantageous to alert the user if a filter blockage has occurred so that the user can take remedial actions to relieve the blockage. For example, in embodiments where the filter is contained within a wound dressing, a filter blockage may be triggered if the wound dressing is at or nearing capacity for storing wound exudate and requires replacement. In some embodiments, the rate of execution of the method 1800 can be based on (or be the same as) the pressure sampling rate for the pump system. In other embodiments, the method 1800 can be performed at a rate different from the pressure sampling rate for the pump system.

Transition of the pump system to an active state, such as the IPD state 1314 or the MPD state 1354 is illustrated in FIG. 70 by the active state 1802. Upon transitioning to the active state 1802, the pump system can activate a source of negative pressure, such as a pump assembly as shown in step 1804.

In some embodiments, while the pump assembly is in the active state 1802, the pump system can intermittently and/or continuously monitor the pressure within the pump system or some portion thereof, such as a fluid flow path between a source of negative pressure and a wound dressing. Based on the measured pressure within the pump system or some portion thereof, the pump system can calculate a rate of pressure change based on a difference between two or more pressure values and the amount of time between the measurements. As shown in the illustrated embodiment, the process 1800 can transition from step 1804 to step 1806, where the process 1800 can determine whether the calculated rate of pressure change or drop exceeds a threshold value. For example, the threshold value can be approximately −50 mmHg/second (6,750 Pa/s). The threshold value can be between approximately −20 mmHg/second and approximately −200 mmHg/second, between approximately −40 mmHg/second and approximately −100 mmHg/second, between approximately −50 mmHg/second and approximately −75 mmHg/second, approximately −70 mmHg/second, any value or subrange within these ranges, or any other threshold as desired.

The threshold value can be calculated based on the volume of the fluid flow pathway between the source of negative pressure and the wound dressing, such as the manifold (e.g., manifold 300 of pump system 100) and conduit (e.g., conduits 904, 906), the volume of the wound dressing, and the flow rate of the source of negative pressure. For a given flow rate of the source of negative pressure, the rate of pressure change within the fluid flow path between the source of negative pressure and the wound dressing would vary depending on the amount of exudate or other incompressible fluids within the wound dressing. As the amount of exudate or other incompressible fluids within the wound dressing increases, the rate of pressure change within the fluid flow path would increase as a result of the reduced volume of compressible fluids within the wound dressing. Accordingly, it is possible to estimate the remaining capacity of the wound dressing based on the calculated rate of pressure change. As such, it is possible to estimate the remaining capacity without use of other sensors, such as a dressing sensor, flow sensor, and the like. The threshold value can be set at or around the rate of pressure change exhibited by a wound dressing at or near capacity.

Should the process 1800 determine that the rate of pressure change satisfies (e.g., exceeds) the threshold rate, the process 1800 can transition from step 1806 to step 1808 and increase the value of a filter block detection counter. In some embodiments, the process 1800 can increase the value of the counter by 1 although any other value can be used. Moreover, in some embodiments, the increase in value of the counter can be based on other factors, such as the calculated rate of pressure drop.

In some circumstances, it is possible that the calculated rate of pressure change or drop can greatly exceed the threshold rate of pressure change. For example, in circumstances where the conduit is kinked or blocked proximate the manifold, the rate of pressure change can be significant. It can be advantageous to differentiate between such a transient blockage condition and a more permanent filter blocked condition. As such, in some embodiments, when the process 1800 determines that a calculated rate of pressure change exceeds a maximum rate of pressure change, the process 1800 may not increase the counter and/or may provide a different indication to the user. In some embodiments, the maximum rate can be equal to or greater than approximately 110% of the threshold rate, equal to or greater than approximately 120% of the threshold rate, equal to or greater than approximately 130% of the threshold rate, equal to or greater than approximately 140% of the threshold rate, equal to or greater than approximately 150% of the threshold rate, or any other percentage of the threshold rate.

When the process 1800 determines that the rate of pressure change does not satisfy (e.g., does not exceed) the threshold rate, the process 1800 can advance to step 1810 and, in some embodiments, decrease the value of the counter. In some embodiments, the process 1800 can decrease the value of the counter by 1 although any other value can be used. For example, the process 1800 can reset the counter to its initial value, such as 0, 1, or any other suitable value. In some embodiments, the decrease in value of the counter can be based on other factors, such as the calculated rate of pressure drop. In some embodiments, the process 1800 can ensure that the value of the counter does not decrease below the initial value, such as 0.

During step 1812, the process 1800 can determine whether the counter has reached a set value that represents a threshold number of times that the rate of pressure change has satisfied the threshold rate. The set value can be a preset value from the factory, can be a variable value based on other parameters of the pump, or can be set by the user. In some embodiments, the set value can beneficially be set to a value higher than 1. A value higher than 1 can be advantageous as it can reduce the likelihood of a false positive which may be caused by a factor other than a filter blockage, such as an outlier pressure reading, a kink in the conduit located in the fluid flow path between the pump system and the wound dressing, or other similar factors. If the process 1800 determines that the counter satisfies the set value (e.g., is equal to the set value), the process 1800 can transition to a filter blocked state 1814. In some embodiments, in state 1814, the pump system can perform the operations discussed in connection with state 1318 discussed in connection with FIG. 63.

If the process 1800 determines that the counter does not satisfy the set value (e.g., is smaller than the set value), the process 1800 system can transition to step 1816 where it determines whether the pressure within the pump system or some portion thereof is at or near a low pressure threshold. If not, the process can continue to maintain the pump in an active state and transition to step 1804. If the process 1800 determines that the pressure within the pump system or some portion thereof is at or near a low pressure threshold, the process 1800 can transition to the monitor state 1818, which can be the same as or similar to the monitor state 1352 discussed in connection with FIG. 63. Accordingly, in some embodiments, the pump system can deactivate the pump and monitor the pressure within the pump system or some portion thereof. As is explained above, the process 1800 can transition to step 1820 where it determines if the pressure within the pump system or some portion thereof is at or near a high pressure threshold. In case that the pressure has reached the high pressure threshold, the process 1800 can then proceed to step 1804 and perform operations explained above.

Figure 71:
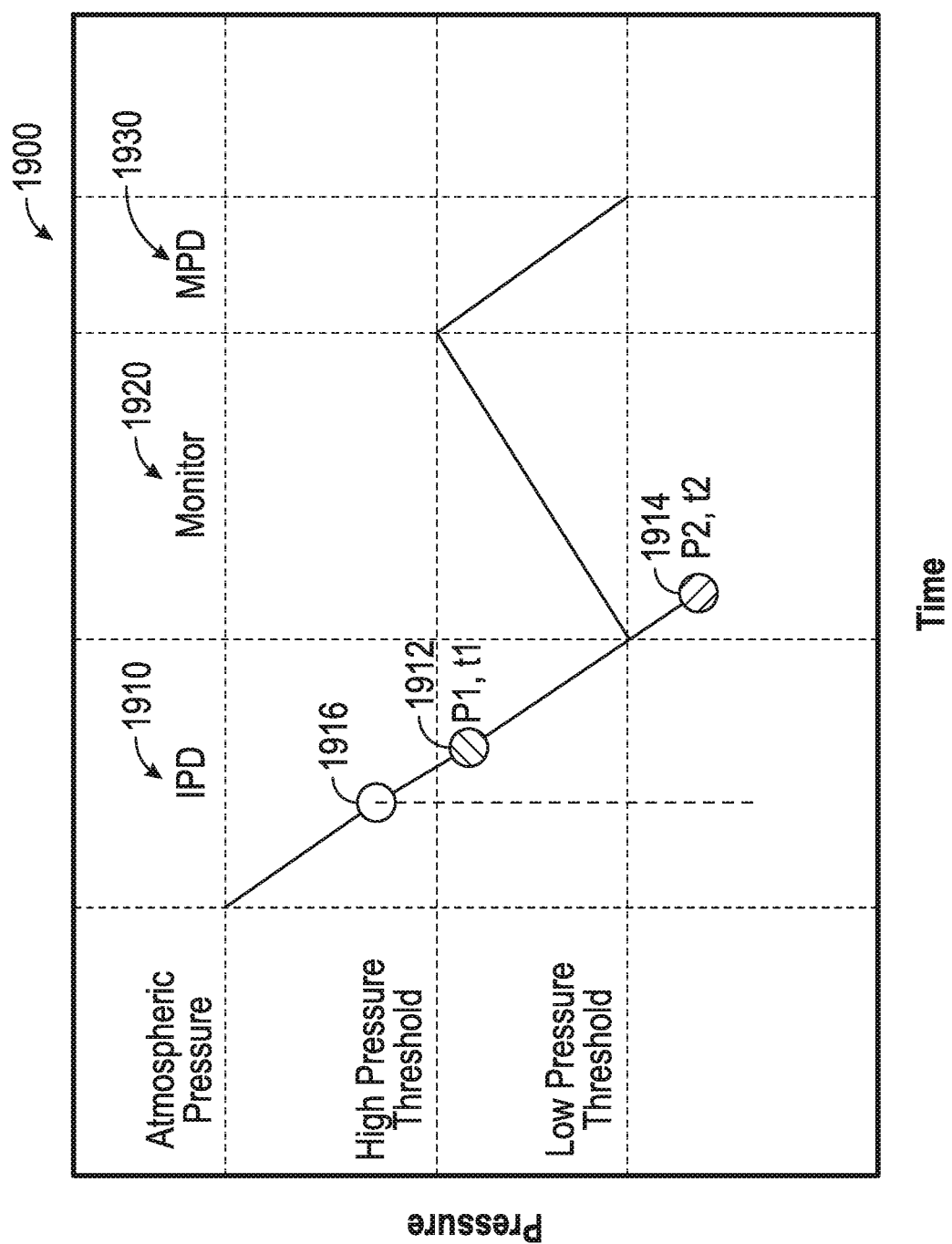
FIG. 71 is an exemplary pressure versus time graph according to some embodiments.

An exemplary graph 1900 of pressure versus time during the IPD state 1910, monitor state 1920, and MPD state 1930 is illustrated in FIG. 71. As shown in the illustrated embodiment, during the IPD state 1910, the pump system can sample the pressure at two or more points in time represented on the graph as points 1912, 1914 corresponding to pressures P1 at time t1 and P2 at time t2 respectively. The rate of change of pressure between these two points can be calculated according to: (P2−P1)/(t2−t1).

In some circumstances, the abrupt pressure drops from point 1916 to point 1914 represents a transient blockage, such as a kinked conduit in the fluid flow path. As is explained above, the process 1800 can detect this condition by determining that the rate of change of pressure greatly exceeds the threshold, and can refrain from updating the counter.

Figure 72:
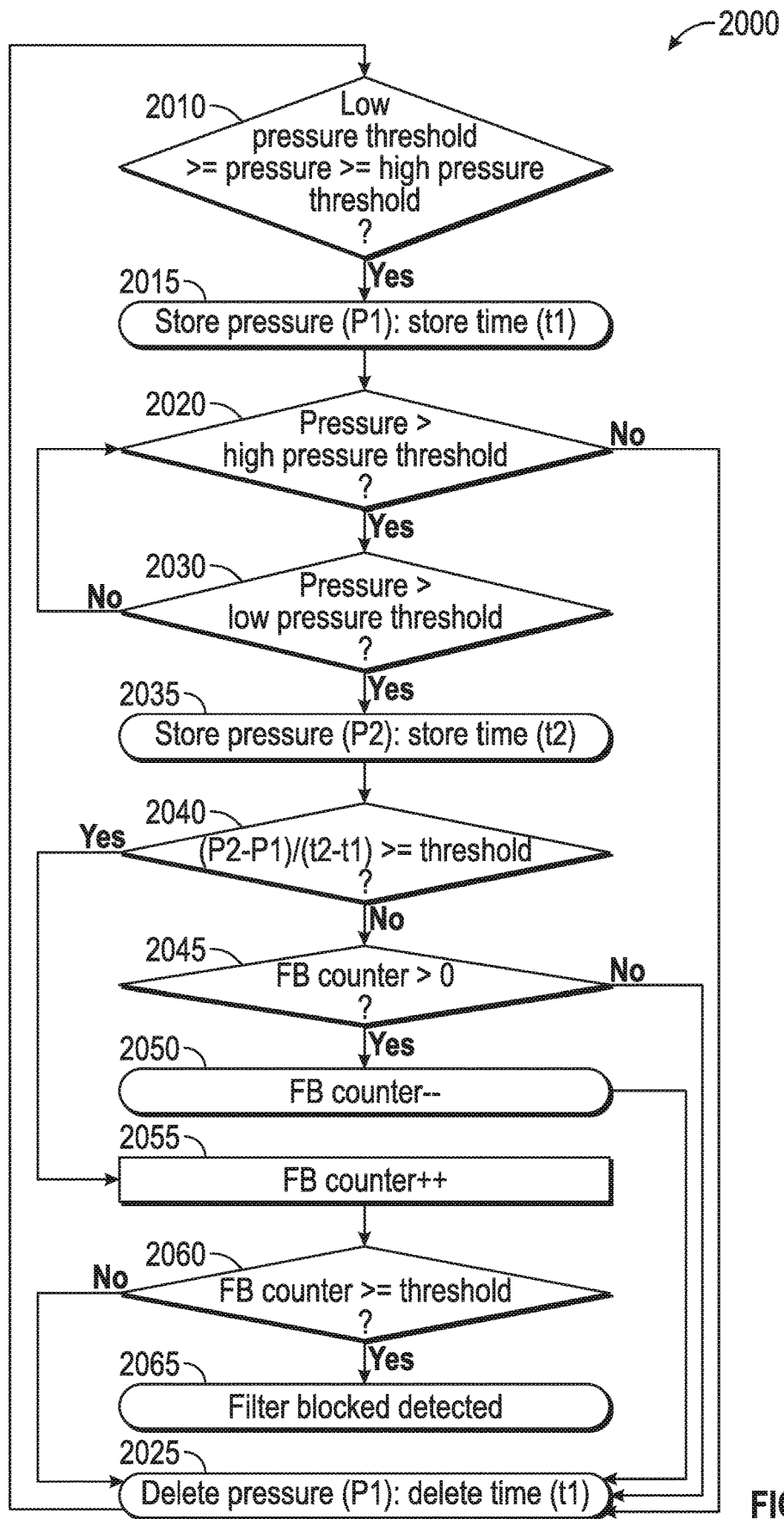
FIG. 72 is another embodiment of a method for determining a filter blockage.
Figure 74:
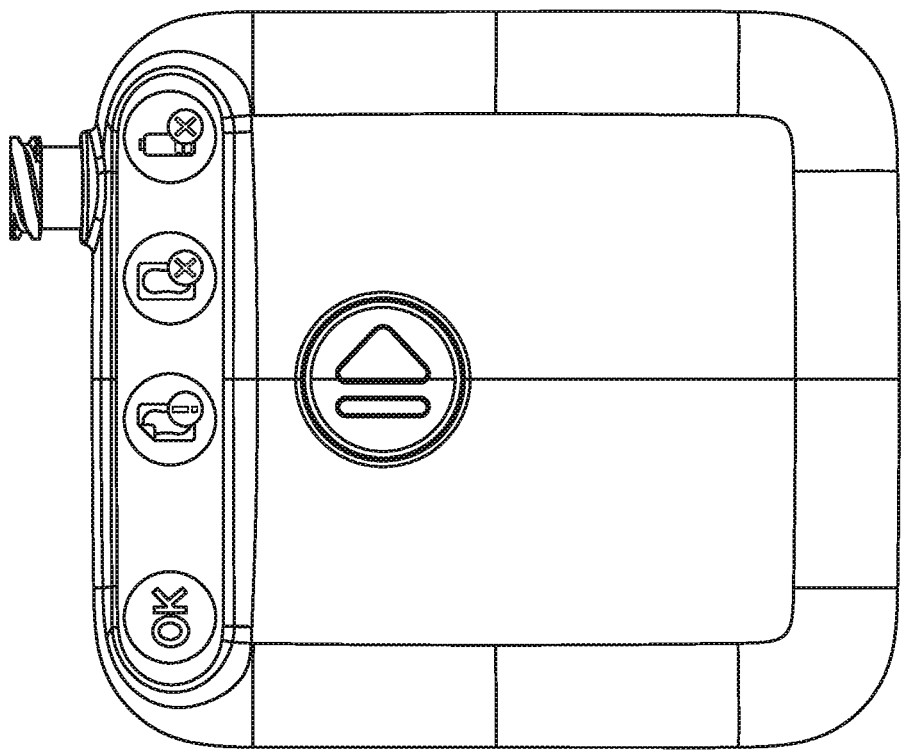
FIG. 74 is a front view of the pump system of FIG. 73.
Figure 73:
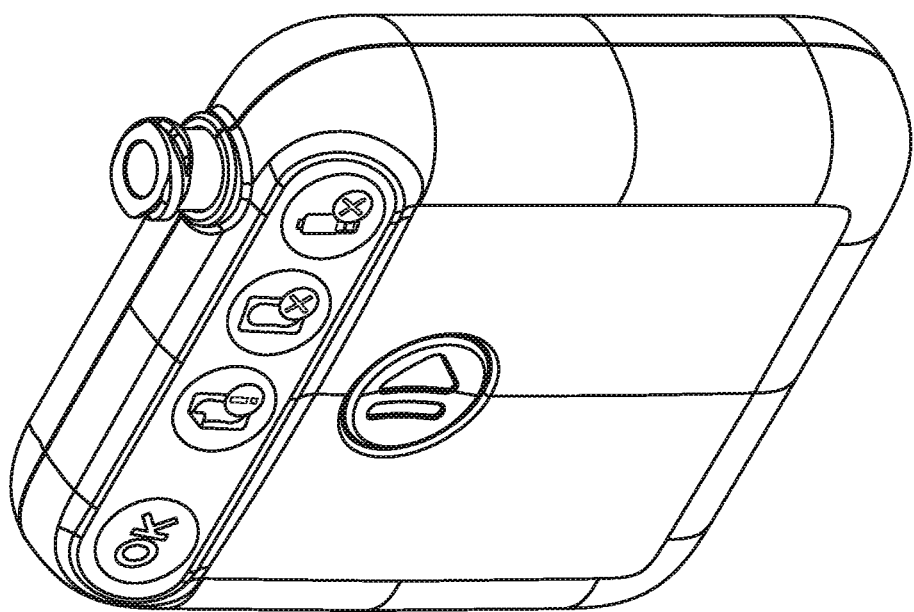
FIG. 73 is a front perspective view of the pump system of FIG. 1 without the optional mounting component attached.
Figure 76:
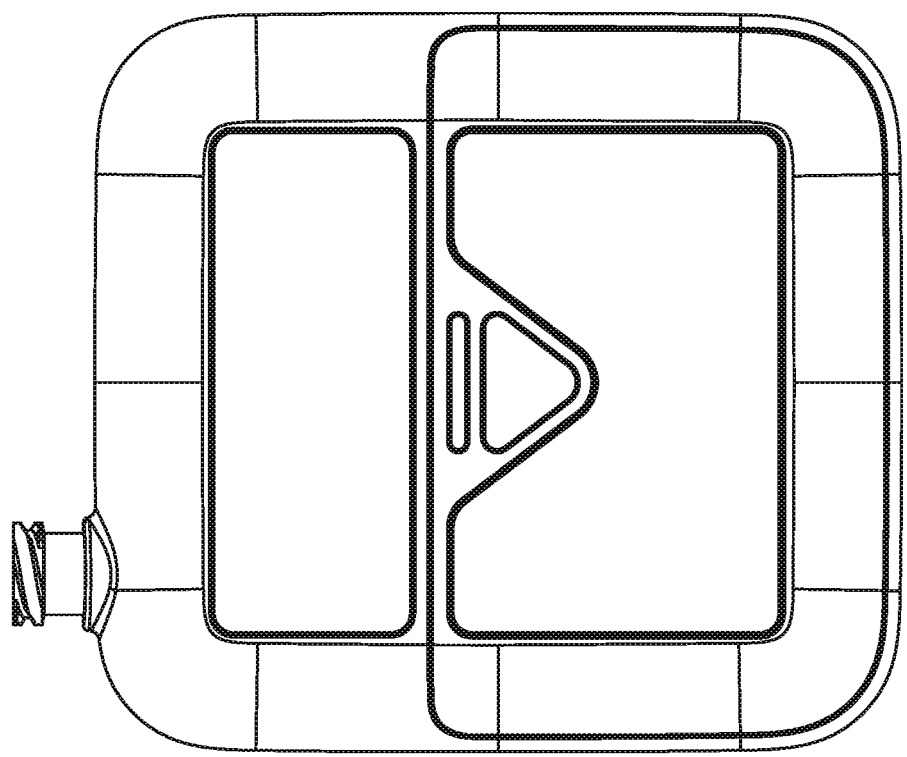
FIG. 76 is a rear view of the pump system of FIG. 73.
Figure 75:
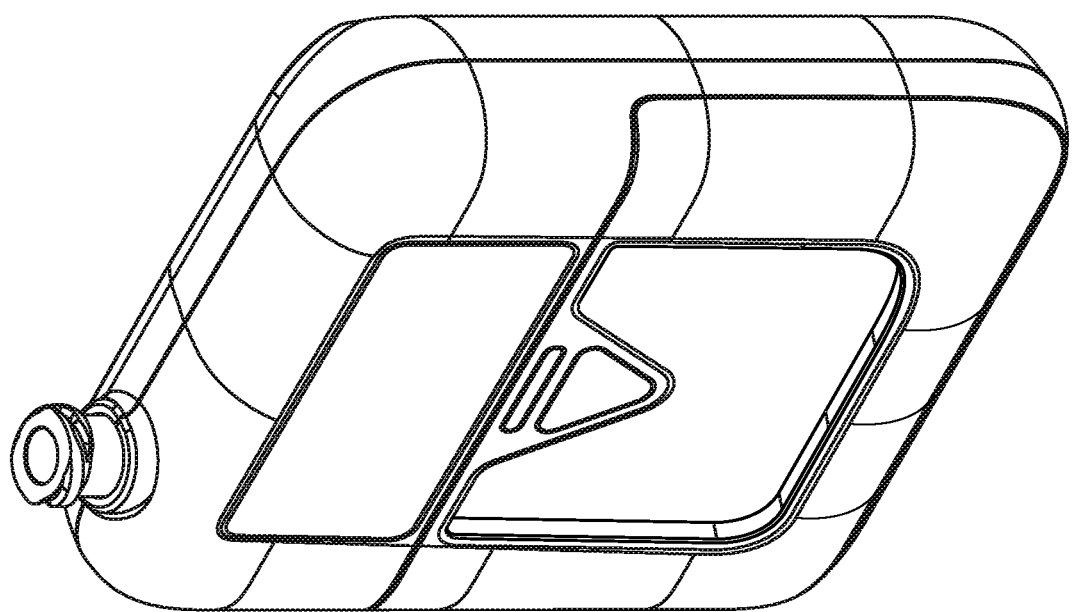
FIG. 75 is a rear perspective view of the pump system of FIG. 73.
Figure 77:
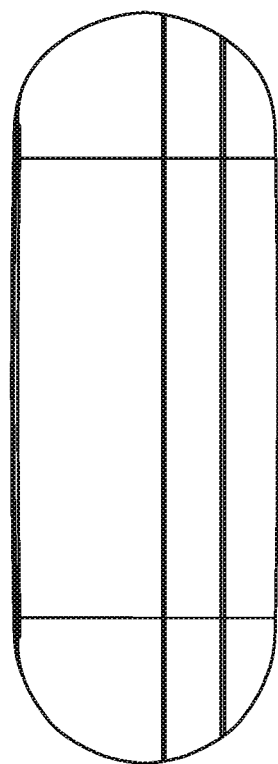
FIG. 77 is a top view of the pump system of FIG. 73.
Figure 78:
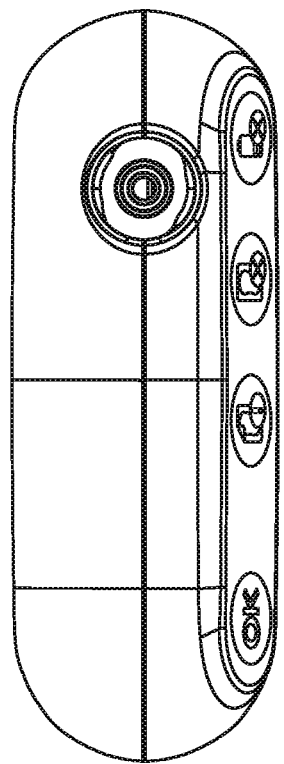
FIG. 78 is a bottom view of the pump system of FIG. 73.
Figure 80:
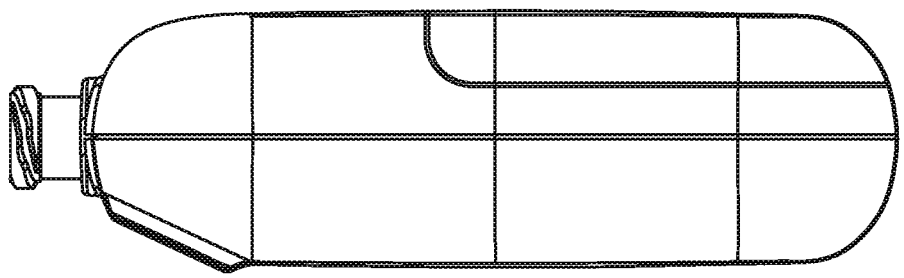
FIG. 80 is a left side view of the pump system of FIG. 73.
Figure 79:
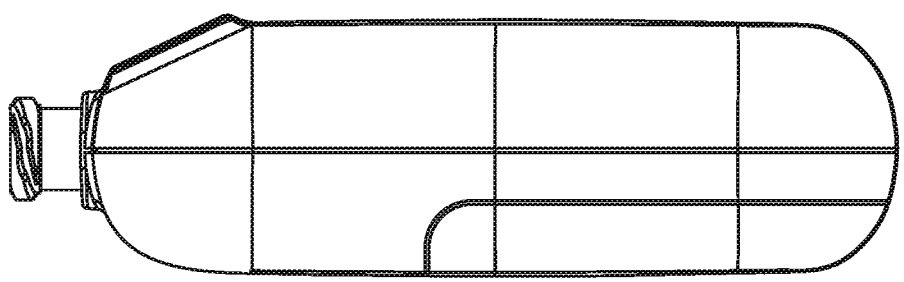
FIG. 79 is a right side view of the pump system of FIG. 73.
Figure 82:
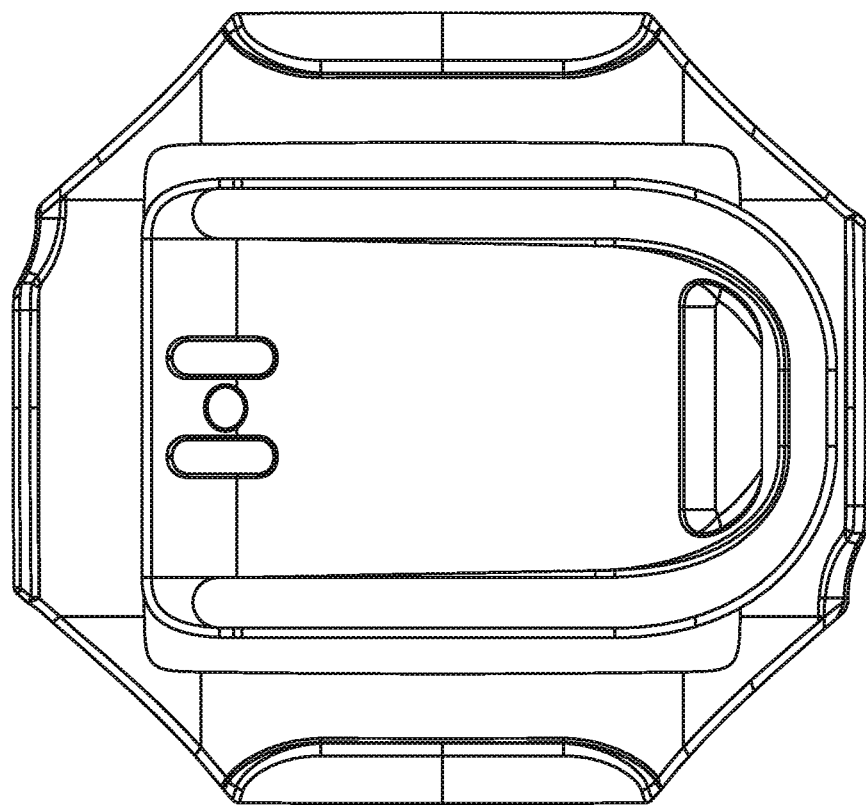
FIG. 82 is a front view of the pump mounting component of FIG. 81.
Figure 81:
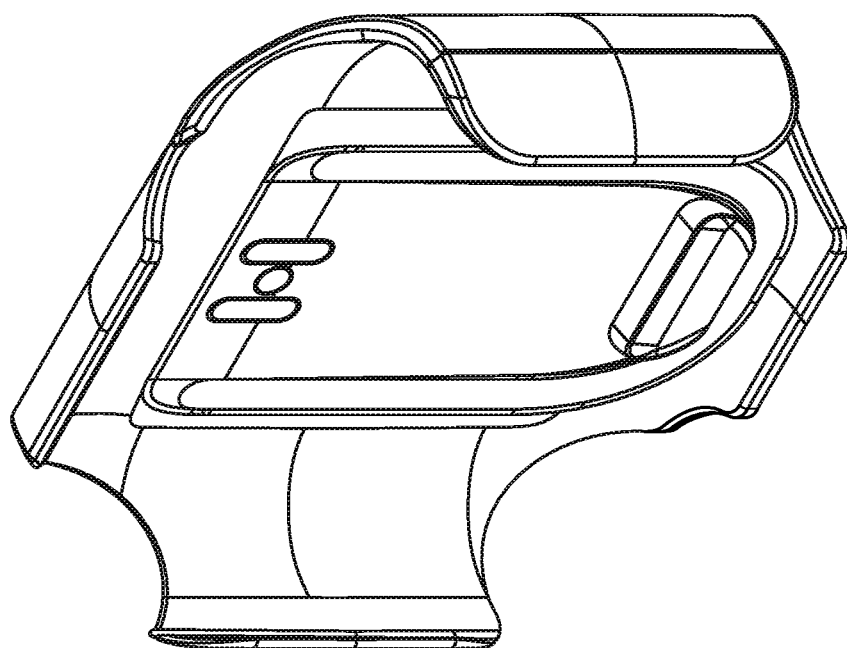
FIG. 81 is a front perspective view of a pump mounting component.
Figure 84:
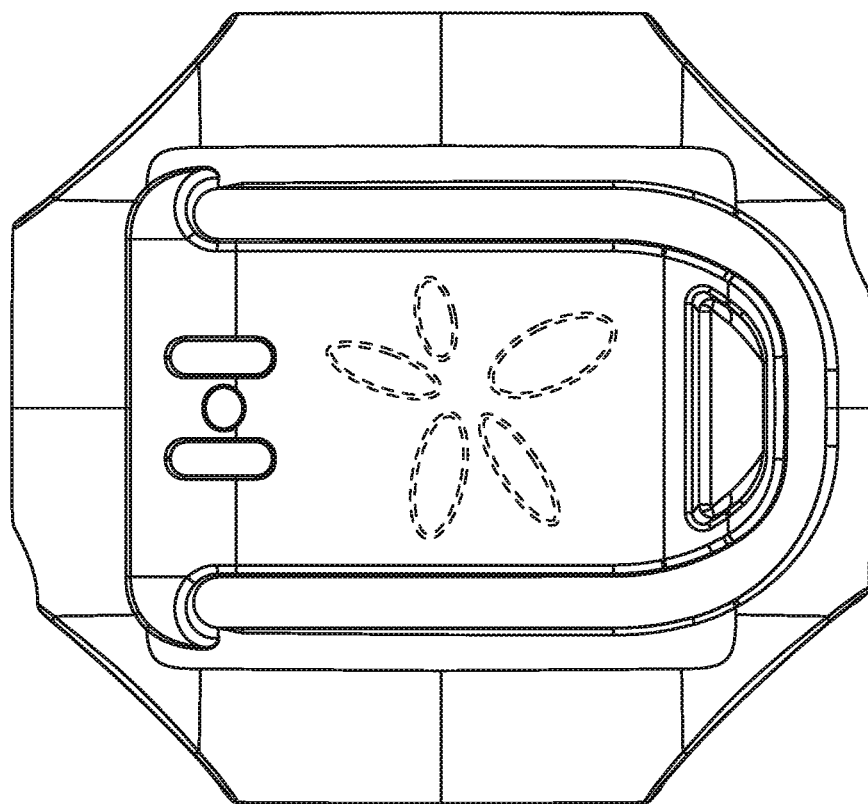
FIG. 84 is a rear view of the pump mounting component of FIG. 81.
Figure 83:
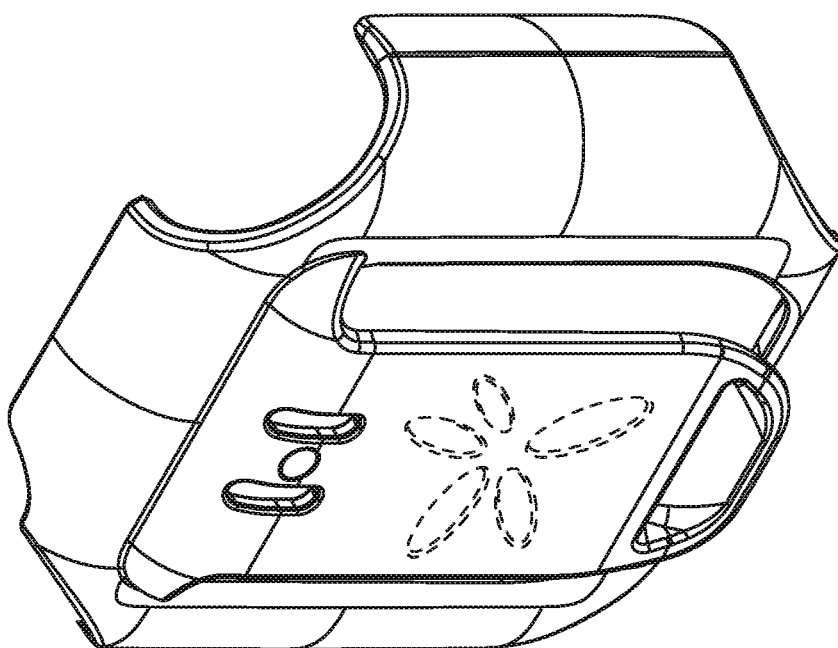
FIG. 83 is a rear perspective view of the pump mounting component of FIG. 81.
Figure 86:
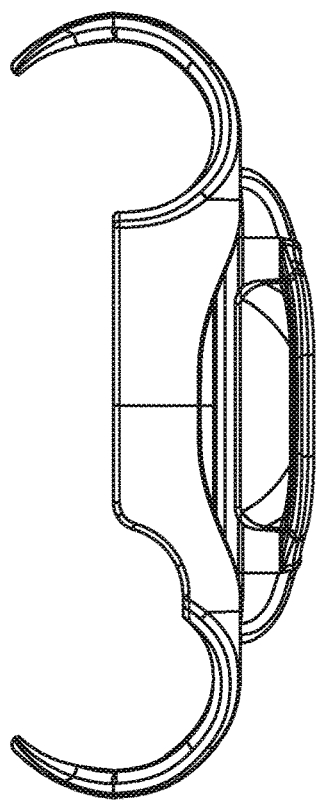
FIG. 86 is a bottom view of the pump mounting component of FIG. 81.
Figure 85:
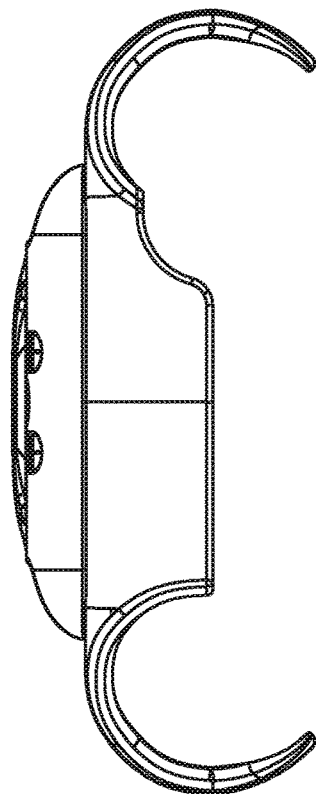
FIG. 85 is a top view of the pump mounting component of FIG. 81.
Figure 88:
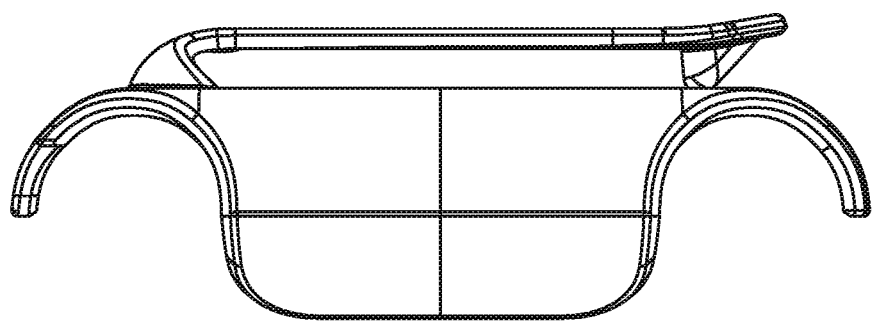
FIG. 88 is a left side view of the pump mounting component of FIG. 81.
Figure 87:
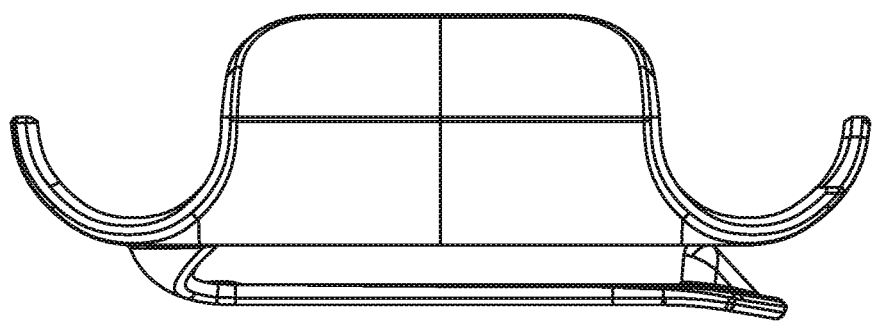
FIG. 87 is a right side view of the pump mounting component of FIG. 81.

FIG. 72 illustrates another process or method 2000 for determining whether a filter blockage is present in a pump system according to some embodiments. The process 2000 can be implemented by the controller of a pump system, such as controllers 1114, 1202, and the process 2000 can be implemented as part of executing the state diagram 1300. The method 2000 can be used to determine the existence of a filter blockage for any of the pump embodiments disclosed herein. In some embodiments, it can be advantageous to alert the user if a filter blockage has occurred so that the user can take remedial actions to relieve the blockage. For example, in embodiments where the filter is contained within a wound dressing, a filter blockage may be triggered if the wound dressing is at or nearing capacity and requires replacement. In some embodiments, the rate of execution of the method 2000 can be based on (or be the same as) the pressure sampling rate for the pump system. In other embodiments, the method 2000 can be performed at a rate different from the pressure sampling rate for the pump system.

As shown in the illustrated embodiment, during step 2010 the pump system can determine whether a measured negative pressure within the pump system or some portion thereof pressure is greater than or equal to a high pressure threshold and/or less than or equal to a low pressure threshold. If so, the pump system can store the measured pressure (P1) and the time (t1), such as in memory, as shown in step 2015. The pump system can then transition to step 2020.

During step 2020, the pump system can determine whether the measured negative pressure is greater than a high pressure threshold. If not, the pump system can transition to step 2025 and delete the stored pressure (P1) and time (t1) and transition back to step 2010. If the pump system determines that the measured negative pressure is greater than the high pressure threshold, the pump system can transition to step 2030. During step 2030, the pump system can determine whether the measured negative pressure is greater than a low pressure threshold. If not, the pump system can transition back to step 2020. If the pump system determines that the measured negative pressure is greater than the low pressure threshold, the pump system can store the measured pressure (P2) and time (t2) that this occurs as shown in step 2035. The pump system can then transition to step 2040.

During step 2040, the pump system can determine a rate of pressure change or drop between the two stored pressures. The pump system can determine whether the calculated rate of pressure change or drop exceeds a threshold value. For example, the threshold value can be approximately −50 mmHg/second (6,750 Pa/s). The threshold value can be between approximately −20 mmHg/second and approximately −200 mmHg/second, between approximately −40 mmHg/second and approximately −100 mmHg/second, between approximately −50 mmHg/second and approximately −75 mmHg/second, approximately −70 mmHg/second, any value or subrange within these ranges, or any other threshold as desired.

When the process 2000 determines that the rate of pressure change does not satisfy (e.g., does not exceed) the threshold rate, the process 2000 can advance to step 2045 and, in some embodiments, decrease the value of a filter block detection counter. For example, if the process 2000 determines that the counter is greater than 0, the pump system can transition to step 2050 and decrease the value of the counter. In some embodiments, the pump system can decrease the value of the counter by 1 although any other value can be used. For example, the process 2000 can reset the counter to its initial value, such as 0, 1, or any other suitable value. In some embodiments, the decrease in value of the counter can be based on other factors, such as the calculated rate of pressure drop. As shown in the illustrated embodiment, the process 2000 can ensure that the value of the counter does not decrease below the initial value, such as 0, as a result of step 2045. Accordingly, if during step

2045 the process 2000 determines that the counter is not greater than 0, the process 2000 can transition to step 2025.

Should the process 2000 determine that the rate of pressure change, shown as (P2–P1)/(t2–t1), satisfies (e.g., exceeds) the threshold rate, the process 2000 can transition from step 2040 to step 2055 and increase the value of the counter. In some embodiments, the process 2000 can increase the value of the counter by 1 although any other value can be used. Moreover, in some embodiments, the increase in value of the counter can be based on other factors, such as the calculated rate of pressure drop.

As noted above in connection with process 1800 described in connection with FIG. 70, in some circumstances, it is possible that the calculated rate of pressure change or drop can greatly exceed the threshold rate of pressure change. As such, in some embodiments, when the process 2000 determines that a calculated rate of pressure change exceeds a maximum rate of pressure change, the process 2000 may not increase the counter and/or may provide a different indication to the user. In some embodiments, the maximum rate can be equal to or greater than approximately 110% of the threshold rate, equal to or greater than approximately 120% of the threshold rate, equal to or greater than approximately 130% of the threshold rate, equal to or greater than approximately 140% of the threshold rate, equal to or greater than approximately 150% of the threshold rate, or any other percentage of the threshold rate.

During step 2060, the process 2000 can determine whether the counter has reached a set value that represents a threshold number of times that the rate of pressure change has satisfied the threshold rate. The set value can be a preset value from the factory, can be a variable value based on other parameters of the pump, or can be set by the user. In some embodiments, the set value can beneficially be set to a value higher than 1. If the process 2000 determines that the counter satisfies the set value (e.g., is greater than or equal to the set value), the process 2000 can transition to a filter blocked state 2065. In some embodiments, in state 2065, the pump system can perform the operations discussed in connection with state 1318 discussed in connection with FIG. 63. If the process 2000 determines that the counter does not satisfy the set value (e.g., is not greater than or equal to the set value), the process 2000 can transition to step 2025.

With respect to the method 2000, the rate of pressure change is calculated based on two measured negative pressures, the first of which is measured when the negative pressure is between a high pressure threshold and a low pressure threshold and the second of which is measured when the negative pressure is greater than the low pressure threshold. In some instances, the duration of time between the first and second measured negative pressures can be greater than, if not significantly greater than, a sampling rate of the pump system. Accordingly, there can be a lower likelihood of a false positive which may be caused by a factor other than a filter blockage, such as an outlier pressure reading, a kink in the fluid flow path between the pump system and the wound dressing, or other similar factors which may cause a transient pressure change of significant magnitude.

Other processes or methods for determining whether a filter blockage is present in a pump system are also appreciated, which can be implemented by the controller of a pump system, such as controllers 1114 or 1202, and which can be implemented as part of executing the state diagram 1300. For example, in some embodiments, the presence of a blockage can be determined based on the level of activity of the pump, such as measured duty cycle. In some embodiments, the processes or methods can compare the level of activity of the pump, such as measured duty cycle, to a blockage threshold, which can be adjusted based on whether the pump is operating without or with a canister. In some embodiments, the detection of whether a canister is present can be performed automatically, for example, by the controllers 1114 or 1202. Automatic detection can be performed using one or more of the following approaches: characteristics of pressure distribution in a fluid flow path (including characteristics of decaying pressure, settling pressure, etc.), sensor indicating attachment and/or presence of the canister, RFID detection, actuating a switch indicating attachment and/or presence of the canister, and the like.

In any embodiments disclosed herein, the drive signal for the source of negative pressure can be attenuated upon start up to slowly ramp up or "soft start" the source of negative pressure. For example, in some embodiments, parameters such as the offset and/or amplitude of the drive signal can be reduced when the source of negative pressure is first activated after having previously been inactive for some period of time. In soft starting the source of negative pressure, the forces applied to one or more components of the source of negative pressure can be reduced.

As noted above, at a lower negative pressure, such as 0 mmHg, a lower amplitude for the drive signal may be desirable since the piston will exhibit a greater degree of movement for a given amplitude at the lower vacuum condition whereas at a higher negative pressure, such as −70 mmHg, a higher amplitude may be desirable since the piston will exhibit a lesser degree of movement for a given amplitude at the higher vacuum condition. Accordingly, should the source of negative pressure be subject to a drive signal with amplitude and offset calculated for the target pressure of, for instance −70 mmHg, when the pressure within the diaphragm pump is at 0 mmHg, there is a potential that the source of negative pressure can be over driven, thereby causing a reduction in efficiency. Further, over driving the source of negative pressure can cause contact between one or more components within the source of negative pressure. For example, for a source of negative pressure which utilizes a voice coil actuator, over driving the voice coil actuator can cause components such as a support, shaft, or piston to contact mechanical stops which can cause noise, vibration, and harshness.

Soft starting the source of negative pressure can be done any time the source of negative pressure is being activated after being inactive. In some embodiments, soft starting can be performed only after the source of negative pressure has been inactive for a set period of time. The set period can be a preset value, a variable parameter based on operating conditions of the pump system, and/or input by the user.

As noted above, in some embodiments, the pump system can calculate the offset and/or amplitude for the drive signal based at least on part on the stored parameters in the pump system. In some embodiments, during a soft start, the pump system can activate the source of negative pressure with a drive signal corresponding to a lower negative pressure than the measured negative pressure, such as approximately −15 mmHg (−2 kPa) when the measured negative pressure is −70 mmHg. In some embodiments, the pump system can activate the source of negative pressure with other drive signals, such as a drive signal between approximately 0 mmHg and approximately −100 mmHg, between approximately −5 mmHg and approximately −75 mmHg, between approximately −10 mmHg and approximately −50 mmHg, between approximately −15 mmHg and approximately −25 mmHg, any value or subrange within these ranges, or any other pressure as desired. The pressure can be a preset value, a variable parameter based on operating conditions of the pump system, and/or input by the user.

In some embodiments, the pump system can actuate the source of negative pressure with a soft start drive signal for a set duration of time. The set duration of time can be sufficient to ensure that the source of negative pressure is at or near the measured pressure in the pump system or some portion thereof, such that application of a drive signal at the measured pressure would be less likely to over drive the source of negative pressure. For example, the duration can be approximately 100 ms. In some embodiments, the duration can be between approximately 10 ms and approximately 1000 ms, between approximately 50 ms and approximately 500 ms, between approximately 75 ms and approximately 250 ms, approximately 100 ms, any value or subrange within these ranges, and any other duration as desired. The duration can be a preset value, a variable parameter based on operating conditions of the pump system, and/or input by the user.

Other Embodiments

The following described embodiments are other embodiments contemplated by this disclosure:

1. An apparatus for use in negative pressure wound therapy, comprising:
   a pump assembly, comprising:
   a pump housing;
   a magnet positioned within the pump housing;
   an electrically conductive coil positioned within the pump housing; and
   a diaphragm, wherein the coil is directly or indirectly coupled with the diaphragm and is configured to move at least a portion of the diaphragm to pump a fluid through the pump assembly; and
   a dampener positioned within the pump assembly configured to reduce sound generated by the pump assembly during operation of the pump assembly.

2. The apparatus of claim 1, wherein the dampener comprises a porous material configured to allow fluid to flow through the dampener.

3. The apparatus of claim 2, wherein the porous material is urethane foam.

4. The apparatus of claim 1, wherein the pump housing comprises a chamber, and wherein the dampener is positioned within the chamber.

5. The apparatus of claim 4, wherein the chamber is integrally formed with the pump housing.

6. The apparatus of claim 4, further comprising a diffuser positioned within the chamber, the diffuser configured to facilitate expansion of fluid as it enters the chamber.

7. The apparatus of claim 4 or 5, wherein the pump housing further comprises an exhaust channel configured to communicate fluid flow out of the pump assembly, and wherein the chamber is in communication with the exhaust channel.

8. The apparatus of claim 7, wherein the exhaust channel comprises an opening along the channel configured to redirect a portion of a fluid flow from the exhaust channel back into an internal volume of the housing, wherein said redirection is configured to reduce sound generated by the pump assembly during operation of the pump assembly.

9. The apparatus of claim 8, wherein the portion of the fluid flow from the exhaust channel comprises an entirety of a fluid flow from the exhaust channel.

10. The apparatus of any previous claim, further comprising a manifold positioned such that the manifold is between the pump assembly and a wound dressing when the apparatus is in use.

11. The apparatus of claim 10, further comprising a diffuser positioned within the manifold.

12. The apparatus of claim 10, further comprising a second dampener within the manifold.

13. The apparatus of claim 12, wherein the second dampener comprises a porous material configured to allow fluid to flow through the dampener.

14. The apparatus of claim 13, wherein the porous material of the second dampener is urethane foam.

15. The apparatus of any previous claim, further comprising a control board.

16. The apparatus of claim 15, further comprising an electrical conduit for connecting the control board to the electrically conductive coil.

17. The apparatus of any previous claim, wherein the pump assembly further comprises:
   an upper pole;
   a lower pole spaced apart from the upper pole; and
   one or more valves configured to control a flow of fluid through the pump assembly;
   wherein at least a portion of the coil is positioned between the upper and the lower pole, and
   wherein the magnet is positioned between at least a portion of the upper pole and the lower pole.

18. The apparatus of claim 17, wherein a portion of each of the one or more valves comprises a rib extending away from a surface of the valve, the rib being configured to compress or deform to increase a seal with a corresponding sealing surface.

19. The apparatus of claim 17, wherein the pump assembly further comprises a pump chamber body configured to receive the one or more valves in one or more corresponding valve recesses.

20. The apparatus of claim 19, wherein a sealant is positioned between the pump chamber body and the housing.

21. The apparatus of claim 19, wherein the pump assembly further comprises one or more valve chambers formed in part by a union between a portion of an outer surface of the pump chamber body and a portion of an inner surface of the housing.

22. The apparatus of claim 19, wherein the one or more valve recesses further comprise one or more indexing features configured to receive one or more corresponding alignment features of the one or more valves to inhibit improper valve installation into the pump chamber body.

23. The apparatus of any previous claim, further comprising a wound dressing configured to sealingly surround a wound.

24. The apparatus of any previous claim, comprising a spring member, wherein:
   a periphery of the spring member is supported within the pump assembly so as to be in a fixed position relative to the diaphragm; and
   a middle portion of the spring member is configured to deflect relative to the periphery of the spring member when a middle portion of the diaphragm axially deflects.

25. The apparatus of any previous claim, further comprising an illumination source disposed within the housing, wherein part of the housing is transparent or translucent such that light emitted from the illumination source passes through the housing.

26. The apparatus of any previous claim, wherein the dampener is a filter configured to filter fluid as it flows through the dampener.

27. The apparatus of claim 1, further comprising a dampener positioned on an exterior surface of the pump housing.

28. A pump apparatus, comprising:
- a housing having a first section and a second section; and
- an illumination source disposed within the housing adjacent the first section;
- wherein the illumination source is configured to illuminate the first section,
- wherein the first section is one of transparent and translucent, and
- wherein the first section is thinner than the second section as measured perpendicularly from inside to outside the housing.

29. The pump apparatus of claim 28, wherein the second section is opaque.

30. The pump apparatus of claim 28, wherein the illumination source comprises light emitting diodes (LED).

31. The pump apparatus of claim 28, wherein the first section comprises an icon.

32. The pump apparatus of claim 28, further comprising a pump assembly disposed within the housing configured for negative pressure wound therapy.

33. The pump apparatus of claim 32, wherein the first section comprises four icons.

34. The pump apparatus of claim 33, wherein one of the four icons comprises an indicator configured to illuminate when the pump assembly is operating properly, a second of the four icons comprises an indicator configured to illuminate when there is a leak, a third of the four icons comprises an indicator configured to illuminate when a dressing connected to the wound apparatus is full, and a fourth of the four icons comprises an indicator indicating that a battery level is low.

35. The pump apparatus according claim 28, further comprising a baffle configured to control an illumination of the first section by absorbing light.

36. The pump apparatus of claim 35, wherein the baffle is configured to inhibit an illumination of one part of the first section from illuminating another part of the first section, wherein illumination comprises light passing through a transparent or translucent portion of the of the first section.

37. The pump apparatus of claim 35 or 36, wherein the baffle is directly or indirectly connected to or integrally formed with at least one of the first and second sections.

38. A pump apparatus, comprising:
- a pump casing with one or more transparent portions configured to allow a laser to pass therethrough; and
- a component housing configured to be laser welded to the pump casing, the component housing comprising one or more laser absorbing portions configured to be melted by the laser.

39. The pump apparatus of claim 38, wherein the one or more laser absorbing portions are darker than the one or more transparent portions.

40. The pump apparatus of claim 38 or 39, wherein the one or more laser absorbing portions comprises at least one of nontransparent material and laser absorbing material.

41. The pump apparatus of claim 40, wherein the at least one of nontransparent material and laser absorbing material is positioned on the surface of the component housing or extends through a thickness of the component housing.

42. The pump apparatus of claim 40 or 41, wherein the at least one of nontransparent material and laser absorbing material comprises 5% to 100% black pigment.

43. The pump apparatus according to any of claims 38-42, wherein at least a portion of the pump casing is transparent and wherein at least a portion of the component housing is at least one of nontransparent and laser absorbent.

44. The pump apparatus according to any of claims 38-43, wherein the one or more laser absorbing portions of the component housing represent a weld contour to which the laser is configured to be applied.

45. The pump apparatus according to any of claims 38-44, wherein the component housing houses at least one of one or more valves, a diaphragm, a magnet, and an electrically conductive coil.

46. The pump apparatus according to any of claims 38-45, wherein a portion of the one or more transparent portions of the pump casing comprises part of an intake channel and an outtake channel on the exterior of the pump casing, the intake and outtake channels having sloped surfaces to prevent sudden laser diffraction during laser welding.

47. A pump apparatus, comprising:
- a transparent pump component configured to allow a laser to pass through during laser welding; and
- a housing configured to be laser welded to the transparent pump component, the housing comprising one or more laser absorbing portions configured to be melted by the laser.

48. The pump apparatus of claim 47, wherein the housing comprises one or more weld surfaces comprising the one or more laser absorbing portions.

49. The pump apparatus of claim 48, wherein the one or more weld surfaces comprises at least six circumferential weld surfaces.

50. The pump apparatus of claim 49, wherein the at least six circumferential weld surfaces are equally spaced apart.

51. The pump apparatus according to any of claims 47-50, the housing further comprising one or more vertical flanges, wherein each vertical flange comprises two weld surfaces and one stop, the stop configured to control a collapse of the transparent pump component into the housing during welding.

52. The pump apparatus of claim 51, wherein the two weld surfaces of each of the one or more vertical flanges comprises the one or more laser absorbing portions.

53. The pump apparatus according to any of claims 47-52, wherein the transparent pump component comprises a bushing.

54. The pump apparatus according to any of claims 47-52, wherein the housing comprises a pump chamber body.

55. An apparatus for use in negative pressure wound therapy, comprising:
- a pump system configured for negative pressure wound therapy, comprising:
  - an outer housing;
  - a pump assembly positioned within the outer housing, the pump assembly comprising a pump housing that receives a plurality of pump components therein; and
  - a connector for connecting a tube or conduit to the pump system to deliver negative pressure from the pump assembly to a wound.

56. The apparatus of claim 55, further comprising an intake manifold within the outer housing providing fluid communication between the connector and the pump assembly.

57. The apparatus of claim 55, further comprising a circuit board positioned within the outer housing configured to control the pump assembly.

58. The apparatus of claim 55, further comprising a wound dressing configured to connect to the tube or conduit.

59. The apparatus of claim 55, wherein the pump housing comprises a chamber formed integrally with the pump housing, wherein the chamber receives a dampening component.

60. The apparatus of claim 55, wherein the pump housing comprises an exhaust channel, the exhaust channel configured to redirect a fluid flow from the exhaust channel into an internal volume of the pump housing to reduce sound generated by the pump assembly during operation.

61. The apparatus of claim 55, wherein the pump assembly comprises a noise reduction system.

62. The apparatus of claim 55, wherein the pump components received within the pump housing comprise a magnet, an electrically conductive coil, a diaphragm, and a dampener.

63. The apparatus of claim 62, wherein the pump components received within the pump housing comprise a spring configured to interact with the diaphragm.

64. The apparatus of claim 62, wherein the pump components received within the pump housing comprise an upper pole, a lower pole, and a valve, wherein the magnet and a portion of the electrically conductive coil are disposed between the upper and lower poles.

65. The apparatus of claim 64, wherein the valve comprises a rib configured to better seal the rib against a sealing surface.

66. The apparatus of claim 55, wherein the outer housing comprises a display comprising a plurality of indicators.

67. The apparatus of claim 55, wherein the outer housing comprises relatively thinner material, transparent material, or translucent material overlying an illumination component on the inside of the outer housing.

68. The apparatus of claim 67, further comprising baffles attached to or formed integrally with interior surfaces of the outer housing to prevent illumination of one indicator from bleeding into and onto another indicator.

69. The apparatus of claim 55, further comprising one or more user input features on an outside surface of the outer housing.

70. The apparatus of claim 55, wherein one or more of the pump housing and the pump components are transparent to facilitate laser welding during assembly of the pump system.

71. A negative pressure pump system comprising:
   a pump assembly comprising:
      an actuator; and
      a diaphragm; and
   a controller configured to control operation of the pump system, the controller further configured to:
      calculate at least one of an amplitude and an offset for a drive signal based at least in part on previously calculated parameters and a negative pressure setting;
      generate the drive signal with the at least one calculated amplitude and offset; and
      apply the drive signal to the pump system, thereby causing delivery of negative pressure wound therapy.

72. The negative pressure pump system of embodiment 71, wherein the previously calculated parameters comprise a plurality of calibrated amplitudes at a plurality of negative pressure settings.

73. The negative pressure pump system of embodiment 71 or 72, wherein the previously calculated parameters comprise a plurality of calibrated offsets at a plurality of negative pressure settings.

74. The negative pressure pump system according to any of embodiments 71-73, wherein the controller is further configured to calculate both the amplitude and the offset for the drive signal.

75. The negative pressure pump system according to any of embodiments 71-74, wherein the controller is further configured to interpolate between at least two previously calculated amplitudes or offsets.

76. The negative pressure pump system of embodiment 75, wherein the controller is further configured to linearly interpolate between at least two previously calculated amplitudes or offsets.

77. The negative pressure pump system according to any of embodiments 71-76, wherein the previously calculated parameters comprises at least 3 parameters.

78. The negative pressure pump system according to any of embodiments 71-77, wherein the previously calculated parameters are dependent on one or more properties of the pump system.

79. The negative pressure pump system according to any of embodiments 71-78, wherein the actuator comprises a voice coil actuator, the voice coil actuator being connected to the diaphragm.

80. The negative pressure pump system according to any of embodiments 71-79, wherein the pump assembly further comprises a spring configured to affect a resonant frequency of the pump assembly.

81. The negative pressure pump system according to any of embodiments 71-80, wherein the controller is further configured to apply a start up signal when the pump system has been activated after a period of inactivity, the start up signal comprising at least one of an amplitude and an offset different from at least one of the amplitude and the offset of the drive signal.

82. The negative pressure pump system according to embodiment 81, wherein the controller is further configured to:
   calculate at least one of an amplitude and an offset for the start up signal based at least in part on previously calculated parameters and a soft start negative pressure setting that is less than the negative pressure setting; and
   apply the start up signal to the pump system.

83. The negative pressure pump system according to embodiment 82, wherein the controller is further configured to apply the start up signal to the pump system over a start up time period until the soft start negative pressure setting is reached under a wound dressing configured to be placed over a wound, and subsequently apply the drive signal to the pump system.

84. The negative pressure pump system according to embodiment 83, wherein the controller is configured to apply the drive signal to the pump system until the negative pressure setting is reached under the wound dressing.

85. The negative pressure pump system according to embodiment 83 or 84, wherein the start up time period is approximately 100 milliseconds.

86. The negative pressure pump system according to embodiment 83 or 84, wherein the start up time period is between approximately 10 milliseconds and approximately 1000 milliseconds.

87. The negative pressure pump system according to embodiment 83 or 84, wherein the start up time period is between approximately 50 milliseconds and approximately 500 milliseconds.

88. The negative pressure pump system according to embodiment 83 or 84, wherein the start up time period is between approximately 75 milliseconds and approximately 250 milliseconds.

89. A calibration system for calibrating a pump system configured for negative pressure wound therapy, the calibration system comprising:
- a sensor; and
- a controller configured to control operation of the calibration system, the controller further configured to:
  - cause generation of a drive signal;
  - cause actuation of the pump system with the drive signal;
  - measure movement of a component of the pump system with the sensor;
  - calculate a first dimension based on the measured movement of the component; and
  - determine whether a first convergence condition has been satisfied by determining that the first dimension is within a first tolerance of a first target value.

90. The calibration system of embodiment 89, wherein the controller is further configured to:
- calculate a second dimension based on the measured movement of the component; and
- determine whether a second convergence condition has been satisfied by determining that the second dimension is within a second tolerance of a second target value.

91. The calibration system of embodiment 90, wherein the controller is further configured to determine that the first and second convergence conditions are satisfied substantially simultaneously.

92. The calibration system according to any of embodiments 89-91, wherein, upon determining that at least one of the first or second convergence conditions is met, the controller is further configured to store a set of parameters associated with the drive signal in a memory of the pump system.

93. The calibration system according to any of embodiments 89-92, wherein, upon determining that at least one of the first or second convergence conditions is not satisfied, the controller is further configured to:
- cause adjustment of one or more parameters of the drive signal based at least in part on the measured movement of the component;
- cause generation of an adjusted drive signal;
- cause actuation of the pump system with the adjusted drive signal;
- measure the movement of the component of the pump assembly with the sensor; and
- determine whether the convergence condition has been satisfied.

94. The calibration system according to any of embodiments 89-93, wherein the controller is further configured to cause selection of an amplitude of the drive signal for generation of at least one of the drive signal and the adjusted drive signal.

95. The calibration system according to any of embodiments 89-94, wherein the controller is further configured to cause selection of an offset of the drive signal for generation of at least one of the drive signal and the adjusted drive signal.

96. The calibration system according to any of embodiments 90-95, wherein at least one of the first and second dimensions comprises a travel of the component.

97. The calibration system according to any of embodiments 90-96, wherein at least one of the first and second dimensions comprises an average position of the component.

98. The calibration system according to any of embodiments 90-97, wherein the component comprises a piston connected to a diaphragm.

99. A method for controlling a pump system configured for negative pressure wound therapy, the method comprising:
- calculating at least one of an amplitude and an offset for a drive signal based at least in part on previously calculated parameters and a negative pressure setting;
- generating the drive signal with the at least one calculated amplitude and offset; and
- applying the drive signal to the pump system, and thereby causing delivery of negative pressure wound therapy;
- wherein the method is performed under control of a controller of the pump system.

100. The method of embodiment 99, wherein the previously calculated parameters comprise a plurality of calibrated amplitudes at a plurality of negative pressure settings.

101. The method of embodiment 99 or 100, wherein the previously calculated parameters comprise a plurality of calibrated offsets at a plurality of negative pressure settings.

102. The method of according to any of embodiments 99-101, wherein calculating the at least one of the amplitude and the offset for a drive signal comprises calculating both the amplitude and the offset for the drive signal.

103. The method according to any of embodiments 99-102, wherein calculating the at least one of the amplitude and the offset for the drive signal further comprises interpolating between at least two previously calculated amplitudes or offsets.

104. The method of embodiment 103, wherein the interpolation is a linear interpolation.

105. The method according to any of embodiments 99-104, wherein the previously calculated parameters comprises at least 3 parameters.

106. The method according to any of embodiments 99-105, wherein the previously calculated parameters are dependent on one or more properties of the pump system.

107. The method according to any of embodiments 99-106, wherein the pump system comprises a voice coil actuator connected to a diaphragm.

108. The method according to any of embodiments 99-107, wherein the pump system further comprises a spring configured to affect a resonant frequency of the pump system.

109. The method according to any of embodiments 99-108, further comprising applying a start up signal when the pump system has been activated after a period of inactivity, the start up signal comprising at least one of an amplitude and an offset different from at least one of the amplitude and the offset of the drive signal.

110. The method according to embodiment 108, further comprising:
- calculating at least one of the amplitude and the offset for the start up signal based at least in part on previously calculated parameters and a soft start negative pressure setting that is less than the negative pressure setting; and
- applying the start up signal to the pump system.

111. The method according to embodiment 110, wherein applying the start up signal comprises applying the start up signal to the pump system over a start up time period until the soft start negative pressure setting is reached under a wound dressing configured to be placed over a wound, and subsequently applying the drive signal to the pump system.

112. The method according to embodiment 111, wherein the drive signal is applied to the pump system until the negative pressure setting is reached under the wound dressing.

113. The method according to embodiment 111 or 112, wherein the start up time period is approximately 100 milliseconds.

114. The method according to embodiment 111 or 112, wherein the start up time period is between approximately 10 milliseconds and approximately 1000 milliseconds.

115. The method according to embodiment 111 or 112, wherein the start up time period is between approximately 50 milliseconds and approximately 500 milliseconds.

116. The method according to embodiment 111 or 112, wherein the start up time period is between approximately 75 milliseconds and approximately 250 milliseconds.

117. A method for calibrating a pump system configured for negative pressure wound therapy, the method comprising:
  causing generation of a drive signal;
  causing actuation of the pump system with the drive signal;
  measuring movement of a component of the pump system;
  calculating a first dimension based on the measured movement of the component; and
  determining whether a first convergence condition has been satisfied by determining that the first dimension is within a first tolerance of a first target value, wherein the method is performed under control of a controller of a calibration system.

118. The method of embodiment 117, further comprising:
  calculating a second dimension based on the measured movement of the component; and
  determining whether a second convergence condition is satisfied by determining that the second dimension is within a second tolerance of a second target value.

119. The method of embodiment 118, further comprising determining that the first and second convergence conditions are satisfied substantially simultaneously.

120. The method according to any of embodiments 117-119, further comprising in response to determining that at least one of the first or second convergence conditions is met, storing in a memory of the pump system a set of parameters associated with the drive signal.

121. The method according to any of embodiments 117-120, wherein the method further comprises in response to determining that at least one of the first or second convergence conditions is not satisfied:
  causing adjustment of one or more parameters of the drive signal based at least in part on the measured movement of the component;
  causing generation of an adjusted drive signal;
  causing actuation of the pump system with the adjusted drive signal;
  measuring the movement of the component of the pump assembly; and
  determining whether the convergence condition has been satisfied.

122. The method according to any of embodiments 117-121, wherein causing generation of the drive signal or the adjusted drive signal comprises selecting an amplitude of the drive signal.

123. The method according to any of embodiments 117-122, wherein causing generation of the drive signal or the adjusted drive signal comprises selecting an offset of the drive signal.

124. The method according to any of embodiments 118-123, wherein at least one of the first and second dimensions comprises a travel of the component.

125. The method according to any of embodiments 118-124, wherein at least one of the first and second dimensions comprises an average position of the component.

126. The method according to any of embodiments 118-125, wherein the component comprises a piston connected to a diaphragm.

127. A pump system configured for negative pressure wound therapy, the pump system comprising:
  a pump assembly configured to provide a negative pressure, via a flow path, to a wound dressing configured to be positioned over a wound, the flow path configured to fluidically connect the pump system to the wound dressing;
  a sensor configured to measure a pressure in the flow path; and
  a controller configured to control operation of the pump system, the controller further configured to:
    measure a first pressure value in the flow path at a first time;
    measure a second pressure value in the flow path at a second time;
    calculate a first rate of pressure change using the first and second pressure values; and
    provide an indication that the wound dressing is full in response to determining that the calculated first rate of pressure change satisfies a threshold rate of change.

128. The pump system of claim 127, wherein the controller is further configured to:
  measure a third pressure value in the flow path at a third time;
  measure a fourth pressure value within the flow path at a fourth time;
  calculate a second rate of pressure change using the third and fourth pressure values; and
  provide the indication that the wound dressing is full in response to determining that the calculated first and second rates of pressure change satisfy the threshold rate of change.

129. The pump system of claim 127 or 128, wherein the pressure in the fluid flow path is between a maximum pressure and a minimum pressure.

130. The pump system of any of claims 127 to 129, wherein the controller is further configured to determine whether the second pressure value is less than a minimum pressure.

131. The pump system of any of claims 127 to 130, wherein the controller is further configured to provide an indication that the wound dressing is full in response to determining that the calculated first rate of pressure change equals or exceeds the threshold rate of change.

132. The pump system of any of claims 127 to 131, wherein the threshold rate of change is approximately −50 mmHg/second.

133. The pump system of any of claims 127 to 131, wherein the threshold rate of change is approximately −70 mmHg/second.

134. The pump system of any of claims 127 to 131, wherein the threshold rate of change is between approximately −20 mmHg/second and approximately −200 mmHg/second.

135. The pump system of any of claims 127 to 131, wherein the threshold rate of change is between approximately −40 mmHg/second and approximately −100 mmHg/second.

136. The pump system of any of claims 127 to 131, wherein the threshold rate of change is between approximately −50 mmHg/second and approximately −75 mmHg/second.

137. The pump system of any of claims 127 to 136, wherein the controller is further configured to provide an indication of a transient blockage condition in response to determining that the calculated first rate of pressure change satisfies a maximum rate of change.

138. The pump system of any of claims 127 to 137, wherein the controller is further configured to provide an indication of a transient blockage condition in response to determining that the calculated first and second rates of pressure change satisfy a maximum rate of change.

139. The pump system of claim 137 or 138, wherein the transient blockage condition comprises at least one of a kink in the flow path and an occlusion in the flow path.

140. The pump system of any of claims 137 to 138, wherein the maximum rate of change comprises about 110%, about 120%, about 130%, about 140%, or about 150% of the threshold rate.

141. The pump system of any of claims 137 to 138, wherein the maximum rate of change comprises between about 105% and about 155% of the threshold rate of change.

142. The pump system of any of claims 137 to 141, wherein the controller is further configured to provide an indication of a transient blockage condition in response to determining that the calculated first rate of pressure change equals or exceeds the maximum rate of change.

143. The pump system of any of claims 127 to 142 wherein the controller is further configured to sample a pressure within the fluid flow path during one or more time intervals.

144. The pump system of claim 143, wherein the controller is further configured to sample the pressure at least twice during each of the one or more time intervals.

145. The pump system of claim 143 or 144, wherein the controller is further configured to average the pressure samples during each of the one or more time intervals.

146. A method for controlling a pump system configured for negative pressure wound therapy, the method comprising:
causing provision of negative pressure, via a flow path, to a wound dressing configured to be positioned over a wound, the flow path configured to fluidically connect the pump system to the wound dressing;
measuring a first pressure value in the flow path at a first time;
measuring a second pressure value in the flow path at a second time;
calculating a first rate of pressure change using the first and second pressure values; and
in response to determining that the calculated first rate of pressure change satisfies a threshold rate of change, providing an indication that the wound dressing is full, wherein the method is performed under control of a controller of the pump system.

147. The method of claim 146, further comprising:
measuring a third pressure value in the flow path at a third time;
measuring a fourth pressure value within the flow path at a fourth time;
calculating a second rate of pressure change using the third and fourth pressure values; and
providing the indication that the wound dressing is full in response to determining that the calculated first and second rates of pressure change satisfy the threshold rate of change.

148. The method of claim 146 or 147, wherein the pressure in the fluid flow path is between a maximum pressure and a minimum pressure.

149. The method of any of claims 146 to 148, further comprising determining whether the second pressure value is less than a minimum pressure.

150. The method of any of claims 146 to 149, wherein satisfying the threshold rate of change comprises equaling or exceeding the threshold rate of change.

151. The method of any of claims 146 to 150, wherein the threshold rate of change is approximately −50 mmHg/second.

152. The method of any of claims 146 to 150, wherein the threshold rate of change is approximately −70 mmHg/second.

153. The method of any of claims 146 to 150, wherein the threshold rate of change is between approximately −20 mmHg/second and approximately −200 mmHg/second.

154. The method of any of claims 146 to 150, wherein the threshold rate of change is between approximately −40 mmHg/second and approximately −100 mmHg/second.

155. The method of any of claims 146 to 150, wherein the threshold rate of change is between approximately −50 mmHg/second and approximately −75 mmHg/second.

156. The method of any of claims 146 to 155, further comprising providing an indication of a transient blockage condition in response to determining that the calculated first rate of pressure change satisfies a maximum rate of change.

157. The method of any of claims 146 to 156, further comprising providing an indication of a transient blockage condition in response to determining that the calculated first and second rates of pressure change satisfy a maximum rate of change.

158. The method of claim 156 or 157, wherein the transient blockage condition comprises at least one of a kink in the flow path and an occlusion in the flow path.

159. The method of any of claims 156 to 158, wherein the maximum rate of change comprises about 110%, about 120%, about 130%, about 140%, or about 150% of the threshold rate of change.

160. The method of any of claims 156 to 158, wherein the maximum rate of change comprises between about 105% and about 155% of the threshold rate of change.

161. The method of claim any of claims 156 to 160, wherein satisfying the maximum rate of change comprises equaling or exceeding the maximum rate of change.

162. The method of any of claims 146 to 161, wherein measuring the pressure values within the flow path comprises sampling a pressure within the fluid flow path during one or more time intervals.

163. The method of claim 162, further comprising sampling the pressure at least twice during each of the one or more time intervals.

164. The method of claim 162 or 163, further comprising averaging the pressure samples during each of the one or more time intervals.

165. A pump system configured for negative pressure wound therapy, the pump system comprising:
a pump assembly comprising:
an actuator; and
a diaphragm; and a controller configured to control operation of the pump system, the controller further configured to:
apply a drive signal to the pump assembly, the drive signal alternating between a positive amplitude and a negative amplitude and the drive signal having an offset; and
sample a pressure within a fluid flow path configured to connect the pump assembly to a wound dressing configured to be placed over a wound during one or more time intervals, wherein each of the one or more time intervals occurs when the drive signal is approximately at an amplitude equal to one or more sampling amplitudes.

166. The pump system of claim 165, wherein the sampling amplitude comprises a local maxima of the amplitude.

167. The pump system of claim 165 or 166, wherein the sampling amplitude comprises a local minima of the amplitude.

168. The pump system according to any of claims 165-167, wherein the sampling amplitude comprises a zero crossing of the amplitude.

169. The pump system according to any of claims 165-168, wherein the sampling amplitude comprises an offset crossing of the amplitude.

170. The pump system according to any of claims 165-169, wherein the controller is further configured to sample the pressure at least twice during each of the one or more time intervals.

171. The pump system of claim 170, wherein the controller is further configured to average the pressure samples during each time interval.

172. The pump system of any of claims 165-171, wherein the controller is further configured to adjust at least one parameter of the drive signal based on the pressure samples.

173. A method for controlling a pump system configured for negative pressure wound therapy, the method comprising:
applying a drive signal to a pump assembly of the pump system, the drive signal alternating between a positive amplitude and a negative amplitude and the drive signal having an offset; and
sampling a pressure within a fluid flow path configured to connect the pump system to a wound dressing configured to be placed over a wound during one or more time intervals, wherein each of the one or more time intervals occurs when the drive signal is approximately at an amplitude equal to one or more sampling amplitudes,
wherein the method is performed under control of a controller of the pump system.

174. The method of claim 173, wherein the sampling amplitude comprises a local maxima of the amplitude.

175. The method of claim 173 or 174, wherein the sampling amplitude comprises a local minima of the amplitude.

176. The method according to any of claims 173-175, wherein the sampling amplitude comprises a zero crossing of the amplitude.

177. The method according to any of claims 173-176, wherein the sampling amplitude comprises an offset crossing of the amplitude.

178. The method according to any of claims 173-177, further comprising sampling the pressure at least twice during each of the one or more time intervals.

179. The method of claim 178, further comprising averaging the pressure samples during each time interval.

180. The method of any of claims 173-179, further comprising adjusting at least one parameter of the drive signal based on the pressure samples.

Any apparatus and method described in this application can include any combination of the preceding features described in this and other paragraphs, among other features and combinations described herein, including features and combinations described in subsequent paragraphs, and including any features and combinations described in any application incorporated by reference herein.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

While certain embodiments have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present disclosure is defined only by reference to the claims presented herein or as presented in the future.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Various components illustrated in the figures may be implemented as software and/or firmware on a processor, controller, ASIC, FPGA, and/or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A pump system configured for negative pressure wound therapy, the pump system comprising:
   a pump assembly configured to provide a negative pressure, via a flow path, to a wound dressing configured to be positioned over a wound, the flow path configured to fluidically connect the pump assembly to the wound dressing;
   a sensor configured to measure a pressure in the flow path; and
   a controller configured to control operation of the pump assembly, the controller further configured to:
      determine a first pressure value in the flow path at a first time;
      determine a second pressure value in the flow path at a second time; and
      in response to determining that the first and second pressure values are between high and low pressure thresholds:
         calculate a first rate of pressure change using the first and second pressure values; and
         provide an indication that the wound dressing is full in response to determining that the calculated first rate of pressure change satisfies a threshold rate of change.

2. The pump system of claim 1, wherein the controller is further configured to:
   measure a third pressure value in the flow path at a third time;
   measure a fourth pressure value within the flow path at a fourth time;
   calculate a second rate of pressure change using the third and fourth pressure values; and
   provide the indication that the wound dressing is full in response to determining that the calculated first and second rates of pressure change satisfy the threshold rate of change.

3. The pump system of claim 2, wherein the controller is further configured to provide an indication of a transient blockage condition in response to determining that the calculated first and second rates of pressure change satisfy a maximum rate of change, the maximum rate of change being greater than the threshold rate of change.

4. The system of claim 2, wherein the controller is configured to calculate the second rate of pressure change using the third and fourth pressure values in response to determining that the third and fourth pressure values are between the high and low pressure thresholds.

5. The pump system of claim 1, wherein the pressure in the fluid flow path is maintained between the high and low pressure thresholds.

6. The pump system of claim 1, wherein the controller is further configured to: activate the pump assembly in response to determining that pressure in the flow path satisfies the high pressure threshold and deactivate the pump assembly in response to determining that pressure in the flow path satisfies the low pressure threshold.

7. The pump system of claim 1, wherein the controller is configured to provide the indication that the wound dressing is full in response to determining that the calculated first rate of pressure change equals or exceeds the threshold rate of change.

8. The pump system of claim 1, wherein the threshold rate of change is approximately −50 mmHg/second.

9. The pump system of claim 1, wherein the threshold rate of change is approximately −70 mmHg/second.

10. The pump system of claim 1, wherein the threshold rate of change is between approximately −20 mmHg/second and approximately −200 mmHg/second.

11. The pump system of claim 1, wherein the threshold rate of change is between approximately −40 mmHg/second and approximately −100 mmHg/second.

12. The pump system of claim 1, wherein the threshold rate of change is between approximately −50 mmHg/second and approximately −75 mmHg/second.

13. The pump system of claim 1, wherein the controller is further configured to provide an indication of a transient blockage condition in response to determining that the calculated first rate of pressure change satisfies a maximum rate of change the maximum rate of change being greater than the threshold rate of change.

14. The pump system of claim 13, wherein the transient blockage condition comprises at least one of a kink in the flow path and or an occlusion in the flow path.

15. The pump system of claim 13, wherein the maximum rate of change comprises about 110%, about 120%, about 130%, about 140%, or about 150% of the threshold rate of change.

16. The pump system of claim 13, wherein the maximum rate of change comprises between about 105% and about 155% of the threshold rate of change.

17. The pump system of claim 13, wherein the controller is further configured to provide an indication of the transient blockage condition in response to determining that the calculated first rate of pressure change equals or exceeds the maximum rate of change.

18. The pump system of claim 1, wherein the controller is further configured to sample a pressure within the fluid flow path during one or more time intervals.

19. The pump system of claim 18, wherein the controller is further configured to sample the pressure at least twice during each of the one or more time intervals.

20. The pump system of claim 18, wherein the controller is further configured to average the pressure samples during each of the one or more time intervals.

21. A method for controlling a pump system configured for negative pressure wound therapy, the method comprising:
    causing provision of negative pressure, via a flow path, to a wound dressing configured to be positioned over a wound, the flow path configured to fluidically connect the pump system to the wound dressing;
    measuring a first pressure value in the flow path at a first time;
    measuring a second pressure value in the flow path at a second time; and
    in response to determining that the first and second pressure values are between high and low pressure thresholds:
        calculating a first rate of pressure change using the first and second pressure values; and
        in response to determining that the calculated first rate of pressure change satisfies a threshold rate of change, providing an indication that the wound dressing is full,
    wherein the method is performed under control of a controller of the pump system.

22. The method of claim 21, further comprising maintaining the pressure in the fluid flow path between the high and low pressure thresholds.

23. The method of claim 21, further comprising:
    causing provision of negative pressure in response to determining that pressure in the flow path satisfies the high pressure threshold; and
    stopping provision of negative pressure in response to determining that pressure in the flow path satisfies the low pressure threshold.

24. The method of claim 21, wherein providing the indication that the wound dressing is full comprises providing the indication in response to determining that the calculated first rate of pressure change equals or exceeds the threshold rate of change.

25. The method of claim 21, wherein the threshold rate of change is approximately −50 mmHg/second, approximately −70 mmHg/second, between approximately −20 mmHg/second and approximately −200 mmHg/second, between approximately −40 mmHg/second and approximately −100 mmHg/second, or between approximately −50 mmHg/second and approximately −75 mmHg/second.

26. The method of claim 21, further comprising providing an indication of a transient blockage condition indicating at least one of a kink in the flow path or an occlusion in the flow path in response to determining that the calculated first rate of pressure change satisfies a maximum rate of change, the maximum rate of change being greater than the threshold rate of change.

27. The method of claim 26, wherein the maximum rate of change comprises about 110%, about 120%, about 130%, about 140%, about 150%, or between about 105% and about 155% of the threshold rate of change.

28. The method of claim 26, further comprising providing an indication of the transient blockage condition in response to determining that the calculated first rate of pressure change equals or exceeds the maximum rate of change.

29. The method of claim 21, further comprising:
    measuring a third pressure value in the flow path at a third time;
    measuring a fourth pressure value within the flow path at a fourth time;
    calculating a second rate of pressure change using the third and fourth pressure values; and
    providing the indication that the wound dressing is full in response to determining that the calculated first and second rates of pressure change satisfy the threshold rate of change.

30. The method of claim 29, further comprising calculating the second rate of pressure change using the third and fourth pressure values in response to determining that the third and fourth pressure values are between the high and low pressure thresholds.

* * * * *

UNITED STATES PATENT AND TRADEMARK OFFICE
CERTIFICATE OF CORRECTION

PATENT NO. : 10,682,446 B2
APPLICATION NO. : 15/536260
DATED : June 16, 2020
INVENTOR(S) : Ben Alan Askem It is certified that error appears in the above-identified patent and that said Letters Patent is hereby corrected as shown below:

In the Specification

In Column 37, Line 44, delete "650`'" and insert --650'--.

In Column 39, Line 12, delete "can by" and insert --can be--.

In Column 40, Line 58, delete "DRAM." and insert --DRAM,--.

In Column 75, Line 37, delete "according" and insert --of--.

In Column 75, Line 44, delete "of the of the" and insert --of the--.

In the Claims

In Column 88, Line 60, Claim 4, delete "system" and insert --pump system--.

In Column 89, Line 29, Claim 13, delete "change" and insert --change,--.

In Column 89, Line 33, Claim 14, delete "and or" and insert --or--.

Signed and Sealed this
Third Day of November, 2020

Andrei Iancu
*Director of the United States Patent and Trademark Office*